(12) United States Patent
Abend et al.

(10) Patent No.: US 11,433,132 B2
(45) Date of Patent: Sep. 6, 2022

(54) POLYOMAVIRUS NEUTRALIZING ANTIBODIES

(71) Applicant: Novartis AG, Basel (CH)

(72) Inventors: Johanna Abend, Emeryville, CA (US); Vanessa Cornacchione, Basel (CH); John Michael Lindner, Basel (CH); Elisabetta Traggiai, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/768,429

(22) PCT Filed: Nov. 28, 2018

(86) PCT No.: PCT/IB2018/059429
§ 371 (c)(1),
(2) Date: May 29, 2020

(87) PCT Pub. No.: WO2019/106578
PCT Pub. Date: Jun. 6, 2019

(65) Prior Publication Data
US 2020/0384109 A1    Dec. 10, 2020

Related U.S. Application Data

(60) Provisional application No. 62/727,168, filed on Sep. 5, 2018, provisional application No. 62/593,566, filed on Dec. 1, 2017.

(51) Int. Cl.
| | |
|---|---|
| *A61K 39/42* | (2006.01) |
| *A61P 31/20* | (2006.01) |
| *A61K 31/343* | (2006.01) |
| *A61K 31/436* | (2006.01) |
| *A61K 31/52* | (2006.01) |
| *A61K 38/13* | (2006.01) |
| *C07K 16/08* | (2006.01) |

(52) U.S. Cl.
CPC ............ *A61K 39/42* (2013.01); *A61K 31/343* (2013.01); *A61K 31/436* (2013.01); *A61K 31/52* (2013.01); *A61K 38/13* (2013.01); *A61P 31/20* (2018.01); *C07K 16/084* (2013.01); *C07K 2317/33* (2013.01); *C07K 2317/51* (2013.01); *C07K 2317/515* (2013.01); *C07K 2317/565* (2013.01); *C07K 2317/622* (2013.01); *C07K 2317/70* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 8,470,979 | B2 | 6/2013 | Bondensgaard et al. |
| 9,862,760 | B2 | 1/2018 | Abend et al. |
| 10,435,460 | B2 | 10/2019 | Abend et al. |
| 10,450,366 | B2 | 10/2019 | Abend et al. |
| 10,654,914 | B2 | 5/2020 | Abend et al. |
| 2010/0215662 | A1 | 8/2010 | Bradbury |
| 2013/0337438 | A1* | 12/2013 | Mori ................... G01N 33/6854 435/5 |
| 2015/0056188 | A1 | 2/2015 | Simon et al. |
| 2017/0088605 | A1 | 3/2017 | Abend et al. |
| 2018/0079799 | A1 | 3/2018 | Abend et al. |
| 2019/0002533 | A1 | 1/2019 | Abend et al. |
| 2019/0071488 | A1 | 3/2019 | Abend et al. |
| 2020/0190167 | A1 | 6/2020 | Abend et al. |

FOREIGN PATENT DOCUMENTS

| | | |
|---|---|---|
| WO | WO-2003/105894 | 12/2003 |
| WO | WO-2013/142299 | 9/2013 |
| WO | WO-2014/002035 | 1/2014 |
| WO | WO-2014/102399 | 7/2014 |
| WO | WO-2015/095770 | 6/2015 |
| WO | WO-2017/046676 | 3/2017 |
| WO | WO-2019/106578 | 6/2019 |

OTHER PUBLICATIONS

Abend et al. (2007). "Inhibitory Effect of Gamma Interferon on BK Virus Gene Expression and Replication" J. Virology 81 :272-279.
Antinori et al. (2003). "Clinical epidemiology and survival of progressive multifocal leukoencephalopathy in the era of highly active antiretroviral therapy: Data from the Italian Registry Investigative Neuro Aids (IRINA)" Journal of NeuroVirology 9(supplemental 1): 47-53.
Astrom et al. (1958). "Progressive Multifocal Leuko-Encephalopathy a Hitherto Unrecognized Complication of Chronic Lymphatic Leukemia and Hodgkin's Disease" Brain 81(1): 93-111.
Bennett et al. (2012). "BK polyomavirus: emerging pathogen" Microbes and Infection 14(9):672-683.
Binet et al. (1999). "Polyomavirus Disease Under New Immunosuppressive Drugs: A Cause of Renal Graft Dysfunction and Graft Loss" Transplantation 67(6):918-922.
Brennan et al. (2005). "Incidence of BK with tacrolimus versus cyclosporine and impact of preemptive immunosuppression reduction" Am. J. Transplant 5(3):582-594.
Bressollette-Bodin et al. (2005). "A Prospective Longitudinal Study of BK Virus Infection in 104 Renal Transplant Recipients" American Journal of Transplantation 5(8): 1926-1933.
Broekema et al. (2010). "A system for the analysis of BKV non-coding control regions: Application to clinical isolates from an HIV/AIDS patient" Virology 407:368-373.
Carter et al. (2003). "Lack of Serologic Evidence for Prevalent Simian Virus 40 Infection in Humans" J. Natl. Cancer Inst. 95:1522-1530.
Chatterjee et al. (2000). "Identification of Archetype and Rearranged Forms of BK Virus in Leukocytes From Healthy Individuals" Journal of Medical Virology 60:353-362.

(Continued)

*Primary Examiner* — Adam Weidner
(74) *Attorney, Agent, or Firm* — Cooley LLP

(57) ABSTRACT

The present invention relates to anti-polyomavirus antibodies, antibody fragments, and their uses for the prevention and treatment of BK or JC virus infection and associated diseases.

34 Claims, 10 Drawing Sheets

Specification includes a Sequence Listing.

(56) References Cited

OTHER PUBLICATIONS

Chen et al. (2015). "Synthetic antibodies and peptides recognizing progressive multifocal leukoencephalopathyspecific point mutations in polyomavirus JC capsid viral protein 1" mABS 7(4):681-692.
Derienzo et al. (2000). "Evaluation of the Half-Life of Intravenous Human Cytomegalovirus Immune Globulin in Patients Receiving Partially Mismatched Related Donor Bone Marrow Transplantation" Pharmacotherapy 20: 1175-1178.
Garcia-Suarez et al. (2005). "Changes in the Natural History of Progressive Multifocal Leukoencephalopathy in HIV-negative Lymphoproliferative Disorders: Impact of Novel Therapies" Am. J Hematol 80(4):271-281.
Gardner. (1971). "New human papovavirus (B.K.) isolated from urine after renal transplantation" Lancet 297(7712):1253-1257.
Gorelik et al. (2011). "Progressive Multifocal Leukoencephalopathy (PML) Development is Associated with Mutations in JC Virus Capsid Protein VP1 that Change its Receptor Specificity" Journal of Infectious Diseases 204:237-244.
Goudsmit et al. (1982). "The role of BK virus in acute respiratory tract disease and the presence of BKV DNA in tonsils" Journal of Medical Virology 10:91-99.
Heritage et al. (1981). "The persistence of papovavirus BK DNA sequences in normal human renal tissue" Journal of Medical Virology 8:143-150.
Hirsch. (2002). "Polyomavirus BK nephropathy: a (re-)emerging complication in renal transplantation" Am. J. Transplant 2 (1):25-30.
Hirsch et al. (2002). "Prospective Study of Polyomavirus Type BK Replication and Nephropathy in Renal-Transplant Recipients" New England J. Medicine 347(7):488-496.
Hirsch et al. (2005). "Polyomavirus-Associated Nephropathy in Renal Transplantation: Interdisciplinary Analyses and Recommendations" Transplantation 79(1):1277-1286.
Jiang et al. (2009). "The Role of Polyomaviruses in Human Disease" Virology 384(2): 266-273.
Johne et al. (2004). "Nuclear Localization of Avian Polyomavirus Structural Protein VP1 Is a Prerequisite for the Formation of Virus-Like Particles." Journal of Virology, 78(2): 930-937.
Johne et al. (2011). "Taxonomical Developments in the Family Polyomaviridae" Arch. Virol. 156(9):1627-1634.
Knowles et al. (2006). "Discovery and Epidemiology of the Human Polyomaviruses BK Virus (BKV) and JC Virus (JCV)" Adv. Exp. Med. Biol. 577: 19-45.
Lipshutz et al. (2004). "BK Nephropathy in Kidney Transplant Recipients Treated with a Calcineurin Inhibitor-Free Immunosuppression Regimen" American Journal of Transplantation 2004; 4: 2132-2134.
Liu. (2015). "Antibody Glycosylation and its Impact on the Pharmacokinetics and Pharmacodynamics of Monoclonal Antibodies and Fc-fusion Proteins" J. Pharm. Sci. 104(6): 1866-1884.
Mengelle et al. (2011). "JC Virus DNA in the Peripheral Blood of Renal Transplant Patients: a 1-Year Prospective Follow-up in France" J. Med. Viral. 83(1):132-136.
Neu et al. (2013). Pios Pathogens 9(10):e1003714 and e1003688.
Nickeleit et al. (1999). "Polyomavirus Infection of Renal Allograft Recipients: From Latent Infection to Manifest Disease" J. Am. Seo. Neprol. 10(5):1080-1089.
O'Hara et al. (2014). "Gallic acid-based small-molecule inhibitors of JC and BK polyomaviral infection" Virus Research 189:280-285.
Padgett et al. (1971). "Cultivation of Papova-Like Virus from Human Brain with Progressive Multifocal Leucoencephalopathy" Lancet 297(7712):1257-1260.
Padgett et al. (1973). "Prevalence of Antibodies in Human Sera against JC Virus, an Isolate from a Case of Progressive Multifocal Leukoencephalopathy" Journal of Infectious Diseases 127(4):467-470.
Pastrana et al. (2012). "Neutralization Serotyping of BK Polyomavirus Infection in Kidney Transplant Recipients" PLoS Pathogens vol. 8(4)e1002650.
Purighalla et al. (1995). "BK Virus Infection in a Kidney Allograft Diagnosed by Needle Biopsy" American Journal of Kidney Diseases 26(4):671-673.
Qian et al. (2010). "Lipids and Proteins Act in Opposing Manners To Regulate Polyomavirus Infection" Journal of Virology 84(19):9840-9852.
Randhawa et al. (1999). "Human Polyoma Virus-Associated Interstital Nephritis in the Allograft Kidney" Transplantation 67:103-109.
Randhawa et al. (2006). "BK Virus Infection in Transplant Recipients: An Overview and Update" American Journal of Transplantation 6(9):2000-2005.
Randhawa et al. (2009). "Identification of Species-Specific and Cross-Reactive Epitopes in Human Polyomavirus Capsids Using Monoclonal Antibodies" Journal of General Virology 90:634-639.
Randhawa et al. (2015). "Commercially Available Immunoglobulins Contain Virus Neutralizing Antibodies Against all Major Genotypes of Polyomavirus" BK. Am J Transplant. 15(4):1014-20.
Reid et al. (2011). "Sequencing and Analysis of JC Virus DNA From Natalizumab-Treated PML Patients" J Infect Dis. 204:237-244.
Reploeg et al. (2001). "BK Virus: A Clinical Review" Clin Infect. Dis. 33(2):191-202.
Richardson. (1961). "Progressive Multifocal Leukoencephalopathy." New England Journal of Medicine 265(17):815-823.
Rudikoff et al. (1982). "Single Amino Acid Substitution Altering Antigen-Binding Specificity" Proc. Natl. Acad. Sci. U.S.A. 79:1979-1983.
Sabath et al. (2002). "Traffic of JC Virus from Sites of Initial Infection to the Brain: The Path to Progressive Multifocal Leukoencephalopathy" Journal Infectious Diseases 186:S180-S186.
Shinohara et al. (1993). "BK Virus Infection of the Human Urinary Tract" Journal of Medical Virology 41(4):301-305.
Wiseman et al. (2009). "Polyomavirus Nephropathy: A Current Perspective and Clinical Considerations" Am.J. Kidney Dis 54 (1):131-142.

* cited by examiner

FIGURE 1

| | Clone | ELISA binding | | Subclass | IgG1 viral neutralization EC$_{50}$ (nM) | | | | |
|---|---|---|---|---|---|---|---|---|---|
| | | BKV-ST1 | BKV-ST4 | | ST1 | ST2 | ST3 | ST4 | JCV |
| IgG CD27$^+$CD73$^+$ | NOV219 | ● | ● | IgG3 | 0.5 | 17 | | | |
| | NOV399 | ● | ● | IgG3 | 0.2 | | | | |
| | NOV675 | ● | ● | IgG3 | 0.2 | | | | |
| | NOV567 | ● | ● | IgG3 | 0.4 | 38 | | 18 | |
| | NOV581 | ● | ● | IgG1 | 0.7 | 0.7 | 2.8 | 0.3 | 250 |
| | NOV487 | ● | ● | IgG1 | 4.5 | 14 | 4.1 | 20 | |
| IgG CD27$^+$CD73$^-$ | NOV796 | ● | ● | IgG1 | 0.4 | 3.5 | 3.3 | 0.3 | 0.4 |
| IgG CD27$^-$CD73$^+$ | NOV530 | ● | ● | IgG3 | 0.3 | 0.5 | 2.8 | 0.1 | 0.05 |
| | NOV638 | ● | | IgG1 | 0.03 | | | | |

```
                   PENTAMER B₂
              316---------330
      ST1     RVDGQPMYGMESQVE     (SEQ ID NO:386)
      ST2     KVDGQPMYGMESQVE     (SEQ ID NO:387)
BKV   ST3     KVDGQPMYGMESQVE     (SEQ ID NO:388)
      ST4     RVDGQPMYGMESQVE     (SEQ ID NO:389)
      JCV     RVDGQPMYGMDAQVE     (SEQ ID NO:390)
      MCV     KVSGQPMEGKDNQVE     (SEQ ID NO:391)
```

FIGURE 3E

PENTAMER A₄

```
          169  182------193
     ST1  Y/   NPTAQSQVMNTD  (SEQ ID NO:392)
     ST2  Y/   NPTAQSQVMNTD  (SEQ ID NO:393)
BKV  ST3  Y/   NPTAQSQVMNTD  (SEQ ID NO:394)
     ST4  Y/   NPTAQSQVMNTD  (SEQ ID NO:395)
     JCV  Y/   NATVQSQVMNTE  (SEQ ID NO:396)
     MCV  Y/   KMTPKNQGLDPQ  (SEQ ID NO:397)
```

FIGURE 3F

PENTAMER A₃

BKV {
ST1  59--64  PDENLR (SEQ ID NO:398)   81---87  PERKMLP (SEQ ID NO:404)
ST2         PDDNLR (SEQ ID NO:399)            PDRKMLP (SEQ ID NO:405)
ST3         PDDNLR (SEQ ID NO:400)            PDRKMLP (SEQ ID NO:406)
ST4         PDNNLR (SEQ ID NO:401)            PDRKMLP (SEQ ID NO:407)
JCV         PDEHLR (SEQ ID NO:402)            PSNDMLP (SEQ ID NO:408)
MCV         NSPDLP (SEQ ID NO:403)            PIKENLP (SEQ ID NO:409)

BKV {
ST1  172-176  KYPDG (SEQ ID NO:410)   198-201  LDKN (SEQ ID NO:416)
ST2          KYPQG (SEQ ID NO:411)            LDKN (SEQ ID NO:417)
ST3          KYPQG (SEQ ID NO:412)            LDKN (SEQ ID NO:418)
ST4          KYPEG (SEQ ID NO:413)            LDKN (SEQ ID NO:419)
JCV          KYPDG (SEQ ID NO:414)            LDKN (SEQ ID NO:420)
MCV          EYPKT (SEQ ID NO:415)            LDKD (SEQ ID NO:421)

FIGURE 3G

NOV530 VH4-31

```
              S
CDR1  GGSISGGGYYWS         (SEQ ID NO:422)
            SGS
CDR2  YIYYNRGT             (SEQ ID NO:423)
                I
CDR3  ARCVLGGYGSDAFDR      (SEQ ID NO:424)
```

FIGURE 3H

```
                      Y
NOV530 VK3-11   CDR1  RASQSVSSHLA      (SEQ ID NO: 425)
                        N T
                CDR2  (Y)DASSRAN       (SEQ ID NO: 426)
                         N
                CDR3  QQRSSWPPSLT      (SEQ ID NO: 427)
```

POLYOMAVIRUS NEUTRALIZING ANTIBODIES

CROSS REFERENCE TO RELATED APPLICATIONS

This application is the national stage of PCT Application No PCT/IB2018/059429 filed Nov. 28, 2018, which claims priority to U.S. provisional applications No. 62/727,168 filed Sep. 5, 2018 and No. 62/593,566 filed Dec. 1, 2017. The entire content of these applications is hereby incorporated by reference.

SEQUENCE LISTING

The instant application contains a Sequence Listing which has been submitted in ASCII format via EFS-Web and is hereby incorporated by reference in its entirety. Said ASCII copy, created on May 14, 2020 is named "APMX-002_02WO—PCT Sequence Listing.TXT" and is 493.8 kilobytes in size.

FIELD OF THE INVENTION

The present disclosure is directed to anti-polyomavirus antibodies, antibody fragments, and their uses for the reducing the likelihood or treatment of polyomaviral infection.

BACKGROUND OF THE INVENTION

Of the human polyomaviruses, BK virus (BKV) and JC virus (JCV) were the first two identified. These two polyomaviruses were isolated from immunosuppressed patients and published in the same issue of Lancet in 1971 (Gardner et al., Lancet 1971 1:1253-1527, and Padgett et al., Lancet 1971 1:1257-1260). Polyomaviruses are icosahedral, non-enveloped, double-stranded DNA viruses. They measure 40-45 nm in diameter and are comprised of 88% protein and 12% DNA.

The BKV genome is a circular double-stranded DNA of approximately 5000 base pairs in length and contains three major divisions: the early coding region, the late coding region, and a non-coding control region. The early coding region encodes for the three regulatory proteins (large tumor antigen [TAg], small tumor antigen [tAg], and truncated tumor antigen [truncTAg]), which are the first viral proteins expressed in a newly infected cell and are responsible for facilitating viral DNA replication and establishing a favorable cellular environment. The late coding region encodes the three structural proteins (VP1, VP2, and VP3) that make up the viral capsid, as well as the agnoprotein, the role of which during viral replication is less well-defined. The non-coding control region contains the genomic origin of replication as well as the early and late promoters that drive expression of the viral gene products.

BKV has been detected in many different cell types, including epithelial cells of the kidney, bladder, and ureter (typical sites of persistence), tonsillar tissue, and lymphocytes (proposed sites of primary infection and dissemination) (Chatterjee et al., J. Med. Virol. 2000; 60:353-362, Goudsmit et al., J. Med. Virol. 1982; 10:91-99, Heritage et al., J. Med. Virol. 1981; 8:143-150, Shinohara et al., J. Med. Virol. 1993; 41(4):301-305). The primary cell surface receptors for BKV are the gangliosides GT1b, GD1b, and GD3, all of which have a terminal α2,8-linked sialic acid and are fairly ubiquitous, allowing infection of various cell types (Neu et al., PLos Patholog. 2013; 9(10):e1003714 and e1003688, see also, O'Hara et al., Virus Res. 2014; 189: 208-285). The non-enveloped icosahedral virion of BKV is composed of three distinct viral proteins: 360 copies of the major viral capsid protein VP1 arranged in 72 pentamers and 72 copies combined of the minor viral capsid proteins VP2 and VP3, with one VP2 or VP3 molecule associated with each VP1 pentamer. Only VP1 is exposed on the virion surface at entry and each pentamer has five low-affinity binding sites for the ganglioside receptor. Binding of VP1 pentamers to ganglioside receptors on the cell surface initiates internalization through a caveolae-mediated endocytic pathway, followed by trafficking of the virus to the endoplasmic reticulum and finally, to the nucleus (Tsai and Qian, J. Virol 2010; 84(19):9840-9852).

Infection with BKV is essentially ubiquitous, with estimates ranging between 80% and 90% of the population globally infected (Knowles W. A., Adv. Exp. Med. Biol. 2006; 577:19-45). Primary infection most often occurs during childhood (i.e., before age 10) and results in either a mild, non-specific, self-limited illness or no symptoms at all. Persistent infection is established in the epithelial cells of the renal tubules, ureters, and bladder, and is effectively controlled by the immune system. Transient asymptomatic viral shedding in the urine of immunocompetent adults occurs sporadically but results in no disease or sequelae. However, compromised immune function, particularly upon immunosuppression following renal or hematopoietic stem cell transplantation, can lead to uncontrolled BKV replication and ultimately to BKV-associated nephropathy (BKVAN) or hemorrhagic cystitis (HC), a painful disease of the bladder. There are no effective antiviral therapies against BKV and the current standard of care is reduction of immunosuppression, which increases the risk of acute rejection. Even with the current, more aggressive approaches to monitoring and prevention, up to 10% of renal transplant recipients will develop BKVAN and 15-30% of those patients will suffer graft loss due to BKVAN. Among those undergoing reduction in immunosuppressive regimen upon detection of BK viremia, up to 30% will experience an acute rejection episode as a result.

Although BKV was first described in 1971 (supra), it was not until the 1990s that BKVAN was reported in the literature as a cause of kidney transplant injury (Purighalla et al., Am. J. Kidney Dis. 1995; 26:671-673 and Randhawa et al., Transplantation 1999; 67:103-109). In early management of BKVAN, testing positive for BK had severe consequences, with more than 50% of the patients having graft dysfunction and graft loss (Hirsch et al., New Engl. J. Med. 2002; 347:488-496). BKV reactivation and replication follows a well-established clinical course in kidney transplant patients, evidenced first by detection of virus and viral DNA in the urine (viruria), followed by detection of virus in the bloodstream (viremia), and finally signs of nephropathy and diminished kidney function as a result of viral replication. Approximately 30-40% of all kidney transplant recipients will have viruria and 10-20% of recipients will have BK viremia, typically within the first 3 months post-tranpslantation (Sawinski and Goral, Nephrol Dial Transplant. 2015; 30:209-217; Hirsch et al., Am J Transplant. 2013; 13:136-145; Dharnidharka et al., Pediatr Nephrol. 2011; 26:1763-1774; Babel et al., Transplantation. 2009; 88:89-95). Approximately 1-10% of all kidney transplant recipients will progress to BKVAN, typically within the first year post-transplant (Bohl and Brennan, Clin J Am Soc Nephrol. 2007; 2(Suppl 1): S36-46; Sawinski and Goral, Nephrol Dial Transplant. 2015; 30:209-217). BKV replication in the renal tubular epithelial cells causes necrosis and lytic destruction, leading to denudation of the basement membrane, accumulation of tubular fluid in the interstitum, and ultimately results in interstitial fibrosis and tubular atrophy (Nickeleit et al., J. Am. Soc. Neprol. 1999; 10(5):1080-1089). Patients may present with deterioration of renal function, tubule-interstitial nephritis and ureteric stenosis (Garner et al., Lancet 1971; 1(7712):1253-1257 and Hirsch Am. J. Transplant 2002; 2(1)25-30).

BKV can also cause pneumonitis, retinitis, and meningoencephalitis in immunocompromised hosts (Reploeg et al., Clin. Infect. Dis. 2001; 33(2):191-202). BKV disease in hematopoietic stem cell transplant (HSCT) recipients typically manifests as hemorrhagic cystitis (HC), which can vary in severity. Viruria (but not always viremia) and painful hematuria are associated with the clinical presentation of HC. The current standard of care is supportive in nature, involving primarily forced hydration/diuresis and pain management measures. The most severe cases require blood transfusions, clot evacuation, and can lead to death in some instances. HC of any cause (e.g. drug, radiation, viral) is relatively common among HSCT recipients but BKV-associated HC occurs in approximately 10-12% of patients usually within 6 months post-transplantation. There are other viral etiologies of HC, with adenovirus being a more common cause of HC among pediatric HSCT recipients compared with adult HSCT recipients. BK virus has also been observed in other immunocompromised conditions such as solid organ transplants and in HIV/AIDS patients (Jiang et al., Virol. 2009; 384:266-273).

At this point, the standard of care treatment of BKVAN is the reduction of immunosuppression in an attempt to prevent graft dysfunction and graft loss (Wiseman et al., Am. J. Kidney Dis. 2009; 54(1): 131-142 and Hirsch et al., Transplantation 2005; 79(1): 1277-1286). There are no fixed clinical regimes for the reduction, as reduction of the immunosuppression may help to prevent progression from viremia to the extensive damage associated with clinical nephropathy, but this also increases the risk of acute organ rejection (Brennan et al., Am. J. Transplant 2005; 5(3):582-594). Clinicians have reported the use of therapeutics such as cidofovir, leflunomide, or quinolones in combination with the reduction of immunosuppressants; however, the reports find this approach ineffective, with the added burden of managing additional side effects (Randhawa and Brennan Am. J. Transplant 2006; 6(9):2000-2005). As such, there is an unmet and useful need in the field for therapies that neutralize polyoma viruses such as BKV and that can be used in an immunocompromised host.

JC virus (JCV) is another human polyomavirus which is highly prevalent in the population (80%), although JCV is generally acquired later than BKV (Padgett et al., J. Infect. Dis. 1973; 127(4):467-470 and Sabath et al., J. Infect. Dis. 2002; 186 Suppl. 2:5180-5186). After initial infection, JCV establishes latency in the lymphoid organs and kidneys and when reactivated, invades the central nervous system (CNS) via infected B lymphocytes. Once in the CNS, the JCV causes progressive multifocal leukoencephalopathy (PML), which is a progressive demyelinating CNS disorder. Most cases of PML are associated with immunomodulatory therapies used for the treatment of multiple sclerosis (e.g., natalizumab, fingolimod) or rheumatoid arthritis (e.g., rituximab) and disease progression is usually halted by cessation of treatment. Given the progressive nature of PML, it may be possible to document significant improvement in patients receiving JCV neutralizing antibodies over several months, either by clinical criteria or by MRI, which is already routinely used to monitor multiple sclerosis, in patients receiving JCV neutralizing antibodies over several months. PML may also manifest in HIV/AIDS patients and has also been reported in immunosuppressed patients (Angstrom et al., Brain 1958; 81(1):93-111 and Garcia-Suarez et al., Am. J. Hematol. 2005; 80(4):271-281). PML patients present with confusion, mental status changes, gait ataxia, focal neurological defects such as hemi paresis, limb paresis, and visual changes (Richardson E. P., N. Eng. J. Med. 1961; 265:815-823). The prognosis of patients with PML is poor and is especially poor in patients with HIV/AIDS (Antinori et al., J. Neurovirol. 2003; 9 suppl. 1:47-53). This further highlights the unmet and useful need in the field for therapies that neutralize polyomaviruses such as JCV.

SUMMARY OF THE INVENTION

The present disclosure is directed to neutralizing antibodies to human polyomaviruses and/or fragments thereof, antibodies that recognize BK virus and/or JC virus.

An antibody, wherein said antibody or antigen binding fragment thereof specifically binds BK virus and/or JC virus.

The antibody wherein said antibody or antigen binding fragment thereof specifically binds BK virus and/or JC virus. In one embodiment, the antibody or antigen binding fragment thereof binds to BKV serotype I, BKV serotype II, BKV serotype III or BKV serotype IV or a combination of serotypes I-IV. In another embodiment, the antibody or antigen binding fragment thereof further binds to JC virus.

The antibody wherein said antibody or antigen binding fragment specifically binds to and neutralizes BK and/or JC virus. In one embodiment, the antibody or antigen binding fragment thereof binds to and neutralizes BK serotype I. In one embodiment, the antibody or antigen binding fragment thereof binds to and neutralizes BKV serotype I and BKV serotype II. In another embodiment, the antibody or antigen binding fragment thereof binds to and neutralizes BKV serotype I and BKV serotype III. In another embodiment, the antibody or antigen binding fragment thereof binds to and neutralizes BKV serotype I and BKV serotype IV. In another embodiment, the antibody or antigen binding fragment thereof binds to and neutralizes BKV serotype II and BKV serotype III. In another embodiment, the antibody or antigen binding fragment thereof binds to and neutralizes BKV serotype II and BKV serotype IV. In another embodiment, the antibody or antigen binding fragment thereof binds to an neutralizes BKV serotype I and JCV. In a preferred embodiment, the antibody or antigen binding fragment thereof binds to and neutralizes BKV serotypes I, II, III and IV. Furthermore, the antibody or antigen binding fragment thereof binds to and neutralizes BKV serotypes I, II, III and IV and JCV.

An isolated antibody or antigen binding fragment thereof, wherein said antibody or antigen binding fragment thereof comprises: (i) a heavy chain region and (ii) a light chain region set forth in Table 2.

An isolated antibody, wherein said antibody or antigen binding fragment thereof comprises:
(i) a heavy chain variable region that comprises (a) a HCDR1 (CDR-Complementarity Determining Region) of SEQ ID NO: 9, (b) a HCDR2 of SEQ ID NO:10, (c) a HCDR3 of SEQ ID NO:11 and a light chain variable region that comprises: (d) a LCDR1 of SEQ ID NO:25, (e) a LCDR2 of SEQ ID NO:26, and (f) a LCDR3 of SEQ ID NO:27;
(ii) a heavy chain variable region that comprises (a) a HCDR1 of SEQ ID NO:41, (b) a HCDR2 of SEQ ID NO:42, (c) a HCDR3 of SEQ ID NO:43; and a light chain variable region that comprises: (d) a LCDR1 of SEQ ID NO:57, (e) a LCDR2 of SEQ ID NO:58, and (f) a LCDR3 of SEQ ID NO:59;
(iii) a heavy chain variable region that comprises (a) a HCDR1 of SEQ ID NO:73, (b) a HCDR2 of SEQ ID NO:74, (c) a HCDR3 of SEQ ID NO:75; and a light chain variable region that comprises: (d) a LCDR1 of SEQ ID NO:89, (e) a LCDR2 of SEQ ID NO:90, and (f) a LCDR3 of SEQ ID NO:91; (iv) a heavy chain variable region that comprises: (a) a HCDR1 of SEQ ID NO:105, (b) a HCDR2 of SEQ ID NO:106, (c) a HCDR3 of SEQ ID NO:107; and a light chain variable region that comprises: (d) a LCDR1 of SEQ ID NO:121, (e) a LCDR2 of SEQ ID NO:122, and (f) a LCDR3 of SEQ ID NO:123;
(v) a heavy chain variable region that comprises: (a) a HCDR1 of SEQ ID NO:137, (b) a HCDR2 of SEQ ID NO:138, (c) a HCDR3 of SEQ ID NO:139; and a light chain variable region that comprises: (d) a LCDR1 of SEQ ID NO:153, (e) a LCDR2 of SEQ ID NO:154, and (f) a LCDR3 of SEQ ID NO:155;
(vi) a heavy chain variable region that comprises: (a) a HCDR1 of SEQ ID NO:169, (b) a HCDR2 of SEQ ID NO:170, (c) a HCDR3 of SEQ ID NO:171; and a light chain variable region that comprises: (d) a LCDR1 of SEQ ID NO:185, (e) a LCDR2 of SEQ ID NO:186, and (f) a LCDR3 of SEQ ID NO:187;
(vii) a heavy chain variable region that comprises: (a) a HCDR1 of SEQ ID NO:201, (b) a HCDR2 of SEQ ID NO: 202, (c) a HCDR3 of SEQ ID NO:203; and a light chain variable region that comprises: (d) a LCDR1 of SEQ ID NO:217, (e) a LCDR2 of SEQ ID NO:218, and (f) a LCDR3 of SEQ ID NO:219;
(viii) a heavy chain variable region that comprises: (a) a HCDR1 of SEQ ID NO:233, (b) a HCDR2 of SEQ ID NO:234, (c) a HCDR3 of SEQ ID NO:235; and a light chain variable region that comprises: (d) a LCDR1 of SEQ ID NO:249, (e) a LCDR2 of SEQ ID NO:250, and (f) a LCDR3 of SEQ ID NO:251; and
(ix) a heavy chain variable region that comprises: (a) a HCDR1 of SEQ ID NO:265, (b) a HCDR2 of SEQ ID NO: 266, (c) a HCDR3 of SEQ ID NO:267; and a light chain variable region that comprises: (d) a LCDR1 of SEQ ID NO:281, (e) a LCDR2 of SEQ ID NO:282, and (f) a LCDR3 of SEQ ID NO: 283.

The antibody wherein one or two amino acids within a CDR have been modified, deleted, or substituted.

The antibody that retains at least 90, 91, 92, 93, 94, 95, 96, 97, 98 or 99% identity over either the variable heavy chain region or the variable light chain region.

The antibody wherein the antibody is a monoclonal antibody, a chimeric antibody, a humanized antibody, a human engineered antibody, a human antibody, a single chain antibody (scFv), or an antibody fragment.

An isolated antibody or antigen binding fragment thereof, wherein said antibody or antigen binding fragment thereof comprises:
(i) a heavy chain variable region (vH) that comprises SEQ ID NO:18, and a light chain variable region (vL) that comprises SEQ ID NO: 34;
(ii) a heavy chain variable region (vH) that comprises SEQ ID NO: 50, and a light chain variable region (vL) that comprises SEQ ID NO: 66;
(iii) a heavy chain variable region (vH) that comprises SEQ ID NO: 82, and a light chain variable region (vL) that comprises SEQ ID NO:98;
(iv) a heavy chain variable region (vH) that comprises SEQ ID NO:114, and a light chain variable region (vL) that comprises SEQ ID NO:130;
(v) a heavy chain variable region (vH) that comprises SEQ ID NO:146, and a light chain variable region (vL) that comprises SEQ ID NO:162;
(vi) a heavy chain variable region (vH) that comprises SEQ ID NO:178, and a light chain variable region (vL) that comprises SEQ ID NO:194;
(vii) a heavy chain variable region (vH) that comprises SEQ ID NO:210, and a light chain variable region (vL) that comprises SEQ ID NO:226;
(viii) a heavy chain variable region (vH) that comprises SEQ ID NO: 242, and a light chain variable region (vL) that comprises SEQ ID NO:258; and
(ix) a heavy chain variable region (vH) that comprises SEQ ID NO:274, and a light chain variable region (vL) that comprises SEQ ID NO:290.

The antibody or fragment thereof, that retains at least 90, 91, 92, 93, 94, 95, 96, 97, 98 or 99% identity over either the variable light or variable heavy region.

The antibody wherein one, two, three, four or five, but less than 10 amino acids within the variable light or variable heavy region have been modified, deleted or substituted.

The antibody wherein the antibody is a monoclonal antibody, a chimeric antibody, a humanized antibody, a human engineered antibody, a human antibody, a single chain antibody (scFv) or an antibody fragment.

The method of isolating and producing the antibody, in which the natural signal/leader peptide sequence matching the appropriate VH and/or VL gene segments is used.

The method of isolating and producing the antibody, in which a synthetic and/or optimized signal/leader peptide sequence is used to improve expression and yield.

The antibody wherein the antibody or fragment thereof has reduced glycosylation or no glycosylation or is hypofucosylated.

A pharmaceutical composition comprising the antibody or fragment thereof, further comprising a pharmaceutically acceptable carrier.

The pharmaceutical composition, wherein the pharmaceutically acceptable carrier contains histadine or a sugar.

The pharmaceutical composition, wherein the sugar is sucrose.

A pharmaceutical composition comprising a plurality of an antibody or antigen binding fragment, wherein at least 0.05%, 0.1%, 0.5%, 1%, 2%, 3%, 5% or more or more of the antibodies in the composition have an α2,3-linked sialic acid residue.

A pharmaceutical composition comprising a plurality of an antibody or antigen binding fragment, wherein none of the antibodies comprise a bisecting GlcNAc.

The pharmaceutical composition comprising the antibody or fragment thereof, wherein the composition is prepared as a lyophilisate.

A method of neutralizing a BK virus or JC virus infection comprising administering via injection or infusion to a patient in need an effective amount of the antibody.

The method wherein the patient in need is diagnosed with BK viruria or BK viremia.

The method wherein the patient in need is diagnosed with JC viruria or JC viremia.

A method of treating or reducing the likelihood of a BK virus or JC virus associated disorder, comprising administering via injection or infusion to a patient in need an effective amount of the antibody, and wherein the disorder is: nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

The method wherein the antibody or composition is reconstituted prior to injection or infusion.

The method wherein the antibody or the pharmaceutical composition is administered in combination with another therapeutic agent.

The method wherein the therapeutic agent is an immunosuppressive agent.

The method wherein the immune suppressive agent is: a monophosphate dehydrogenase inhibitor, a purine synthesis inhibitor, a calcineurin inhibitor or an mTOR inhibitor.

The method wherein the immunosuppressive agent is mycophenolate mofetil (MMF), mycophenolate sodium, azathioprine, tacrolimus, sirolimus or cyclosporine.

The method wherein the therapeutic agent is an additional anti-VP1 antibody.

The method wherein the PML is associated with the treatment of multiple sclerosis or rheumatoid arthritis, or psoriasis.

The method wherein the multiple sclerosis treatment is natalizumab, fingolimod, or dimethyl fumarate, fumaric acid esters, or alemtuzumab.

The method wherein the rheumatoid arthritis treatment is rituximab.

The method wherein the psoriasis treatment is efalizumab.

The antibody or fragment thereof for use as a medicament.

The antibody or fragment thereof for use in the neutralization of a BK virus or JC virus infection.

The antibody or fragment thereof, for use in the treatment or reducing the likelihood of: nephropathy, BKVAN hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

The use of the antibody or fragment thereof, administered in combination with another therapeutic agent.

The use of the antibody or fragment thereof wherein the therapeutic agent is an immunosuppressive agent.

The use of the antibody or fragment thereof wherein the immunosuppressive agent is a monophosphate dehydrogenase inhibitor, a purine synthesis inhibitor, a calcineurin inhibitor or an mTOR inhibitor.

The use of the antibody or fragment thereof wherein the immunosuppressive agent is: mycophenolate mofetil (MMF), mycophenolate sodium, azathioprine, tacrolimus, sirolimus or cyclosporine.

The use of the antibody or fragment thereof, wherein the therapeutic agent is an additional anti-BK antibody.

The use of the antibody or fragment thereof, the PML is associated with the treatment of multiple sclerosis, rheumatoid arthritis or psoriasis.

The use wherein the multiple sclerosis treatment is natalizumab, fingolimod, or dimethyl fumarate, fumaric acid esters, or alemtuzumab.

The use wherein the rheumatoid arthritis treatment is rituximab.

The use wherein the psoriasis treatment is efalizumab.

A nucleic acid that encodes the antibody or antigen binding fragment.

A vector comprising the nucleic acid.

A host cell comprising the vector.

A diagnostic reagent comprising the antibody or antigen binding fragment thereof, which is labeled.

The diagnostic reagent, wherein the label is selected from the group consisting of a radiolabel, a fluorophore, a chromophore, an imaging agent, and a metal ion.

Definitions

Unless stated otherwise, the following terms and phrases as used herein are intended to have the following meanings:

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementarity-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting in total about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, IMGT, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Lefranc, M. P., Nucleic Acids Res., 29:207-209 (2001); Al-Lazikani et al., J. Mol. Biol., 273: 927-748 (1997)). Definitions of antigen combining sites are also described in the following: Ruiz et al., Nucleic Acids Res., 28:219-221 (2000); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HC CDR1), 50-65 (HC CDR2), and 95-102 (HC CDR3) in a VH, e.g., a mammalian VH, e.g., a human VH; and amino acid residues 24-34 (LC CDR1), 50-56 (LC CDR2), and 89-97 (LC CDR3) in a VL, e.g., a mammalian VL, e.g., a human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2, or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment," as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR, and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody," as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)), or electron microscopy. A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known or inferred variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91% 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically, a specific or selective binding reaction will produce a signal at least twice over the background signal and, more typically, at least 10 to 100 times over the background.

The term "equilibrium dissociation constant (KD, M)" refers to the dissociation rate constant (kd, time−1) divided by the association rate constant (ka, time−1, M−1). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an anti-BK or JC antibody of the present disclosure. In some aspects, the phrase "consisting essentially of" expressly excludes the inclusion of one or more additional active agents other than an anti-BK or JC antibody of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, (Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, (J. Mol. Biol. 48:444-453, 1970), algorithm which has been incorporated into the GAP program in the GCG software package (available from University of South Florida), using either a BLOSUM 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "subject" includes human and non-human animals Non-human animals include all vertebrates, e g, mammals and non-mammals, such as non-human primates, sheep, dog, cow, chickens, amphibians, and reptiles. Except when noted, the terms "patient" or "subject" are used herein interchangeably.

The terms "BKV" or "BK virus" refer to a member of the family Polyomaviridae, genus *Orthopolyomavirus*. Polyomaviruses are icosahedral, non-enveloped, double-stranded DNA viruses with a genome of approximately 5,000 base pairs. They measure approximately 40-45 nM in diameter (Bennett et al., Microbes and Infection. 2012:14(9):672-683).

"JCV" or "JC virus" refers to a member of the family Polyomaviridae, genus *Orthopolyomavirus*. JCV is related to BKV, and is also an icosahedral, non-enveloped, double-stranded DNA virus with a genome of approximately 5,000 base pairs. They measure approximately 40-45 nM in diameter (Johne et al., Arch. Virol. 2011; 156(9):1627-1634).

The terms "BKV nephropathy" or "BKV-associated nephropathy" or "BKVAN" refer to the inflammatory interstitial nephropathy resulting from the lytic infection with BKV, characterized by viral cytopathogenic changes and viral gene expression, primarily in the renal tubular epithelium.

The term "VP1" refers to the major polyoma virus capsid subunit protein. "VP1 pentamers" are composed of five monomers of VP1.

TABLE 1

VP1 sequences

| Name | Sequence | SEQ ID NO |
|---|---|---|
| VP1 BKV serotype I | MAPTKRKGECPGAAPKKPKEPVQVPKLLIKGGVEVLEV KTGVDAITEVECFLNPEMGDPDENLRGFSLKLSAENDFS SDSPERKMLPCYSTARIPLPNLNEDLTCGNLLMWEAVTV QTEVIGITSMLNLHAGSQKVHEHGGGKPIQGSNFHFFAV GGDPLEMQGVLMNYRTKYPEGTITPKNPTAQSQVMNTD HKAYLDKNNAYPVECWIPDPSRNENTRYFGTFTGGENV PPVLHVTNTATTVLLDEQGVGPLCKADSLYVSAADICGL FTNSSGTQQWRGLARYFKIRLRKRSVKNPYPISFLLSDL INRRTQRVDGQPMYGMESQVEEVRVFDGTERLPGDPDMI RYIDKQGQLQTKML | (SEQ ID NO: 1) |

TABLE 1-continued

VP1 sequences

| Name | Sequence | SEQ ID NO |
|---|---|---|
| VP1 BKV sero- type II | MAPTKRKGECPGAAPKKPKEPVQVPKLLIKGGVEVLEV KTGVDAITEVECFLNPEMGDPDDNLRGYSLKLTAENAFD SDSPDKKMLPCYSTARIPLPNLNEDLTCGNLLMWEAVTV KTEVIGITSMLNLHAGSQKVHENGGGKPVQGSNFHFFAV GGDPLEMQGVLMNYRTKYPQGTITPKNPTAQSQVMNTD HKAYLDKNNAYPVECWIPDPSRNENTRYFGTYTGGENV PPVLHVTNTATTVLLDEQGVGPLCKADSLYVSAADICGL FTNSSGTQQWRGLARYFKIRLRKRSVKNPYPISFLLSDL INRRTQKVDGQPMYGMESQVEEVRVFDGTEQLPGDPDMI RYIDRQGQLQTKMV | (SEQ ID NO: 2) |
| VP1 BKV sero- type III | MAPTKRKGECPGAAPKKPKEPVQVPKLLIKGGVEVLEV KTGVDAITEVECFLNPEMGDPDDHLRGYSQHLSAENAF DSDSPDKKMLPCYSTARIPLPNLNEDLTCGNLLMWEAVT VKTEVIGITSMLNLHAGSQKVHENGGGKPVQGSNFHFFA VGGDPLEMQGVLMNYRTKYPQGTITPKNPTAQSQVMNT DHKAYLDKNNAYPVECWIPDPSKNENTRYFGTYTGGEN VPPVLHVTNTATTVLLDEQGVGPLCKADSLYVSAADICG LFTNSSGTQQWRGLARYFKIRLRKRSVKNPYPISFLLSD LINRRTQKVDGQPMYGMESQVEEVRVFDGTEQLPGDPDM IRYIDRQGQLQTKMV | (SEQ ID NO: 3) |
| VP1 BKV sero- type IV | MAPTKRKGECPGAAPKKPKEPVQVPKLLIKGGVEVLEV KTGVDAITEVECFLNPEMGDPDNDLRGYSLRLTAETAFD SDSPDRKMLPCYSTARIPLPNLNEDLTCGNLLMWEAVTV KTEVIGITSMLNLHAGSQKVHENGGGKPIQGSNFHFFAV GGDPLEMQGVLMNYRTKYPEGTVTPKNPTAQSQVMNT DHKAYLDKNNAYPVECWIPDPSRNENTRYFGTYTGGEN VPPVLHVTNTATTVLLDEQGVGPLCKADSLYVSAADICG LFTNSSGTQQWRGLPRYFKIRLRKRSVKNPYPISFLLSD LINRRTQRVDGQPMYGMESQVEEVRVFDGTEQLPGDPDM IRYIDRQGQLQTKMV | (SEQ ID NO: 4) |
| JCV VP1 | MAPTKRKGERKDPVQVPKLLIRGGVEVLEVKTGVDSITE VECFLTPEMGDPDEHLRGFSKSISISDTFESDSPNKDML PCYSVARIPLPNLNEDLTCGNILMWEAVTLKTEVIGVTT LMNVHSNGQATHDNGAGKPVQGTSFHFFSVGGEALELQG VVFNYRTKYPDGTIFPKNATVQSQVMNTEHKAYLDKNK AYPVECWVPDPTRNENTRYFGTLTGGENVPPVLHITNTA TTVLLDEFGVGPLCKGDNLYLSAVDVCGMFTNRSGSQQ WRGLSRYFKVQLRKRRVKNPYPISFLLTDLINRRTPRVD GQPMYGMDAQVEEVRVFEGTEELPGDPDMMRYVDRYG QLQTKML | (SEQ ID NO: 5) |

"Virus-like particles" or "VLP" are an assembly of VP1 pentamers into viral capsids. VLPs are composed of 72 VP1 pentamers. VLPs are structurally very similar to actual virus but lack the minor capsid proteins (VP2 and VP3) as well as the viral DNA genome, and therefore are non-infectious. VLPs are useful as viral epitopes are presented in a similar conformation to the actual virus.

"IC50" (half-maximal inhibitory concentration) refers to the concentration of a particular antibody which induces a signal halfway (50%) between the baseline control and the maximum possible signal. For example, the IC50 is the concentration of antibody at which 50% of the available binding sites on the VP1 antigen are occupied.

"EC50" (half-maximal effective concentration) refers to the concentration of a particular antibody which induces a response halfway (50%) between the baseline control and the maximum possible effect after a specific exposure or treatment time. For example, the EC50 is the concentration of antibody at which virus infection is neutralized by 50%.

"EC90" refers to the concentration of a particular antibody which induces a response corresponding to 90% of the maximum possible effect after a specific exposure or treatment time. For example, the EC90 is the concentration of antibody at which virus infection is neutralized by 90%.

"Neutralization" refers to the inhibition of viral infection of a host cell, as demonstrated by the absence of viral gene expression. Without being held to any one theory, mechanisms of neutralization by a particular antibody could include blocking the interaction of viral capsid proteins with cell surface receptors or disruption of any stage of the entry and trafficking process prior to delivery of the viral genome to the nucleus of the host cell.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both.

The phrase "reducing the likelihood" refers to delaying the onset or development or progression of the disease, infection or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated polyoma viral infection.

The term "co-administer" refers to the simultaneous presence of two active agents in the blood of an individual. Active agents that are co-administered can be concurrently or sequentially delivered.

BRIEF DESCRIPTION OF THE DRAWINGS

FIG. 1 graphically represents ELISA binding properties and viral neutralization capacity of a panel of antibodies, with the IC50 in nM given for each serotype neutralized.

FIGS. 3D-F are amino acid alignments of the BKV subtypes 1-4, JCV, and Merkel cell virus (MCV) VP1 protein at positions contributing to the NOV530 epitope on BKV ST1 (numbering). Highlighted residues represent conserved positions predicted to be located within a 5 Å radius of the scFv. The highlighted residues from 316-330 in FIG. 3D correspond match the VP1 chain Pentamer $B_2$ depicted in FIG. 3B. The highlighted residues 169, 182-193 in FIG. 3E correspond with Pentamer $A_4$ from FIG. 3B. The highlighted residues 59-64, 81-87, 172-176 and 198-201 in FIG. 3F correspond to Pentamer $A_3$ from FIG. 3B. FIG. 3G and FIG. 3H depict the NOV530 heavy and light chain complementarity-determining variable regions, except tyrosine-49 (in parentheses), which belongs to VK-FR2. Residues in bold text are predicted to be located within a 5 Å radius from viral amino acids. Somatically hypermutated residues are indicated by the germline amino acid above the mutated position. Underlined residues indicate CDR3 sequences generated by junctional diversity during V(D)J recombination processes.

DETAILED DESCRIPTION

Figures 2A, 2B:
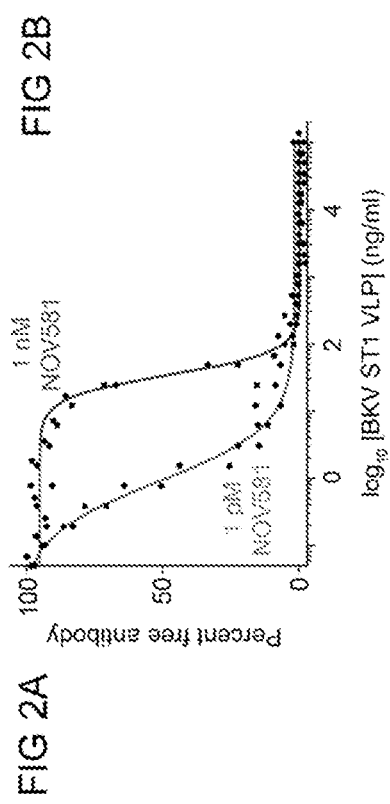
FIG. 2A shows a 4-parameter fitting of a $K_d$-controlled curve (based on the low concentration of the antibody NOV581), and a fitting of a stoichiometry-controlled curve.
FIG. 2B shows the $K_d$ in pM for three antibodies across all four BK serotypes.

The present disclosure provides for antibodies, antibody fragments (e.g., antigen binding fragments), that bind and neutralize BKV. Furthermore, the present disclosure provides antibodies that have desirable pharmacokinetic characteristics and other desirable attributes, and thus can be used for reducing the likelihood of or treating BK virus-associated nephropathy (e.g. BKVAN) and/or JC virus-associated progressive multifocal leukoencephalopathy (PML). The present disclosure further provides pharmaceutical compositions comprising the antibodies and methods of making and using such pharmaceutical compositions for the prevention and treatment of polyomavirus infection and associated disorders.

Anti-Polyomavirus Antibodies

The present disclosure provides for antibodies or antibody fragments (e.g., antigen binding fragments) that specifically bind to BK virus or JC virus. Antibodies or antibody fragments (e.g., antigen binding fragments) of the present disclosure include, but are not limited to, the human monoclonal antibodies or fragments thereof, isolated as described, in the Examples below.

The present disclosure in certain aspects provides antibodies or antibody fragments (e.g., antigen binding fragments) that specifically bind to BK or JC virus, said antibodies or antibody fragments (e.g., antigen binding fragments) comprise a VH domain having an amino acid sequence of SEQ ID NO: 18, 50, 82, 114, 146, 178, 210, 242 and 274 (Table 2). The present disclosure also provides antibodies or antibody fragments (e.g., antigen binding fragments) that specifically bind to BK or JC virus, said antibodies or antibody fragments (e.g., antigen binding fragments) comprise a VH CDR having an amino acid sequence of any one of the VH CDRs listed in Table 2. In particular aspects, the present disclosure provides antibodies or antibody fragments (e.g., antigen binding fragments) that specifically bind to BK or JC virus, said antibodies comprising (or alternatively, consist of) one, two, three, or more VH CDRs having an amino acid sequence of any of the VH CDRs listed in Table 2.

The present disclosure provides antibodies or antibody fragments (e.g., antigen binding fragments) that specifically bind to BK or JC virus, said antibodies or antibody fragments (e.g., antigen binding fragments) comprise a VL domain having an amino acid sequence of SEQ ID NO: 34, 66, 98, 130, 162, 194, 226, 258 and 290 (Table 2). The present disclosure also provides antibodies or antibody fragments (e.g., antigen binding fragments) that specifically bind to BK or JC virus, said antibodies or antibody fragments (e.g., antigen binding fragments) comprise a VL CDR having an amino acid sequence of any one of the VL CDRs listed in Table 2. In particular, the disclosure provides antibodies or antibody fragments (e.g., antigen binding fragments) that specifically bind to BK or JC virus, said antibodies or antibody fragments (e.g., antigen binding fragments) comprise (or alternatively, consist of) one, two, three or more VL CDRs having an amino acid sequence of any of the VL CDRs listed in Table 2.

Other antibodies or antibody fragments (e.g., antigen binding fragments) of the present disclosure include amino acids that have been mutated, yet have at least 60, 70, 80, 90 or 95 percent identity in the CDR regions with the CDR regions depicted in the sequences described in Table 2. In some aspects, it includes mutant amino acid sequences wherein no more than 1, 2, 3, 4 or 5 amino acids have been mutated in the CDR regions when compared with the CDR regions depicted in the sequence described in Table 2.

The present disclosure also provides nucleic acid sequences that encode VH, VL, the full length heavy chain, and the full length light chain of the antibodies that specifically bind to BK or JC virus. Such nucleic acid sequences can be optimized for expression in mammalian cells.

TABLE 2

| Anti-Polyoma virus Antibodies | | |
|---|---|---|
| NOV530 | | |
| SEQ ID NO: 6 (Combined) | HCDR1 | GGSISGGGYYWS |
| SEQ ID NO: 7 (Combined) | HCDR2 | YIYYNRGTYYNPALKS |
| SEQ ID NO: 8 (Combined) | HCDR3 | CVLGGYGSDAFDR |
| SEQ ID NO: 9 (Kabat) | HCDR1 | GGGYYWS |

TABLE 2-continued

Anti-Polyoma virus Antibodies

SEQ ID NO: 10 HCDR2 YIYYNRGTYYNPALKS
(Kabat)

SEQ ID NO: 11 HCDR3 CVLGGYGSDAFDR
(Kabat)

SEQ ID NO: 12 HCDR1 GGSISGGGY
(Chothia)

SEQ ID NO: 13 HCDR2 YYNRG
(Chothia)

SEQ ID NO: 14 HCDR3 CVLGGYGSDAFDR
(Chothia)

SEQ ID NO: 15 HCDR1 GGSISGGGYY
(IMGT)

SEQ ID NO: 16 HCDR2 IYYNRGT
(IMGT)

SEQ ID NO: 17 HCDR3 ARCVLGGYGSDAFDR
(IMGT)

SEQ ID NO: 18 VH QVQLQESGPGLVKPSQTLSLTCTVSGGSISGGGYYWSWIR
QHPGKGLEFIGYIYYNRGTYYNPALKSRLTISVDTSKNDF
SLKLSSVSAADTAVYYCARCVLGGYGSDAFDRWGQGTTVT
VAS

SEQ ID NO: 19 DNA VH CAGGTGCAGCTGCAGGAGTCGGGCCCAGGACTGGTGAAGC
CTTCACAGACCCTGTCCCTCACCTGCACTGTCTCTGGTGG
CTCCATCAGCGGTGGTGGTTACTACTGGAGCTGGATCCGC
CAGCACCCAGGGAAGGGCCTGGAGTTCATTGGATACATAT
ATTATAATAGGGGCACCTACTACAATCCGGCCCTCAAGAG
TCGACTTACCATATCAGTAGACACCTCTAAGAATGACTTC
TCCCTGAAGCTGAGCTCTGTGAGTGCCGCGGACACGGCCG
TGTATTACTGTGCGAGATGTGTCCTTGGTGGCTACGGTTC
TGATGCTTTTGATAGGTGGGGCCAAGGGACAACGGTCACC
GTCGCTTCA

SEQ ID NO: 20 Heavy QVQLQESGPGLVKPSQTLSLTCTVSGGSISGGGYYWSWIR
Chain QHPGKGLEFIGYIYYNRGTYYNPALKSRLTISVDTSKNDF
SLKLSSVSAADTAVYYCARCVLGGYGSDAFDRWGQGTTVT
VASASTKGPSVFPLAPCSRSTSGGTAALGCLVKDYFPEPV
TVSWNSGALTSGVHTFPTVLQSSGLYSLSSVVTVPSSSLG
TQTYICNVNHKPSNTKVDKRVEPKSCDKTHTCPPCPAPEL
LGGPSVFLFPPKPKDTLMISRTPEVTCVVVDVSHEDPEVK
FNWYVDGVEVHNAKTKPREEQYNSTYRVVSVLTVLHQDWL
NGKEYKCKVSNKALPAPIEKTISKAKGQPREPQVYTLPPS
REEMTKNQVSLTCLVKGFYPSDIAVEWESNGQPENNYKTT
PPVLDSDGSFFLYSKLTVDKSRWQQGNVFSCSVMHEALHN
HYTQKSLSLSPGK SEQ ID NO: 21 DNA CAGGTGCAGCTGCAGGAGTCGGGCCCAGGACTGGTGAAGC
Heavy CTTCACAGACCCTGTCCCTCACCTGCACTGTCTCTGGTGG
Chain CTCCATCAGCGGTGGTGGTTACTACTGGAGCTGGATCCGC
CAGCACCCAGGGAAGGGCCTGGAGTTCATTGGATACATAT
ATTATAATAGGGGCACCTACTACAATCCGGCCCTCAAGAG
TCGACTTACCATATCAGTAGACACCTCTAAGAATGACTTC
TCCCTGAAGCTGAGCTCTGTGAGTGCCGCGGACACGGCCG
TGTATTACTGTGCGAGATGTGTCCTTGGTGGCTACGGTTC
TGATGCTTTTGATAGGTGGGGCCAAGGGACAACGGTCACC
GTCGCTTCAGCTTCCACCAAGGGCCCATCGGTCTTCCCCC
TGGCGCCCTGCTCCAGGAGCACCTCTGGGGGCACAGCGGC
CCTGGGCTGCCTGGTCAAGGACTACTTCCCCGAACCGGTG
ACGGTGTCGTGGAACTCAGGCGCCCTGACCAGCGGCGTGC
ACACCTTCCCGACTGTCCTACAGTCCTCAGGACTCTACTC
CCTCAGCAGCGTGGTGACCGTGCCCTCCAGCAGCTTGGGC
ACCCAGACCTACATCTGCAACGTGAACCACAAGCCCAGCA
ACACCAAGGTGGACAAGAGAGTGGAGCCCAAGAGCTGCGA
CAAGACCCACACCTGCCCCCCTGCCCAGCCCAGAGCTG
CTGGGCGGACCCTCCGTGTTCCTGTTCCCCCCCAAGCCCA
AGGACACCCTGATGATCAGCAGGACCCCCGAGGTGACCTG
CGTGGTGGTGGACGTGAGCCACGAGGACCCAGAGGTGAAG
TTCAACTGGTACGTGGACGGCGTGGAGGTGCACAACGCCA
AGACCAAGCCCAGAGAGGAGCAGTACAACAGCACCTACAG
GGTGGTGTCCGTGCTGACCGTGCTGCACCAGGACTGGCTG TABLE 2-continued Anti-Polyoma virus Antibodies

```
AACGGCAAGGAATACAAGTGCAAGGTCTCCAACAAGGCCC
TGCCAGCCCCCATCGAAAAGACCATCAGCAAGGCCAAGGG
CCAGCCACGGGAGCCCCAGGTGTACACCCTGCCCCCCTCC
CGGGAGGAGATGACCAAGAACCAGGTGTCCCTGACCTGTC
TGGTGAAGGGCTTCTACCCCAGCGACATCGCCGTGGAGTG
GGAGAGCAACGGCCAGCCCGAGAACAACTACAAGACCACC
CCCCCAGTGCTGGACAGCGACGGCAGCTTCTTCCTGTACA
GCAAGCTGACCGTGGACAAGTCCAGGTGGCAGCAGGGCAA
CGTGTTCAGCTGCAGCGTGATGCACGAGGCCCTGCACAAC
CACTACACCCAGAAGAGCCTGAGCCTGTCCCCCGGCAAG
```

| SEQ ID NO: 22 (Combined) | LCDR1 | RASQSVSSHLA |
|---|---|---|
| SEQ ID NO: 23 (Combined) | LCDR2 | DASSRAN |
| SEQ ID NO: 24 (Combined) | LCDR3 | QQRSSWPPSLT |
| SEQ ID NO: 25 (Kabat) | LCDR1 | RASQSVSSHLA |
| SEQ ID NO: 26 (Kabat) | LCDR2 | DASSRAN |
| SEQ ID NO: 27 (Kabat) | LCDR3 | QQRSSWPPSLT |
| SEQ ID NO: 28 (Chothia) | LCDR1 | SQSVSSH |
| SEQ ID NO: 29 (Chothia) | LCDR2 | DAS |
| SEQ ID NO: 30 (Chothia) | LCDR3 | RSSWPPSL |
| SEQ ID NO: 31 (IMGT) | LCDR1 | QSVSSH |
| SEQ ID NO: 32 (IMGT) | LCDR2 | DASSRANGIP |
| SEQ ID NO: 33 (IMGT) | LCDR3 | QQRSSWPPSLT |

SEQ ID NO: 34    VL
EIVLTQSPVTLSLSPGERAILSCRASQSVSSHLAWYQQKP
GQAPRLLIYDASSRANGIPARFSGSGSGTDFTLTISSLAP
EDFAVYYCQQRSSWPPSLTFGGGTKVEIR

SEQ ID NO: 35    DNA VL
```
GAAATTGTGTTGACACAGTCCCCAGTCACCCTGTCTTTGT
CTCCAGGGGAAAGAGCCATCCTCTCCTGTAGGGCCAGTCA
GAGTGTTAGCAGCCACTTAGCCTGGTACCAACAGAAGCCT
GGCCAGGCTCCCAGGCTCCTCATCTATGATGCATCCAGCA
GGGCCAATGGCATCCCAGCCAGGTTCAGTGGCAGTGGGTC
TGGGACAGACTTCACTCTCACCATCAGCAGCCTAGCGCCT
GAAGATTTTGCAGTTTATTACTGTCAGCAGCGTAGCAGCT
GGCCTCCGTCCCTCACTTTCGGCGGAGGGACCAAGGTGGA
GATCAGA
```

SEQ ID NO: 36    Light Chain
EIVLTQSPVTLSLSPGERAILSCRASQSVSSHLAWYQQKP
GQAPRLLIYDASSRANGIPARFSGSGSGTDFTLTISSLAP
EDFAVYYCQQRSSWPPSLTFGGGTKVEIRRTVAAPSVFIF
PPSDEQLKSGTASVVCLLNNFYPREAKVQWKVDNALQSGN
SQESVTEQDSKDSTYSLSSTLTLSKADYEKHKVYACEVTH
QGLSSPVTKSFNRGEC SEQ ID NO: 37    DNA Light Chain
```
GAAATTGTGTTGACACAGTCCCCAGTCACCCTGTCTTTGT
CTCCAGGGGAAAGAGCCATCCTCTCCTGTAGGGCCAGTCA
GAGTGTTAGCAGCCACTTAGCCTGGTACCAACAGAAGCCT
GGCCAGGCTCCCAGGCTCCTCATCTATGATGCATCCAGCA
GGGCCAATGGCATCCCAGCCAGGTTCAGTGGCAGTGGGTC
TGGGACAGACTTCACTCTCACCATCAGCAGCCTAGCGCCT
GAAGATTTTGCAGTTTATTACTGTCAGCAGCGTAGCAGCT
GGCCTCCGTCCCTCACTTTCGGCGGAGGGACCAAGGTGGA
GATCAGACGAACTGTGGCTGCACCATCTGTCTTCATCTTC
CCGCCATCTGATGAGCAGTTGAAATCTGGAACTGCCTCTG
```

TABLE 2-continued

Anti-Polyoma virus Antibodies

```
TTGTGTGCCTGCTGAATAACTTCTATCCCAGAGAGGCCAA
AGTACAGTGGAAGGTGGACAACGCCCTGCAGAGCGGCAAC
AGCCAGGAGAGCGTCACCGAGCAGGACAGCAAGGACTCCA
CCTACAGCCTGAGCAGCACCCTGACCCTGAGCAAGGCCGA
CTACGAGAAGCATAAGGTGTACGCCTGCGAGGTGACCCAC
CAGGGCCTGTCCAGCCCCGTGACCAAGAGCTTCAACAGGG
GCGAGTGC
```

NOV399

SEQ ID NO: 38  HCDR1  GFTFRSYMMN
(Combined)

SEQ ID NO: 39  HCDR2  YISGSGGTKYYVDSVKG
(Combined)

SEQ ID NO: 40  HCDR3  DLDCSGGTCYDGMDV
(Combined)

SEQ ID NO: 41  HCDR1  SYMMN
(Kabat)

SEQ ID NO: 42  HCDR2  YISGSGGTKYYVDSVKG
(Kabat)

SEQ ID NO: 43  HCDR3  DLDCSGGTCYDGMDV
(Kabat)

SEQ ID NO: 44  HCDR1  GFTFRSY
(Chothia)

SEQ ID NO: 45  HCDR2  SGSGGT
(Chothia)

SEQ ID NO: 46  HCDR3  DLDCSGGTCYDGMDV
(Chothia)

SEQ ID NO: 47  HCDR1  GFTFRSYM
(IMGT)

SEQ ID NO: 48  HCDR2  ISGSGGTK
(IMGT)

SEQ ID NO: 49  HCDR3  ARDLDCSGGTCYDGMDV
(IMGT)

SEQ ID NO: 50  VH     EVQLVESGGGLVQPGGSLRLSCAASGFTFRSYMMNWVRQA
                      PGKGLEWVSYISGSGGTKYYVDSVKGRFTISRDNAKNSLY
                      LQMHSLRAEDTAVYYCARDLDCSGGTCYDGMDVWGQGTTV
                      TVSS

SEQ ID NO: 51  DNA VH GAGGTGCAGCTGGTGGAGTCGGGGGGAGGCTTGGTACAGC
                      CTGGGGGGTCCCTGAGACTCTCCTGTGCAGCCTCTGGATT
                      CACCTTCAGGAGTTATATGATGAATTGGGTCCGCCAGGCT
                      CCAGGGAAGGGGCTGGAGTGGGTTTCATATATTAGTGGTA
                      GTGGTGGAACCAAATACTACGTAGACTCTGTGAAGGGCCG
                      ATTCACCATATCCAGAGACAACGCCAAGAACTCACTGTAT
                      CTGCAAATGCACAGCCTGAGAGCCGAGGACACGGCTGTGT
                      ATTACTGTGCGAGAGATCTCGATTGCAGTGGTGGGACCTG
                      CTACGACGGTATGGACGTCTGGGGCCAAGGGACCACGGTC
                      ACCGTCTCCTCA

SEQ ID NO: 52  Heavy  EVQLVESGGGLVQPGGSLRLSCAASGFTFRSYMMNWVRQA
               Chain  PGKGLEWVSYISGSGGTKYYVDSVKGRFTISRDNAKNSLY
                      LQMHSLRAEDTAVYYCARDLDCSGGTCYDGMDVWGQGTTV
                      TVSSASTKGPSVFPLAPCSRSTSGGTAALGCLVKDYFPEP
                      VTVSWNSGALTSGVHTFPAVLQSSGLYSLSSVVTVPSSSL
                      GTQTYICNVNHKPSNTKVDKRVEPKSCDKTHTCPPCPAPE
                      LLGGPSVFLFPPKPKDTLMISRTPEVTCVVVDVSHEDPEV
                      KFNWYVDGVEVHNAKTKPREEQYNSTYRVVSVLTVLHQDW
                      LNGKEYKCKVSNKALPAPIEKTISKAKGQPREPQVYTLPP
                      SREEMTKNQVSLTCLVKGFYPSDIAVEWESNGQPENNYKT
                      TPPVLDSDGSFFLYSKLTVDKSRWQQGNVESCSVMHEALH
                      NHYTQKSLSLSPGK SEQ ID NO: 53  DNA    GAGGTGCAGCTGGTGGAGTCGGGGGGAGGCTTGGTACAGC
               Heavy  CTGGGGGGTCCCTGAGACTCTCCTGTGCAGCCTCTGGATT
               Chain  CACCTTCAGGAGTTATATGATGAATTGGGTCCGCCAGGCT
```

TABLE 2-continued

Anti-Polyoma virus Antibodies

```
CCAGGGAAGGGGCTGGAGTGGGTTTCATATATTAGTGGTA
GTGGTGGAACCAAATACTACGTAGACTCTGTGAAGGGCCG
ATTCACCATATCCAGAGACAACGCCAAGAACTCACTGTAT
CTGCAAATGCACAGCCTGAGAGCCGAGGACACGGCTGTGT
ATTACTGTGCGAGAGATCTCGATTGCAGTGGTGGGACCTG
CTACGACGGTATGGACGTCTGGGGCCAAGGGACCACGGTC
ACCGTCTCCTCAGCTTCCACCAAGGGCCCATCGGTCTTCC
CCCTGGCGCCCTGCTCCAGGAGCACCTCTGGGGGCACAGC
GGCCCTGGGCTGCCTGGTCAAGGACTACTTCCCCGAACCG
GTGACGGTGTCGTGGAACTCAGGCGCCCTGACCAGCGGCG
TGCACACCTTCCCGGCTGTCCTACAGTCCTCAGGACTCTA
CTCCCTCAGCAGCGTGGTGACCGTGCCCTCCAGCAGCTTG
GGCACCCAGACCTACATCTGCAACGTGAATCACAAGCCCA
GCAACACCAAGGTGGACAAGAGAGTGGAGCCCAAGAGCTG
CGACAAGACCCACACCTGCCCCCCCTGCCCAGCCCCAGAG
CTGCTGGGCGGACCCTCCGTGTTCCTGTTCCCCCCCAAGC
CCAAGGACACCCTGATGATCAGCAGGACCCCCGAGGTGAC
CTGCGTGGTGGTGGACGTGAGCCACGAGGACCCAGAGGTG
AAGTTCAACTGGTACGTGGACGGCGTGGAGGTGCACAACG
CCAAGACCAAGCCCAGAGAGGAGCAGTACAACAGCACCTA
CAGGGTGGTGTCCGTGCTGACCGTGCTGCACCAGGACTGG
CTGAACGGCAAGGAATACAAGTGCAAGGTCTCCAACAAGG
CCCTGCCAGCCCCCATCGAAAAGACCATCAGCAAGGCCAA
GGGCCAGCCACGGGAGCCCCAGGTGTACACCCTGCCCCCC
TCCCGGGAGGAGATGACCAAGAACCAGGTGTCCCTGACCT
GTCTGGTGAAGGGCTTCTACCCCAGCGACATCGCCGTGGA
GTGGGAGAGCAACGGCCAGCCCGAGAACAACTACAAGACC
ACCCCCCCAGTGCTGGACAGCGACGGCAGCTTCTTCCTGT
ACAGCAAGCTGACCGTGGACAAGTCCAGGTGGCAGCAGGG
CAACGTGTTCAGCTGCAGCGTGATGCACGAGGCCCTGCAC
AACCACTACACCCAGAAGAGCCTGAGCCTGTCCCCGGCA
AG
```

| SEQ ID NO: 54 (Combined) | LCDR1 | SGDKLGNKYVY |
|---|---|---|
| SEQ ID NO: 55 (Combined) | LCDR2 | QHTKRPS |
| SEQ ID NO: 56 (Combined) | LCDR3 | QAWDSSIVI |
| SEQ ID NO: 57 (Kabat) | LCDR1 | SGDKLGNKYVY |
| SEQ ID NO: 58 (Kabat) | LCDR2 | QHTKRPS |
| SEQ ID NO: 59 (Kabat) | LCDR3 | QAWDSSIVI |
| SEQ ID NO: 60 (Chothia) | LCDR1 | DKLGNKY |
| SEQ ID NO: 61 (Chothia) | LCDR2 | QHT |
| SEQ ID NO: 62 (Chothia) | LCDR3 | WDSSIV |
| SEQ ID NO: 63 (IMGT) | LCDR1 | KLGNKY |
| SEQ ID NO: 64 (IMGT) | LCDR2 | QHT |
| SEQ ID NO: 65 (IMGT) | LCDR3 | QAWDSSIVI |
| SEQ ID NO: 66 | VL | SYELTQPPSVSVSPGQTATITCSGDKLGNKYVYWFQHRPG QSPVLVIYQHTKRPSGIPERFSGSNSGNTATLTISGTQAM DEADYYCQAWDSSIVIFGGGTKLTVL |
| SEQ ID NO: 67 | DNA VL | TCCTATGAGCTGACTCAGCCACCCTCAGTGTCCGTGTCCC CTGGACAGACAGCCACCATCACCTGCTCTGGAGATAAATT GGGTAATAAATATGTTTACTGGTTTCAGCACAGGCCAGGC CAGTCCCCTGTGCTGGTCATCTATCAACATACCAAGCGGC CCTCAGGGATCCCTGAGCGATTCTCTGGCTCCAACTCTGG |

TABLE 2-continued

Anti-Polyoma virus Antibodies

|  |  |  |
|---|---|---|
|  |  | GAACACAGCCACTCTGACCATCAGCGGGACCCAGGCTATG<br>GATGAGGCTGACTATTACTGTCAGGCGTGGGACAGTAGCA<br>TTGTGATATTCGGCGGAGGGACCAAGCTGACCGTCCTA |
| SEQ ID NO: 68 | Light<br>Chain | SYELTQPPSVSVSPGQTATITCSGDKLGNKYVYWFQHRPG<br>QSPVLVIYQHTKRPSGIPERFSGSNSGNTATLTISGTQAM<br>DEADYYCQAWDSSIVIFGGGTKLTVLGQPKAAPSVTLFPP<br>SSEELQANKATLVCLISDFYPGAVTVAWKADSSPVKAGVE<br>TTTPSKQSNNKYAASSYLSLTPEQWKSHRSYSCQVTHEGS<br>TVEKTVAPTECS |
| SEQ ID NO: 69 | DNA<br>Light<br>Chain | TCCTATGAGCTGACTCAGCCACCCTCAGTGTCCGTGTCCC<br>CTGGACAGACAGCCACCATCACCTGCTCTGGAGATAAATT<br>GGGTAATAAATATGTTTACTGGTTTCAGCACAGGCCAGGC<br>CAGTCCCCTGTGCTGGTCATCTATCAACATACCAAGCGGC<br>CCTCAGGGATCCCTGAGCGATTCTCTGGCTCCAACTCTGG<br>GAACACAGCCACTCTGACCATCAGCGGGACCCAGGCTATG<br>GATGAGGCTGACTATTACTGTCAGGCGTGGGACAGTAGCA<br>TTGTGATATTCGGCGGAGGGACCAAGCTGACCGTCCTAGG<br>TCAGCCCAAGGCTGCCCCCTCGGTCACTCTGTTCCCGCCC<br>TCCTCTGAGGAGCTTCAAGCCAACAAGGCCACACTGGTGT<br>GTCTCATAAGTGACTTCTACCCGGGAGCCGTGACAGTGGC<br>CTGGAAGGCAGATAGCAGCCCCGTCAAGGCGGGAGTGGAG<br>ACCACCACACCCTCCAAACAAAGCAACAACAAGTACGCCG<br>CCAGCAGCTACCTGAGCCTGACCCCCGAGCAGTGGAAGAG<br>CCACAGAAGCTACAGCTGCCAGGTCACCCACGAGGGCAGC<br>ACCGTGGAGAAAACCGTGGCCCCCACCGAGTGCAGC |

NOV567

| SEQ ID NO: 70<br>(Combined) | HCDR1 | GYTFTAYYMH |
| SEQ ID NO: 71<br>(Combined) | HCDR2 | WINPNTGVTNFAQKFQG |
| SEQ ID NO: 72<br>(Combined) | HCDR3 | DRDASMASYYYYGMDV |
| SEQ ID NO: 73<br>(Kabat) | HCDR1 | AYYMH |
| SEQ ID NO: 74<br>(Kabat) | HCDR2 | WINPNTGVTNFAQKFQG |
| SEQ ID NO: 75<br>(Kabat) | HCDR3 | DRDASMASYYYYGMDV |
| SEQ ID NO: 76<br>(Chothia) | HCDR1 | GYTFTAY |
| SEQ ID NO: 77<br>(Chothia) | HCDR2 | NPNTGV |
| SEQ ID NO: 78<br>(Chothia) | HCDR3 | DRDASMASYYYYGMDV |
| SEQ ID NO: 79<br>(IMGT) | HCDR1 | GYTFTAYY |
| SEQ ID NO: 80<br>(IMGT) | HCDR2 | INPNTGVT |
| SEQ ID NO: 81<br>(IMGT) | HCDR3 | ARDRDASMASYYYYGMDV |
| SEQ ID NO: 82 | VH | QVQLVQSGAEVKKPGASVKVSCKASGYTFTAYYMHWVRQA<br>PGQGLEWMGWINPNTGVTNFAQKFQGRVTMTRDTSIGTAY<br>IELSWLRSDDTAVYYCARDRDASMASYYYYGMDVWGQGTT<br>VTVSS |
| SEQ ID NO: 83 | DNA VH | CAGGTGCAGCTGGTGCAGTCTGGGGCTGAGGTGAAGAAGC<br>CTGGGGCCTCAGTGAAGGTCTCCTGCAAGGCTTCTGGATA<br>CACCTTCACCGCCTATTATATGCACTGGGTGCGACAGGCC<br>CCTGGACAAGGGCTTGAGTGGATGGGCTGGATCAACCCTA<br>ACACTGGTGTCACAAACTTTGCACAGAAGTTTCAGGGCAG<br>GGTCACCATGACCAGGGACACGTCCATCGGCACAGCCTAC<br>ATTGAATTGAGCTGGCTGAGATCTGACGACACGGCCGTGT |

TABLE 2-continued

Anti-Polyoma virus Antibodies

|  |  |  |
|---|---|---|
|  |  | ATTACTGTGCGAGGGATAGGGATGCATCTATGGCCTCCTA<br>CTACTACTACGGTATGGACGTCTGGGGCCAAGGGACCACG<br>GTCACCGTCTCCTCA |
| SEQ ID NO: 84 | Heavy<br>Chain | QVQLVQSGAEVKKPGASVKVSCKASGYTFTAYYMHWVRQA<br>PGQGLEWMGWINPNTGVTNFAQKFQGRVTMTRDTSIGTAY<br>IELSWLRSDDTAVYYCARDRDASMASYYYYGMDVWGQGTT<br>VTVSSASTKGPSVFPLAPCSRSTSGGTAALGCLVKDYFPE<br>PVTVSWNSGALTSGVHTFPAVLQSSGLYSLSSVVTVPSSS<br>LGTQTYICNVNHKPSNTKVDKRVEPKSCDKTHTCPPCPAP<br>ELLGGPSVFLFPPKPKDTLMISRTPEVTCVVVDVSHEDPE<br>VKFNWYVDGVEVHNAKTKPREEQYNSTYRVVSVLTVLHQD<br>WLNGKEYKCKVSNKALPAPIEKTISKAKGQPREPQVYTLP<br>PSREEMTKNQVSLTCLVKGFYPSDIAVEWESNGQPENNYK<br>TTPPVLDSDGSFFLYSKLTVDKSRWQQGNVFSCSVMHEAL<br>HNHYTQKSLSLSPGK |
| SEQ ID NO: 85 | DNA<br>Heavy<br>Chain | CAGGTGCAGCTGGTGCAGTCTGGGGCTGAGGTGAAGAAGC<br>CTGGGGCCTCAGTGAAGGTCTCCTGCAAGGCTTCTGGATA<br>CACCTTCACCGCCTATTATATGCACTGGGTGCGACAGGCC<br>CCTGGACAAGGGCTTGAGTGGATGGGCTGGATCAACCCTA<br>ACACTGGTGTCACAAACTTTGCACAGAAGTTTCAGGGCAG<br>GGTCACCATGACCAGGGACACGTCCATCGGCACAGCCTAC<br>ATTGAATTGAGCTGGCTGAGATCTGACGACACGGCCGTGT<br>ATTACTGTGCGAGGGATAGGGATGCATCTATGGCCTCCTA<br>CTACTACTACGGTATGGACGTCTGGGGCCAAGGGACCACG<br>GTCACCGTCTCCTCAGCTTCCACCAAGGGCCCATCGGTCT<br>TCCCCCTGGCGCCCTGCTCCAGGAGCACCTCTGGGGGCAC<br>AGCGGCCCTGGGCTGCCTGGTCAAGGACTACTTCCCCGAA<br>CCGGTGACGGTGTCGTGGAACTCAGGCGCCCTGACCAGCG<br>GCGTGCACACCTTCCCGGCTGTCCTACAGTCCTCAGGACT<br>CTACTCCCTCAGCAGCGTGGTGACCGTGCCCTCCAGCAGC<br>TTGGGCACCCAGACCTACATCTGCAACGTGAACCACAAGC<br>CCAGCAACACCAAGGTGGACAAGAGAGTGGAGCCCAAGAG<br>CTGCGACAAGACCCACACCTGCCCCCCCTGCCCAGCCCCA<br>GAGCTGCTGGGCGGACCCTCCGTGTTCCTGTTCCCCCCA<br>AGCCCAAGGACACCCTGATGATCAGCAGGACCCCCGAGGT<br>GACCTGCGTGGTGGTGGACGTGAGCCACGAGGACCCAGAG<br>GTGAAGTTCAACTGGTACGTGGACGGCGTGGAGGTGCACA<br>ACGCCAAGACCAAGCCCAGAGAGGAGCAGTACAACAGCAC<br>CTACAGGGTGGTGTCCGTGCTGACCGTGCTGCACCAGGAC<br>TGGCTGAACGGCAAGGAATACAAGTGCAAGGTCTCCAACA<br>AGGCCCTGCCAGCCCCCATCGAAAAGACCATCAGCAAGGC<br>CAAGGGCCAGCCACGGGAGCCCCAGGTGTACACCCTGCCC<br>CCCTCCCGGGAGGAGATGACCAAGAACCAGGTGTCCCTGA<br>CCTGTCTGGTGAAGGGCTTCTACCCCAGCGACATCGCCGT<br>GGAGTGGGAGAGCAACGGCCAGCCCGAGAACAACTACAAG<br>ACCACCCCCCCAGTGCTGGACAGCGACGGCAGCTTCTTCC<br>TGTACAGCAAGCTGACCGTGGACAAGTCCAGGTGGCAGCA<br>GGGCAACGTGTTCAGCTGCAGCGTGATGCACGAGGCCCTG<br>CACAACCACTACACCCAGAAGAGCCTGAGCCTGTCCCCCG<br>GCAAG |
| SEQ ID NO: 86<br>(Combined) | LCDR1 | SGSSSNIGNNYVS |
| SEQ ID NO: 87<br>(Combined) | LCDR2 | DNYKRPS |
| SEQ ID NO: 88<br>(Combined) | LCDR3 | GTWDRSLSAVV |
| SEQ ID NO: 89<br>(Kabat) | LCDR1 | SGSSSNIGNNYVS |
| SEQ ID NO: 90<br>(Kabat) | LCDR2 | DNYKRPS |
| SEQ ID NO: 91<br>(Kabat) | LCDR3 | GTWDRSLSAVV |
| SEQ ID NO: 92<br>(Chothia) | LCDR1 | SSSNIGNNY |
| SEQ ID NO: 93<br>(Chothia) | LCDR2 | DNY |

TABLE 2-continued

Anti-Polyoma virus Antibodies

SEQ ID NO: 94 LCDR3 WDRSLSAV
(Chothia)

SEQ ID NO: 95 LCDR1 SSNIGNNY
(IMGT)

SEQ ID NO: 96 LCDR2 DNY
(IMGT)

SEQ ID NO: 97 LCDR3 GTWDRSLSAVV
(IMGT)

SEQ ID NO: 98 VL QSVLTQPPSVSAAAGQKVTISCSGSSSNIGNNYVSWYQHL
PGTAPKLLIYDNYKRPSGIPDRFSGSKSGTSATLGITGLQ
TGDEADYYCGTWDRSLSAVVFGGGTKLTVL

SEQ ID NO: 99 DNA VL CAGTCTGTGCTGACGCAGCCGCCCTCAGTGTCTGCGGCCG
CAGGACAGAAGGTCACCATCTCCTGCTCTGGAAGCAGTTC
CAACATTGGGAATAATTATGTATCCTGGTACCAGCACCTC
CCAGGAACAGCCCCCAAACTCCTCATTTATGACAATTATA
AGCGACCCTCAGGGATTCCTGACCGATTCTCTGGCTCCAA
GTCTGGCACGTCAGCCACCCTGGGCATCACCGGACTCCAG
ACTGGGGACGAGGCCGACTATTATTGCGGAACATGGGATA
GGAGCCTGAGTGCTGTGGTATTCGGCGGAGGGACCAAGCT
GACCGTCCTA

SEQ ID NO: 100 Light QSVLTQPPSVSAAAGQKVTISCSGSSSNIGNNYVSWYQHL
Chain PGTAPKLLIYDNYKRPSGIPDRFSGSKSGTSATLGITGLQ
TGDEADYYCGTWDRSLSAVVFGGGTKLTVLGQPKAAPSVT
LFPPSSEELQANKATLVCLISDFYPGAVTVAWKADSSPVK
AGVETTTPSKQSNNKYAASSYLSLTPEQWKSHRSYSCQVT
HEGSTVEKTVAPTECS SEQ ID NO: 101 DNA CAGTCTGTGCTGACGCAGCCGCCCTCAGTGTCTGCGGCCG
Light CAGGACAGAAGGTCACCATCTCCTGCTCTGGAAGCAGTTC
Chain CAACATTGGGAATAATTATGTATCCTGGTACCAGCACCTC
CCAGGAACAGCCCCCAAACTCCTCATTTATGACAATTATA
AGCGACCCTCAGGGATTCCTGACCGATTCTCTGGCTCCAA
GTCTGGCACGTCAGCCACCCTGGGCATCACCGGACTCCAG
ACTGGGGACGAGGCCGACTATTATTGCGGAACATGGGATA
GGAGCCTGAGTGCTGTGGTATTCGGCGGAGGGACCAAGCT
GACCGTCCTAGGTCAGCCCAAGGCTGCCCCCTCGGTCACT
CTGTTCCCGCCCTCCTCTGAGGAGCTTCAAGCCAACAAGG
CCACACTGGTGTGTCTCATAAGTGACTTCTACCCGGGAGC
CGTGACAGTGGCCTGGAAGGCAGATAGCAGCCCCGTCAAG
GCGGGAGTGGAGACCACCACACCCTCCAAACAAAGCAACA
ACAAGTACGCCGCCAGCAGCTATCTGAGCCTGACGCCTGA
GCAGTGGAAGTCCCACAGAAGCTACAGCTGCCAGGTCACC
CACGAGGGCAGCACCGTGGAGAAAACCGTGGCCCCCACCG
AGTGCAGC

NOV675

SEQ ID NO: 102 HCDR1 GYRFTSHWIS
(Combined)

SEQ ID NO: 103 HCDR2 RIDPSDSYIKYSPSFQG
(Combined)

SEQ ID NO: 104 HCDR3 LGYSSGWYYFDY
(Combined)

SEQ ID NO: 105 HCDR1 SHWIS
(Kabat)

SEQ ID NO: 106 HCDR2 RIDPSDSYIKYSPSFQG
(Kabat)

SEQ ID NO: 107 HCDR3 LGYSSGWYYFDY
(Kabat)

SEQ ID NO: 108 HCDR1 GYRFTSH
(Chothia)

SEQ ID NO: 109 HCDR2 DPSDSY
(Chothia)

TABLE 2-continued

Anti-Polyoma virus Antibodies

SEQ ID NO: 110 HCDR3    LGYSSGWYYFDY
(Chothia)

SEQ ID NO: 111 HCDR1    GYRFTSHW
(IMGT)

SEQ ID NO: 112 HCDR2    IDPSDSYI
(IMGT)

SEQ ID NO: 113 HCDR3    ARLGYSSGWYYFDY
(IMGT)

SEQ ID NO: 114 VH       EVQLVQSGAEVKKPGESLRISCKGSGYRFTSHWISWVRQM
                        PGKGLEWVARIDPSDSYIKYSPSFQGHVTISADKSTSTAF
                        LQWSSLKASDTAMYYCARLGYSSGWYYFDYWGQGTLVTVS
                        S

SEQ ID NO: 115 DNA VH   GAAGTGCAGCTGGTGCAGTCTGGAGCAGAGGTGAAAAAGC
                        CCGGGGAGTCTCTGAGGATCTCTTGTAAGGGTTCTGGATA
                        CAGGTTTACCAGCCACTGGATCAGCTGGGTGCGCCAGATG
                        CCCGGGAAAGGCCTGGAGTGGGTGGCGAGGATTGATCCTA
                        GTGACTCTTATATCAAGTACAGCCCGTCCTTCCAAGGCCA
                        CGTCACCATCTCAGCTGACAAGTCCACCAGCACAGCCTTC
                        CTGCAGTGGAGCAGCCTGAAGGCCTCGGACACCGCCATGT
                        ATTACTGTGCGAGACTAGGGTATAGCAGTGGCTGGTACTA
                        TTTTGACTACTGGGGCCAGGGAACCCTGGTCACCGTCTCC
                        TCA

SEQ ID NO: 116 Heavy    EVQLVQSGAEVKKPGESLRISCKGSGYRFTSHWISWVRQM
               Chain    PGKGLEWVARIDPSDSYIKYSPSFQGHVTISADKSTSTAF
                        LQWSSLKASDTAMYYCARLGYSSGWYYFDYWGQGTLVTVS
                        SASTKGPSVFPLAPCSRSTSGGTAALGCLVKDYFPEPVTV
                        SWNSGALTSGVHTFPAVLQSSGLYSLSSVVTVPSSSLGTQ
                        TYICNVNHKPSNTKVDKRVEPKSCDKTHTCPPCPAPELLG
                        GPSVFLFPPKPKDTLMISRTPEVTCVVVDVSHEDPEVKFN
                        WYVDGVEVHNAKTKPREEQYNSTYRVVSVLTVLHQDWLNG
                        KEYKCKVSNKALPAPIEKTISKAKGQPREPQVYTLPPSRE
                        EMTKNQVSLTCLVKGFYPSDIAVEWESNGQPENNYKTTPP
                        VLDSDGSFFLYSKLTVDKSRWQQGNVFSCSVMHEALHNHY
                        TQKSLSLSPGK SEQ ID NO: 117 DNA      GAAGTGCAGCTGGTGCAGTCTGGAGCAGAGGTGAAAAAGC
               Heavy    CCGGGGAGTCTCTGAGGATCTCTTGTAAGGGTTCTGGATA
               Chain    CAGGTTTACCAGCCACTGGATCAGCTGGGTGCGCCAGATG
                        CCCGGGAAAGGCCTGGAGTGGGTGGCGAGGATTGATCCTA
                        GTGACTCTTATATCAAGTACAGCCCGTCCTTCCAAGGCCA
                        CGTCACCATCTCAGCTGACAAGTCCACCAGCACAGCCTTC
                        CTGCAGTGGAGCAGCCTGAAGGCCTCGGACACCGCCATGT
                        ATTACTGTGCGAGACTAGGGTATAGCAGTGGCTGGTACTA
                        TTTTGACTACTGGGGCCAGGGAACCCTGGTCACCGTCTCC
                        TCAGCTTCCACCAAGGGCCCATCGGTCTTCCCCCTGGCGC
                        CCTGCTCCAGGAGCACCTCTGGGGGCACAGCGGCCCTGGG
                        CTGCCTGGTCAAGGACTACTTCCCCGAACCGGTGACGGTG
                        TCGTGGAACTCAGGCGCCCTGACCAGCGGCGTGCACACCT
                        TCCCGGCTGTCCTACAGTCCTCAGGACTCTACTCCCTCAG
                        CAGCGTGGTGACCGTGCCCTCCAGCAGCTTGGGCACCCAG
                        ACCTACATCTGCAACGTGAACCACAAGCCCAGCAACACCA
                        AGGTGGACAAGAGAGTGGAGCCCAAGAGCTGCGACAAGAC
                        CCACACCTGCCCCCCCTGCCCAGCCCCAGAGCTGCTGGGC
                        GGACCCTCCGTGTTCCTGTTCCCCCCCAAGCCCAAGGACA
                        CCCTGATGATCAGCAGGACCCCCGAGGTGACCTGCGTGGT
                        GGTGGACGTGAGCCACGAGGACCCAGAGGTGAAGTTCAAC
                        TGGTACGTGGACGGCGTGGAGGTGCACAACGCCAAGACCA
                        AGCCCAGAGAGGAGCAGTACAACAGCACCTACAGGGTGGT
                        GTCCGTGCTGACCGTGCTGCACCAGGACTGGCTGAACGGC
                        AAGGAATACAAGTGCAAGGTCTCCAACAAGGCCCTGCCAG
                        CCCCCATCGAAAAGACCATCAGCAAGGCCAAGGGCCAGCC
                        ACGGGAGCCCCAGGTGTACACCCTGCCCCCCTCCCGGGAG
                        GAGATGACCAAGAACCAGGTGTCCCTGACCTGTCTGGTGA
                        AGGGCTTCTACCCCAGCGACATCGCCGTGGAGTGGGAGAG
                        CAACGGCCAGCCCGAGAACAACTACAAGACCACCCCCCCA
                        GTGCTGGACAGCGACGGCAGCTTCTTCCTGTACAGCAAGC
                        TGACCGTGGACAAGTCCAGGTGGCAGCAGGGCAACGTGTT
                        CAGCTGCAGCGTGATGCACGAGGCCCTGCACAACCACTAC
                        ACCCAGAAGAGCCTGAGCCTGTCCCCCGGCAAG TABLE 2-continued Anti-Polyoma virus Antibodies SEQ ID NO: 118 LCDR1  SGSRTNIGSNAVN
(Combined)

SEQ ID NO: 119 LCDR2  SSDQRPS
(Combined)

SEQ ID NO: 120 LCDR3  AAWDDSLHGWV
(Combined)

SEQ ID NO: 121 LCDR1  SGSRTNIGSNAVN
(Kabat)

SEQ ID NO: 122 LCDR2  SSDQRPS
(Kabat)

SEQ ID NO: 123 LCDR3  AAWDDSLHGWV
(Kabat)

SEQ ID NO: 124 LCDR1  SRTNIGSNA
(Chothia)

SEQ ID NO: 125 LCDR2  SSD
(Chothia)

SEQ ID NO: 126 LCDR3  WDDSLHGW
(Chothia)

SEQ ID NO: 127 LCDR1  RTNIGSNA
(IMGT)

SEQ ID NO: 128 LCDR2  SSD
(IMGT)

SEQ ID NO: 129 LCDR3  AAWDDSLHGWV
(IMGT)

SEQ ID NO: 130 VL     SPVLTQPPSASGTPGQRVTISCSGSRTNIGSNAVNWYQQV
                      PGTAPKLLIYSSDQRPSGVSDRFSGSKSGTSGSLAISGLQ
                      SEDETDYYCAAWDDSLHGWVFGGGTKLTVL

SEQ ID NO: 131 DNA VL TCGCCTGTGCTGACTCAGCCGCCCTCAGCGTCTGGGACCC
                      CCGGGCAGAGGGTCACCATCTCTTGTTCTGGAAGCAGGAC
                      CAACATCGGAAGTAATGCTGTAAACTGGTACCAGCAGGTC
                      CCAGGAACGGCCCCCAAACTCCTCATCTATAGTAGTGATC
                      AGCGGCCCTCAGGGGTCTCTGACCGATTCTCTGGCTCCAA
                      GTCTGGCACCTCAGGCTCCCTGGCCATCAGTGGCCTCCAG
                      TCTGAGGATGAAACTGATTATTACTGTGCAGCATGGGATG
                      ACAGCCTGCATGGTTGGGTGTTCGGCGGAGGGACCAAGCT
                      GACCGTCCTA

SEQ ID NO: 132 Light  SPVLTQPPSASGTPGQRVTISCSGSRTNIGSNAVNWYQQV
               Chain  PGTAPKLLIYSSDQRPSGVSDRFSGSKSGTSGSLAISGLQ
                      SEDETDYYCAAWDDSLHGWVFGGGTKLTVLGQPKAAPSVT
                      LFPPSSEELQANKATLVCLISDFYPGAVTVAWKADSSPVK
                      AGVETTTPSKQSNNKYAASSYLSLTPEQWKSHRSYSCQVT
                      HEGSTVEKTVAPTECS SEQ ID NO: 133 DNA    TCGCCTGTGCTGACTCAGCCGCCCTCAGCGTCTGGGACCC
               Light  CCGGGCAGAGGGTCACCATCTCTTGTTCTGGAAGCAGGAC
               Chain  CAACATCGGAAGTAATGCTGTAAACTGGTACCAGCAGGTC
                      CCAGGAACGGCCCCCAAACTCCTCATCTATAGTAGTGATC
                      AGCGGCCCTCAGGGGTCTCTGACCGATTCTCTGGCTCCAA
                      GTCTGGCACCTCAGGCTCCCTGGCCATCAGTGGCCTCCAG
                      TCTGAGGATGAAACTGATTATTACTGTGCAGCATGGGATG
                      ACAGCCTGCATGGTTGGGTGTTCGGCGGAGGGACCAAGCT
                      GACCGTCCTAGGTCAGCCCAAGGCTGCCCCCTCGGTCACT
                      CTGTTCCCGCCCTCCTCTGAGGAGCTTCAAGCCAACAAGG
                      CCACACTGGTGTGTCTCATAAGTGACTTCTACCCGGGAGC
                      CGTGACAGTGGCCTGGAAGGCAGATAGCAGCCCCGTCAAG
                      GCGGGAGTGGAGACCACCACACCCTCCAAACAAAGCAACA
                      ACAAGTACGCCGCCAGCAGCTACCTGAGCCTGACCCCCGA
                      GCAGTGGAAGAGCCACAGAAGCTACAGCTGCCAGGTCACC
                      CACGAGGGCAGCACCGTGGAGAAAACCGTGGCCCCCACCG
                      AGTGCAGC TABLE 2-continued Anti-Polyoma virus Antibodies

NOV219

SEQ ID NO: 134 HCDR1    GYRFTSHWIS
(Combined)

SEQ ID NO: 135 HCDR2    RIDPSDSYTKYSPSFQG
(Combined)

SEQ ID NO: 136 HCDR3    LGYHSGWYYFDY
(Combined)

SEQ ID NO: 137 HCDR1    SHWIS
(Kabat)

SEQ ID NO: 138 HCDR2    RIDPSDSYTKYSPSFQG
(Kabat)

SEQ ID NO: 139 HCDR3    LGYHSGWYYFDY
(Kabat)

SEQ ID NO: 140 HCDR1    GYRFTSH
(Chothia)

SEQ ID NO: 141 HCDR2    DPSDSY
(Chothia)

SEQ ID NO: 142 HCDR3    LGYHSGWYYFDY
(Chothia)

SEQ ID NO: 143 HCDR1    GYRFTSHW
(IMGT)

SEQ ID NO: 144 HCDR2    IDPSDSYT
(IMGT)

SEQ ID NO: 145 HCDR3    ARLGYHSGWYYFDY
(IMGT)

SEQ ID NO: 146 VH       QVQLVESGAEVKKPGESLRISCKGSGYRFTSHWISWVRQM
                        PGKGLEWVARIDPSDSYTKYSPSFQGHVTISTDKSTSTAY
                        LHWSSLKASDTAMYYCARLGYHSGWYYFDYWGQGTLVTVS
                        S

SEQ ID NO: 147 DNA VH   CAGGTGCAGCTGGTGGAGTCTGGAGCAGAGGTGAAAAAGC
                        CCGGGGAGTCTCTGAGGATCTCCTGTAAGGGTTCTGGATA
                        CAGGTTTACCAGCCACTGGATCAGCTGGGTGCGCCAGATG
                        CCCGGGAAAGGCCTGGAGTGGGTGGCGAGGATTGATCCTA
                        GTGACTCTTATACCAAGTACAGCCCGTCCTTCCAAGGCCA
                        CGTCACCATCTCAACTGACAAGTCCACCAGCACAGCCTAC
                        CTGCACTGGAGCAGCCTGAAGGCCTCGGACACCGCCATGT
                        ATTACTGTGCGAGACTAGGGTATCACAGTGGCTGGTACTA
                        CTTTGACTACTGGGGCCAGGGAACCCTGGTCACCGTCTCC
                        TCA

SEQ ID NO: 148 Heavy    QVQLVESGAEVKKPGESLRISCKGSGYRFTSHWISWVRQM
               Chain    PGKGLEWVARIDPSDSYTKYSPSFQGHVTISTDKSTSTAY
                        LHWSSLKASDTAMYYCARLGYHSGWYYFDYWGQGTLVTVS
                        SASTKGPSVFPLAPCSRSTSGGTAALGCLVKDYFPEPVTV
                        SWNSGALTSGVHTFPAVLQSSGLYSLSSVVTVPSSSLGTQ
                        TYICNVNHKPSNTKVDKRVEPKSCDKTHTCPPCPAPELLG
                        GPSVFLFPPKPKDTLMISRTPEVTCVVVDVSHEDPEVKFN
                        WYVDGVEVHNAKTKPREEQYNSTYRVVSVLTVLHQDWLNG
                        KEYKCKVSNKALPAPIEKTISKAKGQPREPQVYTLPPSRE
                        EMTKNQVSLTCLVKGFYPSDIAVEWESNGQPENNYKTTPP
                        VLDSDGSFFLYSKLTVDKSRWQQGNVFSCSVMHEALHNHY
                        TQKSLSLSPGK SEQ ID NO: 149 DNA      CAGGTGCAGCTGGTGGAGTCTGGAGCAGAGGTGAAAAAGC
               Heavy    CCGGGGAGTCTCTGAGGATCTCCTGTAAGGGTTCTGGATA
               Chain    CAGGTTTACCAGCCACTGGATCAGCTGGGTGCGCCAGATG
                        CCCGGGAAAGGCCTGGAGTGGGTGGCGAGGATTGATCCTA
                        GTGACTCTTATACCAAGTACAGCCCGTCCTTCCAAGGCCA
                        CGTCACCATCTCAACTGACAAGTCCACCAGCACAGCCTAC
                        CTGCACTGGAGCAGCCTGAAGGCCTCGGACACCGCCATGT
                        ATTACTGTGCGAGACTAGGGTATCACAGTGGCTGGTACTA
                        CTTTGACTACTGGGGCCAGGGAACCCTGGTCACCGTCTCC
                        TCAGCTTCCACCAAGGGCCCATCGGTCTTCCCCCTGGCGC

TABLE 2-continued

Anti-Polyoma virus Antibodies

```
CCTGCTCCAGGAGCACCTCTGGGGGCACAGCGGCCCTGGG
CTGCCTGGTCAAGGACTACTTCCCCGAACCGGTGACGGTG
TCGTGGAACTCAGGCGCCCTGACCAGCGGCGTGCACACCT
TCCCGGCTGTCCTACAGTCCTCAGGACTCTACTCCCTCAG
CAGCGTGGTGACCGTGCCCTCCAGCAGCTTGGGCACCCAG
ACCTACATCTGCAACGTGAACCACAAGCCCAGCAACACCA
AGGTGGACAAGAGAGTGGAGCCCAAGAGCTGCGACAAGAC
CCACACCTGCCCCCCCTGCCCAGCCCCAGAGCTGCTGGGC
GGACCCTCCGTGTTCCTGTTCCCCCCCAAGCCCAAGGACA
CCCTGATGATCAGCAGGACCCCCGAGGTGACCTGCGTGGT
GGTGGACGTGAGCCACGAGGACCCAGAGGTGAAGTTCAAC
TGGTACGTGGACGGCGTGGAGGTGCACAACGCCAAGACCA
AGCCCAGAGAGGAGCAGTACAACAGCACCTACAGGGTGGT
GTCCGTGCTGACCGTGCTGCACCAGGACTGGCTGAACGGC
AAGGAATACAAGTGCAAGGTCTCCAACAAGGCCCTGCCAG
CCCCCATCGAAAAGACCATCAGCAAGGCCAAGGGCCAGCC
ACGGGAGCCCCAGGTGTACACCCTGCCCCCCTCCCGGGAG
GAGATGACCAAGAACCAGGTGTCCTGACCTGTCTGGTGA
AGGGCTTCTACCCCAGCGACATCGCCGTGGAGTGGGAGAG
CAACGGCCAGCCCGAGAACAACTACAAGACCACCCCCCCA
GTGCTGGACAGCGACGGCAGCTTCTTCCTGTACAGCAAGC
TGACCGTGGACAAGTCCAGGTGGCAGCAGGGCAACGTGTT
CAGCTGCAGCGTGATGCACGAGGCCCTGCACAACCACTAC
ACCCAGAAGAGCCTGAGCCTGTCCCCCGGCAAG
```

SEQ ID NO: 150 LCDR1    SGSSSNIGSNAVN
(Combined)

SEQ ID NO: 151 LCDR2    SSDQRPS
(Combined)

SEQ ID NO: 152 LCDR3    AAWDDSLHGWI
(Combined)

SEQ ID NO: 153 LCDR1    SGSSSNIGSNAVN
(Kabat)

SEQ ID NO: 154 LCDR2    SSDQRPS
(Kabat)

SEQ ID NO: 155 LCDR3    AAWDDSLHGWI
(Kabat)

SEQ ID NO: 156 LCDR1    SSSNIGSNA
(Chothia)

SEQ ID NO: 157 LCDR2    SSD
(Chothia)

SEQ ID NO: 158 LCDR3    WDDSLHGW
(Chothia)

SEQ ID NO: 159 LCDR1    SSNIGSNA
(IMGT)

SEQ ID NO: 160 LCDR2    SSD
(IMGT)

SEQ ID NO: 161 LCDR3    AAWDDSLHGWI
(IMGT)

SEQ ID NO: 162 VL       QSALTQPPSASGTPGQRVTISCSGSSSNIGSNAVNWYQQL
                        PGTAPKLLIYSSDQRPSGVPDRFSGSKSGTSGSLAISGLH
                        SEDETDYYCAAWDDSLHGWIFGGGTKLTVI

SEQ ID NO: 163 DNA VL   CAGTCTGCCCTGACTCAGCCACCCTCAGCGTCTGGGACCC
                        CCGGGCAGAGGGTCACCATCTCTTGTTCTGGAAGCAGCTC
                        CAACATCGGAAGTAATGCTGTAAACTGGTACCAGCAGCTC
                        CCAGGAACGGCCCCCAAACTCCTCATCTATAGTAGTGATC
                        AGCGGCCCTCAGGGGTCCCTGACCGATTCTCTGGCTCCAA
                        GTCTGGCACCTCAGGCTCCCTGGCCATCAGTGGGCTCCAC
                        TCTGAGGATGAGACTGATTATTACTGTGCAGCATGGGATG
                        ACAGCCTGCATGGTTGGATATTCGGCGGAGGGACCAAGCT
                        GACCGTCATA

SEQ ID NO: 164 Light    QSALTQPPSASGTPGQRVTISCSGSSSNIGSNAVNWYQQL
               Chain    PGTAPKLLIYSSDQRPSGVPDRFSGSKSGTSGSLAISGLH
                        SEDETDYYCAAWDDSLHGWIFGGGTKLTVIGQPKAAPSVT TABLE 2-continued Anti-Polyoma virus Antibodies LFPPSSEELQANKATLVCLISDFYPGAVTVAWKADSSPVK
AGVETTTPSKQSNNKYAASSYLSLTPEQWKSHRSYSCQVT
HEGSTVEKTVAPTECS SEQ ID NO: 165 DNA   CAGTCTGCCCTGACTCAGCCACCCTCAGCGTCTGGGACCC
               Light CCGGGCAGAGGGTCACCATCTCTTGTTCTGGAAGCAGCTC
               Chain CAACATCGGAAGTAATGCTGTAAACTGGTACCAGCAGCTC
CCAGGAACGGCCCCCAAACTCCTCATCTATAGTAGTGATC
AGCGGCCCTCAGGGGTCCCTGACCGATTCTCTGGCTCCAA
GTCTGGCACCTCAGGCTCCCTGGCCATCAGTGGGCTCCAC
TCTGAGGATGAGACTGATTATTACTGTGCAGCATGGGATG
ACAGCCTGCATGGTTGGATATTCGGCGGAGGGACCAAGCT
GACCGTCATAGGTCAGCCCAAGGCTGCCCCCTCGGTCACT
CTGTTCCCGCCCTCCTCTGAGGAGCTTCAAGCCAACAAGG
CCACACTGGTGTGTCTCATAAGTGACTTCTACCCGGGAGC
CGTGACAGTGGCCTGGAAGGCAGATAGCAGCCCCGTCAAG
GCGGGAGTGGAGACCACCACACCCTCCAAACAAAGCAACA
ACAAGTACGCCGCCAGCAGCTACCTGAGCCTGACGCCTGA
GCAGTGGAAGTCCCACAGAAGCTACAGCTGCCAGGTCACC
CACGAGGGCAGCACCGTGGAGAAAACCGTGGCCCCCACCG
AGTGCAGC

NOV487

SEQ ID NO: 166 HCDR1  GASISSGSDYWS
(Combined)

SEQ ID NO: 167 HCDR2  RIYTSGRNSYNPSLKS
(Combined)

SEQ ID NO: 168 HCDR3  NSRRYGGYDLFDV
(Combined)

SEQ ID NO: 169 HCDR1  SGSDYWS
(Kabat)

SEQ ID NO: 170 HCDR2  RIYTSGRNSYNPSLKS
(Kabat)

SEQ ID NO: 171 HCDR3  NSRRYGGYDLFDV
(Kabat)

SEQ ID NO: 172 HCDR1  GASISSGSD
(Chothia)

SEQ ID NO: 173 HCDR2  YTSGR
(Chothia)

SEQ ID NO: 174 HCDR3  NSRRYGGYDLFDV
(Chothia)

SEQ ID NO: 175 HCDR1  GASISSGSDY
(IMGT)

SEQ ID NO: 176 HCDR2  IYTSGRN
(IMGT)

SEQ ID NO: 177 HCDR3  ARNSRRYGGYDLFDV
(IMGT)

SEQ ID NO: 178 VH     QVQLQESGPGLVKPSQTLSLTCTVSGASISSGSDYWSWIR
QPAGKGLEWIGRIYTSGRNSYNPSLKSRVTIAVDTSKNQF
SLKLSSVSATDTAVYYCARNSRRYGGYDLFDVWGQGTMVT
VSS

SEQ ID NO: 179 DNA VH CAGGTGCAGCTGCAGGAGTCGGGCCCAGGACTGGTGAAGC
CTTCACAGACCCTGTCCCTCACCTGCACTGTCTCTGGTGC
CTCCATCAGCAGTGGTAGTGACTACTGGAGCTGGATCCGG
CAGCCCGCCGGGAAGGGACTGGAGTGGATTGGGCGTATCT
ATACCAGTGGGAGGAACAGCTACAACCCCTCCCTCAAGAG
TCGAGTCACCATAGCAGTAGACACGTCCAAGAACCAGTTC
TCCCTGAAGCTGAGTAGTGTGAGTGCCACAGACACGGCCG
TGTATTACTGTGCGAGGAATAGCAGAAGATATGGTGGCTA
CGATCTGTTTGATGTCTGGGGCCAAGGGACAATGGTCACC
GTCTCTTCA

TABLE 2-continued

Anti-Polyoma virus Antibodies

SEQ ID NO: 180 Heavy Chain
QVQLQESGPGLVKPSQTLSLTCTVSGASISSGSDYWSWIR
QPAGKGLEWIGRIYTSGRNSYNPSLKSRVTIAVDTSKNQF
SLKLSSVSATDTAVYYCARNSRRYGGYDLFDVWGQGTMVT
VSSASTKGPSVFPLAPSSKSTSGGTAALGCLVKDYFPEPV
TVSWNSGALTSGVHTFPAVLQSSGLYSLSSVVTVPSSSLG
TQTYICNVNHKPSNTKVDKRVEPKSCDKTHTCPPCPAPEL
LGGPSVFLFPPKPKDTLMISRTPEVTCVVVDVSHEDPEVK
FNWYVDGVEVHNAKTKPREEQYNSTYRVVSVLTVLHQDWL
NGKEYKCKVSNKALPAPIEKTISKAKGQPREPQVYTLPPS
REEMTKNQVSLTCLVKGFYPSDIAVEWESNGQPENNYKTT
PPVLDSDGSFFLYSKLTVDKSRWQQGNVFSCSVMHEALHN
HYTQKSLSLSPGK SEQ ID NO: 181 DNA Heavy Chain
CAGGTGCAGCTGCAGGAGTCGGGCCCAGGACTGGTGAAGC
CTTCACAGACCCTGTCCCTCACCTGCACTGTCTCTGGTGC
CTCCATCAGCAGTGGTAGTGACTACTGGAGCTGGATCCGG
CAGCCCGCCGGGAAGGGACTGGAGTGGATTGGGCGTATCT
ATACCAGTGGGAGGAACAGCTACAACCCCTCCCTCAAGAG
TCGAGTCACCATAGCAGTAGACACGTCCAAGAACCAGTTC
TCCCTGAAGCTGAGTAGTGTGAGTGCCACAGACACGGCCG
TGTATTACTGTGCGAGGAATAGCAGAAGATATGGTGGCTA
CGATCTGTTTGATGTCTGGGGCCAAGGGACAATGGTCACC
GTCTCTTCAGCCTCCACCAAGGGCCCATCGGTCTTCCCCC
TGGCACCCTCCTCCAAGAGCACCTCTGGGGGCACAGCGGC
CCTGGGCTGCCTGGTCAAGGACTACTTCCCCGAACCGGTG
ACGGTGTCGTGGAACTCAGGCGCCCTGACCAGCGGCGTGC
ACACCTTCCCGGCTGTCCTACAGTCCTCAGGACTCTACTC
CCTCAGCAGCGTGGTGACCGTGCCCTCCAGCAGCTTGGGC
ACCCAGACCTACATCTGCAACGTGAACCACAAGCCCAGCA
ACACCAAGGTGGACAAGAGAGTGGAGCCCAAGAGCTGCGA
CAAGACCCACACCTGCCCCCCCTGCCCAGCCCCAGAGCTG
CTGGGCGGACCCTCCGTGTTCCTGTTCCCCCCCAAGCCCA
AGGACACCCTGATGATCAGCAGGACCCCCGAGGTGACCTG
CGTGGTGGTGGACGTGAGCCACGAGGACCCAGAGGTGAAG
TTCAACTGGTACGTGGACGGCGTGGAGGTGCACAACGCCA
AGACCAAGCCCAGAGAGGAGCAGTACAACAGCACCTACAG
GGTGGTGTCCGTGCTGACCGTGCTGCACCAGGACTGGCTG
AACGGCAAGGAATACAAGTGCAAGGTCTCCAACAAGGCCC
TGCCAGCCCCCATCGAAAAGACCATCAGCAAGGCCAAGGG
CCAGCCACGGGAGCCCCAGGTGTACACCCTGCCCCCCTCC
CGGGAGGAGATGACCAAGAACCAGGTGTCCCTGACCTGTC
TGGTGAAGGGCTTCTACCCCAGCGACATCGCCGTGGAGTG
GGAGAGCAACGGCCAGCCCGAGAACAACTACAAGACCACC
CCCCCAGTGCTGGACAGCGACGGCAGCTTCTTCCTGTACA
GCAAGCTGACCGTGGACAAGTCCAGGTGGCAGCAGGGCAA
CGTGTTCAGCTGCAGCGTGATGCACGAGGCCCTGCACAAC
CACTACACCCAGAAGAGCCTGAGCCTGTCCCCCGGCAAG SEQ ID NO: 182 LCDR1 (Combined)  GGNNIGSKSVH SEQ ID NO: 183 LCDR2 (Combined)  YDGDRPS SEQ ID NO: 184 LCDR3 (Combined)  QVWDTSSDHPV SEQ ID NO: 185 LCDR1 (Kabat)  GGNNIGSKSVH SEQ ID NO: 186 LCDR2 (Kabat)  YDGDRPS SEQ ID NO: 187 LCDR3 (Kabat)  QVWDTSSDHPV SEQ ID NO: 188 LCDR1 (Chothia)  NNIGSKS SEQ ID NO: 189 LCDR2 (Chothia)  YDG SEQ ID NO: 190 LCDR3 (Chothia)  WDTSSDHP

SEQ ID NO: 191 LCDR1 (IMGT)  NIGSKS

TABLE 2-continued

Anti-Polyoma virus Antibodies

SEQ ID NO: 192 LCDR2 YDG
(IMGT)

SEQ ID NO: 193 LCDR3 QVWDTSSDHPV
(IMGT)

SEQ ID NO: 194 VL SYVLTQPPSVSEAPGKTARITCGGNNIGSKSVHWYQQKPG
QAPVLVIYYDGDRPSGIPERFSGSNSGNTATLTISRVEAG
DEADYYCQVWDTSSDHPVFGGGTKLTVL

SEQ ID NO: 195 DNA VL TCCTATGTGCTGACTCAGCCACCCTCAGTGTCAGAGGCCC
CAGGAAAGACGGCCAGGATTACCTGTGGGGGAAACAACAT
TGGAAGTAAAAGTGTGCACTGGTACCAGCAGAAGCCAGGC
CAGGCCCCTGTGCTGGTCATCTATTATGATGGCGACCGGC
CCTCAGGGATCCCTGAGCGATTCTCTGGCTCCAACTCTGG
GAACACGGCCACCCTGACCATCAGCAGGGTCGAAGCCGGG
GATGAGGCCGACTATTACTGTCAGGTGTGGGATACTAGTA
GTGATCACCCGGTGTTCGGCGGAGGGACCAAGCTGACCGT
CCTA

SEQ ID NO: 196 Light SYVLTQPPSVSEAPGKTARITCGGNNIGSKSVHWYQQKPG
Chain QAPVLVIYYDGDRPSGIPERFSGSNSGNTATLTISRVEAG
DEADYYCQVWDTSSDHPVFGGGTKLTVLGQPKAAPSVTLF
PPSSEELQANKATLVCLISDFYPGAVTVAWKADSSPVKAG
VETTTPSKQSNNKYAASSYLSLTPEQWKSHRSYSCQVTHE
GSTVEKTVAPTECS SEQ ID NO: 197 DNA TCCTATGTGCTGACTCAGCCACCCTCAGTGTCAGAGGCCC
Light CAGGAAAGACGGCCAGGATTACCTGTGGGGGAAACAACAT
Chain TGGAAGTAAAAGTGTGCACTGGTACCAGCAGAAGCCAGGC
CAGGCCCCTGTGCTGGTCATCTATTATGATGGCGACCGGC
CCTCAGGGATCCCTGAGCGATTCTCTGGCTCCAACTCTGG
GAACACGGCCACCCTGACCATCAGCAGGGTCGAAGCCGGG
GATGAGGCCGACTATTACTGTCAGGTGTGGGATACTAGTA
GTGATCACCCGGTGTTCGGCGGAGGGACCAAGCTGACCGT
CCTAGGTCAGCCCAAGGCTGCCCCCTCGGTCACTCTGTTC
CCGCCCTCCTCTGAGGAGCTTCAAGCCAACAAGGCCACAC
TGGTGTGTCTCATAAGTGACTTCTACCCGGGAGCCGTGAC
AGTGGCCTGGAAGGCAGATAGCAGCCCCGTCAAGGCGGGA
GTGGAGACCACCACACCCTCCAAACAAAGCAACAACAAGT
ACGCCGCCAGCAGCTACCTGAGCCTGACCCCCGAGCAGTG
GAAGAGCCACAGAAGCTACAGCTGCCAGGTCACCCACGAG
GGCAGCACCGTGGAGAAAACCGTGGCCCCCACCGAGTGCA
GC

NOV581

SEQ ID NO: 198 HCDR1 GFTFSGYNMH
(Combined)

SEQ ID NO: 199 HCDR2 YISNSGRTIYYADSVKG
(Combined)

SEQ ID NO: 200 HCDR3 DRDPQWLGNDALQI
(Combined)

SEQ ID NO: 201 HCDR1 GYNMH
(Kabat)

SEQ ID NO: 202 HCDR2 YISNSGRTIYYADSVKG
(Kabat)

SEQ ID NO: 203 HCDR3 DRDPQWLGNDALQI
(Kabat)

SEQ ID NO: 204 HCDR1 GFTFSGY
(Chothia)

SEQ ID NO: 205 HCDR2 SNSGRT
(Chothia)

SEQ ID NO: 206 HCDR3 DRDPQWLGNDALQI
(Chothia)

SEQ ID NO: 207 HCDR1 GFTFSGYN
(IMGT)

TABLE 2-continued

Anti-Polyoma virus Antibodies

SEQ ID NO: 208 HCDR2  ISNSGRTI
(IMGT)

SEQ ID NO: 209 HCDR3  ARDRDPQWLGNDALQI
(IMGT)

SEQ ID NO: 210 VH     QVQLVESGGGLVQPGGSLRLSCVASGFTFSGYNMHWVRQA
                      PGKGLEWVSYISNSGRTIYYADSVKGRFTLSRDNAKNSLY
                      LQMNSLRAEDTAVYFCARDRDPQWLGNDALQIWGQGTMVT
                      VSS

SEQ ID NO: 211 DNA VH CAGGTGCAGCTGGTGGAGTCTGGGGGAGGCTTGGTACAGC
                      CTGGGGGGTCCCTGAGGCTCTCCTGTGTAGCCTCTGGATT
                      CACCTTCAGTGGCTATAACATGCACTGGGTCCGCCAGGCT
                      CCAGGGAAGGGGCTGGAGTGGGTCTCATACATTAGTAATA
                      GTGGTAGAACCATATACTACGCAGACTCTGTGAAGGGCCG
                      ATTCACCCTGTCCAGAGACAACGCCAAGAACTCACTGTAT
                      CTGCAGATGAACAGCCTGAGAGCCGAGGACACGGCTGTCT
                      ATTTTTGTGCGAGAGATCGGGATCCCCAGTGGCTGGGAAA
                      TGATGCTCTTCAAATCTGGGGCCAAGGGACAATGGTCACC
                      GTCTCTTCA

SEQ ID NO: 212 Heavy  QVQLVESGGGLVQPGGSLRLSCVASGFTFSGYNMHWVRQA
               Chain  PGKGLEWVSYISNSGRTIYYADSVKGRFTLSRDNAKNSLY
                      LQMNSLRAEDTAVYFCARDRDPQWLGNDALQIWGQGTMVT
                      VSSASTKGPSVFPLAPSSKSTSGGTAALGCLVKDYFPEPV
                      TVSWNSGALTSGVHTFPAVLQSSGLYSLSSVVTVPSSSLG
                      TQTYICNVNHKPSNTKVDKRVEPKSCDKTHTCPPCPAPEL
                      LGGPSVFLFPPKPKDTLMISRTPEVTCVVVDVSHEDPEVK
                      FNWYVDGVEVHNAKTKPREEQYNSTYRVVSVLTVLHQDWL
                      NGKEYKCKVSNKALPAPIEKTISKAKGQPREPQVYTLPPS
                      REEMTKNQVSLTCLVKGFYPSDIAVEWESNGQPENNYKTT
                      PPVLDSDGSFFLYSKLTVDKSRWQQGNVFSCSVMHEALHN
                      HYTQKSLSLSPGK SEQ ID NO: 213 DNA    CAGGTGCAGCTGGTGGAGTCTGGGGGAGGCTTGGTACAGC
               Heavy  CTGGGGGGTCCCTGAGGCTCTCCTGTGTAGCCTCTGGATT
               Chain  CACCTTCAGTGGCTATAACATGCACTGGGTCCGCCAGGCT
                      CCAGGGAAGGGGCTGGAGTGGGTCTCATACATTAGTAATA
                      GTGGTAGAACCATATACTACGCAGACTCTGTGAAGGGCCG
                      ATTCACCCTGTCCAGAGACAACGCCAAGAACTCACTGTAT
                      CTGCAGATGAACAGCCTGAGAGCCGAGGACACGGCTGTCT
                      ATTTTTGTGCGAGAGATCGGGATCCCCAGTGGCTGGGAAA
                      TGATGCTCTTCAAATCTGGGGCCAAGGGACAATGGTCACC
                      GTCTCTTCAGCCTCCACCAAGGGCCCATCGGTCTTCCCCC
                      TGGCACCCTCCTCCAAGAGCACCTCTGGGGGCACAGCGGC
                      CCTGGGCTGCCTGGTCAAGGACTACTTCCCCGAACCGGTG
                      ACGGTGTCGTGGAACTCAGGCGCCCTGACCAGCGGCGTGC
                      ACACCTTCCCGGCTGTCCTACAGTCCTCAGGACTCTACTC
                      CCTCAGCAGCGTGGTGACCGTGCCCTCCAGCAGCTTGGGC
                      ACCCAGACCTACATCTGCAACGTGAATCACAAGCCCAGCA
                      ACACCAAGGTGGACAAGAGAGTGGAGCCCAAGAGCTGCGA
                      CAAGACCCACACCTGCCCCCCCTGCCCAGCCCCAGAGCTG
                      CTGGGCGGACCCTCCGTGTTCCTGTTCCCCCCCAAGCCCA
                      AGGACACCCTGATGATCAGCAGGACCCCCGAGGTGACCTG
                      CGTGGTGGTGGACGTGAGCCACGAGGACCCAGAGGTGAAG
                      TTCAACTGGTACGTGGACGGCGTGGAGGTGCACAACGCCA
                      AGACCAAGCCCAGAGAGGAGCAGTACAACAGCACCTACAG
                      GGTGGTGTCCGTGCTGACCGTGCTGCACCAGGACTGGCTG
                      AACGGCAAGGAATACAAGTGCAAGGTCTCCAACAAGGCCC
                      TGCCAGCCCCCATCGAAAAGACCATCAGCAAGGCCAAGGG
                      CCAGCCACGGGAGCCCCAGGTGTACACCCTGCCCCCCTCC
                      CGGGAGGAGATGACCAAGAACCAGGTGTCCCTGACCTGTC
                      TGGTGAAGGGCTTCTACCCCAGCGACATCGCCGTGGAGTG
                      GGAGAGCAACGGCCAGCCCGAGAACAACTACAAGACCACC
                      CCCCCAGTGCTGGACAGCGACGGCAGCTTCTTCCTGTACA
                      GCAAGCTGACCGTGGACAAGTCCAGGTGGCAGCAGGGCAA
                      CGTGTTCAGCTGCAGCGTGATGCACGAGGCCCTGCACAAC
                      CACTACACCCAGAAGAGCCTGAGCCTGTCCCCCGGCAAG SEQ ID NO: 214 LCDR1  RASQSVSSGYLA
(Combined)

SEQ ID NO: 215 LCDR2  GASSRAT
(Combined)

SEQ ID NO: 216 LCDR3  QQYGTSRKT
(Combined)

TABLE 2-continued

Anti-Polyoma virus Antibodies

SEQ ID NO: 217 LCDR1 RASQSVSSGYLA
(Kabat)

SEQ ID NO: 218 LCDR2 GASSRAT
(Kabat)

SEQ ID NO: 219 LCDR3 QQYGTSRKT
(Kabat)

SEQ ID NO: 220 LCDR1 SQSVSSGY
(Chothia)

SEQ ID NO: 221 LCDR2 GAS
(Chothia)

SEQ ID NO: 222 LCDR3 YGTSRK
(Chothia)

SEQ ID NO: 223 LCDR1 QSVSSGY
(IMGT)

SEQ ID NO: 224 LCDR2 GAS
(IMGT)

SEQ ID NO: 225 LCDR3 QQYGTSRKT
(IMGT)

SEQ ID NO: 226 VL  EIVLTQSPGTLSLSPGERATLSCRASQSVSSGYLAWYQQK
PGQAPRLLIYGASSRATGIPDRFSGSGSGTDFTLTISRLE
PEDFAVYYCQQYGTSRKTFGQGTKVEIK

SEQ ID NO: 227 DNA VL  GAAATTGTTTTGACGCAGTCTCCAGGCACCCTGTCTTTGT
CTCCAGGGGAAAGAGCCACCCTCTCCTGCAGGGCCAGTCA
GAGTGTTAGCAGTGGCTACTTAGCCTGGTATCAGCAGAAA
CCTGGCCAGGCTCCCAGGCTCCTCATCTATGGTGCATCCA
GCAGGGCCACTGGCATCCCAGACAGGTTCAGTGGCAGTGG
GTCTGGGACAGACTTCACTCTCACCATCAGCAGACTGGAG
CCTGAAGATTTTGCAGTGTATTATTGTCAGCAGTATGGTA
CCTCACGTAAGACGTTCGGCCAAGGGACCAAGGTGGAAAT
CAAA

SEQ ID NO: 228 Light  EIVLTQSPGTLSLSPGERATLSCRASQSVSSGYLAWYQQK
Chain  PGQAPRLLIYGASSRATGIPDRFSGSGSGTDFTLTISRLE
PEDFAVYYCQQYGTSRKTFGQGTKVEIKRTVAAPSVFIFP
PSDEQLKSGTASVVCLLNNFYPREAKVQWKVDNALQSGNS
QESVTEQDSKDSTYSLSSTLTLSKADYEKHKVYACEVTHQ
GLSSPVTKSFNRGEC SEQ ID NO: 229 DNA  GAAATTGTTTTGACGCAGTCTCCAGGCACCCTGTCTTTGT
Light  CTCCAGGGGAAAGAGCCACCCTCTCCTGCAGGGCCAGTCA
Chain  GAGTGTTAGCAGTGGCTACTTAGCCTGGTATCAGCAGAAA
CCTGGCCAGGCTCCCAGGCTCCTCATCTATGGTGCATCCA
GCAGGGCCACTGGCATCCCAGACAGGTTCAGTGGCAGTGG
GTCTGGGACAGACTTCACTCTCACCATCAGCAGACTGGAG
CCTGAAGATTTTGCAGTGTATTATTGTCAGCAGTATGGTA
CCTCACGTAAGACGTTCGGCCAAGGGACCAAGGTGGAAAT
CAAACGAACTGTGGCTGCACCATCTGTCTTCATCTTCCCG
CCATCTGATGAGCAGTTGAAATCTGGAACTGCCTCTGTTG
TGTGCCTGCTGAATAACTTCTATCCCAGAGAGGCCAAAGT
ACAGTGGAAGGTGGACAACGCCCTGCAGAGCGGCAACAGC
CAGGAGAGCGTCACCGAGCAGGACAGCAAGGACTCCACCT
ACAGCCTGAGCAGCACCCTGACCCTGAGCAAGGCCGACTA
CGAGAAGCATAAGGTGTACGCCTGCGAGGTGACCCACCAG
GGCCTGTCCAGCCCCGTGACCAAGAGCTTCAACAGGGGCG
AGTGC

NOV796

SEQ ID NO: 230 HCDR1 GGSISGYYWS
(Combined)

SEQ ID NO: 231 HCDR2 LIYESGSANYNPSLKS
(Combined)

SEQ ID NO: 232 HCDR3 RVRGWSYGMDV
(Combined)

TABLE 2-continued

Anti-Polyoma virus Antibodies

SEQ ID NO: 233 HCDR1  GYYWS
(Kabat)

SEQ ID NO: 234 HCDR2  LIYESGSANYNPSLKS
(Kabat)

SEQ ID NO: 235 HCDR3  RVRGWSYGMDV
(Kabat)

SEQ ID NO: 236 HCDR1  GGSISGY
(Chothia)

SEQ ID NO: 237 HCDR2  YESGS
(Chothia)

SEQ ID NO: 238 HCDR3  RVRGWSYGMDV
(Chothia)

SEQ ID NO: 239 HCDR1  GGSISGYY
(IMGT)

SEQ ID NO: 240 HCDR2  IYESGSA
(IMGT)

SEQ ID NO: 241 HCDR3  ARRVRGWSYGMDV
(IMGT)

SEQ ID NO: 242 VH     QVQLVQSGPGLVKPSETLSLTCSVSGGSISGYYWSWIRQP
                      PGKGLEWIGLIYESGSANYNPSLKSRVTISLDTSKNQFSL
                      KLKSVTAADTAVYYCARRVRGWSYGMDVWGQGTTVAVSS

SEQ ID NO: 243 DNA VH CAGGTGCAGCTGGTGCAGTCTGGCCCAGGACTGGTGAAGC
                      CTTCGGAGACCCTGTCCCTCACCTGCAGTGTCTCTGGTGG
                      CTCCATCAGTGGTTACTACTGGAGCTGGATCCGGCAGCCC
                      CCAGGGAAGGGACTGGAGTGGATCGGCTTAATTTATGAGA
                      GTGGGAGCGCCAACTACAATCCCTCCCTCAAGAGTCGAGT
                      CACCATATCGCTAGACACGTCCAAGAATCAGTTCTCCCTG
                      AAGCTGAAGTCTGTGACCGCCGCGGACACGGCCGTGTATT
                      ACTGTGCGAGACGAGTCCGTGGCTGGTCTTACGGTATGGA
                      CGTCTGGGGCCAAGGGACCACGGTCGCCGTCTCCTCA

SEQ ID NO: 244 Heavy  QVQLVQSGPGLVKPSETLSLTCSVSGGSISGYYWSWIRQP
               Chain  PGKGLEWIGLIYESGSANYNPSLKSRVTISLDTSKNQFSL
                      KLKSVTAADTAVYYCARRVRGWSYGMDVWGQGTTVAVSSA
                      STKGPSVFPLAPSSKSTSGGTAALGCLVKDYFPEPVTVSW
                      NSGALTSGVHTFPAVLQSSGLYSLSSVVTVPSSSLGTQTY
                      ICNVNHKPSNTKVDKRVEPKSCDKTHTCPPCPAPELLGGP
                      SVFLFPPKPKDTLMISRTPEVTCVVVDVSHEDPEVKFNWY
                      VDGVEVHNAKTKPREEQYNSTYRVVSVLTVLHQDWLNGKE
                      YKCKVSNKALPAPIEKTISKAKGQPREPQVYTLPPSREEM
                      TKNQVSLTCLVKGFYPSDIAVEWESNGQPENNYKTTPPVL
                      DSDGSFFLYSKLTVDKSRWQQGNVFSCSVMHEALHNHYTQ
                      KSLSLSPGK SEQ ID NO: 245 DNA    CAGGTGCAGCTGGTGCAGTCTGGCCCAGGACTGGTGAAGC
               Heavy  CTTCGGAGACCCTGTCCCTCACCTGCAGTGTCTCTGGTGG
               Chain  CTCCATCAGTGGTTACTACTGGAGCTGGATCCGGCAGCCC
                      CCAGGGAAGGGACTGGAGTGGATCGGCTTAATTTATGAGA
                      GTGGGAGCGCCAACTACAATCCCTCCCTCAAGAGTCGAGT
                      CACCATATCGCTAGACACGTCCAAGAATCAGTTCTCCCTG
                      AAGCTGAAGTCTGTGACCGCCGCGGACACGGCCGTGTATT
                      ACTGTGCGAGACGAGTCCGTGGCTGGTCTTACGGTATGGA
                      CGTCTGGGGCCAAGGGACCACGGTCGCCGTCTCCTCAGCC
                      TCCACCAAGGGCCCATCGGTCTTCCCCCTGGCACCCTCCT
                      CCAAGAGCACCTCTGGGGGCACAGCGGCCCTGGGCTGCCT
                      GGTCAAGGACTACTTCCCCGAACCGGTGACGGTGTCGTGG
                      AACTCAGGCGCCCTGACCAGCGGCGTGCACACCTTCCCGG
                      CTGTCCTACAGTCCTCAGGACTCTACTCCCTCAGCAGCGT
                      GGTGACCGTGCCCTCCAGCAGCTTGGGCACCCAGACCTAC
                      ATCTGCAACGTGAACCACAAGCCCAGCAACACCAAGGTGG
                      ACAAGAGAGTGGAGCCCAAGAGCTGCGACAAGACCCACAC
                      CTGCCCCCCTGCCCAGCCCCAGAGCTGCTGGGCGGACCC
                      TCCGTGTTCCTGTTCCCCCCAAGCCCAAGGACACCCTGA
                      TGATCAGCAGGACCCCCGAGGTGACCTGCGTGGTGGTGGA
                      CGTGAGCCACGAGGACCCAGAGGTGAAGTTCAACTGGTAC
                      GTGGACGGCGTGGAGGTGCACAACGCCAAGACCAAGCCCA
                      GAGAGGAGCAGTACAACAGCACCTACAGGGTGGTGTCCGT
                      GCTGACCGTGCTGCACCAGGACTGGCTGAACGGCAAGGAA TABLE 2-continued Anti-Polyoma virus Antibodies

```
                       TACAAGTGCAAGGTCTCCAACAAGGCCCTGCCAGCCCCCA
                       TCGAAAAGACCATCAGCAAGGCCAAGGGCCAGCCACGGGA
                       GCCCCAGGTGTACACCCTGCCCCCCTCCCGGGAGGAGATG
                       ACCAAGAACCAGGTGTCCCTGACCTGTCTGGTGAAGGGCT
                       TCTACCCCAGCGACATCGCCGTGGAGTGGGAGAGCAACGG
                       CCAGCCCGAGAACAACTACAAGACCACCCCCCCAGTGCTG
                       GACAGCGACGGCAGCTTCTTCCTGTACAGCAAGCTGACCG
                       TGGACAAGTCCAGGTGGCAGCAGGGCAACGTGTTCAGCTG
                       CAGCGTGATGCACGAGGCCCTGCACAACCACTACACCCAG
                       AAGAGCCTGAGCCTGTCCCCCGGCAAG
```

SEQ ID NO: 246 LCDR1    RASQILSSSFLA
(Combined)

SEQ ID NO: 247 LCDR2    AASSRAT
(Combined)

SEQ ID NO: 248 LCDR3    QHYGSSPPWT
(Combined)

SEQ ID NO: 249 LCDR1    RASQILSSSFLA
(Kabat)

SEQ ID NO: 250 LCDR2    AASSRAT
(Kabat)

SEQ ID NO: 251 LCDR3    QHYGSSPPWT
(Kabat)

SEQ ID NO: 252 LCDR1    SQILSSSF
(Chothia)

SEQ ID NO: 253 LCDR2    AAS
(Chothia)

SEQ ID NO: 254 LCDR3    YGSSPPW
(Chothia)

SEQ ID NO: 255 LCDR1    QILSSSF
(IMGT)

SEQ ID NO: 256 LCDR2    AAS
(IMGT)

SEQ ID NO: 257 LCDR3    QHYGSSPPWT
(IMGT)

SEQ ID NO: 258 VL       DIVLTQSPGTLSLSPGETATLSCRASQILSSSFLAWFQQI
                        PGQAPRLLIYAASSRATGIPDRFSGSGSGTDFSLTISRLE
                        PEDFAVYYCQHYGSSPPWTFGQGTKVEIK

SEQ ID NO: 259 DNA VL   GATATTGTGTTGACGCAGTCTCCAGGCACCCTGTCTTTGT
                        CTCCAGGGGAGACAGCCACCCTCTCCTGCAGGGCCAGTCA
                        GATTCTTAGCAGCAGCTTCTTAGCCTGGTTCCAGCAGATA
                        CCTGGCCAGGCTCCCAGACTCCTCATCTATGCTGCATCCA
                        GCAGGGCCACTGGCATCCCAGACAGGTTCAGTGGCAGTGG
                        GTCTGGGACAGACTTCAGTCTCACCATCAGCAGACTGGAG
                        CCTGAAGATTTTGCAGTGTATTACTGTCAGCACTATGGTA
                        GCTCACCTCCTTGGACGTTCGGCCAAGGGACCAAGGTGGA
                        AATCAAA

SEQ ID NO: 260 Light    DIVLTQSPGTLSLSPGETATLSCRASQILSSSFLAWFQQI
               Chain    PGQAPRLLIYAASSRATGIPDRFSGSGSGTDFSLTISRLE
                        PEDFAVYYCQHYGSSPPWTFGQGTKVEIKRTVAAPSVFIF
                        PPSDEQLKSGTASVVCLLNNFYPREAKVQWKVDNALQSGN
                        SQESVTEQDSKDSTYSLSSTLTLSKADYEKHKVYACEVTH
                        QGLSSPVTKSFNRGEC SEQ ID NO: 261 DNA      GATATTGTGTTGACGCAGTCTCCAGGCACCCTGTCTTTGT
               Light    CTCCAGGGGAGACAGCCACCCTCTCCTGCAGGGCCAGTCA
               Chain    GATTCTTAGCAGCAGCTTCTTAGCCTGGTTCCAGCAGATA
                        CCTGGCCAGGCTCCCAGACTCCTCATCTATGCTGCATCCA
                        GCAGGGCCACTGGCATCCCAGACAGGTTCAGTGGCAGTGG
                        GTCTGGGACAGACTTCAGTCTCACCATCAGCAGACTGGAG
                        CCTGAAGATTTTGCAGTGTATTACTGTCAGCACTATGGTA
                        GCTCACCTCCTTGGACGTTCGGCCAAGGGACCAAGGTGGA
                        AATCAAACGAACTGTGGCTGCACCATCTGTCTTCATCTTC
                        CCGCCATCTGATGAGCAGTTGAAATCTGGAACTGCCTCTG
```

TABLE 2-continued

Anti-Polyoma virus Antibodies

```
TTGTGTGCCTGCTGAATAACTTCTATCCCAGAGAGGCCAA
AGTACAGTGGAAGGTGGACAACGCCCTGCAGAGCGGCAAC
AGCCAGGAGAGCGTCACCGAGCAGGACAGCAAGGACTCCA
CCTACAGCCTGAGCAGCACCCTGACCCTGAGCAAGGCCGA
CTACGAGAAGCATAAGGTGTACGCCTGCGAGGTGACCCAC
CAGGGCCTGTCCAGCCCCGTGACCAAGAGCTTCAACAGGG
GCGAGTGC
```

NOV638

SEQ ID NO: 262 HCDR1 GYTFTSYDII
(Combined)

SEQ ID NO: 263 HCDR2 RMNPTGGNTDYVPKFQG
(Combined)

SEQ ID NO: 264 HCDR3 GVKSLGVSEIDY
(Combined)

SEQ ID NO: 265 HCDR1 SYDII
(Kabat)

SEQ ID NO: 266 HCDR2 RMNPTGGNTDYVPKFQG
(Kabat)

SEQ ID NO: 267 HCDR3 GVKSLGVSEIDY
(Kabat)

SEQ ID NO: 268 HCDR1 GYTFTSY
(Chothia)

SEQ ID NO: 269 HCDR2 NPTGGN
(Chothia)

SEQ ID NO: 270 HCDR3 GVKSLGVSEIDY
(Chothia)

SEQ ID NO: 271 HCDR1 GYTFTSYD
(IMGT)

SEQ ID NO: 272 HCDR2 MNPTGGNT
(IMGT)

SEQ ID NO: 273 HCDR3 ARGVKSLGVSEIDY
(IMGT)

SEQ ID NO: 274 VH    QVQLVQSGAEVKKPGASVKVSCKASGYTFTSYDIIWVRQA
                     TGQGLEWMGRMNPTGGNTDYVPKFQGRVTMTRDISLSTAY
                     MELRSLTSEDTAVFYCARGVKSLGVSEIDYWGQGTLVTVS
                     S

SEQ ID NO: 275 DNA VH CAGGTGCAGCTGGTGCAGTCTGGGGCTGAGGTGAAGAAAC
                     CTGGGGCCTCAGTGAAGGTCTCCTGCAAGGCTTCTGGATA
                     CACCTTCACCAGTTATGATATCATCTGGGTGCGACAGGCC
                     ACTGGACAAGGGCTTGAGTGGATGGGAAGGATGAACCCTA
                     CCGGTGGTAACACAGACTATGTACCGAAGTTCCAGGGCAG
                     AGTCACCATGACCAGGGACATCTCCTTAAGTACAGCCTAC
                     ATGGAGCTGCGCAGCCTGACATCTGAGGACACGGCCGTGT
                     TTTACTGTGCGAGAGGCGTAAAGTCTTTAGGAGTTTCGGA
                     AATTGACTACTGGGGCCAGGGAACCCTGGTCACCGTCTCC
                     TCA

SEQ ID NO: 276 Heavy QVQLVQSGAEVKKPGASVKVSCKASGYTFTSYDIIWVRQA
               Chain TGQGLEWMGRMNPTGGNTDYVPKFQGRVTMTRDISLSTAY
                     MELRSLTSEDTAVFYCARGVKSLGVSEIDYWGQGTLVTVS
                     SASTKGPSVFPLAPSSKSTSGGTAALGCLVKDYFPEPVTV
                     SWNSGALTSGVHTFPAVLQSSGLYSLSSVVTVPSSSLGTQ
                     TYICNVNHKPSNTKVDKRVEPKSCDKTHTCPPCPAPELLG
                     GPSVFLFPPKPKDTLMISRTPEVTCVVVDVSHEDPEVKFN
                     WYVDGVEVHNAKTKPREEQYNSTYRVVSVLTVLHQDWLNG
                     KEYKCKVSNKALPAPIEKTISKAKGQPREPQVYTLPPSRE
                     EMTKNQVSLTCLVKGFYPSDIAVEWESNGQPENNYKTTPP
                     VLDSDGSFFLYSKLTVDKSRWQQGNVFSCSVMHEALHNHY
                     TQKSLSLSPGK TABLE 2-continued Anti-Polyoma virus Antibodies SEQ ID NO: 277 DNA Heavy Chain
CAGGTGCAGCTGGTGCAGTCTGGGGCTGAGGTGAAGAAAC
CTGGGGCCTCAGTGAAGGTCTCCTGCAAGGCTTCTGGATA
CACCTTCACCAGTTATGATATCATCTGGGTGCGACAGGCC
ACTGGACAAGGGCTTGAGTGGATGGGAAGGATGAACCCTA
CCGGTGGTAACACAGACTATGTACCGAAGTTCCAGGGCAG
AGTCACCATGACCAGGGACATCTCCTTAAGTACAGCCTAC
ATGGAGCTGCGCAGCCTGACATCTGAGGACACGGCCGTGT
TTTACTGTGCGAGAGGCGTAAAGTCTTTAGGAGTTTCGGA
AATTGACTACTGGGGCCAGGGAACCCTGGTCACCGTCTCC
TCAGCCTCCACCAAGGGCCCATCGGTCTTCCCCCTGGCAC
CCTCCTCCAAGAGCACCTCTGGGGGCACAGCGGCCCTGGG
CTGCCTGGTCAAGGACTACTTCCCCGAACCGGTGACGGTG
TCGTGGAACTCAGGCGCCCTGACCAGCGGCGTGCACACCT
TCCCGGCTGTCCTACAGTCCTCAGGACTCTACTCCCTCAG
CAGCGTGGTGACCGTGCCCTCCAGCAGCTTGGGCACCCAG
ACCTACATCTGCAACGTGAACCACAAGCCCAGCAACACCA
AGGTGGACAAGAGAGTGGAGCCCAAGAGCTGCGACAAGAC
CCACACCTGCCCCCCCTGCCCAGCCCCAGAGCTGCTGGGC
GGACCCTCCGTGTTCCTGTTCCCCCCCAAGCCCAAGGACA
CCCTGATGATCAGCAGGACCCCCGAGGTGACCTGCGTGGT
GGTGGACGTGAGCCACGAGGACCCAGAGGTGAAGTTCAAC
TGGTACGTGGACGGCGTGGAGGTGCACAACGCCAAGACCA
AGCCCAGAGAGGAGCAGTACAACAGCACCTACAGGGTGGT
GTCCGTGCTGACCGTGCTGCACCAGGACTGGCTGAACGGC
AAGGAATACAAGTGCAAGGTCTCCAACAAGGCCCTGCCAG
CCCCCATCGAAAAGACCATCAGCAAGGCCAAGGGCCAGCC
ACGGGAGCCCCAGGTGTACACCCTGCCCCCCTCCCGGGAG
GAGATGACCAAGAACCAGGTGTCCCTGACCTGTCTGGTGA
AGGGCTTCTACCCCAGCGACATCGCCGTGGAGTGGGAGAG
CAACGGCCAGCCCGAGAACAACTACAAGACCACCCCCCCA
GTGCTGGACAGCGACGGCAGCTTCTTCCTGTACAGCAAGC
TGACCGTGGACAAGTCCAGGTGGCAGCAGGGCAACGTGTT
CAGCTGCAGCGTGATGCACGAGGCCCTGCACAACCACTAC
ACCCAGAAGAGCCTGAGCCTGTCCCCCGGCAAG SEQ ID NO: 278 LCDR1 (Combined)    SGSTSNIANNYVL SEQ ID NO: 279 LCDR2 (Combined)    DNNKRPS SEQ ID NO: 280 LCDR3 (Combined)    GTWDNSLSVGV SEQ ID NO: 281 LCDR1 (Kabat)    SGSTSNIANNYVL SEQ ID NO: 282 LCDR2 (Kabat)    DNNKRPS SEQ ID NO: 283 LCDR3 (Kabat)    GTWDNSLSVGV SEQ ID NO: 284 LCDR1 (Chothia)    STSNIANNY SEQ ID NO: 285 LCDR2 (Chothia)    DNN SEQ ID NO: 286 LCDR3 (Chothia)    WDNSLSVG

SEQ ID NO: 287 LCDR1 (IMGT)    TSNIANNY

SEQ ID NO: 288 LCDR2 (IMGT)    DNN

SEQ ID NO: 289 LCDR3 (IMGT)    GTWDNSLSVGV

SEQ ID NO: 290 VL
QSALTQPPSVSAAPGQKVTISCSGSTSNIANNYVLWYQQL
PGTAPKLLIYDNNKRPSGIPDRFSGSKSGTSATLGITGLQ
TADEADYYCGTWDNSLSVGVFGGGTKLTVL

TABLE 2-continued

Anti-Polyoma virus Antibodies

SEQ ID NO: 291 DNA VL  CAGTCTGCCCTGACTCAGCCTCCCTCAGTGTCTGCGGCCC
CAGGACAGAAGGTCACCATCTCCTGCTCTGGAAGCACCTC
CAACATTGCGAATAATTATGTCTTATGGTACCAGCAACTC
CCAGGAACAGCCCCCAAAACTCCTCATTTATGACAATAATA
AGCGACCCTCAGGGATTCCTGACCGATTCTCCGGCTCCAA
GTCTGGCACGTCAGCCACCCTGGGCATCACCGGACTCCAG
ACTGCGGACGAGGCCGATTACTACTGCGGAACATGGGATA
ACAGCCTGAGTGTTGGGGTGTTCGGCGGCGGGACCAAGTT
GACCGTCCTA

SEQ ID NO: 292 Light Chain  QSALTQPPSVSAAPGQKVTISCSGSTSNIANNYVLWYQQL
PGTAPKLLIYDNNKRPSGIPDRFSGSKSGTSATLGITGLQ
TADEADYYCGTWDNSLSVGVFGGGTKLTVLGQPKAAPSVT
LFPPSSEELQANKATLVCLISDFYPGAVTVAWKADSSPVK
AGVETTTPSKQSNNKYAASSYLSLTPEQWKSHRSYSCQVT
HEGSTVEKTVAPTECS SEQ ID NO: 293 DNA Light Chain  CAGTCTGCCCTGACTCAGCCTCCCTCAGTGTCTGCGGCCC
CAGGACAGAAGGTCACCATCTCCTGCTCTGGAAGCACCTC
CAACATTGCGAATAATTATGTCTTATGGTACCAGCAACTC
CCAGGAACAGCCCCCAAAACTCCTCATTTATGACAATAATA
AGCGACCCTCAGGGATTCCTGACCGATTCTCCGGCTCCAA
GTCTGGCACGTCAGCCACCCTGGGCATCACCGGACTCCAG
ACTGCGGACGAGGCCGATTACTACTGCGGAACATGGGATA
ACAGCCTGAGTGTTGGGGTGTTCGGCGGCGGGACCAAGTT
GACCGTCCTAGGTCAGCCCAAGGCTGCCCCCTCGGTCACT
CTGTTCCCGCCCTCCTCTGAGGAGCTTCAAGCCAACAAGG
CCACACTGGTGTGTCTCATAAGTGACTTCTACCCGGGAGC
CGTGACAGTGGCCTGGAAGGCAGATAGCAGCCCCGTCAAG
GCGGGAGTGGAGACCACCACACCCTCCAAACAAAGCAACA
ACAAGTACGCCGCCAGCAGCTACCTGAGCCTGACGCCTGA
GCAGTGGAAGTCCCACAGAAGCTACAGCTGCCAGGTCACC
CACGAGGGCAGCACCGTGGAGAAAACCGTGGCCCCCACCG
AGTGCAGC

NOV527

SEQ ID NO: 294 Heavy Chain  MELGLCWLLLVAILKGVQCEVQLLESGGGLVQPGGSLRLS
CAASGFIFRNYGMSWLRQAPGKGLEWVSAISGSGANTYYT
DSVKGRFTISRDNSKNTLYLQIYSLTAEDTALYYCAKSKG
DGGADAFDVWGQGTLVTVSSGSASAPTLFPLVSCENSPSD
TSSVAVGCLAQDFLPDSITFSWKYKNNSDISSTRGFPSVL
RGGKYAATSQVLLPSKDVMQGTDEHVVCKVQHPNGNKEKN
VPLPVIAELPPKVSVFVPPRDGFFGNPRKSKLICQATGFS
PRQIQVSWLREGKQVGSGVTTDQVQAEAKESGPTTYKVTS
TLTIKESDWLGQSMFTCRVDHRGLTFQQNASSMCVPDQDT
AIRVFAIPPSFASIFLTKSTKLTCLVTDLTTYDSVTISWT
RQNGEAVKTHTNISESHPNATFSAVGEASICEDDWNSGER
FTCTVTHTDLPSPLKQTISRPKGVALHRPDVYLLPPAREQ
LNLRESATITCLVTGFSPADVFVQWMQRGQPLSPEKYVTS
APMPEPQAPGRYFAHSILTVSEEEWNTGETYTCVVAHEAL
PNRVTERTVDKSTGKPTLYNVSLVMSDTAGTCY SEQ ID NO: 295 Light chain  MRLPAQLLGLLLLWLPGAKCDIRMTQSPSTLSASVGDRVT
ITCRASQSISRWLAWYQQKPGKAPKLLIYKASSLESGVPS
RFSGSGSATEFTLTISSLQPDDFATYYCQQYNSFWTFGQG
TKVEIKRTVAAPSVFIFPPSDEQLKSGTASVVCLLNNFYP
REAKVQWKVDNALQSGNSQESVTEQDSKDSTYSLSSTLTL
SKADYEKHKVYACEVTHQGLSSPVTKSFNRGEC

NOV280

SEQ ID NO: 296 Heavy Chain  MELGLCWVFLVALLRGVQCQVQLVESGGGVVQPGRSLRLS
CAASGFTFSSYGMHWVRQAPGKGLEWVAVIWYDGSNKYYA
DSVKGRFTISRDNSKNTLYLQMNSLRAEDTAVYYCARDPL
IVVVPAAIYYYYGMDVWGQGTTVTVSSGSASAPTLFPLVS
CENSPSDTSSVAVGCLAQDFLPDSITFSWKYKNNSDISST
RGFPSVLRGGKYAATSQVLLPSKDVMQGTDEHVVCKVQHP
NGNKEKNVPLPVIAELPPKVSVFVPPRDGFFGNPRKSKLI
CQATGFSPRQIQVSWLREGKQVGSGVTTDQVQAEAKESGP
TTYKVTSTLTIKESDWLGQSMFTCRVDHRGLTFQQNASSM
CVPDQDTAIRVFAIPPSFASIFLTKSTKLTCLVTDLTTYD
SVTISWTRQNGEAVKTHTNISESHPNATFSAVGEASICED
DWNSGERFTCTVTHTDLPSPLKQTISRPKGVALHRPDVYL
LPPAREQLNLRESATITCLVTGFSPADVFVQWMQRGQPLS
PEKYVTSAPMPEPQAPGRYFAHSILTVSEEEWNTGETYTC
VVAHEALPNRVTERTVDKSTGKPTLYNVSLVMSDTAGTCY TABLE 2-continued Anti-Polyoma virus Antibodies SEQ ID NO: 297 Light chain
MDMRVPAQLLGLLLLWLRGARCDIQMTQSPSSLSASVGDR
VTITCRTSQSISSYLNWYQQKPGKAPKLLIYAASSLQSGV
PSRFSGSGSGTDFTLTISSLQPEDFATYYCQQSYSTPITF
GQGTRLEIKRTVAAPSVFIFPPSDEQLKSGTASVVCLLNN
FYPREAKVQWKVDNALQSGNSQESVTEQDSKDSTYSLSST
LTLSKADYEKHKVYACEVTHQGLSSPVTKSFNRGEC

NOV756

SEQ ID NO: 298 Heavy Chain
MKHLWFFLLLVAAPRWVLSQLQLQESGPGLVKPSETLSLT
CTVSGGSISSSSYYWGWIRQPPGKGLEWIGSIYYSGSTYY
NPSLKSRVTISVDTSKNQFSLKLSSVTAADTAVYYCARLG
YYYYMDVWGKGTTVTVSSGSASAPTLFPLVSCENSPSDTS
SVAVGCLAQDFLPDSITFSWKYKNNSDISSTRGFPSVLRG
GKYAATSQVLLPSKDVMQGTDEHVVCKVQHPNGNKEKNVP
LPVIAELPPKVSVFVPPRDGFFGNPRKSKLICQATGFSPR
QIQVSWLREGKQVGSGVTTDQVQAEAKESGPTTYKVTSTL
TIKESDWLGQSMFTCRVDHRGLTFQQNASSMCVPDQDTAI
RVFAIPPSFASIFLTKSTKLTCLVTDLTTYDSVTISWTRQ
NGEAVKTHTNISESHPNATFSAVGEASICEDDWNSGERFT
CTVTHTDLPSPLKQTISRPKGVALHRPDVYLLPPAREQLN
LRESATITCLVTGFSPADVFVQWMQRGQPLSPEKYVTSAP
MPEPQAPGRYFAHSILTVSEEEWNTGETYTCVVAHEALPN
RVTERTVDKSTGKPTLYNVSLVMSDTAGTCY SEQ ID NO: 299 Light chain
MVLQTQVFISLLLWISGAYGDIVMTQSPDSLAVSLGERAT
INCKSSQSVLYSSNNKNYLAWYQQKPGQPPKLLIYWASTR
ESGVPDRFSGSGSGTDFTLTISSLQAEDVAVYYCQQYYST
PPTFGGGTKVEIKRTVAAPSVFIFPPSDEQLKSGTASVVC
LLNNFYPREAKVQWKVDNALQSGNSQESVTEQDSKDSTYS
LSSTLTLSKADYEKHKVYACEVTHQGLSSPVTKSFNRGEC

NOV252

SEQ ID NO: 300 Heavy Chain
MEFGLSWVFLVAILKGVQCEVQVVESGGGLVQPGESLRLS
CAASGFTFSNYFMHWVRQAPGMGLEWVARINTDGSVTMYA
DSVKGRFTISRDNAKNTVYLQMNSLRAEDTAVYYCVRPNS
VHDKLLENWGQGTLVTVSSGSASAPTLFPLVSCENSPSDT
SSVAVGCLAQDFLPDSITFSWKYKNNSDISSTRGFPSVLR
GGKYAATSQVLLPSKDVMQGTDEHVVCKVQHPNGNKEKNV
PLPVIAELPPKVSVFVPPRDGFFGNPRKSKLICQATGFSP
RQIQVSWLREGKQVGSGVTTDQVQAEAKESGPTTYKVTST
LTIKESDWLGQSMFTCRVDHRGLTFQQNASSMCVPDQDTA
IRVFAIPPSFASIFLTKSTKLTCLVTDLTTYDSVTISWTR
QNGEAVKTHTNISESHPNATFSAVGEASICEDDWNSGERF
TCTVTHTDLPSPLKQTISRPKGVALHRPDVYLLPPAREQL
NLRESATITCLVTGFSPADVFVQWMQRGQPLSPEKYVTSA
PMPEPQAPGRYFAHSILTVSEEEWNTGETYTCVVAHEALP
NRVTERTVDKSTGKPTLYNVSLVMSDTAGTCY SEQ ID NO: 301 Light chain
MRLPAQLLGLLLLWLPGAKCDIQMTQSPSTLSASVGDRVT
ITCRASQSISSWLAWYQQKPGKAPKLLINKASSLESGVPS
RFSGSGSGTEFTLTINSLQPDDFATYYCQQYYTSSYRFG
QGTKLEIKRTVAAPSVFIFPPSDEQLKSGTASVVCLLNNF
YPREAKVQWKVDNALQSGNSQESVTEQDSKDSTYSLSSTL
TLSKADYEKHKVYACEVTHQGLSSPVTKSFNRGEC

NOV157

SEQ ID NO: 302 Heavy Chain
MSVSFLLLVAAPRWVLSQQQLQESGPGLVKPSETLSLTCX
VSGGSISSSSYYWGWIRQPPGKGLEWIGSIYYRGSTYYNP
SLRSRVTASVDTSRNQFSLRLSSVTAADTAVYYCARSYCS
GSCYAVGAFDMWGQGTMVTVSSGSASAPTLFPLVSCENSP
SDTSSVAVGCLAQDFLPDSITFSWKYKNNSDISSTRGFPS
VLRGGKYAATSQVLLPSKDVMQGTDEHVVCKVQHPNGNKE
KNVPLPVIAELPPKVSVFVPPRDGFFGNPRKSKLICQATG
FSPRQIQVSWLREGKQVGSGVTTDQVQAEAKESGPTTYKV
TSTLTIKESDWLGQSMFTCRVDHRGLTFQQNASSMCVPDQ
DTAIRVFAIPPSFASIFLTKSTKLTCLVTDLTTYDSVTIS
WTRQNGEAVKTHTNISESHPNATFSAVGEASICEDDWNSG
ERFTCTVTHTDLPSPLKQTISRPKGVALHRPDVYLLPPAR
EQLNLRESATITCLVTGFSPADVFVQWMQRGQPLSPEKYV
TSAPMPEPQAPGRYFAHSILTVSEEEWNTGETYTCVVAHE
ALPNRVTERTVDKSTGKPTLYNVSLVMSDTAGTCY TABLE 2-continued Anti-Polyoma virus Antibodies SEQ ID NO: 303 Light chain
MAWTPLLFLTLLLHCTGSLSQLVLTQSPSASASLGASVKL
TCTLSSGHSSHAIAWHQQQPEKGPRYLIKLNSDGSHNKGD
GIPDRFSGSSSGAERYLTISSLQSEDEADYYCQTWDTGIV
VFGGGTKLTVLGQPKAAPSVTLFPPSSEELQANKATLVCL
ISDFYPGAVTVAWKADSSPVKAGVETTTPSKQSNNKYAAS
SYLSLTPEQWKSHRSYSCQVTHEGSTVEKTVAPTECS

NOV882

SEQ ID NO: 304 Heavy Chain
MEFGLSWVFLVALLRGVQCQVQLVESGGGVVQPGRSLRLS
CAASGFTFSSYAMHWVRQAPGKGLEWVAVISYDGSNKYYA
DSVKGRFTISRDNSKNTLYLQMNSLRAEDTAVYYCARDFR
GWGGGSGGSCGYWGQGTLVTVSSGSASAPTLFPLVSCENS
PSDTSSVAVGCLAQDFLPDSITFSWKYKNNSDISSTRGFP
SVLRGGKYAATSQVLLPSKDVMQGTDEHVVCKVQHPNGNK
EKNVPLPVIAELPPKVSVFVPPRDGFFGNPRKSKLICQAT
GFSPRQIQVSWLREGKQVGSGVTTDQVQAEAKESGPTTYK
VTSTLTIKESDWLGQSMFTCRVDHRGLTFQQNASSMCVPD
QDTAIRVFAIPPSFASIFLTKSTKLTCLVTDLTTYDSVTI
SWTRQNGEAVKTHTNISESHPNATFSAVGEASICEDDWNS
GERFTCTVTHTDLPSPLKQTISRPKGVALHRPDVYLLPPA
REQLNLRESATITCLVTGFSPADVFVQWMQRGQPLSPEKY
VTSAPMPEPQAPGRYFAHSILTVSEEEWNTGETYTCVVAH
EALPNRVTERTVDKSTGKPTLYNVSLVMSDTAGTCY SEQ ID NO: 305 Light chain
MALTPLLLTLLAHCTGSWANFMLTQPHSVSESPGKTVTIS
CTRSSGSIASNYVQWYQQRPGSSPTTVIYEDNQRPSGVPD
RFSGSIDSSSNSASLTISGLKTEDEADYYCQSYDSSNLYV
FGTGTKVTVLGQPKANPTVTLFPPSSEELQANKATLVCLI
SDFYPGAVTVAWKADGSPVKAGVETTKPSKQSNNKYAASS
YLSLTPEQWKSHRSYSCQVTHEGSTVEKTVAPTECS

NOV578

SEQ ID NO: 306 Heavy Chain
MEFGLSWVFLVAIIKGVQCQVQLVESGGGLVKPGGSLRLS
CAASGFTFSDYFMSWVRQTPGKGLEWLSYMSSDGTIIHHA
DSLKGRFTISRDNAKNSLFLQMNTLRAEDTAVYYCATHIL
ETTIAAFEIWGRGTMVIVSSASTKGPSVFPLAPCSRSTSE
STAALGCLVKDYFPEPVTVSWNSGALTSGVHTFPAVLQSS
GLYSLSSVVTVPSSNFGTQTYICNVNHKPSNTKVDKRVEP
KSCDKTHTCPPCPAPELLGGPSVFLFPPKPKDTLMISRTP
EVTCVVVDVSHEDPEVKFNWYVDGVEVHNAKTKPREEQYN
STYRVVSVLTVLHQDWLNGKEYKCKVSNKALPAPIEKTIS
KAKGQPREPQVYTLPPSREEMTKNQVSLTCLVKGFYPSDI
AVEWESNGQPENNYKTTPPVLDSDGSFFLYSKLTVDKSRW
QQGNVFSCSVMHEALHNHYTQKSLSLSPGK SEQ ID NO: 307 Light chain
MVLQTQVFISLLLWIAGAYGDIVMTQSPDSLALSLGERAT
INCRSSHSVLYRSNNNNYVAWYQQKPGQPPRLLIYWASNR
ASGVPDRFSGSGSGTDFTLTISSLQPEDAAVYFCQQILDT
PFTFGPGTKVEIKRTVAAPSVFIFPPSDEQLKSGTASVVC
LLNNFYPREAKVQWKVDNALQSGNSQESVTEQDSKDSTYS
LSSTLTLSKADYEKHKVYACEVTHQGLSSPVTKSFNRGEC

NOV295

SEQ ID NO: 308 Heavy Chain
MEFGLSWLFLVATLKGVQCEVQLLESGGGLMQPGGSXRLS
CAASGFTFRSYAMNWVRQAPGKGLEWVSTISGNGGTTYYA
DSVRGRFTISRDNSKNTLFLQMNSLRAEDTAIYYCAQGEP
WSGYLEPLFASWGQGTLVTVSSASTKGPSVFPLAPCSRST
SGGTAALGCLVKDYFPEPVTVSWNSGALTSGVHTFPAVLQ
SSGLYSLSSVVTVPSSSLGTQTYICNVNHKPSNTKVDKRV
EPKSCDKTHTCPPCPAPELLGGPSVFLFPPKPKDTLMISR
TPEVTCVVVDVSHEDPEVKFNWYVDGVEVHNAKTKPREEQ
YNSTYRVVSVLTVLHQDWLNGKEYKCKVSNKALPAPIEKT
ISKAKGQPREPQVYTLPPSREEMTKNQVSLTCLVKGFYPS
DIAVEWESNGQPENNYKTTPPVLDSDGSFFLYSKLTVDKS
RWQQGNVFSCSVMHEALHNHYTQKSLSLSPGK SEQ ID NO: 309 Light chain
MAWTPLWLTLLTLCIGSVVSSELTQDPAVSVALGQTVRIT
CQGDSLRNFYASWYQQKPGQAPVLVIYGKNNRPSGIPDRF
SGSSSGNTVSLTITGAQAEDDADYYCNSRDSSGNHVIFGG
GTKLTVLGQPKAAPSVTLFPPSSEELQANKATLVCLISDF
YPGAVTVAWKADSSPVKAGVETTTPSKQSNNKYAASSYLS
LTPEQWKSHRSYSCQVTHEGSTVEKTVAPTECS TABLE 2-continued Anti-Polyoma virus Antibodies

NOV612

SEQ ID NO: 310 Heavy Chain
MELGLCWVFLVAILEGVQCEVQLVESGGGLVHPGGSLRLS
CAASGFTFRTYIMNWVRQAPGKGLEWISYISASSGTIYYA
DSVKGRFTISRDNAKNSLYLQMNSLRAEDTAVYYCARDLD
CSGGTCYDGFDSWGHGTLVTVSSSSTKGPSVFPLAPSSKS
TSGGTAALGCLVKDYFPEPVTVSWNSGALTSGVHTFPAVL
QSSGLYSLSSVVTVPSSSLGTQTYICNVNHKPSNTKVDKR
VEPKSCDKTHTCPPCPAPELLGGPSVFLFPPKPKDTLMIS
RTPEVTCVVVDVSHEDPEVKFNWYVDGVEVHNAKTKPREE
QYNSTYRVVSVLTVLHQDWLNGKEYKCKVSNKALPAPIEK
TISKAKGQPREPQVYTLPPSREEMTKNQVSLTCLVKGFYP
SDIAVEWESNGQPENNYKTTPPVLDSDGSFFLYSKLTVDK
SRWQQGNVFSCSVMHEALHNHYTQKSLSLSPGK SEQ ID NO: 311 Light chain
MAWTPLFLGVLAYCTGSVASYELTQPPSLSVSPGQTASIT
CSGDKLGDKYACWYQQRPGQSPVLVIYQDTKRPSGIPERF
SGSNSGNTATLTISGTQAMDEADYYCQAWDSSTAVFGGGT
RLTVLGQPKAAPSVTLFPPSSEELQANKATLVCLISDFYP
GAVTVAWKADSSPVKAGVETTTPSKQSNNKYAASSYLSLT
PEQWKSHRSYSCQVTHEGSTVEKTVAPTECS

NOV773

SEQ ID NO: 312 Heavy Chain
MEFGLSWIFLLAILKGVQCEVQLVESGGGLVQPGRSLRLS
CAASGFNFDNYAMHWVRQVPGKGLEWVSGINWNSGYEGYA
DSVKGRFTISRDNAQNSLYLQMDSLRTDDTALYYCTKDTI
AAVGRGAFDIWGQGTKVTVSSASTKGPSVFPLAPCSRSTS
GGTAALGCLVKDYFPEPVTVSWNSGALTSGVHTFPAVLQS
SGLYSLSSVVTVPSSSLGTQTYICNVNHKPSNTKVDKRVE
PKSCDKTHTCPPCPAPELLGGPSVFLFPPKPKDTLMISRT
PEVTCVVVDVSHEDPEVKFNWYVDGVEVHNAKTKPREEQY
NSTYRVVSVLTVLHQDWLNGKEYKCKVSNKALPAPIEKTI
SKAKGQPREPQVYTLPPSREEMTKNQVSLTCLVKGFYPSD
IAVEWESNGQPENNYKTTPPVLDSDGSFFLYSKLTVDKSR
WQQGNVFSCSVMHEALHNHYTQKSLSLSPGK SEQ ID NO: 313 Light chain
MAWIPLLLGLLSHCTGSVTSYVLTQPPSVSVAPGKTAMIT
CGGNKIGGKSVHWYQQKPGQAPVLVISYDSDRPSGIPQRF
SGSNSGNTATLTISRVEAGDEADYYCQVWDTSSVHRVFGG
GTKLTVLGQPKAAPSVTLFPPSSEELQANKATLVCLISDF
YPGAVTVAWKADSSPVKAGVETTTPSKQSNNKYAASSYLS
LTPEQWKSHRSYSCQVTHEGSTVEKTVAPTECS

NOV738

SEQ ID NO: 314 Heavy Chain
MKHLWFFLLLVAAPRWVLSQLQLRESGPGLVKPSETLSLT
CSVSGDSISRSSDYWGWIRQPPGRGLEWIGSIYRTGSTYY
NPSLSSRVTISVDTSKSQFSLSLSSVTAADTALYYCARVR
HDYVWGSIYYYGMDVWGQGTTVTVSSPSTKGPSVFPLAPC
SRSTSGGTAALGCLVKDYFPEPVTVSWNSGALTSGVHTFP
AVLQSSGLYSLSSVVTVPSSSLGTQTYICNVNHKPSNTKV
DKRVEPKSCDKTHTCPPCPAPELLGGPSVFLFPPKPKDTL
MISRTPEVTCVVVDVSHEDPEVKFNWYVDGVEVHNAKTKP
REEQYNSTYRVVSVLTVLHQDWLNGKEYKCKVSNKALPAP
IEKTISKAKGQPREPQVYTLPPSREEMTKNQVSLTCLVKG
FYPSDIAVEWESNGQPENNYKTTPPVLDSDGSFFLYSKLT
VDKSRWQQGNVFSCSVMHEALHNHYTQKSLSLSPGK SEQ ID NO: 315 Light chain
MAWSPLLLTQGTGSWAQSALTQPRSVSGSPGQSVTISCTG
TGSDVGGYTYVSWYQQHPDKAPKLVIYDVTKRPSGVPDRF
SGSKSGNTASLTISGLRADDEADYYCCSYAGRYSWVFGGG
TKLTVLGQPKAAPSVTLFPPSSEELQANKATLVCLISDFY
PGAVTVAWKADSSPVKAGVETTTPSKQSNNKYAASSYLSL
TPEQWKSHRSYSCQVTHEGSTVEKTVAPTECS

NOV151

SEQ ID NO: 316 Heavy Chain
MEFGLSWLFLVAILKGVHCEVDLLESGGGLIQPGGSLRLS
CAASGFTFRNYAMNWVRQVPGKGLEWVSSVSGSGGTTYYA
DSVKGRFSISRDNSKNTLYLQMNGLRAGDTAIYYCAKGEA
WSGYLEPLCDFWGHGTLVTVSSASTKGPSVFPLAPSSKST
SGGTAALGCLVKDYFPEPVTVSWNSGALTSGVHTFPAVLQ
SSGLYSLSSVVTVPSSSLGTQTYICNVNHKPSNTKVDKRV
EPKSCDKTHTCPPCPAPELLGGPSVFLFPPKPKDTLMISR
TPEVTCVVVDVSHEDPEVKFNWYVDGVEVHNAKTKPREEQ
YNSTYRVVSVLTVLHQDWLNGKEYKCKVSNKALPAPIEKT TABLE 2-continued Anti-Polyoma virus Antibodies

```
                      ISKAKGQPREPQVYTLPPSREEMTKNQVSLTCLVKGFYPS
                      DIAVEWESNGQPENNYKTTPPVLDSDGSFFLYSKLTVDKS
                      RWQQGNVFSCSVMHEALHNHYTQKSLSLSPGK

SEQ ID NO: 317 Light  MALTPLWLTLLTLCIGSVVSSELTQDPAVSVALGQTVRIT
               chain  CQGDSLRDFYGSWYQQKPGQAPVLVNFGYNNRPSGIPDRF
                      SGSRSGNTASLTITGAQAEDEADYYCNSRDISGNRVVFGG
                      GTKLTVVGQPEAAPSVTLFPPSSEELQANKATLVCLISDF
                      YPGAVTVAWKADSSPVKAGVETTTPSKQSNNKYAASSYLS
                      LTPEQWKSHRSYSCQVTHEGSTVEKTVAPTECS
```

NOV212

```
SEQ ID NO: 318 Heavy  MKHLWFFLLLVAAPRWVLSQLQLQESGSGLVRPSQTLSLT
               Chain  CAVSGASISSGGYSWSWIRQPPGKGLEWIGYIYHSGSTSY
                      NPSLKSRVTISEDKSNNQFSLKLSSVTAADTAVYYCARVW
                      ASFYYGSWTPPTWFDPWGPGTLVTVSSASTKGPSVFPLAP
                      CSRSTSGGTAALGCLVKDYFPEPVTVSWNSGALTSGVHTF
                      PAVLQSSGLYSLSSVVTVPSSSLGTQTYICNVNHKPSNTK
                      VDKRVEPKSCDKTHTCPPCPAPELLGGPSVFLFPPKPKDT
                      LMISRTPEVTCVVVDVSHEDPEVKFNWYVDGVEVHNAKTK
                      PREEQYNSTYRVVSVLTVLHQDWLNGKEYKCKVSNKALPA
                      PIEKTISKAKGQPREPQVYTLPPSREEMTKNQVSLTCLVK
                      GFYPSDIAVEWESNGQPENNYKTTPPVLDSDGSFFLYSKL
                      TVDKSRWQQGNVFSCSVMHEALHNHYTQKSLSLSPGK SEQ ID NO: 319 Light  MAWIPLLLTQGTGSWAQSALTQPRSVSGSPGQSVTISCTG
               chain  TGSNVGGYTYVSWYQQHPGKAPKLLIYDVSKRPSGVPDRF
                      SGSKSGNTASLTISGLQADDEADYHCCSYAGGYTLVFGGG
                      TKLTVLGQPKAAPSVTLFPPSSEELQANKATLVCLISDFY
                      PGAVTVAWKADSSPVKAGVETTTPSKQSNNKYAASSYLSL
                      TPEQWKSHRSYSCQVTHEGSTVEKTVAPTECS
```

NOV624

```
SEQ ID NO: 320 Heavy  MELGLSWVFLVAILEGVQCEVQLVESGGGLVQPGGSLRLS
               Chain  CSASGFTFRSYIINWVRQAPGKGLEWVSYISGSSGTKNYA
                      DSVKGRFTISRDNAKNSVYLQMNSLRAEDTAVYYCARDLD
                      CSGGSCYDGMDVWGQGTTVTVSSASTKGPSVFPLAPCSRS
                      TSGGTAALGCLVKDYFPEPVTVSWNSGALTSGVHTFPAVL
                      QSSGLYSLSSVVTVPSSSLGTQTYICNVNHKPSNTKVDKR
                      VEPKSCDKTHTCPPCPAPELLGGPSVFLFPPKPKDTLMIS
                      RTPEVTCVVVDVSHEDPEVKFNWYVDGVEVHNAKTKPREE
                      QYNSTYRVVSVLTVLHQDWLNGKEYKCKVSNKALPAPIEK
                      TISKAKGQPREPQVYTLPPSREEMTKNQVSLTCLVKGFYP
                      SDIAVEWESNGQPENNYKTTPPVLDSDGSFFLYSKLTVDK
                      SRWQQGNVFSCSVMHEALHNHYTQKSLSLSPGK SEQ ID NO: 321 Light  MAWTPLLLGVLAYCTGSVASFELTQPPSVSVSPGQTASIT
               chain  CSGDKLGHHYAYWFQQRPGQSPVLVIYQHTKRPSGIPERF
                      SGSKSGNTATLTISGTQAMDEADYYCQAWDSSTYVVFGGG
                      TKVTVLGQPKAAPSVTLFPPSSEELQANKATLVCLISDFY
                      PGAVTVAWKADSSPVKAGVETTTPSKQSNNKYAASSYLSL
                      TPEQWKSHRSYSCQVTHEGSTVEKTVAPTECS
```

NOV696

```
SEQ ID NO: 322 Heavy  MKHLWFFLLLVAAPRWVLSQVQLQESGPGLVKPSQTLSLT
               Chain  CSVSGGSISSGSHYWSWIRQPAGEALEWIGRTYTSGRTSY
                      NPSLKSRVTISVDTSKNQFSLKLTSVTAADTAVYYCARNS
                      RIYGGYELFDIWGQGTMVTVSSASTKGPSVFPLAPSSKST
                      SGGTAALGCLVKDYFPEPVTVSWNSGALTSGVHTFPAVLQ
                      SSGLYSLSSVVTVPSSSLGTQTYICNVNHKPSNTKVDKRV
                      EPKSCDKTHTCPPCPAPELLGGPSVFLFPPKPKDTLMISR
                      TPEVTCVVVDVSHEDPEVKFNWYVDGVEVHNAKTKPREEQ
                      YNSTYRVVSVLTVLHQDWLNGKEYKCKVSNKALPAPIEKT
                      ISKAKGQPREPQVYTLPPSREEMTKNQVSLTCLVKGFYPS
                      DIAVEWESNGQPENNYKTTPPVLDSDGSFFLYSKLTVDKS
                      RWQQGNVFSCSVMHEALHNHYTQKSLSLSPGK SEQ ID NO: 323 Light  MAWTPLLLGLLSHCTGSLTSYVLTQPPSVSVAPGKTARIP
               chain  CGGDNIGNKGVHWYQQKSGQAPVLLIHYDSDRPSGIPERF
                      SGSNSGNTATLSISRVELGDEADYYCQVWDTSSDQPVFGG
                      GTKLTVLGQPKAAPSVTLFPPSSEELQANKATLVCLISDF
                      YPGAVTVAWKADSSPVKAGVETTTPSKQSNNKYAASSYLS
                      LTPEQWKSHRSYSCQVTHEGSTVEKTVAPTECS
```

TABLE 2-continued

Anti-Polyoma virus Antibodies

NOV474

SEQ ID NO: 324 Heavy Chain
MEFGLSWVFLVAILEGVQCEVQLVESGGGLVQPGGSLRLS
CAASGFTFRSYMMNWVRQAPGKGLEWVSYISGSGGTKYYV
DSVKGRFTISRDNAKNSLYLQMHSLRAEDTAVYYCARDLD
CSGGTCYDGMDVWGQGTTVTVSSASTKGPSVFPLAPCSRS
TSGGTAALGCLVKDYFPEPVTVSWNSGALTSGVHTFPAVL
QSSGLYSLSSVVTVPSSSLGTQTYICNVNHKPSNTKVDKR
VEPKSCDKTHTCPPCPAPELLGGPSVFLFPPKPKDTLMIS
RTPEVTCVVVDVSHEDPEVKFNWYVDGVEVHNAKTKPREE
QYNSTYRVVSVLTVLHQDWLNGKEYKCKVSNKALPAPIEK
TISKAKGQPREPQVYTLPPSREEMTKNQVSLTCLVKGFYP
SDIAVEWESNGQPENNYKTTPPVLDSDGSFFLYSKLTVDK
SRWQQGNVFSCSVMHEALHNHYTQKSLSLSPGK SEQ ID NO: 325 Light chain
MAWAPLLLGVLAYCTGSVASYELIQPPSVSVSPGQTASIT
CSGDKLGNKYVYWFQHRPGQSPVLVIYQHTKRPSGIPERF
SGSKSGNTATLIISGTQAMDEADYYCQAWDSSVVIFGGGT
KLTVLGQPKAAPSVTLFPPSSEELQANKATLVCLISDFYP
GAVTVAWKADSSPVKAGVETTTPSKQSNNKYAASSYLSLT
PEQWKSHRSYSCQVTHEGSTVEKTVAPTECS

NOV126

SEQ ID NO: 326 Heavy Chain
MKHLWFFLLLVAAPRWVLSQLQLQESGPGLVKPSETLSLT
CSVSGDSISRSSDYWGWIRQPPGRGLEWIGSIYRTGSTYY
NPSLSSRVTISVDTSKSQFSLSLSSVTAADTALYYCARVR
HDYVWGSIYYYGMDVWGQGTTVTVSSPSTKGPSVFPLAPC
SRSTSGGTAALGCLVKDYFPEPVTVSWNSGALTSGVHTFP
AVLQSSGLYSLSSVVTVPSSSLGTQTYICNVNHKPSNTKV
DKRVEPKSCDKTHTCPPCPAPELLGGPSVFLFPPKPKDTL
MISRTPEVTCVVVDVSHEDPEVKFNWYVDGVEVHNAKTKP
REEQYNSTYRVVSVLTVLHQDWLNGKEYKCKVSNKALPAP
IEKTISKAKGQPREPQVYTLPPSREEMTKNQVSLTCLVKG
FYPSDIAVEWESNGQPENNYKTTPPVLDSDGSFFLYSKLT
VDKSRWQQGNVFSCSVMHEALHNHYTQKSLSLSPGK SEQ ID NO: 327 Light chain
MAWIPLLLTQGTGSWAQSALTQPRSVSGSPGQSVTISCTG
TGSDVGGYTYVSWYQQHPDKAPKLVIYDVTKRPSGVPDRF
SGSKSGNTASLTISGLRADDEADYYCCSYAGRYSWVFGGG
TKLTVLGQPKAAPSVTLFPPSSEELQANKATLVCLISDFY
PGAVTVAWKADSSPVKAGVETTTPSKQSNNKYAASSYLSL
TPEQWKSHRSYSCQVTHEGSTVEKTVAPTECS

NOV128

SEQ ID NO: 328 Heavy Chain
MDWTWRILFLVAAATGAHSQVQLVQSGAEVKKPGASVKVS
CKTSGYTFTAYHLHWVRQTPGQGLEWMGWINPNSGGTNYA
LKFQGRVTVTRDTSISTVYMELTRLRSDDTAVYYCAREKE
PLMASYYYYGMDVWGQGTTVTVSSASTKGPSVFPLAPCSR
STSGGTAALGCLVKDYFPEPVTVSWNSGALTSGVHTFPAV
LQSSGLYSLSSVVTVPSSSLGTQTYICNVNHKPSNTKVDK
RVEPKSCDKTHTCPPCPAPELLGGPSVFLFPPKPKDTLMI
SRTPEVTCVVVDVSHEDPEVKFNWYVDGVEVHNAKTKPRE
EQYNSTYRVVSVLTVLHQDWLNGKEYKCKVSNKALPAPIE
KTISKAKGQPREPQVYTLPPSREEMTKNQVSLTCLVKGFY
PSDIAVEWESNGQPENNYKTTPPVLDSDGSFFLYSKLTVD
KSRWQQGNVFSCSVMHEALHNHYTQKSLSLSPGK SEQ ID NO: 329 Light chain
MAWAPLWLTLLTLCIGSVVSSEVTQDPAVSVALGQTVRIT
CQGDSLRNYYTRWYQQKPGQAPVLVIYRENNRPSGIPDRF
SGSSSGNTASLTITGAQAEDEADYYCTSRATNTDHLVFGG
GTKLTVLGQPKAAPSVTLFPPSSEELQANKATLVCLISDF
YPGAVTVAWKADSSPVKAGVETTTPSKQSNNKYAASSYLS
LTPEQWKSHRSYSCQVTHEGSTVEKTVAPTECS

NOV265

SEQ ID NO: 330 Heavy Chain
MKHLWFFLLLVAAPRWVLSQLQLQESGSGLVRPSQTLSLT
CAVSGASINSGGYSWSWIRQPPGKGLEWIGYIYHSGSTSY
NPSLKSRVTISEDRSKNQFSLKLSSVTAADTAVYYCARVW
ASFYYGSWTPPTWLDPWGPGTLVTVSSASTKGPSVFPLAP
CSRSTSGGTAALGCLVKDYFPEPVTVSWNSGALTSGVHTF
PAVLQSSGLYSLSSVVTVPSSSLGTQTYICNVNHKPSNTK
VDKRVEPKSCDKTHTCPPCPAPELLGGPSVFLFPPKPKDT
LMISRTPEVTCVVVDVSHEDPEVKFNWYVDGVEVHNAKTK
PREEQYNSTYRVVSVLTVLHQDWLNGKEYKCKVSNKALPA TABLE 2-continued Anti-Polyoma virus Antibodies

|  |  |  |
|---|---|---|
|  |  | PIEKTISKAKGQPREPQVYTLPPSREEMTKNQVSLTCLVK GFYPSDIAVEWESNGQPENNYKTTPPVLDSDGSFFLYSKL TVDKSRWQQGNVFSCSVMHEALHNHYTQKSLSLSPGK |
| SEQ ID NO: 331 | Light chain | MAWSPLLLTQGTGSWAQSALTQPRSVSGSPGQSVTISCTG TGSDVGGYTYVSWYQQHPGKAPKLMIYDVSKRPSGVPDRF SGSKSGNTASLTISGLQADDEADYYCCSYAGGYTLVFGGG TKLTVLGQPKAAPSVTLFPPSSEELQANKATLVCLISDFY PGAVTVAWKADSSPVKAGVETTTPSKQSNNKYAASSYLSL TPEQWKSHRSYSCQVTHEGSTVEKTVAPTECS |

NOV864

| SEQ ID NO: 332 | Heavy Chain | MEFGLSWIFLLAILKGVQCEVQLVESGGGLVQPGRSLRLS CAASGFNFDNYAMHWVRQVPGKGLEWVSGINWNSGYEAYA DSVKGRFIISRDNAQNSLYLQMNSLRADDTAFYYCTKDTI AAVGRGAFDIWGQGTGVSVSPASTKGPSVFPLAPCSRSTS GGTAALGCLVKDYFPEPVTVSWNSGALTSGVHTFPAVLQS SGLYSLSSVVTVPSSSLGTQTYICNVNHKPSNTKVDKRVE PKSCDKTHTCPPCPAPELLGGPSVFLFPPKPKDTLMISRT PEVTCVVVDVSHEDPEVKFNWYVDGVEVHNAKTKPREEQY NSTYRVVSVLTVLHQDWLNGKEYKCKVSNKALPAPIEKTI SKAKGQPREPQVYTLPPSREEMTKNQVSLTCLVKGFYPSD IAVEWESNGQPENNYKTTPPVLDSDGSFFLYSKLTVDKSR WQQGNVFSCSVMHEALHNHYTQKSLSLSPGK |
|---|---|---|
| SEQ ID NO: 333 | Light chain | MAWIPLLLGLLSHCTGSVTSYLLTQPPSVSVAPGKTAMIT CGGSKIGGKSVHWYQQKPGQAPVLVISYDSDRPSGIPKRF SGSNSGNTATLTISGVEAGDEADYYCQVWDSSNVHRVFGG GTKLTVLSQPKAAPSVTLFPPSSEELQANKATLVCLISDF YPGAVTVAWKADSSPVKAGVETTTPSKQSNNKYAASSYLS LTPEQWKSHRSYSCQVTHEGSTVEKTVAPTECS |

NOV618

| SEQ ID NO: 334 | Heavy Chain | MKHLWFFLLLLVAAPRWVLSQLQLQESGPGLVKPSETLSLT CSVSGDSISRSSDYWGWIRQPPGRGLEWIGSIYRTGSTYY NPSLSSRVTISVDTSKSQFSLSLSSVTAADTALYYCARVR HDYVWGSIYYYGMDVWGQGTTVTVSSPSTKGPSVFPLAPC SRSTSGGTAALGCLVKDYFPEPVTVSWNSGALTSGVHTFP AVLQSSGLYSLSSVVTVPSSSLGTQTYICNVNHKPSNTKV DKRVEPKSCDKTHTCPPCPAPELLGGPSVFLFPPKPKDTL MISRTPEVTCVVVDVSHEDPEVKFNWYVDGVEVHNAKTKP REEQYNSTYRVVSVLTVLHQDWLNGKEYKCKVSNKALPAP IEKTISKAKGQPREPQVYTLPPSREEMTKNQVSLTCLVKG FYPSDIAVEWESNGQPENNYKTTPPVLDSDGSFFLYSKLT VDKSRWQQGNVFSCSVMHEALHNHYTQKSLSLSPGK |
|---|---|---|
| SEQ ID NO: 335 | Light chain | MAWIPLLLTQGTGSWAQSALTQPRSVSGSPGQSVTISCTG TGSDVGGYTYVSWYQQHPDKAPKLVIYDVTKRPSGVPDRF SGSKSGNTASLTISGLRADDEADYYCCSYAGQPKAAPSVT LFPPSSEELQANKATLVCLISDFYPGAVTVAWKADSSPVK AGVETTTPSKQSNNKYAASSYLSLTPEQWKSHRSYSCQVT HEGSTVEKTVAPTECS |

NOV430

| SEQ ID NO: 336 | Heavy Chain | MELGLCWVFLVAILEGVQCEVQLVESGGGLVQPGGSLRLS CSASGFTFRSYIINWVRQAPGKGLEWVSYISGSSGTKNYA DSVKGRFTISRDNAKNSVYLQMNSLRAEDTAVYYCARDLD CSGGSCYDGMDVWGQGTTVTVSSASTKGPSVFPLAPCSRS TSGGTAALGCLVKDYFPEPVTVSWNSGALTSGVHTFPAVL QSSGLYSLSSVVTVPSSSLGTQTYICNVNHKPSNTKVDKR VEPKSCDKTHTCPPCPAPELLGGPSVFLFPPKPKDTLMIS RTPEVTCVVVDVSHEDPEVKFNWYVDGVEVHNAKTKPREE QYNSTYRVVSVLTVLHQDWLNGKEYKCKVSNKALPAPIEK TISKAKGQPREPQVYTLPPSREEMTKNQVSLTCLVKGFYP SDIAVEWESNGQPENNYKTTPPVLDSDGSFFLYSKLTVDK SRWQQGNVFSCSVMHEALHNHYTQKSLSLSPGK |
|---|---|---|
| SEQ ID NO: 337 | Light chain | MAWTPLFLGVLAYCTGSVASFELTQPPSVSVSPGQTASIT CSGDKLGHHYAYWFQQRPGQSPVLVIYQHTKRPSGIPERF SGSKSGNTATLTISGTQAMDEADYYCQAWDSSTYVVFGGG TKLTVLGQPKAAPSVTLFPPSSEELQANKATLVCLISDFY PGAVTVAWKADSSPVKAGVETTTPSKQSNNKYAASSYLSL TPEQWKSHRSYSCQVTHEGSTVEKTVAPTECS |

TABLE 2-continued

Anti-Polyoma virus Antibodies

NOV270

SEQ ID NO: 338 Heavy Chain
MELGLCWVFLVAILEGVQCEVQLVESGGGLVQPGGSLRLS
CAASGFTFRSYMMNWVRQAPGKGLEWVSYISGSGGTKYYV
DSVKGRFTISRDNAKNSLYLQMHSLRAEDTAVYYCARDLD
CSGGTCYDGMDVWGQGTTVTVSSASTKGPSVFPLAPCSRS
TSGGTAALGCLVKDYFPEPVTVSWNSGALTSGVHTFPAVL
QSSGLYSLSSVVTVPSSSLGTQTYICNVNHKPSNTKVDKR
VEPKSCDKTHTCPPCPAPELLGGPSVFLFPPKPKDTLMIS
RTPEVTCVVVDVSHEDPEVKFNWYVDGVEVHNAKTKPREE
QYNSTYRVVSVLTVLHQDWLNGKEYKCKVSNKALPAPIEK
TISKAKGQPREPQVYTLPPSREEMTKNQVSLTCLVKGFYP
SDIAVEWESNGQPENNYKTTPPVLDSDGSFFLYSKLTVDK
SRWQQGNVFSCSVMHEALHNHYTQKSLSLSPGK SEQ ID NO: 339 Light chain
MAWIPLFLGVLAYCTGSVASYELTQPPSVSVSPGQTASIT
CSGDKLGHKYVYWFQHRPGQSPVLVIYQHTKRPSGIPERF
SGSKSGNTATLTISGTQALDEADYYCQAWDSSVVIFGGGT
KLTVLGQPKAAPSVTLEPPSSEELQANKATLVCLISDFYP
GAVTVAWKADSSPVKAGVETTTPSKQSNNKYAASSYLSLT
PEQWKSHRSYSCQVTHEGSTVEKTVAPTECS

NOV024

SEQ ID NO: 340 Heavy Chain
MDWTWRILFLVAAVTGAHSQVQLVQSGPEVKRPGASVKVS
CKASGYTLTTSSIHWVRQAPGQRLEWMGWINTGNDNTMYS
QKFQGRVLITTDTSASTAYLELRSLRSEDTAVFYCARGPL
PYYYDSSGPLDYWGQGTLVTVSSASTKGPSVFPLAPSSKS
TSGGTAALGCLVKDYFPEPVTVSWNSGALTSGVHTFPAVL
QSSGLYSLSSVVTVPSSSLGTQTYICNVNHKPSNTKVDKR
VEPKSCDKTHTCPPCPAPELLGGPSVFLFPPKPKDTLMIS
RTPEVTCVVVDVSHEDPEVKFNWYVDGVEVHNAKTKPREE
QYNSTYRVVSVLTVLHQDWLNGKEYKCKVSNKALPAPIEK
TISKAKGQPREPQVYTLPPSREEMTKNQVSLTCLVKGFYP
SDIAVEWESNGQPENNYKTTPPVLDSDGSFFLYSKLTVDK
SRWQQGNVFSCSVMHEALHNHYTQKSLSLSPGK SEQ ID NO: 341 Light chain
MAWIPLLLGLLSHCTGSVTSYVLTQPPSVSVAPGKTATFT
CGGDNIGTKSVHWYRQKPGQAPVLVVYDDSDRPSGDPERF
SGSNSGNTATLTISRVEAGDEADYFCQVWISSRDHPVFGE
GTRLTVLGQPKAAPSVTLFPPSSEELQANKATLVCLISDF
YPGAVTVAWKADSSPVKAGVETTTPSKQSNNKYAASSYLS
LTPEQWKSHRSYSCQVTHEGSTVEKTVAPTECS

NOV650

SEQ ID NO: 342 Heavy Chain
MDWTWRILFLVAAATGAHSQVQLVQSGAEVKKPGASVKVS
CKTSGYTFTAYHMHWVRQAPGQGLEWMGWINPNSGGTNYA
QNFQGRVTVTRDTSISTVYMELTRLRSDDTAVYYCARERE
PLMASYYYYGMDVWGQGTTVTVSSASTKGPSVFPLAPCSR
STSGGTAALGCLVKDYFPEPVTVSWNSGALTSGVHTFPAV
LQSSGLYSLSSVVTVPSSSLGTQTYICNVNHKPSNTKVDK
RVEPKSCDKTHTCPPCPAPELLGGPSVFLFPPKPKDTLMI
SRTPEVTCVVVDVSHEDPEVKFNWYVDGVEVHNAKTKPRE
EQYNSTYRVVSVLTVLHQDWLNGKEYKCKVSNKALPAPIE
KTISKAKGQPREPQVYTLPPSREEMTKNQVSLTCLVKGFY
PSDIAVEWESNGQPENNYKTTPPVLDSDGSFFLYSKLTVD
KSRWQQGNVFSCSVMHEALHNHYTQKSLSLSPGK SEQ ID NO: 343 Light chain
MAWATLLLTLCIGSVVSSEVTQDPAVSVALGQTVRITCQG
DSLRNYYTRWYQQKPGQAPILVIYRENNRPSGIPDRFSGS
NSGNTASLTITGAQAEDEADYYCTSRASGSDHLVFGGGTK
LTVLGQPKAAPSVTLFPPSSEELQANKATLVCLISDFYPG
AVTVAWKADSSPVKAGVETTTPSKQSNNKYAASSYLSLTP
EQWKSHRSYSCQVTHEGSTVEKTVAPTECS

NOV605

SEQ ID NO: 344 Heavy Chain
MDWTWRILFLVAAATGAHSRVQLVQSGAEVKKPGASVKVS
CKASGYTFTAYHMHWVRQAPGQGLEWMGWINPNSGGTNYA
QRFQGRVTMTRDTSSSTAYMDLTRLRSDDTAVYYCARERE
PLMASFYHYGLGVWGQGTTVAVSSASTKGPSVFPLAPCSR
STSGGTAALGCLVKDYFPEPVTVSWNSGALTSGVHTFPAV
LQSSGLYSLSSVVTVPSSSLGTQTYICNVNHKPSNTKVDK
RVEPKSCDKTHTCPPCPAPELLGGPSVFLFPPKPKDTLMI
SRTPEVTCVVVDVSHEDPEVKFNWYVDGVEVHNAKTKPRE
EQYNSTYRVVSVLTVLHQDWLNGKEYKCKVSNKALPAPIE TABLE 2-continued Anti-Polyoma virus Antibodies KTISKAKGQPREPQVYTLPPSREEMTKNQVSLTCLVKGFY
PSDIAVEWESNGQPENNYKTTPPVLDSDGSFFLYSKLTVD
KSRWQQGNVFSCSVMHEALHNHYTQKSLSLSPGK SEQ ID NO: 345 Light MAWTPLLTLCIGSGGSSELTQDPAVSVALGQTVTITCQGD
chain SLRIYYASWYQQKPGQAPILVIYDTNKRPSGIPDRFSGSS
SGNTASLTITGAQAEDEAEYYCDSRDSSGDHLLFGGGTRV
TVLGQPKAAPSVTLFPPSSEELQANKATLVCLISDFYPGA
VTVAWKADSSPVKAGVETTTPSKQSNNKYAASSYLSLTPE
QWKSHRSYSCQVTHEGSTVEKTVAPTECS

NOV922

SEQ ID NO: 346 Heavy MKHLWFFLLLVAAPRWVLSQLQLQESGPGLVKPSETLSLT
Chain CSVSGDSISRSSDYWGWIRQPPGRGLEWIGSIYRTGSTYY
NPSLSSRVTISVDTSKSQFSLSLSSVTAADTALYYCARVR
HDYVWGSIYYYGMDVWGQGTTVTVSSPSTKGPSVFPLAPC
SRSTSGGTAALGCLVKDYFPEPVTVSWNSGALTSGVHTFP
AVLQSSGLYSLSSVVTVPSSSLGTQTYICNVNHKPSNTKV
DKRVEPKSCDKTHTCPPCPAPELLGGPSVFLFPPKPKDTL
MISRTPEVTCVVVDVSHEDPEVKFNWYVDGVEVHNAKTKP
REEQYNSTYRVVSVLTVLHQDWLNGKEYKCKVSNKALPAP
IEKTISKAKGQPREPQVYTLPPSREEMTKNQVSLTCLVKG
FYPSDIAVEWESNGQPENNYKTTPPVLDSDGSFFLYSKLT
VDKSRWQQGNVFSCSVMHEALHNHYTQKSLSLSPGK SEQ ID NO: 347 Light MAWTVLLLSLLTQGTGSWAQSALTQPRSVSGSPGQSVTIS
chain CTGTGSDVGGYTYVSWYQQHPDKAPKLVIYDVTKRPSGVP
DRFSGSKSGNTASLTISGLRADDEADYYCCSYAGRYSWVF
GGGTKLTVLGQPKAAPSVTLFPPSSEELQANKATLVCLIS
DFYPGAVTVAWKADSSPVKAGVETTTPSKQSNNKYAASSY
LSLTPEQWKSHRSYSCQVTHEGSTVEKTVAPTECS

NOV152

SEQ ID NO: 348 Heavy MDWTWRILFLVAAATGAHSQVQLVQSGAEVKKPGASVKVS
Chain CKTSGYTFTAYHMHWVRQAPGQGLEWMGWINPNSGGTNYA
QKFQGRVTVTRDTSISTVYMELTRLRSDDTAVYYCARERE
PLMASYYYYGMDVWGQGTTVTVSSASTKGPSVFPLAPCSR
STSGGTAALGCLVKDYFPEPVTVSWNSGALTSGVHTFPAV
LQSSGLYSLSSVVTVPSSSLGTQTYICNVNHKPSNTKVDK
RVEPKSCDKTHTCPPCPAPELLGGPSVFLFPPKPKDTLMI
SRTPEVTCVVVDVSHEDPEVKFNWYVDGVEVHNAKTKPRE
EQYNSTYRVVSVLTVLHQDWLNGKEYKCKVSNKALPAPIE
KTISKAKGQPREPQVYTLPPSREEMTKNQVSLTCLVKGFY
PSDIAVEWESNGQPENNYKTTPPVLDSDGSFFLYSKLTVD
KSRWQQGNVFSCSVMHEALHNHYTQKSLSLSPGK SEQ ID NO: 349 Light MAWIPLWLTLLTLCIGSVVSSEVTQDPAVSVALGQTVRIT
chain CQGDSLRNYYTRWYQQKPGQAPVLVIYRENNRPSGIPDRF
SGSSSGNTASLTITGAQAEDEADYYCTSRASSTDHLVFGG
GTKLTVLGQPKAAPSVTLFPPSSEELQANKATLVCLISDF
YPGAVTVAWKADSSPVKAGVETTTPSKQSNNKYAASSYLS
LTPEQWKSHRSYSCQVTHEGSTVEKTVAPTECS

NOV229

SEQ ID NO: 350 Heavy MELGLSWLFLVATLKGVQCEVQLLESGGGLMQPGGSLRLS
Chain CAASGFTFRSYAMNWVRQAPGKGLEWVSTISGNGGTTYYA
DSVRGRFTISRDNSKNTLFLQMNSLRAEDTAIYYCAQGEP
WSGYLEPLFASWGQGTLVTVSSASTKGPSVFPLAPCSRST
SGGTAALGCLVKDYFPEPVTVSWNSGALTSGVHTFPAVLQ
SSGLYSLSSVVTVPSSSLGTQTYICNVNHKPSNTKVDKRV
EPKSCDKTHTCPPCPAPELLGGPSVFLFPPKPKDTLMISR
TPEVTCVVVDVSHEDPEVKFNWYVDGVEVHNAKTKPREEQ
YNSTYRVVSVLTVLHQDWLNGKEYKCKVSNKALPAPIEKT
ISKAKGQPREPQVYTLPPSREEMTKNQVSLTCLVKGFYPS
DIAVEWESNGQPENNYKTTPPVLDSDGSFFLYSKLTVDKS
RWQQGNVFSCSVMHEALHNHYTQKSLSLSPGK SEQ ID NO: 351 Light MALTPLWLTLLTPCIGSVVSSELTQDPAVSVALGQTVRIT
chain CQGDSLRNFYASWYQQKPGQAPVLVIYGKNNRPSGIPDRF
SGSSSGNTVSLTITGAQAEDDADYYCNSRDSSGNHVIFGG
GTKLTVLGQPKAAPSVTLFPPSSEELQANKATLVCLISDF
YPGAVTVAWKADSSPVKAGVETTTPSKQSNNKYAASSYLS
LTPEQWKSHRSYSCQVTHEGSTVEKTVAPTECS TABLE 2-continued Anti-Polyoma virus Antibodies

NOV099

SEQ ID NO: 352 Heavy Chain
MELGLRWVFLVAILEGVHCEVQLVESGGGLVKPGGSLRLS
CAASGFTFSSYSMNWVRQAPGKGLEWVSSISTSKNYKKYA
DSVKGRFTISRDNAENSLYLQMNSLRAEDTAIYYCARVDY
DYIWGSYREKAMDVWGHGTTVTVSSASTKGPSVFPLAPCS
RSTSGGTAALGCLVKDYFPEPVTVSWNSGALTSGVHTFPA
VLQSSGLYSLSSVVTVPSSSLGTQTYICNVNHKPSNTKVD
KRVEPKSCDKTHTCPPCPAPELLGGPSVFLFPPKPKDTLM
ISRTPEVTCVVVDVSHEDPEVKFNWYVDGVEVHNAKTKPR
EEQYNSTYRVVSVLTVLHQDWLNGKEYKCKVSNKALPAPI
EKTISKAKGQPREPQVYTLPPSREEMTKNQVSLTCLVKGF
YPSDIAVEWESNGQPENNYKTTPPVLDSDGSFFLYSKLTV
DKSRWQQGNVFSCSVMHEALHNHYTQKSLSLSPGK SEQ ID NO: 353 Light chain
MAWSPLLLTQGTGSWAQSALTQPRSVSGSPGQSVTISCTG
TGSDVGGYNYVSWYQQHPGKAPKVIIYDVSKRPSGVPDRF
SGSKSGNTASLTISGLQAEDEADYHCCSYAGTYTWVFGGG
TKVTVLGQPKAAPSVTLFPPSSEELQANKATLVCLISDFY
PGAVTVAWKADSSPVKAGVETTTPSKQSNNKYAASSYLSL
TPEQWKSHRSYSCQVTHEGSTVEKTVAPTECS

NOV160

SEQ ID NO: 354 Heavy Chain
MEFGLRWLFLVAILKGVQCEVQLLESGGGSVQPGGSLRLS
CAASGFTFRNYAMNWVRQSPGKGLEWVSTISGTGGTTYYA
DSVKGRFSISRDNSRNTLYLNMNNLRVEDTAIYYCAKGEP
WSNYLEPLFDHWGQGTLVTVSSASTKGPSVFPLAPSSKST
SGGTAALGCLVKDYFPEPVTVSWNSGALTSGVHTFPAVLQ
SSGLYSLSSVVTVPSSSLGTQTYICNVNHKPSNTKVDKRV
EPKSCDKTHTCPPCPAPELLGGPSVFLFPPKPKDTLMISR
TPEVTCVVVDVSHEDPEVKFNWYVDGVEVHNAKTKPREEQ
YNSTYRVVSVLTVLHQDWLNGKEYKCKVSNKALPAPIEKT
ISKAKGQPREPQVYTLPPSREEMTKNQVSLTCLVKGFYPS
DIAVEWESNGQPENNYKTTPPVLDSDGSFFLYSKLTVDKS
RWQQGNVFSCSVMHEALHNHYTQKSLSLSPGK SEQ ID NO: 355 Light chain
MALTPLLLTLCIGSVVSSELTQDPAVSVALGQTVRITCQG
DSLRNFYATWYQQKPGQAPVFVMYDKTNRPSGIPDRFSGS
RSGNTAYLTITGAQAEDEADYYCNSRDSSGNYVIFGGGTK
LTVLGQPKAAPSVTLFPPSSEELQANKATLVCLISDFYPG
AVTVAWKADSSPVKAGVETTTPSKQSNNKYAASSYLSLTP
EQWKSHRSYSCQVTHEGSTVEKTVAPTECS

NOV904

SEQ ID NO: 356 Heavy Chain
MDWTWRILFLVAAATGAHSQVQLVQSGAEVMRPGASLKVS
CKASGYSFTMYSIHWVRQAPGHRLEWMGWINAANGNTIYS
QNFQGRVTISRDTSATTAHMELGSLRSEDTAVYFCARGPI
PYYYDHSGPFDYWGQGTLVTVSSASTKGPSVFPLAPCSRS
TSGGTAALGCLVKDYFPEPVTVSWNSGALTSGVHTFPAVL
QSSGLYSLSSVVTVPSSSLGTQTYICNVNHKPSNTKVDKR
VEPKSCDKTHTCPPCPAPELLGGPSVFLFPPKPKDTLMIS
RTPEVTCVVVDVSHEDPEVKFNWYVDGVEVHNAKTKPREE
QYNSTYRVVSVLTVLHQDWLNGKEYKCKVSNKALPAPIEK
TISKAKGQPREPQVYTLPPSREEMTKNQVSLTCLVKGFYP
SDIAVEWESNGQPENNYKTTPPVLDSDGSFFLYSKLTVDK
SRWQQGNVFSCSVMHEALHNHYTQKSLSLSPGK SEQ ID NO: 357 Light chain
MEAPAQLLFLLLLWLPDTTGEIVMTQSPPTLSVSPGERAI
LSCRASQSVSSDLAWYQQQAGQAPRLLIYGASTRATGIPP
RFSGSGSGTEFTLTISSLQSEDFAVYYCQQYNKWVTFGGG
TKVEIKRTVAAPSVFIFPPSDEQLKSGTASVVCLLNNFYP
REAKVQWKVDNALQSGNSQESVTEQDSKDSTYSLSSTLTL
SKADYEKHKVYACEVTHQGLSSPVTKSFNRGEC

NOV972

SEQ ID NO: 358 Heavy Chain
MDWTWRILFLVAAATGAHSQVQLVQSGAEVKKPGASVKVS
CRTSGYTFTAYHMHWVRQAPGQGLEWMGWINPNSGGTNYA
QKFQGRVTVTRDTSLRTVYMEVTSLRSDDTAVYYCARERE
PLMASYYYYGLDVWGQGTTVTVSSASTKGPSVFPLAPCSR
STSGGTAALGCLVKDYFPEPVTVSWNSGALTSGVHTFPAV
LQSSGLYSLSSVVTVPSSSLGTQTYICNVNHKPSNTKVDK
RVEPKSCDKTHTCPPCPAPELLGGPSVFLFPPKPKDTLMI
SRTPEVTCVVVDVSHEDPEVKFNWYVDGVEVHNAKTKPRE
EQYNSTYRVVSVLTVLHQDWLNGKEYKCKVSNKALPAPIE TABLE 2-continued Anti-Polyoma virus Antibodies

| | | |
|---|---|---|
| | | KTISKAKGQPREPQVYTLPPSREEMTKNQVSLTCLVKGFY<br>PSDIAVEWESNGQPENNYKTTPPVLDSDGSFFLYSKLTVD<br>KSRWQQGNVFSCSVMHEALHNHYTQKSLSLSPGK |
| SEQ ID NO: 359 | Light<br>chain | MAWAPLWLTLLTLCIGSVVSSEVTQDPAVSVALGQTVRIT<br>CQGDSLRNYYTRWYQQKPGQAPILVIYRENNRPSGIPDRF<br>SGTNSGNTASLTITGAQAEDEADYYCTSRASGTDHLVFGR<br>GTKLTVLGQPKAAPSVTLFPPSSEELQANKATLVCLISDF<br>YPGAVTVAWKADSSPVKAGVETTTPSKQSNNKYAASSYLS<br>LTPEQWKSHRSYSCQVTHEGSTVEKTVAPTECS |

NOV364

| | | |
|---|---|---|
| SEQ ID NO: 360 | Heavy<br>Chain | MDWTWRILFLVAAATGAHSQVQLVQSGAEVKKPGASVKVS<br>CKTSGYAFTAFHLHWVRQAPGQGLEWMGWINPNSGDTNYA<br>QKFQGRVTVTRDTSISTVYMELTRLRSDDTAVYYCARERE<br>PLMASYYYYGMDVWGQGTTVTVSSASTKGPSVFPLAPCSR<br>STSGGTAALGCLVKDYFPEPVTVSWNSGALTSGVHTFPAV<br>LQSSGLYSLSSVVTVPSSSLGTQTYICNVNHKPSNTKVDK<br>RVEPKSCDKTHTCPPCPAPELLGGPSVFLFPPKPKDTLMI<br>SRTPEVTCVVVDVSHEDPEVKFNWYVDGVEVHNAKTKPRE<br>EQYNSTYRVVSVLTVLHQDWLNGKEYKCKVSNKALPAPIE<br>KTISKAKGQPREPQVYTLPPSREEMTKNQVSLTCLVKGFY<br>PSDIAVEWESNGQPENNYKTTPPVLDSDGSFFLYSKLTVD<br>KSRWQQGNVFSCSVMHEALHNHYTQKSLSLSPGK |
| SEQ ID NO: 361 | Light<br>chain | MAWAPLLLTLCIGSVVSSEVTQDPAVSVALGQTVRITCQG<br>DSLRKYYTRWYQQKPGQAPVLVIYRENNRPSGIPDRFSGS<br>SSGNTASLTITGAQAEDEADYYCSSRASSTDHLVFGGGTK<br>LTVLGQPKAAPSVTLFPPSSEELQANKATLVCLISDFYPG<br>AVTVAWKADSSPVKAGVETTTPSKQSNNKYAASSYLSLTP<br>EQWKSHRSYSCQVTHEGSTVEKTVAPTECS |

NOV742

| | | |
|---|---|---|
| SEQ ID NO: 362 | Heavy<br>Chain | MKHLWFFLLLVAAPRWVLSQLQLQESGPGLVKPSETLSLT<br>CSVSGDSISRSSDYWGWIRQPPGRGLEWIGSIYRTGSTYY<br>NPSLSSRVTISVDTSKSQFSLSLSSVTAADTALYYCARVR<br>HDYVWGSIYYYGMDVWGQGTTVTVSSPSTKGPSVFPLAPC<br>SRSTSGGTAALGCLVKDYFPEPVTVSWNSGALTSGVHTFP<br>AVLQSSGLYSLSSVVTVPSSSLGTQTYICNVNHKPSNTKV<br>DKRVEPKSCDKTHTCPPCPAPELLGGPSVFLFPPKPKDTL<br>MISRTPEVTCVVVDVSHEDPEVKFNWYVDGVEVHNAKTKP<br>REEQYNSTYRVVSVLTVLHQDWLNGKEYKCKVSNKALPAP<br>IEKTISKAKGQPREPQVYTLPPSREEMTKNQVSLTCLVKG<br>FYPSDIAVEWESNGQPENNYKTTPPVLDSDGSFFLYSKLT<br>VDKSRWQQGNVFSCSVMHEALHNHYTQKSLSLSPGK |
| SEQ ID NO: 363 | Light<br>chain | MAWXXXXXSXLTQGTGSWARSALTQPRSVSGXPGQSVTIS<br>CTGTGSDVGGYTYVSWYQQHPDKAPKLVIYDVTKRPSGVP<br>DRFSGSKSGNTASLTISGLRADDEADYYCCSYAGRYSWVF<br>GGGTKLTVLGQPKAAPSVTLFPPSSEELQANKATLVCLIS<br>DFYPGAVTVAWKADSSPVKAGVETTTPSKQSNNKYAASSY<br>LSLTPEQWKSHRSYSCQVTHEGSTVEKTVAPTECS |

NOV706

| | | |
|---|---|---|
| SEQ ID NO: 364 | Heavy<br>Chain | MKHLWFFLLLVAAPRWVLSQVQLQESGPGLVKPSQTLSLT<br>CTVSGGSISSGSHYWSWIRQPAGKGLEWIGRIYTSGRNSY<br>NPSLKSRVTISVDTFKNQFSLKVSSVTAADTAVYYCARNN<br>RIYGGYELFDIWGQGTTVTVSSASTKGPSVFPLAPSSKST<br>SGGTAALGCLVKDYFPEPVTVSWNSGALTSGVHTFPAVLQ<br>SSGLYSLSSVVTVPSSSLGTQTYICNVNHKPSNTKVDKRV<br>EPKSCDKTHTCPPCPAPELLGGPSVFLFPPKPKDTLMISR<br>TPEVTCVVVDVSHEDPEVKFNWYVDGVEVHNAKTKPREEQ<br>YNSTYRVVSVLTVLHQDWLNGKEYKCKVSNKALPAPIEKT<br>ISKAKGQPREPQVYTLPPSREEMTKNQVSLTCLVKGFYPS<br>DIAVEWESNGQPENNYKTTPPVLDSDGSFFLYSKLTVDKS<br>RWQQGNVFSCSVMHEALHNHYTQKSLSLSPGK |
| SEQ ID NO: 365 | Light<br>chain | MAWSPLLLGLLSHCTVSVTSFVLTQPPSVSVAPGKTARFS<br>CGGDNIGSKPVHWYQQKPGQAPALVIYDSDRPSGIPERF<br>SGSNSGNTATLTISRVEAGDEADYYCQVWDTSGDHPVFGG<br>GTKLTVLGQPKAAPSVTLFPPSSEELQANKATLVCLISDF<br>YPGAVTVAWKADSSPVKAGVETTTPSKQSNNKYAASSYLS<br>LTPEQWKSHRSYSCQVTHEGSTVEKTVAPTECS |

TABLE 2-continued

Anti-Polyoma virus Antibodies

NOV420

SEQ ID NO: 366 Heavy Chain
MELGLCWVFLVAILEGVHCEVQLVESGGGLVKPGGSLRLS
CAASGFTFSSYSMNWVRQAPGKGLEWVSSISTSKNYKKYA
DSVKGRFTISRDNAENSLYLQMNSLRAEDTAIYYCARVDY
DYIWGSYREKAMDVWGHGTTVTVSSASTKGPSVFPLAPCS
RSTSGGTAALGCLVKDYFPEPVTVSWNSGALTSGVHTFPA
VLQSSGLYSLSSVVTVPSSSLGTQTYICNVNHKPSNTKVD
KRVEPKSCDKTHTCPPCPAPELLGGPSVFLFPPKPKDTLM
ISRTPEVTCVVVDVSHEDPEVKFNWYVDGVEVHNAKTKPR
EEQYNSTYRVVSVLTVLHQDWLNGKEYKCKVSNKALPAPI
EKTISKAKGQPREPQVYTLPPSREEMTKNQVSLTCLVKGF
YPSDIAVEWESNGQPENNYKTTPPVLDSDGSFFLYSKLTV
DKSRWQQGNVFSCSVMHEALHNHYTQKSLSLSPGK SEQ ID NO: 367 Light chain
MAWIPLLLTQGTGSWAQSALTQPRSVSGSPGQSVTISCTG
TGSDVGGYNYVSWYQQHPGKAPKVIIYDVSKRPSGVPDRF
SGSKSGNTASLTISGLQAEDEADYHCCSYAGTYTWVFGGG
TKVTVLGQPKAAPSVTLFPPSSEELQANKATLVCLISDFY
PGAVTVAWKADSSPVKAGVETTTPSKQSNNKYAASSYLSL
TPEQWKSHRSYSCQVTHEGSTVEKTVAPTECS

NOV504

SEQ ID NO: 368 Heavy Chain
MDWTWRVFCLLAVAPGVHSQVQLVQSGAEVKKPGASVRVS
CKASGYTFTNYYMHWVRQAPGQGLEWTGIVNPSGGSTNYA
QKLQGRVTMTIDTSTSTVYMELNSLTSEDTAVYYCARARK
HYFGSGTDYKGRYTAHALDLWGQGTMVIVSSASTKGPSVF
PLAPSSKSTSGGTAALGCLVKDYFPEPVTVSWNSGALTSG
VHTFPAVLQSSGLYSLSSVVTVPSSSLGTQTYICNVNHKP
SNTKVDKRVEPKSCDKTHTCPPCPAPELLGGPSVFLFPPK
PKDTLMISRTPEVTCVVVDVSHEDPEVKFNWYVDGVEVHN
AKTKPREEQYNSTYRVVSVLTVLHQDWLNGKEYKCKVSNK
ALPAPIEKTISKAKGQPREPQVYTLPPSREEMTKNQVSLT
CLVKGFYPSDIAVEWESNGQPENNYKTTPPVLDSDGSFFL
YSKLTVDKSRWQQGNVFSCSVMHEALHNHYTQKSLSLSPG
K SEQ ID NO: 369 Light chain
MVLQTQVFISLLLWISGAYGDIVMTQSPDSLAVSLGERAT
INCKSSQSLLYTSNNKNYLAWYQQKAGQPPKLLIYWASTR
ESGVPDRFSGSGSGTDFTLTISSLQSEDVAVYYCQQYYST
PQTFGQGTKVEIKRTVAAPSVFIFPPSDEQLKSGTASVVC
LLNNFYPREAKVQWKVDNALQSGNSQESVTEQDSKDSTYS
LSSTLTLSKADYEKHKVYACEVTHQGLSSPVTKSFNRGEC

NOV647

SEQ ID NO: 370 Heavy Chain
MKHLWFFLLLVAAPRWVLSQVQLQESGPRLVKPSQTLSLT
CSVSGGTVRTGDYYWSWIRQPPGKGLEWIGFIHYSGSTYY
NPSLKSRVTISLDTSRNQFSLKLSSVTAADTAVYFCARIY
YDSSGYLHSLKIIDSWGQGTLVTVSSASTKGPSVFPLAPC
SRSTSGGTAALGCLVKDYFPEPVTVSWNSGALTSGVHTFP
AVLQSSGLYSLSSVVTVPSSSLGTQTYICNVNHKPSNTKV
DKRVEPKSCDKTHTCPPCPAPELLGGPSVFLFPPKPKDTL
MISRTPEVTCVVVDVSHEDPEVKFNWYVDGVEVHNAKTKP
REEQYNSTYRVVSVLTVLHQDWLNGKEYKCKVSNKALPAP
IEKTISKAKGQPREPQVYTLPPSREEMTKNQVSLTCLVKG
FYPSDIAVEWESNGQPENNYKTTPPVLDSDGSFFLYSKLT
VDKSRWQQGNVFSCSVMHEALHNHYTQKSLSLSPGK SEQ ID NO: 371 Heavy Chain
MRLPAQLLFLLLLWLPDTTGEIVLTQSPATLSASPGERAT
LSCRASQSVSSNLAWYRQKPGQSPRLLIYGASARATGIPA
RFGGSGSGTEFTLTISSLQSEDFAVYYCQQYNNWPLTFGG
GTKVEIKRTVAAPSVFIFPPSDEQLKSGTASVVCLLNNFY
PREAKVQWKVDNALQSGNSQESVTEQDSKDSTYSLSSTLT
LSKADYEKHKVYACEVTHQGLSSPVTKSFNRGEC

NOV329

SEQ ID NO: 372 Heavy Chain
MDWTWRILFLVAAATGAHSQVQLVQSGTEVKKPGASVKVS
CKASGYTFNKYAMNWVRQAPGQRLEWMGYINADNGNTKYS
QKFRDRVTITRDTSASIVYMELRSLRSEDTAMYYCARDGG
WSTTVNNQPYYYGMDVWGQGTTVTVSSASTKGPSVFPLAP
SSKSTSGGTAALGCLVKDYFPEPVTVSWNSGALTSGVHTF
PAVLQSSGLYSLSSVVTVPSSSLGTQTYICNVNHKPSNTK
VDKRVEPKSCDKTHTCPPCPAPELLGGPSVFLFPPKPKDT
LMISRTPEVTCVVVDVSHEDPEVKFNWYVDGVEVHNAKTK TABLE 2-continued Anti-Polyoma virus Antibodies

```
                      PREEQYNSTYRVVSVLTVLHQDWLNGKEYKCKVSNKALPA
                      PIEKTISKAKGQPREPQVYTLPPSREEMTKNQVSLTCLVK
                      GFYPSDIAVEWESNGQPENNYKTTPPVLDSDGSFFLYSKL
                      TVDKSRWQQGNVFSCSVMHEALHNHYTQKSLSLSPGK

SEQ ID NO: 373 Light  MRLLAQLLFLLLLWLPDTTGEIVLTQSPGTLSLSPGERAT
               chain  LSCRASQFVGSKYMAWYQQKPGQAPRLLIYGASSRATGIP
                      DRFSGSGSGTDFTLTISRLEPEDFAVYYCQQFGSSPPMYA
                      FGQGTKLEIKRTVAAPSVFIFPPSDEQLKSGTASVVCLLN
                      NFYPREAKVQWKVDNALQSGNSQESVTEQDSKDSTYSLSS
                      TLTLSKADYEKHKVYACEVTHQGLSSPVTKSFNRGEC
```

NOV631

```
SEQ ID NO: 374 Heavy  MKHLWFFLLLVAVPRWVLSQVQLQESGPRLVKPSQTLSLT
               Chain  CTVSGGSISSGDYYWSWIRQAPGTGLEWIGFIYNTETTYY
                      SPSLRSRVSMSLDTSKNQFSLKLSSVTAADTAVYYCARER
                      RPSHYDSGGYSLDYWGQGTLVTVSSASTKGPSVFPLAPSS
                      KSTSGGTAALGCLVKDYFPEPVTVSWNSGALTSGVHTFPA
                      VLQSSGLYSLSSVVTVPSSSLGTQTYICNVNHKPSNTKVD
                      KRVEPKSCDKTHTCPPCPAPELLGGPSVFLFPPKPKDTLM
                      ISRTPEVTCVVVDVSHEDPEVKFNWYVDGVEVHNAKTKPR
                      EEQYNSTYRVVSVLTVLHQDWLNGKEYKCKVSNKALPAPI
                      EKTISKAKGQPREPQVYTLPPSREEMTKNQVSLTCLVKGF
                      YPSDIAVEWESNGQPENNYKTTPPVLDSDGSFFLYSKLTV
                      DKSRWQQGNVFSCSVMHEALHNHYTQKSLSLSPGK SEQ ID NO: 375 Light  MEAPAQLLFLLLLWLPDSTGEIVMTQSPATLSVSPGERAT
               chain  LSCRASQSVSSNLAWYQQKPGQAPRLLIYGASTRATGIPA
                      RFSGSGSGTEFTLAISSLQSEDFALYYCQQYNNWPRTFGQ
                      GTKVEIKRTVAAPSVFIFPPSDEQLKSGTASVVCLLNNFY
                      PREAKVQWKVDNALQSGNSQESVTEQDSKDSTYSLSSTLT
                      LSKADYEKHKVYACEVTHQGLSSPVTKSFNRGEC
```

NOV055

```
SEQ ID NO: 376 Heavy  MELGLCWVFLVAILEGVQCEVQLVESGGGLVKPGGSLRLS
               Chain  CAASGFTFSTYSMNWVRQAPGKGLEWVSSISSSGTYTYYA
                      DSVKGRFTISRDNAKDSLYLQMNSLRADDTAVYYCARAPY
                      DYGDYRGGRYFDLWGRGSLVTVSSASTKGPSVFPLAPCSR
                      STSGGTAALGCLVKDYFPEPVTVSWNSGALTSGVHTFPAV
                      LQSSGLYSLSSVVTVPSSSLGTQTYICNVNHKPSNTKVDK
                      RVEPKSCDKTHTCPPCPAPELLGGPSVFLFPPKPKDTLMI
                      SRTPEVTCVVVDVSHEDPEVKFNWYVDGVEVHNAKTKPRE
                      EQYNSTYRVVSVLTVLHQDWLNGKEYKCKVSNKALPAPIE
                      KTISKAKGQPREPQVYTLPPSREEMTKNQVSLTCLVKGFY
                      PSDIAVEWESNGQPENNYKTTPPVLDSDGSFFLYSKLTVD
                      KSRWQQGNVFSCSVMHEALHNHYTQKSLSLSPGK SEQ ID NO: 377 Light  MRLPAQLLFLLLLWLPDTTGEIVMTQSPATLSVSPGERAT
               chain  LSCRASQSVSSKLAWYQQKPGQAPRLLIFGASTRATGIPA
                      RFSGSGSGTEFTLTISSLQSEDFAVYYCQQYNNWPRTFGQ
                      GTKVEIKRTVAAPSVFIFPPSDEQLKSGTASVVCLLNNFY
                      PREAKVQWKVDNALQSGNSQESVTEQDSKDSTYSLSSTLT
                      LSKADYEKHKVYACEVTHQGLSSPVTKSFNRGEC
```

NOV224

```
SEQ ID NO: 378 Heavy  MDTLCSTLLLLTIPSWVLSQITLKESGPTLVKPTQTLMLT
               Chain  CTFSGFSLSTSGVGVGWIRQPPGKALEWLAFIYWNTDKRY
                      NPSLKTRLTITKDTSKTQVVLTMTNLDPVDTGTYYCVHHD
                      GYLAEYFNHWGQGTLVTVSSASTKGPSVFPLAPSSKSTSG
                      GTAALGCLVKDYFPEPVTVSWNSGALTSGVHTFPAVLQSS
                      GLYSLSSVVTVPSSSLGTQTYICNVNHKPSNTKVDKRVEP
                      KSCDKTHTCPPCPAPELLGGPSVFLFPPKPKDTLMISRTP
                      EVTCVVVDVSHEDPEVKFNWYVDGVEVHNAKTKPREEQYN
                      STYRVVSVLTVLHQDWLNGKEYKCKVSNKALPAPIEKTIS
                      KAKGQPREPQVYTLPPSREEMTKNQVSLTCLVKGFYPSDI
                      AVEWESNGQPENNYKTTPPVLDSDGSFFLYSKLTVDKSRW
                      QQGNVFSCSVMHEALHNHYTQKSLSLSPGK SEQ ID NO: 379 Light  MALTPLLLTLLIHCTGSWAQSVLTQPPSVSAAPGQRVTIS
               chain  CSGTTSNIGNYYVSWYQEVPGTAPKLLIYDNVKRPSGIPD
                      RFSASKSGTSATLGISGLQTGDEADYYCGTWDGRLSAWVF
                      GGGTKLTVLGQPKAAPSVTLFPPSSEELQANKATLVCLIS
                      DFYPGAVTVAWKADSSPVKAGVETTTPSKQSNNKYAASSY
                      LSLTPEQWKSHRSYSCQVTHEGSTVEKTVAPTECS
```

TABLE 2-continued

Anti-Polyoma virus Antibodies

NOV998

SEQ ID NO: 380 Heavy Chain
```
MKHLWFFLLLVAAPRWVLSQVQLQQWGAGLLRPSETLSLT
CGVSGGALSGYIWSWIRQPPGKGLEWIGEINHSGTTNYSP
SLKSRVTISVDTSKNHFSLRLSSVTAADSAMYYCARGGVR
NWQLGPALDFWGQGTLVTVSSASTKGPSVFPLAPSSKSTS
GGTAALGCLVKDYFPEPVTVSWNSGALTSGVHTFPAVLQS
SGLYSLSSVVTVPSSSLGTQTYICNVNHKPSNTKVDKRVE
PKSCDKTHTCPPCPAPELLGGPSVFLFPPKPKDTLMISRT
PEVTCVVVDVSHEDPEVKFNWYVDGVEVHNAKTKPREEQY
NSTYRVVSVLTVLHQDWLNGKEYKCKVSNKALPAPIEKTI
SKAKGQPREPQVYTLPPSREEMTKNQVSLTCLVKGFYPSD
IAVEWESNGQPENNYKTTPPVLDSDGSFFLYSKLTVDKSR
WQQGNVFSCSVMHEALHNHYTQKSLSLSPGK
```

SEQ ID NO: 381 Light chain
```
MRLPAQLLGLLLLWLPGARCAIQLTQSPSSLSASVGDRVT
ITCRASQDISSFLAWFQQKPGRAPKLLLYAASTLQSGVPS
RFSGSGSGTDFSLTIGSLQPEDFATYYCQSLNNYPRSFTF
GPGTKVDIKRTVAAPSVFIFPPSDEQLKSGTASVVCLLNN
FYPREAKVQWKVDNALQSGNSQESVTEQDSKDSTYSLSST
LTLSKADYEKHKVYACEVTHQGLSSPVTKSFNRGEC
```

NOV484

SEQ ID NO: 382 Heavy Chain
```
MKHLWFFLLLVAAPRWVLSQVQLQESGPGLVKPSETLSLT
CSVSGDSMASDYWSWIRQPPGKGLEWIGYVSYSGTTYYIP
SLKSRVTISLDRSRTQFSLKVTSVTSADTAVYYCARGRRG
HSSGGWGIEFFHQWGQGTLVTVSPASTKGPSVFPLAPSSK
STSGGTAALGCLVKDYFPEPVTVSWNSGALTSGVHTFPAV
LQSSGLYSLRSVVTVPSSSLGTQTYICNVNHKPSNTKVDK
RVEPKSCDKTHTCPPCPAPELLGGPSVFLFPPKPKDTLMI
SRTPEVTCVVVDVSHEDPEVKFNWYVDGVEVHNAKTKPRE
EQYNSTYRVVSVLTVLHQDWLNGKEYKCKVSNKALPAPIE
KTISKAKGQPREPQVYTLPPSREEMTKNQVSLTCLVKGFY
PSDIAVEWESNGQPENNYKTTPPVLDSDGSFFLYSKLTVD
KSRWQQGNVFSCSVMHEALHNHYTQKSLSLSPGK
```

SEQ ID NO: 383 Light chain
```
MEAPAQLLFLLLLWLPDTTGEIVMTQSPPTLSVSPGERAT
LSCRASQSVSSDLAWYQQQAGQAPRLLIYDASTRATGIPP
RFSGSGSGTEFTLTISSLQSEDFAVYYCQQYNKWVTFGGG
TKVEIKRTVAAPSVFIFPPSDEQLKSGTASVVCLLNNFYP
REAKVQWKVDNALQSGNSQESVTEQDSKDSTYSLSSTLTL
SKADYEKHKVYACEVTHQGLSSPVTKSFNRGEC
```

NOV178

SEQ ID NO: 384 Heavy Chain
```
MDWTWRILFLVAAATGAHSQVQLVQSGAEVMRPGASLKVS
CKASGYSFTMYSIHWVRQAPGHRLEWMGWINAANGNTIYS
QNFQGRVTISRDTSATTAHMELGSLRSEDTAVYFCARGPI
PYYYDHSGPFDYWGQGTLVTVSSASTKGPSVFPLAPCSRS
TSGGTAALGCLVKDYFPEPVTVSWNSGALTSGVHTFPAVL
QSSGLYSLSSVVTVPSSSLGTQTYICNVNHKPSNTKVDKR
VEPKSCDKTHTCPPCPAPELLGGPSVFLFPPKPKDTLMIS
RTPEVTCVVVDVSHEDPEVKFNWYVDGVEVHNAKTKPREE
QYNSTYRVVSVLTVLHQDWLNGKEYKCKVSNKALPAPIEK
TISKAKGQPREPQVYTLPPSREEMTKNQVSLTCLVKGFYP
SDIAVEWESNGQPENNYKTTPPVLDSDGSFFLYSKLTVDK
SRWQQGNVFSCSVMHEALHNHYTQKSLSLSPGK
```

SEQ ID NO: 385 Light chain
```
MEAPAQLLFLLLLWLPDTTGEIVMTQSPPTLSVSPGERAI
LSCRASQSVSSDLAWYQQQAGQAPRLLIYGASTRATGIPP
RFSGSGSGTEFTLTISSLQSEDFAVYYCQQYNKWVTFGGG
TKVEIKRTVAAPSVFIFPPSDEQLKSGTASVVCLLNNFYP
REAKVQWKVDNALQSGNSQESVTEQDSKDSTYSLSSTLTL
SKADYEKHKVYACEVTHQGLSSPVTKSFNRGEC
```

Other antibodies of the present disclosure include those where the amino acids or nucleic acids encoding the amino acids have been mutated; yet have at least 60, 70, 80, 90 or 95 percent identity to the sequences described in Table 2. In some aspects, it includes mutant amino acid sequences wherein no more than 1, 2, 3, 4 or 5 amino acids have been mutated in the variable regions when compared with the variable regions depicted in the sequence described in Table 2, while retaining substantially the same therapeutic activity.

Since each of these antibodies can bind to VP1, the VH, VL, full length light chain, and full length heavy chain sequences (amino acid sequences and the nucleotide sequences encoding the amino acid sequences) can be "mixed and matched" to create other VP1-binding antibodies. Such "mixed and matched" VP1-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise, a full length light chain sequence from a particular full length heavy chain/full length light chain pairing should be replaced with a structurally similar full length light chain sequence. Accordingly, in one aspect, the disclosure provides for an isolated monoclonal antibody or antigen binding region thereof having: a heavy chain variable region comprising an amino acid sequence selected from the group consisting of SEQ ID NO:18, 50, 82, 114, 146, 178, 210, 242 and 274 (Table 2); and a light chain variable region comprising an amino acid sequence selected from the group consisting of SEQ ID NO: 34, 66, 98, 130, 162, 194, 226, 258 and 290 (Table 2); wherein the antibody specifically binds to BK or JC virus.

In another aspect, the disclosure provides (i) an isolated monoclonal antibody having: a full length heavy chain comprising an amino acid sequence selected from Table 2 and a full length light chain comprising an amino acid sequence selected from Table 2, with the sequences optimized for expression in a mammalian cell. In similar aspect, the disclosure provides (i) an isolated monoclonal antibody having: a full length heavy chain comprising an amino acid sequence that has been optimized for expression in a mammalian cell, selected from the group consisting of SEQ ID NOs: 20, 52, 84, 116, 148, 180, 212, 244 and 276 (Table 2) and a full length light chain comprising an amino acid sequence that has been optimized for expression in a mammalian cell, selected from the group consisting of SEQ ID NOs: 36, 68, 100, 132, 164, 196, 228, 260 and 292 (Table 2) or (ii) a functional protein comprising an antigen binding portion thereof.

In another aspect, the present disclosure provides BK or JC virus binding antibodies that comprise the heavy chain and light chain CDR1s, CDR2s and CDR3s as described in Table 2, or combinations thereof. The amino acid sequences of the VH CDR1s of the antibodies are shown in SEQ ID NOs: 9, 41, 73, 105, 137, 169, 201, 233 and 265. The amino acid sequences of the VH CDR2s of the antibodies and are shown in SEQ ID NOs: 10, 42, 74, 106, 138, 170, 202, 234 and 266. The amino acid sequences of the VH CDR3s of the antibodies are shown in SEQ ID NOs: 11, 43, 75, 107, 139, 171, 203, 235 and 267. The amino acid sequences of the VL CDR1s of the antibodies are shown in SEQ ID NOs: 25, 57, 89, 121, 153, 185, 217, 249 and 281. The amino acid sequences of the VL CDR2s of the antibodies are shown in SEQ ID NOs 26, 58, 90, 122, 154, 186, 218, 250 and 282. The amino acid sequences of the VL CDR3s of the antibodies are shown in SEQ ID NOs: 27, 59, 91, 123, 155, 187, 219, 251 and 283.

Given that each of these antibodies can bind to BK or JC virus and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody must contain a VH CDR1, 2 and 3 and a VL CDR1, 2 and 3 to create other VP1-binding binding molecules. Such "mixed and matched" VP1-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure.

Accordingly, the present disclosure provides an isolated monoclonal antibody or antigen binding region thereof comprising a heavy chain CDR1 comprising an amino acid sequence selected from the group consisting of SEQ ID NOs: 9, 41, 73, 105, 137, 169, 201, 233 and 265; a heavy chain CDR2 comprising an amino acid sequence selected from the group consisting of SEQ ID NOs: 10, 42, 74, 106, 138, 170, 202, 234 and 266; a heavy chain CDR3 comprising an amino acid sequence selected from the group consisting of SEQ ID NOs:11, 43, 75, 107, 139, 171, 203, 235 and 267; a light chain CDR1 comprising an amino acid sequence selected from the group consisting of SEQ ID NOs: 25, 57, 89, 121, 153, 185, 217, 249 and 281; a light chain CDR2 comprising an amino acid sequence selected from the group consisting of SEQ ID NOs: 26, 58, 90, 122, 154, 186, 218, 250 and 282; and a light chain CDR3 comprising an amino acid sequence selected from the group consisting of SEQ ID NOs:27, 59, 91, 123, 155, 187, 219, 251 and 283; wherein the antibody specifically binds to BK or JC virus.

In certain aspects, an antibody that specifically binds to BK or JC virus is an antibody or antibody fragment (e.g., antigen binding fragment) that is described in Table 2.

1. Identification of Antibodies

The present disclosure provides antibodies and antibody fragments (e.g., antigen binding fragments) that bind to BK or JC virus. In certain aspects the antibodies and antibody fragments can bind to the same epitope within all four BKV serotypes and/or JCV.

The present disclosure also provides antibodies and antibody fragments (e.g., antigen binding fragments) that bind to the same epitope as do the anti-BK or JC antibodies described in Table 2. Additional antibodies and antibody fragments (e.g., antigen binding fragments) can therefore be identified based on their ability to cross-compete (e.g., to competitively inhibit the binding of, in a statistically significant manner) with other antibodies in binding assays. The ability of a test antibody to inhibit the binding of antibodies and antibody fragments (e.g., antigen binding fragments) of the present disclosure to BK or JC virus demonstrates that the test antibody can compete with that antibody or antibody fragment (e.g., antigen binding fragments) for binding to BK or JC virus; such an antibody may, according to non-limiting theory, bind to the same or a related (e.g., a structurally similar or spatially proximal) epitope on BK or JC virus as the antibody or antibody fragment (e.g., antigen binding fragments) with which it competes. In a certain aspect, the antibody that binds to the same epitope on BK or JC virus as the antibodies or antibody fragments (e.g., antigen binding fragments) of the present disclosure is a human or humanized monoclonal antibody. Such human or humanized monoclonal antibodies can be prepared and isolated as described herein.

2. Further Alteration of the Framework of Fc Region

The present disclosure disclosed specific anti-BK or JC virus antibodies. These antibodies comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Can et al.

In addition or alternative to modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen binding fragment thereof of the present disclosure are replaced by one or more allotypic amino acid residues, for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγR1, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In order to minimize the ADCC activity of an antibody, specific mutations in the Fc region result in "Fc silent" antibodies that have minimal interaction with effector cells. In general, the "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181: 6664-69) see also Heusser et al., WO2012065950. Examples of silent Fc lgG1 antibodies are the LALA mutant comprising L234A and L235A mutation in the lgG1 Fc amino acid sequence. Another example of a silent lgG1 antibody is the DAPA (D265A, P329A) mutation (U.S. Pat. No. 6,737,056). Another silent lgG1 antibody comprises the N297A mutation, which results in aglycosylated/non-glycosylated antibodies.

Fc silent antibodies result in no or low ADCC activity, meaning that an Fc silent antibody exhibits an ADCC activity that is below 50% specific cell lysis (low ADCC activity), or that is below 1% specific cell lysis (no ADCC activity).

3. Production of the Antibodies

Anti-BK or JC virus antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 19, 51, 83, 115, 147, 179, 211, 243 and 275. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 35, 67, 99, 131, 163, 195, 227, 259 and 291.

In some aspects, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 21, 53, 85, 117, 149, 181, 213, 245 and 277. In some aspects, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 37, 69, 101, 133, 165, 197, 229, 261 and 293.

The polynucleotides of the present disclosure can encode only the variable region sequence of an anti-BK or JC virus antibody. They can also encode both a variable region and a constant region of the antibody. Some of the polynucleotide sequences encode a polypeptide that comprises variable regions of both the heavy chain and the light chain of one of an exemplified anti-BK or JC virus antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence encoding an anti-BK or JC virus antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the present disclosure are expression vectors and host cells for producing the anti-BK or JC virus antibodies described above. Various expression vectors can be employed to express the polynucleotides encoding the anti-BK or JC virus antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-BK or JC virus polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-BK or JC virus antibody chain or fragment. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of an anti-VP1 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-BK antibody sequences. More often, the inserted anti-BK antibody sequences are linked to a signal sequences before inclusion in the vector. Vectors to be used to receive sequences encoding anti-BK antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-BK or JC antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-VP1 polypeptides. Insect cells in combination with baculovirus vectors can also be used.

In other aspects, mammalian host cells are used to express and produce the anti-VP1 polypeptides of the present disclosure. For example, they can be either a hybridoma cell line expressing endogenous immunoglobulin genes (e.g., the myeloma hybridoma clones as described in the Examples) or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-BK or JC virus antibody chains or binding fragments can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments) of the present disclosure are useful in a variety of applications including, but not limited to, polyoma viral infection and disease. In certain aspects, the antibodies, antibody fragments (e.g., antigen binding fragments), and are useful for neutralizing BKV or JCV infection and the prevention or treatment of BK virus nephropathy, for example, BKVAN). The methods of use can be in vitro, ex vivo, or in vivo methods.

In one aspect, the antibodies, antibody fragments (e.g., antigen binding fragments), are useful for detecting the presence of BKV in a biological sample. The term "detecting" as used herein encompasses quantitative or qualitative detection. In certain aspects, a biological sample comprises a cell or tissue. In certain aspects, such tissues include normal and/or cancerous tissues that express BKV at higher levels relative to other tissues.

In one aspect, the present disclosure provides a method of detecting the presence of BK or JC virus in a biological sample. In certain aspects, the method comprises contacting the biological sample with an anti-BK or JC virus antibody under conditions permissive for binding of the antibody to the antigen, and detecting whether a complex is formed between the antibody and the antigen. The biological sample can include, without limitation, urine or blood samples.

Also included is a method of diagnosing a disorder associated with expression of BK or JC virus. In certain aspects, the method comprises contacting a test cell with an anti-BK or JC virus antibody; determining the level of expression (either quantitatively or qualitatively) of BK or JC virus in the test cell by detecting binding of the antibody to the BK or JC virus; and comparing the level of infection in the test cell with the level of infection of BK or JC virus in a control cell (e.g., a normal cell of the same tissue origin as the test cell or a non-virus infected cell), wherein a higher level of presence of BK or JC virus in the test cell as compared to the control cell indicates the presence of a disorder associated with infection with BK or JC virus. In certain aspects, the test cell is obtained from an individual suspected of having a BK or JC virus infection.

In certain aspects, a method of diagnosis or detection, such as those described above, comprises detecting binding of an BK or JC virus antibody to a virus infected cell. An exemplary assay for detecting binding of an anti-BK or JC virus antibody to a BK or JC virus infected cell is a "FACS" assay.

Certain other methods can be used to detect binding of anti-BK or JC virus antibodies. Such methods include, but are not limited to, antigen-binding assays that are well known in the art, such as Western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain aspects, anti-BK or JC virus antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain aspects, anti-BK or JC virus antibodies are immobilized on an insoluble matrix Immobilization entails separating the anti-BK or JC virus antibody from any BKV or JCV proteins that remains free in solution. This conventionally is accomplished by either insolubilizing the anti-BK or JC antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-BK or JC antibody after formation of a complex between the anti-BK or JC antibody and BKV or JCV protein, e.g., by immunoprecipitation.

Any of the above aspects of diagnosis or detection can be carried out using an anti-BK or JC antibody of the present disclosure in place of or in addition to another anti-BK or JC antibody.

In one aspect, the disclosure provides for a method of treating, reducing the likelihood of or ameliorating a disease comprising administering the antibodies, antibody fragments (e.g., antigen binding fragments), to a patient, thereby treating the disease. In certain aspects, the disease treated with the antibodies, antibody fragments (e.g., antigen binding fragments), is a BK viral or JC viral infection. Examples of BKV and JCV diseases which can be treated and/or prevented include, but are not limited to, nephropathy, hemorrhagic cystitis, Progressive Multifocal Leukoencephalopathy (PML), interstitial kidney disease, ureteral stenosis, granule cell neuronopathy (GCN), vasculitis, colitis, retinitis, meningitis, and immune reconstitution inflammatory syndrome (IRIS). In certain aspects, the infection is characterized by BKV or JCV expressing cells to which the anti-BK or JC antibodies, antibody fragments (e.g., antigen binding fragments) can specifically bind.

The present disclosure provides for methods of treating BK viral infection and BKVAN comprising administering a therapeutically effective amount of the antibodies, antibody fragments (e.g., antigen binding fragments). In certain aspects, the subject is a human.

In certain aspects, the method of reducing BK viral infection comprises administering to a subject a therapeutically effective amount of antibodies or antibody fragments (e.g., antigen binding fragments). In certain aspects, the subject is a human. In certain aspects, the subject is immunosuppressed. For immunosuppressed subjects, the amount of immunosuppression can be increased or decreased due to the therapeutic effects of the anti-BK antibodies.

In certain aspects, the transplanted tissue is infected with BK virus to which the anti-BK antibody binds. As the incidence of BK infection in the general population is high, there is a high probability that in the case of kidney transplantation, the patient accepting the kidney is BK virus positive or the donor providing the kidney is BK virus positive or both are BK virus positive. In order to prevent BKVAN, anti-BK antibodies can be administered to the kidney transplant recipient, before and/or after the kidney transplant procedure, depending on the seropositivity of the kidney donor or transplant recipient. In another aspect, the anti-BK antibodies can be administered to the patient when virus is detected in the urine (viruria), or when virus is detected in the blood (viremia).

For the treatment of BK or JC viral infection, the appropriate dosage of the antibodies, or antibody fragments (e.g., antigen binding fragments), depend on various factors, such as the type of infection to be treated, the severity and course of the infection, the responsiveness of the infection, the generation of viral resistance to therapy, previous therapy, patient's clinical history, and so on. The antibody can be administered one time or over a series of treatments lasting from several days to several months, or until a cure is effected or a diminution of the infection is achieved (e.g., reduction in viruria or viral damage to the kidney). Optimal dosing schedules can be calculated from measurements of drug accumulation in the body of the patient and will vary depending on the relative potency of an individual antibody or antibody fragment (e.g., antigen binding fragment). In certain aspects, dosage is from 0.01 mg to 10 mg (e.g., 0.01 mg, 0.05 mg, 0.1 mg, 0.5 mg, 1 mg, 2 mg, 3 mg, 4 mg, 5 mg, 7 mg, 8 mg, 9 mg, or 10 mg) per kg of body weight, and can be given once or more daily, weekly, monthly or yearly. In certain aspects, the antibody or antibody fragment (e.g., antigen binding fragment), of the present disclosure is given once every two weeks or once every three weeks. The treating physician can estimate repetition rates for dosing based on measured half-life and concentrations of the antibody in bodily fluids or tissues.

Combination Therapy

In certain instances, the antibody or antibody fragment (e.g., antigen binding fragment), of the present disclosure is combined with other therapeutic agents, such as other antiviral agents, anti-allergic agents, anti-nausea agents (or anti-emetics), pain relievers, cytoprotective agents, immunosuppressants and combinations thereof.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or infection described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating BKV or JCV infection by administering to a subject in need thereof an antibody in together with immunosuppressant therapies. The anti-BK or JC antibodies will act prophylactically to neutralize BKV or JCV primary infection or viral reactivation resulting from the immunosuppressant therapy prior to or post-transplantation. Examples of immunosuppressant therapy include, but are not limited to; a monophosphate dehydrogenase inhibitor, a purine synthesis inhibitor, a calcineurin inhibitor or an mTOR inhibitor. Specific examples of immunosuppressive therapeutics include but are not limited to; mycophenolate mofetil (MMF), mycophenolate sodium, azathioprine, tacrolimus, sirolimus and cyclosporine.

Pharmaceutical Compositions

To prepare pharmaceutical or sterile compositions including anti-BK or JC antibodies, the antibodies of the present disclosure are mixed with a pharmaceutically acceptable carrier or excipient. The compositions can additionally contain one or more other therapeutic agents that are suitable for neutralizing BKV or JCV infection.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In a specific aspect, the anti-BK or JC antibody is a lyophilisate in a vial containing the antibody. The lyophilisate can be reconstituted with water or a pharmaceutical carrier suitable for injection. For subsequent intravenous administration, the obtained solution will usually be further diluted into a carrier solution.

The antibodies disclosed herein are useful in the neutralization of BKV or JCV in tissue transplant patients who can be immunosuppressed, so a pharmaceutical carrier of sucrose and human albumin as used previously in bone marrow transplant patients receiving CytoGam® can be used (DeRienzo et al. Pharmacotherapy 2000; 20:1175-8). Alternatively, the anti-BK or JC antibodies can be introduced into transplant patients via a pharmaceutical carrier as described for another anti-viral antibody, Synagis®, as described in WO2003/105894. In this publication, the pharmaceutical carrier was comprised of histidine and/or glycine, a saccharide (e.g. sucrose) and a polyol (e.g. polysorbate).

Selecting an administration regimen for a therapeutic depends on several factors, including the severity of the infection, the level of symptoms, and the accessibility of the target cells in the biological matrix. In certain aspects, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., infusion reactions.

Actual dosage levels of the active ingredients in the pharmaceutical compositions with the anti-BK antibodies can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the neutralizing activity of the antibodies, the route of administration, the time of administration, the half-life of the antibody in the patient, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion, or by doses at intervals of, e.g., one day, one week, or 1-7 times per week. Doses can be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the antibodies described herein, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof can be calculated using the patient's weight in kilograms (kg) multiplied by the dose to be administered in mg/kg.

Doses of the antibodies then can be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure can also be administered via one or more routes of administration using one or more of a variety of methods known in the art. As will be appreciated by the skilled artisan, the route and/or mode of administration will vary depending upon the desired results. Selected routes of administration for the antibodies include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically. In one aspect, the antibodies of the present disclosure are administered by infusion. In another aspect, the antibodies are administered subcutaneously.

If the antibodies of the present disclosure are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the antibodies (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly (methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more antibodies of the present disclosure. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rd. Bioact. Mater. 24:853-854, 1997; and Lam et al., Proc. Int'l. Symp. Control Rd. Bioact. Mater. 24:759-760, 1997, each of which is incorporated herein by reference in their entirety.

If the antibodies of the disclosure are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the antibodies are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., an immunosuppressant, a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the anti-BK antibodies may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the anti-VP1 antibodies of the present disclosure. The two or more therapies may be administered within one same patient visit.

In certain aspects, anti-BK antibodies can be formulated to ensure proper distribution in vivo. For example, the blood-brain barrier (BBB) excludes many highly hydrophilic compounds. To ensure that the anti-BK antibodies cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The present disclosure provides protocols for the administration of pharmaceutical composition comprising antibodies alone or in combination with other therapies to a subject in need thereof. The combination therapies (e.g., prophylactic or therapeutic agents) can be administered concomitantly or sequentially to a subject. The therapy (e.g., prophylactic or therapeutic agents) of the combination therapies can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the antibodies can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various aspects, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other aspects, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of Anti-BK or JC Virus Antibodies

B cells expressing anti-BKV and/or anti-JCV antibodies were lysed and the VH (heavy) and VL (light) chains were amplified by RT-PCR and subsequently sequenced and analyzed to identify critical post translational modification (PTM) sites. Plasmids of the VH and VL chains were then transfected in a CHO mammalian cell line in an IgG1 backbone vector for expression of the full IgG1 antibodies.

Example 2: Binding of Anti-BKV Antibodies to VLPs (ELISA)

The binding of antibodies to VLPs were analyzed by ELISA. Briefly, Nunc MaxiSorp 384-well plates (Thermo Scientific) were coated with 100 ng/well BKV VLPs to BK serotype I (ST1) or serotype IV (ST4) overnight. Antibodies were serially diluted in PBS with 0.5% BSA and allowed to bind antigen-coated plates for 2 hours. Plates were washed with PBS and then incubated with secondary antibody (HRP-conjugated goat anti-human IgG, Southern Biotech #2040-01) diluted 1:6000 in 0.5% BSA in PBS for 1 hour. Plates were washed with PBS and tetramethylbenzidine (TMB) microwell peroxidase substrate (SeramunBlau Fast, Seramun, Germany) was used to develop the reactions. The results of ELISA binding can be seen in FIG. 1. For example, the antibody NOV530 bound to both BKV ST1 and BKV ST4. Antibody NOV638 bound only to BKV ST1.

Example 3: Neutralization of Viral Infection Anti-BKV Antibodies

Infectious BKV serotype I (ST1) and chimeric viruses representing serotype II (ST2), III (ST3), and IV (ST4) were pre-incubated with purified antibodies for 1 hour to allow for binding and neutralization. Primary renal proximal tubule epithelial (RPTE) cells (ATCC, cat #PCS-400-010) were then exposed to the virus-antibody mixture for 4 hours, replaced with fresh medium, and incubated for 48 hours to allow for viral entry and gene expression. Cells were fixed with 4% paraformaldehyde and analyzed by immunofluorescence to detect TAg expression (Calbiochem DP02, pAb416 mouse anti-SV40 TAg antibody). The immunofluorescence was analyzed by high content image analysis using the Cellomics ArrayScan® VTI HCS Reader to quantify the percent of BKV-infected cells (TAg-positive, DAP1-positive), with data presented as percent inhibition of infection relative to untreated control wells. Data are presented as EC50, the concentration of antibody at which virus infection is neutralized by 50%, relative to untreated control wells.

Physiologically, antibodies exert several functions which help inhibit a progressing pathogenic reaction, one of which is to directly block the ability of a virus to bind and/or enter its target cell. These "neutralizing" antibodies typically represent only a subset of antigen-binding Ig. Most of the monoclonal IgG anti-BKV antibodies disclosed herein were able to neutralize at least BKV ST1 in a primary renal cell infection assay, while several were also able to neutralize additional BKV subtypes and/or the related JC virus (FIG. 1). For example, antibody NOV638 was able to bind and neutralize BKV ST1, while antibody NOV530 was able to bind and neutralize all four serotypes of BK virus and also showed a sub-nanomolar EC50 of JCV (FIG. 1).

Example 4: BK Virus and Virus-Like Particle (VLP) Generation

Genomic clones of BKV ST1 were obtained from ATCC (pBR322-BKV MM, cat #45026; pBR322-BKV Dunlop, cat #45025). Infectious genomic clones of chimeric viruses for ST2, ST3 and ST4 were generated using the cloning strategy described previously (Broekema et al, Virology 2010 407: 368-373). Briefly, unique restriction sites (SacII, PmlI) were introduced into BKV serotype I genomes flanking the VP1-VP2-VP3 coding region using site-directed mutagenesis. The coding region for VP1 from ST2 isolate SB (GenBank Accession CAA79596.1), serotype III isolate AS (GenBank Accession AAA46882.1) and ST4 isolate ITA-4 (GenBank Accession BAF75132) were synthesized in the context of VP2/VP3 coding region from the ST1 isolates (Genewiz, La Jolla, Calif.), such that the synthesized fragments encompassed the SacII-PmlI region to be used for swap combinations as described in Broekema et al., supra. The resulting chimeric genomic clones were then used to generate high titer infectious viral stocks in primary renal proximal tubule epithelial (RPTE) cells (ATCC, cat #PCS-400-010) as previously described (Abend et al, J. Virology 2007 81:272-279).

VLPs representing each of the four BKV serotypes were generated by expression of VP1 in Sf9 insect cells and extracted from frozen cell pellets from 1 L cultures by microtip sonication (3×45 second pulses, rest 5 min between pulses on ice), isolation by pelleting VLPs through a 20% sucrose cushion (116,000 g for 2.5 hours), and purification by anion exchange with a 5 ml GE HiTrap Q HP column (GE Healthcare, Pittsburgh, Pa.) followed by purification using a 10 ml Capto™ Core700 (GE Healthcare, Pittsburgh, Pa.) resin-based size exclusion column, and finally purification on a GE Sephacryl S500 26/60 (GE Healthcare, Pittsburgh, Pa.) size exclusion column. The prepared VLPs were used in ELISA and SET based binding assays.

Example 5: Affinity Measurements of Anti-BK Antibodies (SET Assay)

Solution equilibration titration (SET) assay was used to determine the interaction affinities ($K_d$) of antibodies with BKV VLPs from all four serotypes. Antibodies were assayed at 1 pM concentration (constant), VLPs were serially diluted from a starting concentration of 10 nM. Antibody:VLP solution was incubated overnight, then assayed for unbound antibody using an MSD array plate (Meso Scale Discovery Cat #L21XA, Rockville Md.) coated with VLPs. The $K_d$ was determined by fitting the plot with a 1:1 fit model (according to Piehler et al. J. Immunol. Methods. 1997; 201(2):189-206).

Sample curve set used for affinity determination via SET of an anti-BKV monoclonal IgG (clone NOV581) against VLPs of the BKV ST1 is shown in FIG. 2A. The lower curve is a 4-parameter fitting of a $K_d$-controlled curve (based on the low concentration of the antibody NOV581), while the upper curve is a fitting of a stoichiometry-controlled curve (higher constant antibody concentration for estimating the effective ligand concentration). Signal strengths were normalized to initial conditions without BKV VLPs in solution ("100% free antibody").

In FIG. 2 B, the binding affinity was determined of cross-neutralizing monoclonal anti-BKV IgG antibodies against BKV virus-like particles (VLPs). All antibodies tested had $K_d$ values below 50 pM against BKV ST1. In this assay, antibody NOV581 had significant affinity to BKV serotypes 1, 2 and 3, but not 4. In contrast, antibody NOV530 had significant affinity to all four serotypes (FIG. 2B).

Example 6: Cryo Electron Microscopy

Figure 3A:
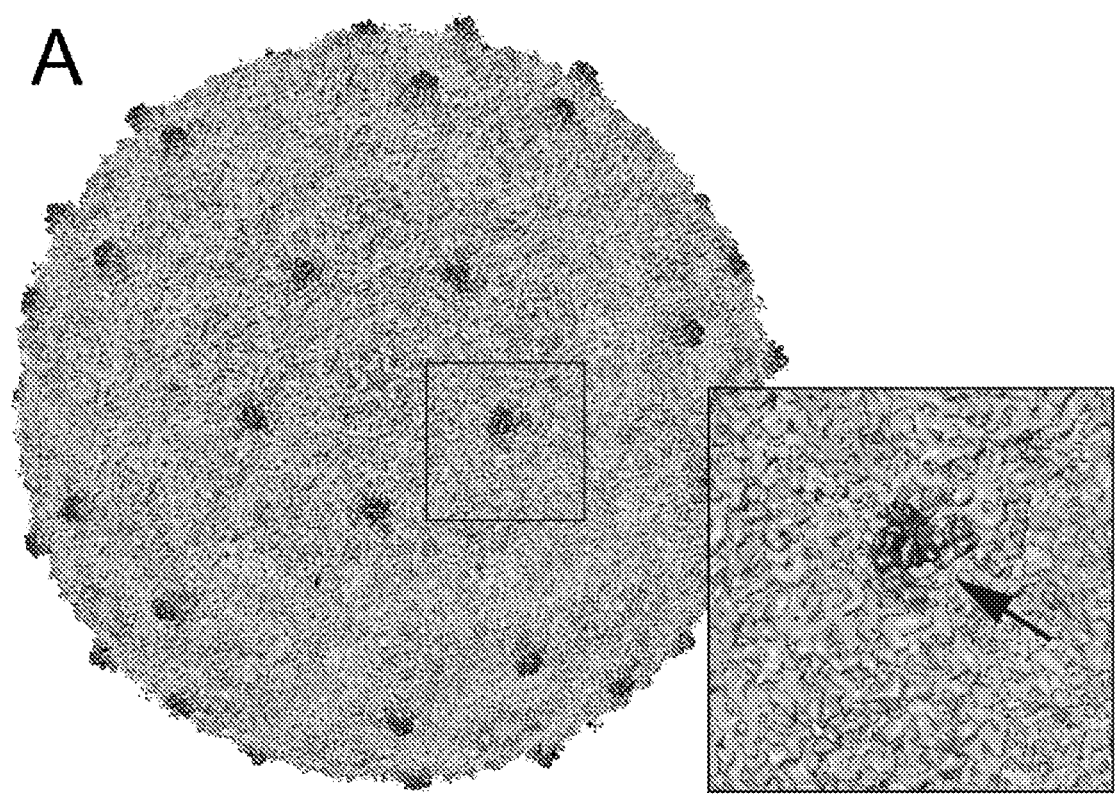
FIG. 3A shows cyro-electron microscopy structure of the interaction between BKV and a cross-neutralizing antibody. It is a 4.24 Å-resolution EM map of BKV ST1 VLP in complex with an scFv of the NOV530 polyomavirus cross-neutralizing antibody. Bound antibody fragments (marked area, black arrow) appear around the viral capsid at the junctions between capsid pentamers. Inset: magnified view of the single scFv bound to its epitope.
Figure 3B:
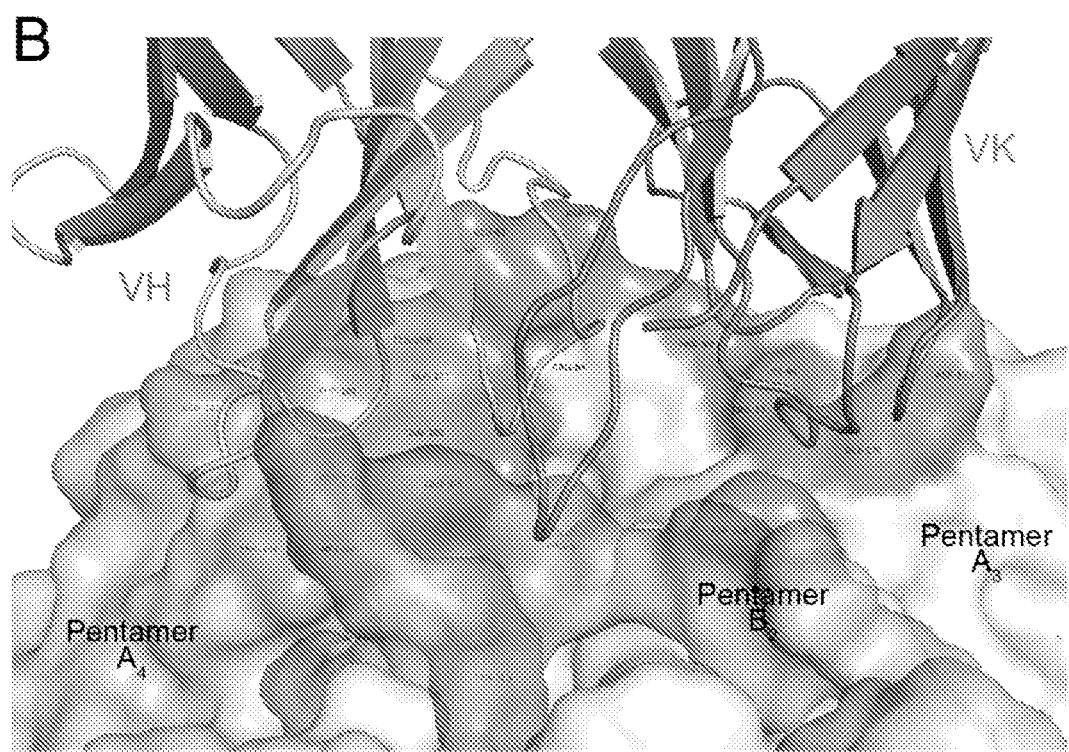
FIG. 3B is a surface and ribbon visualization of the virus-like particle and antibody chains, respectively, of density map-fitted structure models comprising the quaternary viral epitope for NOV530. Individual VP1 monomers from the VLP capsid are labeled to represent their geometric orientation within their respective pentamers. Adjacent pentamers contributing to the epitope are labelled "Pentamer A" (VP1 chains) and "Pentamer B." The VH, heavy chain variable domain and the VK, kappa light chain variable domain are respectively labeled.
Figure 3C:
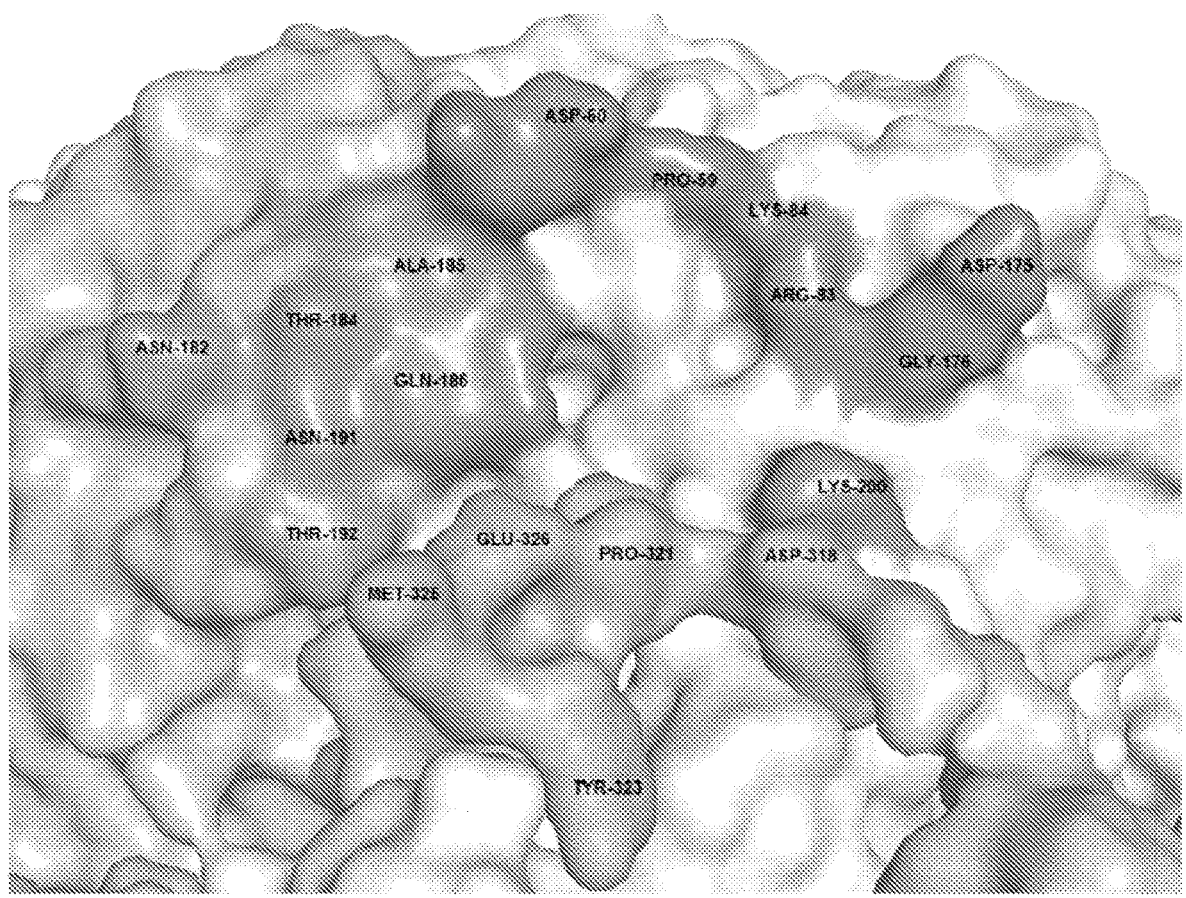
FIG. 3C is an enlargement of FIG. 3B highlighting the critical contact residues.

To understand the mechanism by which the isolated cross-neutralizing antibodies effectively inhibit infection by multiple polyomavirus strains, we performed cryo-electron microscopy (cryoEM) on BKV ST1 VLPs complexed with a single-chain variable fragment (scFv) format of the cross-neutralizing IgG NOV530, and obtained a class-averaged density map at a resolution of 4.24 Å (FIG. 3A). We were able to model the capsid structure of the VLP, including the interlocking pentameric subunits joined together via the C-termini of individual VP1 monomers. Surprisingly, this quaternary structure forms the basis for the complex viral epitope bound by NOV530 (FIG. 3B-C), with three VP1 subunits contributing amino acid residues. In total, 20 viral residues are predicted to be within 5 Å of the antibody; these residues are highly conserved across polyomavirus species, with 3 showing conservative homology and the remaining 17 identical in JCV (FIGS. 3D-F). Interacting positions from the antibody are spread throughout the heavy and light chains, with contributions from both germline-encoded (CDR1 and CDR2) and somatically recombined (CDR3) loops (FIGS. 3G-H). Identifying the complex binding site of NOV530 to the BKV capsid protein would have been impossible with any other method due to its quaternary structural requirement. This binding modality raises additional interesting questions about the mechanism of viral neutralization by NOV530; for example, it is possible that the antibody locks together capsid subunits, thereby blocking viral uncoating processes post-entry. Potential escape mutations may occur only at the cost of reduced virion stability. Indeed, mutations to three amino acid residues within the NOV530 epitope (E61, R64, and R83) have previously been reported to drastically reduce viral fitness, likely due to their effect on receptor binding and capsid structural integrity (Dugan A. S. et al., Identification of amino acid residues in BK virus VP1 that are critical for viability and growth. J Virol 81, 11798-11808 (2007)).

CryoEM Methodologies

BKV ST1 VLPs were incubated with the scFv fragment of NOV530 (360 scFv molecules per VLP, total protein concentration of 1 mg/ml) at room temperature for 1 hour. The sample was then concentrated 10-fold. 4.0 µL of the concentrated VLP-scFv complex was applied onto the grid (R1.2/1.3, Cu 300 mesh, Quantifoil Micro Tools GmbH, Grosslöbichau, Germany) coated with an additional thin amorphous carbon layer. Grids were vitrified using a Leica EM GP plunger. Images were acquired with a Cs-corrected FEI Titan Krios TEM operated at 300 kV equipped with a Quantum-LS Gatan Image Filter (GIF) and recorded on a Gatan K2-Summit direct electron detector (Gatan GmbH). Images were collected automatically (with EPU, Thermo Fisher) in electron-counting mode (nominal post-GIF magnification of ×105,000 and calibrated pixel size of 1.12 Å). Exposures of 7 s were dose-fractionated into 40 frames. The total exposure dose was ~40 e–/Å2. Defocus values varied from −0.8 to −2.5 µm.

The cryoEM data was imaged by using the following protocol. The stage drift and beam-induced motion during exposure were pre-processed and aligned using a pipeline (StackGUI) that automates whole-image drift correction using UNBLUR (Grant, T and Grigorieff N. Measuring the optimal exposure for single particle cryo-EM using a 2.6 Å reconstruction of rotavirus VP6 (eLife. 4(e06980):1-19 (2015)). Contrast transfer function (CTF) parameters were estimated using the program CTFFIND4 (Mindell J A, and Grigorieff N. Accurate determination of local defocus and specimen tilt in electron microscopy. J. Struct. Biol. 142: 334-347 (2003)). Particles were automatically picked up on each micrograph using GAUTOMATCH. A total of 1,400 micrographs were acquired from which 6000 particles were extracted for processing using the Relion software package (Scheres, S. H. RELION: implementation of a Bayesian approach to cryo-EM structure determination. J. Struct. Biol. 180, 519-530, doi:10.1016/j.jsb.2012.09.006 (2012)). Particle sorting included two cycles of reference-free 2D classification. The 5000 particles in the best 2D classes were used for 3D refinement. A sphere was used as an initial model for 3D refinement. We performed particle-based beam-induced movement correction and radiation-damage weighting (known as particle polishing, see Scheres, S. H., Beam-induced motion correction for sub-megadalton cryo-EM particles. Elife 3, e03665, doi:10.7554/eLife.03665 (2014)) on the first 20 frames (corresponding to a total dose of ~20 e–/Å2). The resulting 5000 polished particles gave rise to a reconstruction with an overall resolution of 4.5 Å. Auto-refinement of polished particles with a soft mask around BK-VLP_scFv complex resulted in a 4.24 Å resolution map. The resolution values reported are based on the gold-standard Fourier shell correlation curve (FSC) at 0.143 criterion (Scheres, S. H. RELION: implementation of a Bayesian approach to cryo-EM structure determination. J. Struct. Biol. 180, 519-530, doi:10.1016/j.jsb.2012.09.006 (2012)). The cryo-EM structure of BK virion and crystal structure of scFv (PDB ID codes 5FUA and 4UT7 respectively) were manually fitted into the final cryo-EM map using the program Coot (Emsley P. et al., Features and development of Coot. Acta Crystallogr D Biol Crystallogr 66:486-501 (2010)). The resultant atomic model was subjected to multiple cycles of model rebuilding using the program Coot (Emsley P. et al., supra) and real space refinement against the map using the program Phenix (Adams P D, et al. PHENIX: A comprehensive Python-based system for macromolecular structure solution. Acta Crystallogr D Biol Crystallogr 66:213-221(2010)). This process resulted an atomic model of the pentamer and scFv complex that fit well into the cryo-EM density. Structural illustrations were prepared with PyMOL (available from Schrodinger).

Example 7: Formulation

The anti-BK or JC virus antibodies described herein are monoclonal antibodies, IgG1 isotype with kappa or lambda light chains, and can be lyophilized. These antibodies are soluble and stable in a histidine-sucrose formulation buffer for 4 weeks. In addition, anti-VP1 antibodies were soluble at >200 mg/ml as minimally formulated drug substance (e.g., in histidine buffer in the absence of stabilizers).

For subsequent intravenous administration, the obtained solution will usually be further diluted into a carrier solution to the ready-to-use antibody solution for infusion.

Important stability-indicating analytical methods to select the most stable formulation encompassed, amongst others, size-exclusion chromatography to determine aggregation levels, subvisible particulate matter testing, and potency testing.

It is understood that the examples and aspects described herein are for illustrative purposes only and that various modifications or changes in light thereof will be suggested to persons skilled in the art and are to be included within the spirit and purview of this application and scope of the appended claims.

What is claimed is:

1. An isolated antibody or antigen binding fragment thereof comprising: (i) a heavy chain variable region that comprises (a) a HCDR1 (CDR-Complementarity Determining Region) of SEQ ID NO: 9, (b) a HCDR2 of SEQ ID NO:10, (c) a HCDR3 of SEQ ID NO:11 and a light chain variable region that comprises: (d) a LCDR1 of SEQ ID NO:25, (e) a LCDR2 of SEQ ID NO:26, and (f) a LCDR3 of SEQ ID NO:27;
  (ii) a heavy chain variable region that comprises (a) a HCDR1 of SEQ ID NO:41, (b) a HCDR2 of SEQ ID NO:42, (c) a HCDR3 of SEQ ID NO:43; and a light chain variable region that comprises: (d) a LCDR1 of SEQ ID NO:57, (e) a LCDR2 of SEQ ID NO:58, and (f) a LCDR3 of SEQ ID NO:59;
    (iii) a heavy chain variable region that comprises (a) a HCDR1 of SEQ ID NO:73, (b) a HCDR2 of SEQ ID NO:74, (c) a HCDR3 of SEQ ID NO:75; and a light chain variable region that comprises: (d) a LCDR1 of SEQ ID NO:89, (e) a LCDR2 of SEQ ID NO:90, and (f) a LCDR3 of SEQ ID NO:91;
  (iv) a heavy chain variable region that comprises: (a) a HCDR1 of SEQ ID NO:105, (b) a HCDR2 of SEQ ID NO:106, (c) a HCDR3 of SEQ ID NO:107; and a light chain variable region that comprises: (d) a LCDR1 of SEQ ID NO:121, (e) a LCDR2 of SEQ ID NO:122, and (f) a LCDR3 of SEQ ID NO:123;
  (v) a heavy chain variable region that comprises: (a) a HCDR1 of SEQ ID NO:137, (b) a HCDR2 of SEQ ID NO:138, (c) a HCDR3 of SEQ ID NO:139; and a light chain variable region that comprises: (d) a LCDR1 of SEQ ID NO:153, (e) a LCDR2 of SEQ ID NO:154, and (f) a LCDR3 of SEQ ID NO:155;
  (vi) a heavy chain variable region that comprises: (a) a HCDR1 of SEQ ID NO:169, (b) a HCDR2 of SEQ ID NO:170, (c) a HCDR3 of SEQ ID NO:171; and a light chain variable region that comprises: (d) a LCDR1 of SEQ ID NO:185, (e) a LCDR2 of SEQ ID NO:186, and (f) a LCDR3 of SEQ ID NO:187;
  (vii) a heavy chain variable region that comprises: (a) a HCDR1 of SEQ ID NO:201, (b) a HCDR2 of SEQ ID NO: 202, (c) a HCDR3 of SEQ ID NO:203; and a light chain variable region that comprises: (d) a LCDR1 of SEQ ID NO:217, (e) a LCDR2 of SEQ ID NO:218, and (f) a LCDR3 of SEQ ID NO:219;
  (viii) a heavy chain variable region that comprises: (a) a HCDR1 of SEQ ID NO:233, (b) a HCDR2 of SEQ ID NO:234, (c) a HCDR3 of SEQ ID NO:235; and a light chain variable region that comprises: (d) a LCDR1 of SEQ ID NO:249, (e) a LCDR2 of SEQ ID NO:250, and (f) a LCDR3 of SEQ ID NO:251; or
  (ix) a heavy chain variable region that comprises: (a) a HCDR1 of SEQ ID NO:265, (b) a HCDR2 of SEQ ID NO: 266, (c) a HCDR3 of SEQ ID NO:267; and a light chain variable region that comprises: (d) a LCDR1 of SEQ ID NO:281, (e) a LCDR2 of SEQ ID NO:282, and (f) a LCDR3 of SEQ ID NO: 283.

2. The antibody or antigen binding fragment thereof of claim 1, wherein one or two amino acids within a CDR have been modified.

3. The antibody or antigen binding fragment thereof of claim 1, wherein the antibody or antigen binding fragment thereof retains at least 90, 91, 92, 93, 94, 95, 96, 97, 98 or 99% identity compared to a corresponding human germline sequence of either the variable heavy chain region or the variable light chain region.

4. The antibody or antigen binding fragment thereof of claim 1, wherein the antibody or antigen binding fragment thereof is a monoclonal antibody, a human antibody, a single chain antibody (scFv) or an antibody fragment.

5. An isolated antibody or antigen binding fragment thereof, wherein said antibody or antigen binding fragment thereof comprises:
   (i) a heavy chain variable region (vH) that comprises SEQ ID NO:18, and a light chain variable region (vL) that comprises SEQ ID NO: 34;
   (ii) a heavy chain variable region (vH) that comprises SEQ ID NO: 50, and a light chain variable region (vL) that comprises SEQ ID NO: 66;
   (iii) a heavy chain variable region (vH) that comprises SEQ ID NO: 82, and a light chain variable region (vL) that comprises SEQ ID NO:98;
   (iv) a heavy chain variable region (vH) that comprises SEQ ID NO:114, and a light chain variable region (vL) that comprises SEQ ID NO:130;
   (v) a heavy chain variable region (vH) that comprises SEQ ID NO:146, and a light chain variable region (vL) that comprises SEQ ID NO:162;
   (vi) a heavy chain variable region (vH) that comprises SEQ ID NO:178, and a light chain variable region (vL) that comprises SEQ ID NO:194;
   (vii) a heavy chain variable region (vH) that comprises SEQ ID NO:210, and a light chain variable region (vL) that comprises SEQ ID NO:226;
   (viii) a heavy chain variable region (vH) that comprises SEQ ID NO: 242, and a light chain variable region (vL) that comprises SEQ ID NO:258; or
   (ix) a heavy chain variable region (vH) that comprises SEQ ID NO:274, and a light chain variable region (vL) that comprises SEQ ID NO:290.

6. The antibody or antigen binding fragment thereof of claim 5, wherein the antigen or antigen binding fragment thereof retains at least 90, 91, 92, 93, 94, 95, 96, 97, 98 or 99% identity over either the variable light or variable heavy region.

7. The antibody or antigen binding fragment thereof of claim 5, wherein less than 10 amino acids within the variable light or variable heavy region have been modified.

8. The antibody or antigen binding fragment thereof of claim 5, wherein the antibody or antigen binding fragment thereof is a monoclonal antibody, a chimeric antibody, a human engineered antibody, a human antibody, a single chain antibody (scFv) or an antibody fragment.

9. A nucleic acid that encodes the antibody or antigen binding fragment thereof of claim 1 or 5.

10. A vector comprising the nucleic acid of claim 9.

11. A host cell comprising the vector of claim 10.

12. A diagnostic reagent comprising the antibody or antigen binding fragment thereof of claim 1 or 5, wherein the antibody or antigen binding fragment thereof is labeled.

13. The diagnostic reagent of claim 12, wherein the label is selected from the group consisting of a radiolabel, a fluorophore, a chromophore, an imaging agent, and a metal ion.

14. The antibody or antigen binding fragment thereof of claim 1 or 5 wherein the antibody or antigen binding fragment thereof has reduced glycosylation or no glycosylation or is hypofucosylated.

15. A pharmaceutical composition comprising the antibody or antigen binding fragment thereof of claim 1 or 5 and a pharmaceutically acceptable carrier.

16. The pharmaceutical composition of claim 15, wherein the pharmaceutically acceptable carrier comprises histidine or a sugar.

17. The pharmaceutical composition of claim 16, wherein the sugar is sucrose.

18. A pharmaceutical composition comprising a plurality of antibodies or antigen binding fragments thereof of claim 1 or 5, wherein at least 0.05%, 0.1%, 0.5%, 1%, 2%, 3%, or 5% of the antibodies in the composition have an α2,3-linked sialic acid residue.

19. A pharmaceutical composition comprising a plurality of antibodies or antigen binding fragments thereof of claim 1 or 5, wherein none of the antibodies or antigen binding fragments thereof comprise a bisecting GlcNAc.

20. A pharmaceutical composition comprising the antibody or antigen binding fragment thereof of claim 1 or 5, wherein the composition is a lyophilisate.

21. A method of neutralizing a BK virus or JC virus infection comprising administering via injection or infusion to a patient in need an effective amount of the antibody or antigen binding fragment thereof of claim 1 or 5.

22. The method of claim 21, wherein the patient in need is diagnosed with BK viruria or BK viremia.

23. The method of claim 21, wherein the patient in need is diagnosed with JC viruria or JC viremia.

24. A method of treating or reducing the likelihood of a BK virus or JC virus associated disorder, comprising administering via injection or infusion to a patient in need an effective amount of the antibody or antigen binding fragment thereof of claim 1 or 5, and wherein the disorder is selected from the group consisting of: nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

25. The method of claim 24, wherein the antibody or antigen binding fragment thereof is reconstituted prior to injection or infusion.

26. The method of claim 24, wherein the antibody or the antigen binding fragment thereof is administered in combination with another therapeutic agent.

27. The method of claim 26, wherein the another therapeutic agent is an additional anti-BKV or JCV antibody.

28. The method of claim 26, wherein the another therapeutic agent is an immunosuppressive agent.

29. The method of claim 28, wherein the immune suppressive agent is: a monophosphate dehydrogenase inhibitor, a purine synthesis inhibitor, a calcineurin inhibitor or an mTOR inhibitor.

30. The method of claim 28, wherein the immunosuppressive agent is mycophenolate mofetil (MMF), mycophenolate sodium, azathioprine, tacrolimus, sirolimus or cyclosporine.

31. The method of claim 24, wherein the PML is associated with the treatment of multiple sclerosis, rheumatoid arthritis, or psoriasis.

32. The method of claim 31, wherein treatment of multiple sclerosis is with natalizumab, fingolimod, dimethyl fumarate, fumaric acid esters, or alemtuzumab.

33. The method of claim 31, wherein the treatment of rheumatoid arthritis is with rituximab.

34. The method of claim 31, wherein treatment of psoriasis is with efalizumab.

* * * * *

```
                        SEQUENCE LISTING

<160> NUMBER OF SEQ ID NOS: 427

<210> SEQ ID NO 1
<211> LENGTH: 362
<212> TYPE: PRT
<213> ORGANISM: Human polyomavirus BKV

<400> SEQUENCE: 1

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300
```

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
            325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
            355                 360

<210> SEQ ID NO 2
<211> LENGTH: 362
<212> TYPE: PRT
<213> ORGANISM: Human polyomavirus BKV

<400> SEQUENCE: 2

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
            35                  40                  45

Glu Cys Phe Leu Asn Pro Glu Met Gly Asp Pro Asp Asp Asn Leu Arg
50                  55                  60

Gly Tyr Ser Leu Lys Leu Thr Ala Glu Asn Ala Phe Asp Ser Asp Ser
65                  70                  75                  80

Pro Asp Lys Lys Met Leu Pro Cys Tyr Ser Thr Ala Arg Ile Pro Leu
            85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
            115                 120                 125

Leu His Ala Gly Ser Gln Lys Val His Glu Asn Gly Gly Gly Lys Pro
            130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
            165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
            195                 200                 205

Trp Ile Pro Asp Pro Ser Arg Asn Glu Asn Thr Arg Tyr Phe Gly Thr
210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
            245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
            275                 280                 285

Ile Arg Leu Arg Lys Arg Ser Val Lys Asn Pro Tyr Pro Ile Ser Phe
            290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
            325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
            355                 360

<210> SEQ ID NO 3
<211> LENGTH: 362
<212> TYPE: PRT
<213> ORGANISM: Human polyomavirus BKV

<400> SEQUENCE: 3

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp His Leu Arg
    50                  55                  60

Gly Tyr Ser Gln His Leu Ser Ala Glu Asn Ala Phe Asp Ser Asp Ser
65              70                  75                  80

Pro Asp Lys Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
            115                 120                 125

Leu His Ala Gly Ser Gln Lys Val His Glu Asn Gly Gly Gly Lys Pro
130             135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Lys Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp

```
                         325                 330                 335
Gly Thr Glu Gln Leu Pro Gly Asp Pro Asp Met Ile Arg Tyr Ile Asp
                 340                 345                 350
Arg Gln Gly Gln Leu Gln Thr Lys Met Val
                 355                 360

<210> SEQ ID NO 4
<211> LENGTH: 362
<212> TYPE: PRT
<213> ORGANISM: Human polyomavirus BKV

<400> SEQUENCE: 4

Met Ala Pro Thr Lys Arg Lys Gly Glu Cys Pro Gly Ala Ala Pro Lys
1               5                   10                  15
Lys Pro Lys Glu Pro Val Gln Val Pro Lys Leu Leu Ile Lys Gly Gly
                20                  25                  30
Val Glu Val Leu Glu Val Lys Thr Gly Val Asp Ala Ile Thr Glu Val
            35                  40                  45
Glu Cys Phe Leu Asn Pro Glu Met Gly Asp Pro Asp Asn Asp Leu Arg
    50                  55                  60
Gly Tyr Ser Leu Arg Leu Thr Ala Glu Thr Ala Phe Asp Ser Asp Ser
65                  70                  75                  80
Pro Asp Arg Lys Met Leu Pro Cys Tyr Ser Thr Ala Arg Ile Pro Leu
                85                  90                  95
Pro Asn Leu Asn Glu Asp Leu Thr Cys Gly Asn Leu Leu Met Trp Glu
            100                 105                 110
Ala Val Thr Val Lys Thr Glu Val Ile Gly Ile Thr Ser Met Leu Asn
        115                 120                 125
Leu His Ala Gly Ser Gln Lys Val His Glu Asn Gly Gly Gly Lys Pro
130                 135                 140
Ile Gln Gly Ser Asn Phe His Phe Phe Ala Val Gly Gly Asp Pro Leu
145                 150                 155                 160
Glu Met Gln Gly Val Leu Met Asn Tyr Arg Thr Lys Tyr Pro Glu Gly
                165                 170                 175
Thr Val Thr Pro Lys Asn Pro Thr Ala Gln Ser Gln Val Met Asn Thr
            180                 185                 190
Asp His Lys Ala Tyr Leu Asp Lys Asn Asn Ala Tyr Pro Val Glu Cys
        195                 200                 205
Trp Ile Pro Asp Pro Ser Arg Asn Glu Asn Thr Arg Tyr Phe Gly Thr
    210                 215                 220
Tyr Thr Gly Gly Glu Asn Val Pro Pro Val Leu His Val Thr Asn Thr
225                 230                 235                 240
Ala Thr Thr Val Leu Leu Asp Glu Gln Gly Val Gly Pro Leu Cys Lys
                245                 250                 255
Ala Asp Ser Leu Tyr Val Ser Ala Ala Asp Ile Cys Gly Leu Phe Thr
            260                 265                 270
Asn Ser Ser Gly Thr Gln Gln Trp Arg Gly Leu Pro Arg Tyr Phe Lys
        275                 280                 285
Ile Arg Leu Arg Lys Arg Ser Val Lys Asn Pro Tyr Pro Ile Ser Phe
    290                 295                 300
Leu Leu Ser Asp Leu Ile Asn Arg Arg Thr Gln Arg Val Asp Gly Gln
305                 310                 315                 320
Pro Met Tyr Gly Met Glu Ser Gln Val Glu Glu Val Arg Val Phe Asp
                325                 330                 335
```

```
Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360

<210> SEQ ID NO 5
<211> LENGTH: 354
<212> TYPE: PRT
<213> ORGANISM: Human polyomavirus JCV

<400> SEQUENCE: 5

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65              70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145             150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225             230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305             310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350
```

Met Leu

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Ser Ile Ser Gly Gly Gly Tyr Tyr Trp Ser
1               5                   10

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Tyr Ile Tyr Tyr Asn Arg Gly Thr Tyr Tyr Asn Pro Ala Leu Lys Ser
1               5                   10                  15

<210> SEQ ID NO 8
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Cys Val Leu Gly Gly Tyr Gly Ser Asp Ala Phe Asp Arg
1               5                   10

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Gly Gly Tyr Tyr Trp Ser
1               5

<210> SEQ ID NO 10
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Tyr Ile Tyr Tyr Asn Arg Gly Thr Tyr Tyr Asn Pro Ala Leu Lys Ser
1               5                   10                  15

```
<210> SEQ ID NO 11
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Cys Val Leu Gly Gly Tyr Gly Ser Asp Ala Phe Asp Arg
1               5                   10

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Gly Ser Ile Ser Gly Gly Gly Tyr
1               5

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Tyr Tyr Asn Arg Gly
1               5

<210> SEQ ID NO 14
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Cys Val Leu Gly Gly Tyr Gly Ser Asp Ala Phe Asp Arg
1               5                   10

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Gly Ser Ile Ser Gly Gly Gly Tyr Tyr
1               5                   10

<210> SEQ ID NO 16
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 16

Ile Tyr Tyr Asn Arg Gly Thr
1               5

<210> SEQ ID NO 17
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ala Arg Cys Val Leu Gly Gly Tyr Gly Ser Asp Ala Phe Asp Arg
1               5                   10                  15

<210> SEQ ID NO 18
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Gly Gly
            20                  25                  30

Gly Tyr Tyr Trp Ser Trp Ile Arg Gln His Pro Gly Lys Gly Leu Glu
        35                  40                  45

Phe Ile Gly Tyr Ile Tyr Tyr Asn Arg Gly Thr Tyr Tyr Asn Pro Ala
    50                  55                  60

Leu Lys Ser Arg Leu Thr Ile Ser Val Asp Thr Ser Lys Asn Asp Phe
65                  70                  75                  80

Ser Leu Lys Leu Ser Ser Val Ser Ala Ala Asp Thr Ala Val Tyr Tyr
                85                  90                  95

Cys Ala Arg Cys Val Leu Gly Gly Tyr Gly Ser Asp Ala Phe Asp Arg
            100                 105                 110

Trp Gly Gln Gly Thr Thr Val Thr Val Ala Ser
        115                 120

<210> SEQ ID NO 19
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
caggtgcagc tgcaggagtc gggcccagga ctggtgaagc cttcacagac cctgtccctc      60
acctgcactg tctctggtgg ctccatcagc ggtggtggtt actactggag ctggatccgc     120
cagcacccag ggaagggcct ggagttcatt ggatacatat attataatag gggcacctac     180
```

-continued

```
tacaatccgg ccctcaagag tcgacttacc atatcagtag acacctctaa gaatgacttc    240
tccctgaagc tgagctctgt gagtgccgcg gacacggccg tgtattactg tgcgagatgt    300
gtccttggtg gctacggttc tgatgctttt gataggtggg gccaagggac aacggtcacc    360
gtcgcttca                                                             369
```

<210> SEQ ID NO 20
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Gly Gly
            20                  25                  30

Gly Tyr Tyr Trp Ser Trp Ile Arg Gln His Pro Gly Lys Gly Leu Glu
        35                  40                  45

Phe Ile Gly Tyr Ile Tyr Tyr Asn Arg Gly Thr Tyr Tyr Asn Pro Ala
    50                  55                  60

Leu Lys Ser Arg Leu Thr Ile Ser Val Asp Thr Ser Lys Asn Asp Phe
65                  70                  75                  80

Ser Leu Lys Leu Ser Ser Val Ser Ala Ala Asp Thr Ala Val Tyr Tyr
                85                  90                  95

Cys Ala Arg Cys Val Leu Gly Gly Tyr Gly Ser Asp Ala Phe Asp Arg
            100                 105                 110

Trp Gly Gln Gly Thr Thr Val Thr Val Ala Ser Ala Ser Thr Lys Gly
        115                 120                 125

Pro Ser Val Phe Pro Leu Ala Pro Cys Ser Arg Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Thr Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320
```

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 21
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

```
caggtgcagc tgcaggagtc gggcccagga ctggtgaagc cttcacagac cctgtccctc      60
acctgcactg tctctggtgg ctccatcagc ggtggtggtt actactggag ctggatccgc     120
cagcacccag ggaagggcct ggagttcatt ggatacatat attataatag ggcacctac      180
tacaatccgg ccctcaagag tcgacttacc atatcagtag acacctctaa gaatgacttc     240
tccctgaagc tgagctctgt gagtgccgcg gacacggccg tgtattactg tgcgagatgt     300
gtccttggtg gctacggttc tgatgctttt gataggtggg gccaagggac aacggtcacc     360
gtcgcttcag cttccaccaa gggcccatcg gtcttccccc tggcgccctg ctccaggagc     420
acctctgggg gcacagcggc cctgggctgc ctggtcaagg actacttccc cgaaccggtg     480
acggtgtcgt ggaactcagg cgccctgacc agcggcgtgc acaccttccc gactgtccta     540
cagtcctcag gactctactc cctcagcagc gtggtgaccg tgccctccag cagcttgggc     600
acccagacct acatctgcaa cgtgaaccac aagcccagca acaccaaggt ggacaagaga     660
gtggagccca gagctgcga caagacccac acctgccccc cctgcccagc cccagagctg     720
ctgggcggac cctccgtgtt cctgttcccc ccaagcccca ggacaccct gatgatcagc     780
aggacccccg aggtgacctg cgtggtggtg gacgtgagcc acgaggaccc agaggtgaag     840
ttcaactggt acgtggacgg cgtggaggtg cacaacgcca agaccaagcc cagagaggag     900
cagtacaaca gcacctacag ggtggtgtcc gtgctgaccg tgctgcacca ggactggctg     960
aacggcaagg aatacaagtg caaggtctcc aacaaggccc tgccagcccc catcgaaaag    1020
accatcagca aggccaaggg ccagccacgg gagcccagg tgtacaccct gcccccctcc    1080
cgggaggaga tgaccaagaa ccaggtgtcc ctgacctgtc tggtgaaggg cttctacccc    1140
agcgacatcg ccgtggagtg ggagagcaac ggccagcccg agaacaacta caagaccacc    1200
```

```
cccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagagcct gagcctgtcc cccggcaag                           1359
```

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

```
Arg Ala Ser Gln Ser Val Ser Ser His Leu Ala
1               5                   10
```

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

```
Asp Ala Ser Ser Arg Ala Asn
1               5
```

<210> SEQ ID NO 24
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

```
Gln Gln Arg Ser Ser Trp Pro Pro Ser Leu Thr
1               5                   10
```

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

```
Arg Ala Ser Gln Ser Val Ser Ser His Leu Ala
1               5                   10
```

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asp Ala Ser Ser Arg Ala Asn
1               5

<210> SEQ ID NO 27
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gln Gln Arg Ser Ser Trp Pro Pro Ser Leu Thr
1               5                   10

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ser Gln Ser Val Ser Ser His
1               5

<210> SEQ ID NO 29
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asp Ala Ser
1

<210> SEQ ID NO 30
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Arg Ser Ser Trp Pro Pro Ser Leu
1               5

<210> SEQ ID NO 31
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gln Ser Val Ser Ser His
1               5

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

Asp Ala Ser Ser Arg Ala Asn Gly Ile Pro
1               5                   10

<210> SEQ ID NO 33
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

Gln Gln Arg Ser Ser Trp Pro Pro Ser Leu Thr
1               5                   10

<210> SEQ ID NO 34
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

Glu Ile Val Leu Thr Gln Ser Pro Val Thr Leu Ser Leu Ser Pro Gly
1               5                   10                  15

Glu Arg Ala Ile Leu Ser Cys Arg Ala Ser Gln Ser Val Ser Ser His
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Asn Gly Ile Pro Ala Arg Phe Ser Gly
    50                  55                  60

Ser Gly Ser Gly Thr Asp Phe Thr Leu Thr Ile Ser Ser Leu Ala Pro
65                  70                  75                  80

Glu Asp Phe Ala Val Tyr Tyr Cys Gln Gln Arg Ser Ser Trp Pro Pro
                85                  90                  95

Ser Leu Thr Phe Gly Gly Gly Thr Lys Val Glu Ile Arg
            100                 105

<210> SEQ ID NO 35
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 35
gaaattgtgt tgacacagtc cccagtcacc ctgtctttgt ctccagggga aagagccatc      60
ctctcctgta gggccagtca gagtgttagc agccacttag cctggtacca acagaagcct     120
ggccaggctc ccaggctcct catctatgat gcatccagca gggccaatgg catcccagcc     180

```
aggttcagtg gcagtgggtc tgggacagac ttcactctca ccatcagcag cctagcgcct    240
gaagattttg cagtttatta ctgtcagcag cgtagcagct ggcctccgtc cctcactttc    300
ggcggaggga ccaaggtgga gatcaga                                         327
```

<210> SEQ ID NO 36
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Glu Ile Val Leu Thr Gln Ser Pro Val Thr Leu Ser Leu Ser Pro Gly
1               5                   10                  15

Glu Arg Ala Ile Leu Ser Cys Arg Ala Ser Gln Ser Val Ser Ser His
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Asn Gly Ile Pro Ala Arg Phe Ser Gly
    50                  55                  60

Ser Gly Ser Gly Thr Asp Phe Thr Leu Thr Ile Ser Ser Leu Ala Pro
65                  70                  75                  80

Glu Asp Phe Ala Val Tyr Tyr Cys Gln Gln Arg Ser Ser Trp Pro Pro
                85                  90                  95

Ser Leu Thr Phe Gly Gly Gly Thr Lys Val Glu Ile Arg Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 37
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

```
gaaattgtgt tgacacagtc cccagtcacc ctgtctttgt ctccagggga aagagccatc    60
ctctcctgta gggccagtca gagtgttagc agccacttag cctggtacca acagaagcct    120
ggccaggctc ccaggctcct catctatgat gcatccagca gggccaatgg catcccagcc    180
```

```
aggttcagtg gcagtgggtc tgggacagac ttcactctca ccatcagcag cctagcgcct    240
gaagattttg cagtttatta ctgtcagcag cgtagcagct ggcctccgtc cctcactttc    300
ggcggaggga ccaaggtgga gatcagacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggaca acgccctgca gagcggcaac    480
agccaggaga gcgtcaccga gcaggacagc aaggactcca cctacagcct gagcagcacc    540
ctgaccctga gcaaggccga ctacgagaag cataaggtgt acgcctgcga ggtgacccac    600
cagggcctgt ccagccccgt gaccaagagc ttcaacaggg gcgagtgc                 648
```

```
<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gly Phe Thr Phe Arg Ser Tyr Met Met Asn
1               5                   10

<210> SEQ ID NO 39
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Tyr Ile Ser Gly Ser Gly Gly Thr Lys Tyr Tyr Val Asp Ser Val Lys
1               5                   10                  15

Gly

<210> SEQ ID NO 40
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Asp Leu Asp Cys Ser Gly Gly Thr Cys Tyr Asp Gly Met Asp Val
1               5                   10                  15

<210> SEQ ID NO 41
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ser Tyr Met Met Asn
1               5
```

```
<210> SEQ ID NO 42
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Tyr Ile Ser Gly Ser Gly Gly Thr Lys Tyr Tyr Val Asp Ser Val Lys
1               5                   10                  15

Gly

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Asp Leu Asp Cys Ser Gly Gly Thr Cys Tyr Asp Gly Met Asp Val
1               5                   10                  15

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Phe Thr Phe Arg Ser Tyr
1               5

<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ser Gly Ser Gly Gly Thr
1               5

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Asp Leu Asp Cys Ser Gly Gly Thr Cys Tyr Asp Gly Met Asp Val
1               5                   10                  15

<210> SEQ ID NO 47
<211> LENGTH: 8
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Phe Thr Phe Arg Ser Tyr Met
1               5

<210> SEQ ID NO 48
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Ile Ser Gly Ser Gly Gly Thr Lys
1               5

<210> SEQ ID NO 49
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ala Arg Asp Leu Asp Cys Ser Gly Gly Thr Cys Tyr Asp Gly Met Asp
1               5                   10                  15

Val

<210> SEQ ID NO 50
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Met Met Asn Trp Val Arg Gln Ala Pro Gly Lys Gly Leu Glu Trp Val
        35                  40                  45

Ser Tyr Ile Ser Gly Ser Gly Gly Thr Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Val Tyr Tyr Cys
                85                  90                  95

Ala Arg Asp Leu Asp Cys Ser Gly Gly Thr Cys Tyr Asp Gly Met Asp
            100                 105                 110

Val Trp Gly Gln Gly Thr Thr Val Thr Val Ser Ser
        115                 120
```

<210> SEQ ID NO 51
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51

```
gaggtgcagc tggtggagtc ggggggaggc ttggtacagc ctgggggtc cctgagactc      60
tcctgtgcag cctctggatt caccttcagg agttatatga tgaattgggt ccgccaggct    120
ccagggaagg ggctggagtg ggtttcatat attagtggta gtggtggaac caaatactac    180
gtagactctg tgaagggccg attcaccata tccagagaca acgccaagaa ctcactgtat    240
ctgcaaatgc acagcctgag agccgaggac acggctgtgt attactgtgc gagagatctc    300
gattgcagtg gtgggacctg ctacgacggt atggacgtct ggggccaagg gaccacggtc    360
accgtctcct ca                                                        372
```

<210> SEQ ID NO 52
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Met Met Asn Trp Val Arg Gln Ala Pro Gly Lys Gly Leu Glu Trp Val
        35                  40                  45

Ser Tyr Ile Ser Gly Ser Gly Gly Thr Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Val Tyr Tyr Cys
                85                  90                  95

Ala Arg Asp Leu Asp Cys Ser Gly Gly Thr Cys Tyr Asp Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro

```
                        210                 215                 220
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
        450

<210> SEQ ID NO 53
<211> LENGTH: 1362
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
gaggtgcagc tggtggagtc ggggggaggc ttggtacagc ctgggggtc cctgagactc      60 tcctgtgcag cctctggatt caccttcagg agttatatga tgaattgggt ccgccaggct    120
ccagggaagg ggctggagtg ggtttcatat attagtggta gtggtggaac caaatactac    180
gtagactctg tgaagggccg attcaccata tccagagaca cgccaagaa ctcactgtat     240 ctgcaaatgc acagcctgag agccgaggac acggctgtgt attactgtgc gagagatctc    300
gattgcagtg gtgggacctg ctacgacggt atggacgtct ggggccaagg gaccacggtc    360
accgtctcct cagcttccac caagggccca tcggtcttcc ccctggcgcc ctgctccagg    420
agcacctctg ggggcacagc ggccctgggc tgcctggtca aggactactt ccccgaaccg    480
gtgacggtgt cgtggaactc aggcgccctg accagcggcg tgcacacctt ccgggctgtc    540
ctacagtcct caggactcta ctccctcagc agcgtggtga ccgtgccctc cagcagcttg    600
```

```
ggcacccaga cctacatctg caacgtgaac cacaagccca gcaacaccaa ggtggacaag    660
agagtggagc ccaagagctg cgacaagacc cacacctgcc cccctgccc agccccagag    720 ctgctgggcg gaccctccgt gttcctgttc cccccaagc ccaaggacac cctgatgatc    780
agcaggaccc ccgaggtgac ctgcgtggtg gtggacgtga gccacgagga cccagaggtg    840
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca aggaatacaa gtgcaaggtc tccaacaagg ccctgccagc ccccatcgaa   1020
aagaccatca gcaaggccaa gggccagcca cgggagcccc aggtgtacac cctgcccccc   1080
tcccgggagg agatgaccaa gaaccaggtg tccctgacct gtctggtgaa gggcttctac   1140
cccagcgaca tcgccgtgga gtgggagagc aacggccagc ccgagaacaa ctacaagacc   1200 accccccag tgctggacag cgacggcagc ttcttcctgt acagcaagct gaccgtggac   1260
aagtccaggt ggcagcaggg caacgtgttc agctgcagcg tgatgcacga ggccctgcac   1320
aaccactaca cccagaagag cctgagcctg tcccccggca ag                     1362
```

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 54

Ser Gly Asp Lys Leu Gly Asn Lys Tyr Val Tyr
1               5                   10

<210> SEQ ID NO 55
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 55

Gln His Thr Lys Arg Pro Ser
1               5

<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 56

Gln Ala Trp Asp Ser Ser Ile Val Ile
1               5

<210> SEQ ID NO 57
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

```
Synthetic peptide"

<400> SEQUENCE: 57

Ser Gly Asp Lys Leu Gly Asn Lys Tyr Val Tyr
1               5                   10

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gln His Thr Lys Arg Pro Ser
1               5

<210> SEQ ID NO 59
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Ala Trp Asp Ser Ser Ile Val Ile
1               5

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Asp Lys Leu Gly Asn Lys Tyr
1               5

<210> SEQ ID NO 61
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gln His Thr
1

<210> SEQ ID NO 62
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62
```

Trp Asp Ser Ser Ile Val
1               5

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Lys Leu Gly Asn Lys Tyr
1               5

<210> SEQ ID NO 64
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gln His Thr
1

<210> SEQ ID NO 65
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gln Ala Trp Asp Ser Ser Ile Val Ile
1               5

<210> SEQ ID NO 66
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Ser Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Asn Lys Tyr Val
            20                  25                  30

Tyr Trp Phe Gln His Arg Pro Gly Gln Ser Pro Val Leu Val Ile Tyr
        35                  40                  45

Gln His Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Ile Val Ile
                85                  90                  95

Phe Gly Gly Gly Thr Lys Leu Thr Val Leu

<210> SEQ ID NO 67
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67

```
tcctatgagc tgactcagcc accctcagtg tccgtgtccc ctggacagac agccaccatc    60
acctgctctg gagataaatt gggtaataaa tatgtttact ggtttcagca caggccaggc   120
cagtcccctg tgctggtcat ctatcaacat accaagcggc cctcagggat ccctgagcga   180
ttctctggct ccaactctgg gaacacagcc actctgacca tcagcgggac ccaggctatg   240
gatgaggctg actattactg tcaggcgtgg gacagtagca ttgtgatatt cggcggaggg   300
accaagctga ccgtccta                                                  318
```

<210> SEQ ID NO 68
<211> LENGTH: 212
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

```
Ser Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Asn Lys Tyr Val
            20                  25                  30

Tyr Trp Phe Gln His Arg Pro Gly Gln Ser Pro Val Leu Val Ile Tyr
        35                  40                  45

Gln His Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Ile Val Ile
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

<210> SEQ ID NO 69
<211> LENGTH: 636
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69

```
tcctatgagc tgactcagcc accctcagtg tccgtgtccc ctggacagac agccaccatc    60
acctgctctg gagataaatt gggtaataaa tatgtttact ggtttcagca caggccaggc   120
cagtcccctg tgctggtcat ctatcaacat accaagcggc cctcagggat ccctgagcga   180
ttctctggct ccaactctgg gaacacagcc actctgacca tcagcgggac ccaggctatg   240
gatgaggctg actattactg tcaggcgtgg gacagtagca ttgtgatatt cggcggaggg   300
accaagctga ccgtcctagg tcagcccaag gctgccccct cggtcactct gttcccgccc   360
tcctctgagg agcttcaagc caacaaggcc acactggtgt gtctcataag tgacttctac   420
ccgggagccg tgacagtggc ctggaaggca gatagcagcc ccgtcaaggc gggagtggag   480
accaccacac cctccaaaca aagcaacaac aagtacgccg ccagcagcta cctgagcctg   540
accccgagc agtggaagag ccacagaagc tacagctgcc aggtcaccca cgagggcagc   600
accgtggaga aaaccgtggc ccccaccgag tgcagc                             636
```

<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gly Tyr Thr Phe Thr Ala Tyr Tyr Met His
1               5                   10

<210> SEQ ID NO 71
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Trp Ile Asn Pro Asn Thr Gly Val Thr Asn Phe Ala Gln Lys Phe Gln
1               5                   10                  15

Gly

<210> SEQ ID NO 72
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Asp Arg Asp Ala Ser Met Ala Ser Tyr Tyr Tyr Gly Met Asp Val
1               5                   10                  15

<210> SEQ ID NO 73
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Ala Tyr Tyr Met His
1               5

<210> SEQ ID NO 74
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Trp Ile Asn Pro Asn Thr Gly Val Thr Asn Phe Ala Gln Lys Phe Gln
1               5                   10                  15

Gly

<210> SEQ ID NO 75
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Asp Arg Asp Ala Ser Met Ala Ser Tyr Tyr Tyr Gly Met Asp Val
1               5                   10                  15

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Tyr Thr Phe Thr Ala Tyr
1               5

<210> SEQ ID NO 77
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Asn Pro Asn Thr Gly Val
1               5

```
<210> SEQ ID NO 78
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Asp Arg Asp Ala Ser Met Ala Ser Tyr Tyr Tyr Gly Met Asp Val
1               5                   10                  15

<210> SEQ ID NO 79
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gly Tyr Thr Phe Thr Ala Tyr Tyr
1               5

<210> SEQ ID NO 80
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Ile Asn Pro Asn Thr Gly Val Thr
1               5

<210> SEQ ID NO 81
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Ala Arg Asp Arg Asp Ala Ser Met Ala Ser Tyr Tyr Tyr Gly Met
1               5                   10                  15

Asp Val

<210> SEQ ID NO 82
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
```

```
                    20                  25                  30

Tyr Met His Trp Val Arg Gln Ala Pro Gly Gln Gly Leu Glu Trp Met
        35                  40                  45

Gly Trp Ile Asn Pro Asn Thr Gly Val Thr Asn Phe Ala Gln Lys Phe
    50                  55                  60

Gln Gly Arg Val Thr Met Thr Arg Asp Thr Ser Ile Gly Thr Ala Tyr
65                  70                  75                  80

Ile Glu Leu Ser Trp Leu Arg Ser Asp Thr Ala Val Tyr Tyr Cys
                85                  90                  95

Ala Arg Asp Arg Asp Ala Ser Met Ala Ser Tyr Tyr Tyr Gly Met
                100                 105                 110

Asp Val Trp Gly Gln Gly Thr Thr Val Thr Val Ser Ser
            115                 120                 125

<210> SEQ ID NO 83
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
caggtgcagc tggtgcagtc tggggctgag gtgaagaagc ctggggcctc agtgaaggtc      60
tcctgcaagg cttctggata caccttcacc gcctattata tgcactgggt gcgacaggcc    120
cctggacaag gcttgagtg gatgggctgg atcaaccta acactggtgt cacaaacttt     180
gcacagaagt ttcagggcag ggtcaccatg accagggaca cgtccatcgg cacagcctac    240
attgaattga gctggctgag atctgacgac acggccgtgt attactgtgc gagggatagg    300
gatgcatcta tggcctccta ctactactac ggtatggacg tctggggcca agggaccacg    360
gtcaccgtct cctca                                                     375

<210> SEQ ID NO 84
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Met His Trp Val Arg Gln Ala Pro Gly Gln Gly Leu Glu Trp Met
        35                  40                  45

Gly Trp Ile Asn Pro Asn Thr Gly Val Thr Asn Phe Ala Gln Lys Phe
    50                  55                  60

Gln Gly Arg Val Thr Met Thr Arg Asp Thr Ser Ile Gly Thr Ala Tyr
65                  70                  75                  80

Ile Glu Leu Ser Trp Leu Arg Ser Asp Thr Ala Val Tyr Tyr Cys
                85                  90                  95

Ala Arg Asp Arg Asp Ala Ser Met Ala Ser Tyr Tyr Tyr Gly Met
                100                 105                 110
```

Asp Val Trp Gly Gln Gly Thr Thr Val Thr Val Ser Ser Ala Ser Thr
115                 120                 125

Lys Gly Pro Ser Val Phe Pro Leu Ala Pro Cys Ser Arg Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 85
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 85
caggtgcagc tggtgcagtc tggggctgag gtgaagaagc ctggggcctc agtgaaggtc        60

```
tcctgcaagg cttctggata caccttcacc gcctattata tgcactgggt gcgacaggcc      120
cctggacaag ggcttgagtg gatgggctgg atcaacccta acactggtgt cacaaacttt      180
gcacagaagt ttcagggcag ggtcaccatg accagggaca cgtccatcgg cacagcctac      240
attgaattga gctggctgag atctgacgac acggccgtgt attactgtgc gagggatagg      300
gatgcatcta tggcctccta ctactactac ggtatggacg tctggggcca agggaccacg      360
gtcaccgtct cctcagcttc caccaagggc ccatcggtct tccccctggc gccctgctcc      420
aggagcacct ctgggggcac agcggccctg ggctgcctgg tcaaggacta cttccccgaa      480
ccggtgacgg tgtcgtggaa ctcaggcgcc ctgaccagcg gcgtgcacac cttcccggct      540
gtcctacagt cctcaggact ctactccctc agcagcgtgg tgaccgtgcc ctccagcagc      600
ttgggcaccc agacctacat ctgcaacgtg aaccacaagc ccagcaacac caaggtggac      660
aagagagtgg agcccaagag ctgcgacaag acccacacct gcccccccctg cccagcccca      720 gagctgctgg gcggaccctc cgtgttcctg ttcccccccca gcccaagga cccctgatg      780 atcagcagga cccccgaggt gacctgcgtg gtggtggacg tgagccacga ggacccagag      840
gtgaagttca actggtacgt ggacggcgtg gaggtgcaca cgccaagac caagcccaga      900 gaggagcagt acaacagcac ctacagggtg gtgtccgtgc tgaccgtgct gcaccaggac      960
tggctgaacg gcaaggaata caagtgcaag gtctccaaca aggccctgcc agcccccatc     1020
gaaaagacca tcagcaaggc caagggccag ccacgggagc cccaggtgta caccctgccc     1080
ccctcccggg aggagatgac caagaaccag gtgtccctga cctgtctggt gaagggcttc     1140
taccccagcg acatcgccgt ggagtgggag agcaacggcc agcccgagaa caactacaag     1200
accacccccc cagtgctgga cagcgacggc agcttcttcc tgtacagcaa gctgaccgtg     1260
gacaagtcca ggtggcagca gggcaacgtg ttcagctgca cgtgatgca cgaggccctg     1320 cacaaccact acacccagaa gagcctgagc ctgtccccccg gcaag                   1365
```

<210> SEQ ID NO 86
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Ser Gly Ser Ser Ser Asn Ile Gly Asn Asn Tyr Val Ser
1               5                   10

<210> SEQ ID NO 87
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Asp Asn Tyr Lys Arg Pro Ser
1               5

<210> SEQ ID NO 88
<211> LENGTH: 11
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gly Thr Trp Asp Arg Ser Leu Ser Ala Val Val
1               5                   10

<210> SEQ ID NO 89
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Ser Gly Ser Ser Ser Asn Ile Gly Asn Asn Tyr Val Ser
1               5                   10

<210> SEQ ID NO 90
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Asp Asn Tyr Lys Arg Pro Ser
1               5

<210> SEQ ID NO 91
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Thr Trp Asp Arg Ser Leu Ser Ala Val Val
1               5                   10

<210> SEQ ID NO 92
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Ser Ser Ser Asn Ile Gly Asn Asn Tyr
1               5

<210> SEQ ID NO 93
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 93

Asp Asn Tyr
1

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Trp Asp Arg Ser Leu Ser Ala Val
1               5

<210> SEQ ID NO 95
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ser Ser Asn Ile Gly Asn Asn Tyr
1               5

<210> SEQ ID NO 96
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Asp Asn Tyr
1

<210> SEQ ID NO 97
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Thr Trp Asp Arg Ser Leu Ser Ala Val Val
1               5                   10

<210> SEQ ID NO 98
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Ser Val Leu Thr Gln Pro Pro Ser Val Ser Ala Ala Ala Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln His Leu Pro Gly Thr Ala Pro Lys Leu Leu
        35                  40                  45

Ile Tyr Asp Asn Tyr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Arg Ser Leu
                85                  90                  95

Ser Ala Val Val Phe Gly Gly Gly Thr Lys Leu Thr Val Leu
            100                 105                 110

<210> SEQ ID NO 99
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
cagtctgtgc tgacgcagcc gccctcagtg tctgcggccg caggacagaa ggtcaccatc     60
tcctgctctg gaagcagttc caacattggg aataattatg tatcctggta ccagcacctc    120
ccaggaacag ccccccaaact cctcatttat gacaattata gcgacccctc agggattcct    180
gaccgattct ctggctccaa gtctggcacg tcagccaccc tgggcatcac cggactccag    240
actggggacg aggccgacta ttattgcgga acatgggata ggagcctgag tgctgtggta    300
ttcggcggag ggaccaagct gaccgtccta                                      330

<210> SEQ ID NO 100
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Gln Ser Val Leu Thr Gln Pro Pro Ser Val Ser Ala Ala Ala Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln His Leu Pro Gly Thr Ala Pro Lys Leu Leu
        35                  40                  45

Ile Tyr Asp Asn Tyr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Arg Ser Leu
                85                  90                  95

Ser Ala Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu

```
            115                 120                 125
Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
        210                 215
```

<210> SEQ ID NO 101
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 101

```
cagtctgtgc tgacgcagcc gccctcagtg tctgcggccg caggacagaa ggtcaccatc      60
tcctgctctg gaagcagttc caacattggg aataattatg tatcctggta ccagcaccta    120
ccaggaacag ccccccaaact cctcatttat gacaattata gcgaccctc agggattcct    180
gaccgattct ctggctccaa gtctggcacg tcagccaccc tgggcatcac cggactccag    240
actgggacg aggccgacta ttattgcgga acatgggata ggagcctgag tgctgtggta    300
ttcggcggag ggaccaagct gaccgtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca acaagtacgc cgccagcagc    540
tatctgagcc tgacgcctga gcagtggaag tcccacagaa gctacagctg ccaggtcacc    600
cacgagggca gcaccgtgga gaaaaccgtg gcccccaccg agtgcagc                648
```

<210> SEQ ID NO 102
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 102

```
Gly Tyr Arg Phe Thr Ser His Trp Ile Ser
1               5                   10
```

<210> SEQ ID NO 103
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 103

Arg Ile Asp Pro Ser Asp Ser Tyr Ile Lys Tyr Ser Pro Ser Phe Gln
1               5                   10                  15

Gly

<210> SEQ ID NO 104
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Leu Gly Tyr Ser Ser Gly Trp Tyr Tyr Phe Asp Tyr
1               5                   10

<210> SEQ ID NO 105
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Ser His Trp Ile Ser
1               5

<210> SEQ ID NO 106
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Arg Ile Asp Pro Ser Asp Ser Tyr Ile Lys Tyr Ser Pro Ser Phe Gln
1               5                   10                  15

Gly

<210> SEQ ID NO 107
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Leu Gly Tyr Ser Ser Gly Trp Tyr Tyr Phe Asp Tyr
1               5                   10

<210> SEQ ID NO 108
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 108

Gly Tyr Arg Phe Thr Ser His
1               5

<210> SEQ ID NO 109
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Asp Pro Ser Asp Ser Tyr
1               5

<210> SEQ ID NO 110
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Leu Gly Tyr Ser Ser Gly Trp Tyr Tyr Phe Asp Tyr
1               5                   10

<210> SEQ ID NO 111
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Gly Tyr Arg Phe Thr Ser His Trp
1               5

<210> SEQ ID NO 112
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Ile Asp Pro Ser Asp Ser Tyr Ile
1               5

<210> SEQ ID NO 113
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Ala Arg Leu Gly Tyr Ser Ser Gly Trp Tyr Tyr Phe Asp Tyr
1               5                   10
```

<210> SEQ ID NO 114
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 114

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Arg Phe Thr Ser His
            20                  25                  30

Trp Ile Ser Trp Val Arg Gln Met Pro Gly Lys Gly Leu Glu Trp Val
        35                  40                  45

Ala Arg Ile Asp Pro Ser Asp Ser Tyr Ile Lys Tyr Ser Pro Ser Phe
    50                  55                  60

Gln Gly His Val Thr Ile Ser Ala Asp Lys Ser Thr Ser Thr Ala Phe
65                  70                  75                  80

Leu Gln Trp Ser Ser Leu Lys Ala Ser Asp Thr Ala Met Tyr Tyr Cys
                85                  90                  95

Ala Arg Leu Gly Tyr Ser Ser Gly Trp Tyr Tyr Phe Asp Tyr Trp Gly
            100                 105                 110

Gln Gly Thr Leu Val Thr Val Ser Ser
        115                 120
```

<210> SEQ ID NO 115
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115

```
gaagtgcagc tggtgcagtc tggagcagag gtgaaaaagc ccggggagtc tctgaggatc      60
tcttgtaagg gttctggata caggtttacc agccactgga tcagctgggt gcgccagatg     120
cccgggaaag gcctggagtg gtggcgagg attgatccta gtgactctta tatcaagtac      180
agcccgtcct tccaaggcca cgtcaccatc tcagctgaca agtccaccag cacagccttc     240
ctgcagtgga gcagcctgaa ggcctcggac accgccatgt attactgtgc gagactaggg     300
tatagcagtg gctggtacta ttttgactac tggggccagg gaaccctggt caccgtctcc     360
tca                                                                   363
```

<210> SEQ ID NO 116
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 116

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Arg Phe Thr Ser His
```

-continued

```
             20                  25                  30
Trp Ile Ser Trp Val Arg Gln Met Pro Gly Lys Gly Leu Glu Trp Val
             35                  40                  45
Ala Arg Ile Asp Pro Ser Asp Ser Tyr Ile Lys Tyr Ser Pro Ser Phe
             50                  55                  60
Gln Gly His Val Thr Ile Ser Ala Asp Lys Ser Thr Ser Thr Ala Phe
 65                  70                  75                  80
Leu Gln Trp Ser Ser Leu Lys Ala Ser Asp Thr Ala Met Tyr Tyr Cys
                         85                  90                  95
Ala Arg Leu Gly Tyr Ser Ser Gly Trp Tyr Tyr Phe Asp Tyr Trp Gly
                        100                 105                 110
Gln Gly Thr Leu Val Thr Val Ser Ser Ala Ser Thr Lys Gly Pro Ser
                115                 120                 125
Val Phe Pro Leu Ala Pro Cys Ser Arg Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                    165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Arg Val Glu Pro Lys Ser Cys
        210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                    245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                    325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                    405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
```

Pro Gly Lys
    450

<210> SEQ ID NO 117
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117

```
gaagtgcagc tggtgcagtc tggagcagag gtgaaaaagc ccggggagtc tctgaggatc      60
tcttgtaagg gttctggata caggtttacc agccactgga tcagctgggt gcgccagatg     120
cccgggaaag gcctggagtg ggtggcgagg attgatccta gtgactctta tatcaagtac     180
agcccgtcct tccaaggcca cgtcaccatc tcagctgaca agtccaccag cacagccttc     240
ctgcagtgga gcagcctgaa ggcctcggac accgccatgt attactgtgc gagactaggg     300
tatagcagtg gctggtacta ttttgactac tggggccagg gaaccctggt caccgtctcc     360
tcagcttcca ccaagggccc atcggtcttc cccctggcgc cctgctccag gagcacctct     420
gggggcacag cggccctggg ctgcctggtc aaggactact ccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa ccacaagccc agcaacacca aggtggacaa gagagtggag     660
cccaagagct gcgacaagac ccacacctgc cccccctgcc cagccccaga gctgctgggc     720
ggaccctccg tgttcctgtt cccccccaag cccaaggaca ccctgatgat cagcaggacc     780
cccgaggtga cctgcgtggt ggtggacgtg agccacgagg acccagaggt gaagttcaac     840
tggtacgtgg acggcgtgga ggtgcacaac gccaagacca gcccagaga ggagcagtac     900
aacagcacct acagggtggt gtccgtgctg accgtgctgc accaggactg gctgaacggc     960
aaggaataca agtgcaaggt ctccaacaag gccctgccag cccccatcga aaagaccatc    1020
agcaaggcca agggccagcc acgggagccc caggtgtaca ccctgccccc ctcccgggag    1080
gagatgacca gaaccaggt gtccctgacc tgtctggtga agggcttcta ccccagcgac    1140
atcgccgtgg agtgggagag caacggccag ccgagaaca actacaagac cacccccca    1200
gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaaga gcctgagcct gtcccccggc aag                                1353
```

<210> SEQ ID NO 118
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Ser Gly Ser Arg Thr Asn Ile Gly Ser Asn Ala Val Asn
1               5                   10

<210> SEQ ID NO 119

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Ser Ser Asp Gln Arg Pro Ser
1               5

<210> SEQ ID NO 120
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Ala Ala Trp Asp Asp Ser Leu His Gly Trp Val
1               5                   10

<210> SEQ ID NO 121
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Ser Gly Ser Arg Thr Asn Ile Gly Ser Asn Ala Val Asn
1               5                   10

<210> SEQ ID NO 122
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Ser Ser Asp Gln Arg Pro Ser
1               5

<210> SEQ ID NO 123
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Ala Ala Trp Asp Asp Ser Leu His Gly Trp Val
1               5                   10

<210> SEQ ID NO 124
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 124

Ser Arg Thr Asn Ile Gly Ser Asn Ala
1               5

<210> SEQ ID NO 125
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Ser Ser Asp
1

<210> SEQ ID NO 126
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Trp Asp Asp Ser Leu His Gly Trp
1               5

<210> SEQ ID NO 127
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Arg Thr Asn Ile Gly Ser Asn Ala
1               5

<210> SEQ ID NO 128
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Ser Ser Asp
1

<210> SEQ ID NO 129
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 129

Ala Ala Trp Asp Asp Ser Leu His Gly Trp Val
1               5                   10

<210> SEQ ID NO 130
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Ser Pro Val Leu Thr Gln Pro Pro Ser Ala Ser Gly Thr Pro Gly Gln
1               5                   10                  15

Arg Val Thr Ile Ser Cys Ser Gly Ser Arg Thr Asn Ile Gly Ser Asn
            20                  25                  30

Ala Val Asn Trp Tyr Gln Gln Val Pro Gly Thr Ala Pro Lys Leu Leu
        35                  40                  45

Ile Tyr Ser Ser Asp Gln Arg Pro Ser Gly Val Ser Asp Arg Phe Ser
    50                  55                  60

Gly Ser Lys Ser Gly Thr Ser Gly Ser Leu Ala Ile Ser Gly Leu Gln
65                  70                  75                  80

Ser Glu Asp Glu Thr Asp Tyr Tyr Cys Ala Ala Trp Asp Asp Ser Leu
                85                  90                  95

His Gly Trp Val Phe Gly Gly Gly Thr Lys Leu Thr Val Leu
            100                 105                 110

<210> SEQ ID NO 131
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131
tcgcctgtgc tgactcagcc gcccctcagcg tctgggaccc ccgggcagag ggtcaccatc    60
tcttgttctg gaagcaggac caacatcgga agtaatgctg taaactggta ccagcaggtc   120
ccaggaacgg ccccccaaact cctcatctat agtagtgatc agcggccctc aggggtctct   180
gaccgattct ctggctccaa gtctggcacc tcaggctccc tggccatcag tggcctccag   240
tctgaggatg aaactgatta ttactgtgca gcatgggatg acagcctgca tggttgggtg   300
ttcggcggag ggaccaagct gaccgtccta                                     330

<210> SEQ ID NO 132
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Ser Pro Val Leu Thr Gln Pro Pro Ser Ala Ser Gly Thr Pro Gly Gln
1               5                   10                  15

Arg Val Thr Ile Ser Cys Ser Gly Ser Arg Thr Asn Ile Gly Ser Asn
            20                  25                  30

Ala Val Asn Trp Tyr Gln Gln Val Pro Gly Thr Ala Pro Lys Leu Leu
                35                  40                  45

Ile Tyr Ser Ser Asp Gln Arg Pro Ser Gly Val Ser Asp Arg Phe Ser
    50                  55                  60

Gly Ser Lys Ser Gly Thr Ser Gly Ser Leu Ala Ile Ser Gly Leu Gln
65                  70                  75                  80

Ser Glu Asp Glu Thr Asp Tyr Tyr Cys Ala Ala Trp Asp Asp Ser Leu
                85                  90                  95

His Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 133
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133
tcgcctgtgc tgactcagcc gccctcagcg tctgggaccc ccgggcagag ggtcaccatc      60
tcttgttctg gaagcaggac caacatcgga agtaatgctg taaactggta ccagcaggtc     120
ccaggaacgg ccccccaaact cctcatctat agtagtgatc agcggccctc agggggtctct   180 gaccgattct ctggctccaa gtctggcacc tcaggctccc tggccatcag tggcctccag    240
tctgaggatg aaactgatta ttactgtgca gcatgggatg acagcctgca tggttgggtg    300
ttcggcggag ggaccaagct gaccgtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca acaagtacgc cgccagcagc    540
tacctgagcc tgacccccga gcagtggaag agccacagaa gctacagctg ccaggtcacc    600
cacgagggca gcaccgtgga gaaaaccgtg gccccccaccg agtgcagc                648

<210> SEQ ID NO 134
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 134

Gly Tyr Arg Phe Thr Ser His Trp Ile Ser
1               5                   10

<210> SEQ ID NO 135
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Arg Ile Asp Pro Ser Asp Ser Tyr Thr Lys Tyr Ser Pro Ser Phe Gln
1               5                   10                  15

Gly

<210> SEQ ID NO 136
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Leu Gly Tyr His Ser Gly Trp Tyr Tyr Phe Asp Tyr
1               5                   10

<210> SEQ ID NO 137
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Ser His Trp Ile Ser
1               5

<210> SEQ ID NO 138
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Arg Ile Asp Pro Ser Asp Ser Tyr Thr Lys Tyr Ser Pro Ser Phe Gln
1               5                   10                  15

Gly

<210> SEQ ID NO 139
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:

```
                              Synthetic peptide"

<400> SEQUENCE: 139

Leu Gly Tyr His Ser Gly Trp Tyr Tyr Phe Asp Tyr
1               5                   10

<210> SEQ ID NO 140
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Gly Tyr Arg Phe Thr Ser His
1               5

<210> SEQ ID NO 141
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Asp Pro Ser Asp Ser Tyr
1               5

<210> SEQ ID NO 142
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Leu Gly Tyr His Ser Gly Trp Tyr Tyr Phe Asp Tyr
1               5                   10

<210> SEQ ID NO 143
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Gly Tyr Arg Phe Thr Ser His Trp
1               5

<210> SEQ ID NO 144
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144
```

Ile Asp Pro Ser Asp Ser Tyr Thr
1               5

<210> SEQ ID NO 145
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Ala Arg Leu Gly Tyr His Ser Gly Trp Tyr Tyr Phe Asp Tyr
1               5                   10

<210> SEQ ID NO 146
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Gln Val Gln Leu Val Glu Ser Gly Ala Glu Val Lys Lys Pro Gly Glu
1               5                   10                  15

Ser Leu Arg Ile Ser Cys Lys Gly Ser Gly Tyr Arg Phe Thr Ser His
            20                  25                  30

Trp Ile Ser Trp Val Arg Gln Met Pro Gly Lys Gly Leu Glu Trp Val
        35                  40                  45

Ala Arg Ile Asp Pro Ser Asp Ser Tyr Thr Lys Tyr Ser Pro Ser Phe
    50                  55                  60

Gln Gly His Val Thr Ile Ser Thr Asp Lys Ser Thr Ser Thr Ala Tyr
65                  70                  75                  80

Leu His Trp Ser Ser Leu Lys Ala Ser Asp Thr Ala Met Tyr Tyr Cys
                85                  90                  95

Ala Arg Leu Gly Tyr His Ser Gly Trp Tyr Tyr Phe Asp Tyr Trp Gly
            100                 105                 110

Gln Gly Thr Leu Val Thr Val Ser Ser
        115                 120

<210> SEQ ID NO 147
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 147
caggtgcagc tggtggagtc tggagcagag gtgaaaaagc ccggggagtc tctgaggatc      60
tcctgtaagg gttctggata caggtttacc agccactgga tcagctgggt gcgccagatg     120
cccgggaaag gcctggagtg gtggcgagg attgatccta gtgactctta taccaagtac      180
agcccgtcct tccaaggcca cgtcaccatc tcaactgaca gtccaccag cacagcctac      240 ctgcactgga gcagcctgaa ggcctcggac accgccatgt attactgtgc gagactaggg     300
tatcacagtg gctggtacta ctttgactac tggggccagg gaaccctggt caccgtctcc     360
tca                                                                   363

<210> SEQ ID NO 148
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 148

```
Gln Val Gln Leu Val Glu Ser Gly Ala Glu Val Lys Lys Pro Gly Glu
1               5                   10                  15

Ser Leu Arg Ile Ser Cys Lys Gly Ser Gly Tyr Arg Phe Thr Ser His
            20                  25                  30

Trp Ile Ser Trp Val Arg Gln Met Pro Gly Lys Gly Leu Glu Trp Val
        35                  40                  45

Ala Arg Ile Asp Pro Ser Asp Ser Tyr Thr Lys Tyr Ser Pro Ser Phe
    50                  55                  60

Gln Gly His Val Thr Ile Ser Thr Asp Lys Ser Thr Ser Thr Ala Tyr
65                  70                  75                  80

Leu His Trp Ser Ser Leu Lys Ala Ser Asp Thr Ala Met Tyr Tyr Cys
                85                  90                  95

Ala Arg Leu Gly Tyr His Ser Gly Trp Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 149
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 149

```
caggtgcagc tggtggagtc tggagcagag gtgaaaaagc cggggagtc tctgaggatc      60
tcctgtaagg gttctggata caggtttacc agccactgga tcagctgggt gcgccagatg    120
cccgggaaag gcctggagtg ggtggcgagg attgatccta gtgactctta taccaagtac    180
agcccgtcct tccaaggcca cgtcaccatc tcaactgaca gtccaccag cacagcctac     240
ctgcactgga gcagcctgaa ggcctcggac accgccatgt attactgtgc gagactaggg    300
tatcacagtg gctggtacta cttttgactac tggggccagg gaaccctggt caccgtctcc   360
tcagcttcca ccaagggccc atcggtcttc cccctggcgc cctgctccag gagcacctct   420
gggggcacag cggccctggg ctgcctggtc aaggactact ccccgaacc ggtgacggtg    480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa ccacaagccc agcaacacca aggtggacaa gagagtggag   660
cccaagagct gcgacaagac ccacacctgc ccccctgcc cagccccaga gctgctgggc    720
ggaccctccg tgttcctgtt cccccccaag cccaaggaca ccctgatgat cagcaggacc    780
cccgaggtga cctgcgtggt ggtggacgtg agccacgagg acccagaggt gaagttcaac    840
tggtacgtgg acggcgtgga ggtgcacaac gccaagacca gcccagaga ggagcagtac    900
aacagcacct acagggtggt gtccgtgctg accgtgctgc accaggactg gctgaacggc    960
aaggaataca agtgcaaggt ctccaacaag gccctgccag cccccatcga aaagaccatc   1020
agcaaggcca agggccagcc acgggagccc caggtgtaca ccctgccccc ctcccgggag   1080
gagatgacca gaaccaggt gtccctgacc tgtctggtga agggcttcta ccccagcgac   1140
atcgccgtgg agtgggagag caacggccag ccgagaaca actacaagac caccccccca   1200
gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaaga gcctgagcct gtccccccggc aag                                1353
```

```
<210> SEQ ID NO 150
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Ser Gly Ser Ser Ser Asn Ile Gly Ser Asn Ala Val Asn
1               5                   10

<210> SEQ ID NO 151
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Ser Ser Asp Gln Arg Pro Ser
1               5

<210> SEQ ID NO 152
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Ala Ala Trp Asp Asp Ser Leu His Gly Trp Ile
1               5                   10

<210> SEQ ID NO 153
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Ser Gly Ser Ser Ser Asn Ile Gly Ser Asn Ala Val Asn
1               5                   10

<210> SEQ ID NO 154
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Ser Ser Asp Gln Arg Pro Ser
1               5

<210> SEQ ID NO 155
<211> LENGTH: 11
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Ala Ala Trp Asp Asp Ser Leu His Gly Trp Ile
1               5                   10

<210> SEQ ID NO 156
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Ser Ser Ser Asn Ile Gly Ser Asn Ala
1               5

<210> SEQ ID NO 157
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Ser Ser Asp
1

<210> SEQ ID NO 158
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Trp Asp Asp Ser Leu His Gly Trp
1               5

<210> SEQ ID NO 159
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Ser Ser Asn Ile Gly Ser Asn Ala
1               5

<210> SEQ ID NO 160
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
```

```
            Synthetic peptide"

<400> SEQUENCE: 160

Ser Ser Asp
1

<210> SEQ ID NO 161
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Ala Ala Trp Asp Asp Ser Leu His Gly Trp Ile
1               5                   10

<210> SEQ ID NO 162
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Ser Ser Asp Gln Arg Pro Ser Gly Val Pro Asp Arg Phe Ser
    50                  55                  60

Gly Ser Lys Ser Gly Thr Ser Gly Ser Leu Ala Ile Ser Gly Leu His
65                  70                  75                  80

Ser Glu Asp Glu Thr Asp Tyr Tyr Cys Ala Ala Trp Asp Asp Ser Leu
                85                  90                  95

His Gly Trp Ile Phe Gly Gly Gly Thr Lys Leu Thr Val Ile
            100                 105                 110

<210> SEQ ID NO 163
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 163
cagtctgccc tgactcagcc accctcagcg tctgggaccc ccgggcagag ggtcaccatc      60
tcttgttctg gaagcagctc caacatcgga agtaatgctg taaactggta ccagcagctc    120
ccaggaacgg cccccaaact cctcatctat agtagtgatc agcggccctc aggggtccct    180
gaccgattct ctggctccaa gtctggcacc tcaggctccc tggccatcag tgggctccac    240
tctgaggatg agactgatta ttactgtgca gcatgggatg acagcctgca tggttggata    300
ttcggcggag ggaccaagct gaccgtcata                                     330
```

<210> SEQ ID NO 164
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 164

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Ser Ser Asp Gln Arg Pro Ser Gly Val Pro Asp Arg Phe Ser
    50                  55                  60

Gly Ser Lys Ser Gly Thr Ser Gly Ser Leu Ala Ile Ser Gly Leu His
65                  70                  75                  80

Ser Glu Asp Glu Thr Asp Tyr Tyr Cys Ala Ala Trp Asp Asp Ser Leu
                85                  90                  95

His Gly Trp Ile Phe Gly Gly Gly Thr Lys Leu Thr Val Ile Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 165
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 165
cagtctgccc tgactcagcc accctcagcg tctgggaccc ccgggcagag ggtcaccatc     60
tcttgttctg gaagcagctc caacatcgga agtaatgctg taaactggta ccagcagctc    120
ccaggaacgg cccccaaact cctcatctat agtagtgatc agcggccctc agggggtccct   180 gaccgattct ctggctccaa gtctggcacc tcaggctccc tggccatcag tgggctccac    240
tctgaggatg agactgatta ttactgtgca gcatgggatg acagcctgca tggttggata    300
ttcggcggag ggaccaagct gaccgtcata ggtcagccca ggctgccccc tcggtcact     360 ctgttcccgc cctcctctga ggagcttcaa gccaacaagg ccacactggt gtgtctcata    420

-continued

```
agtgacttct acccgggagc cgtgacagtg gcctggaagg cagatagcag ccccgtcaag     480
gcgggagtgg agaccaccac accctccaaa caaagcaaca acaagtacgc cgccagcagc     540
tacctgagcc tgacgcctga gcagtggaag tcccacagaa gctacagctg ccaggtcacc     600
cacgagggca gcaccgtgga gaaaaccgtg gcccccaccg agtgcagc                  648
```

```
<210> SEQ ID NO 166
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Gly Ala Ser Ile Ser Ser Gly Ser Asp Tyr Trp Ser
1               5                   10

<210> SEQ ID NO 167
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Arg Ile Tyr Thr Ser Gly Arg Asn Ser Tyr Asn Pro Ser Leu Lys Ser
1               5                   10                  15

<210> SEQ ID NO 168
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Asn Ser Arg Arg Tyr Gly Gly Tyr Asp Leu Phe Asp Val
1               5                   10

<210> SEQ ID NO 169
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Ser Gly Ser Asp Tyr Trp Ser
1               5

<210> SEQ ID NO 170
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 170

Arg Ile Tyr Thr Ser Gly Arg Asn Ser Tyr Asn Pro Ser Leu Lys Ser
1               5                   10                  15

<210> SEQ ID NO 171
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Asn Ser Arg Arg Tyr Gly Gly Tyr Asp Leu Phe Asp Val
1               5                   10

<210> SEQ ID NO 172
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Gly Ala Ser Ile Ser Ser Gly Ser Asp
1               5

<210> SEQ ID NO 173
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Tyr Thr Ser Gly Arg
1               5

<210> SEQ ID NO 174
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Asn Ser Arg Arg Tyr Gly Gly Tyr Asp Leu Phe Asp Val
1               5                   10

<210> SEQ ID NO 175
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Gly Ala Ser Ile Ser Ser Gly Ser Asp Tyr
1               5                   10
```

<210> SEQ ID NO 176
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Ile Tyr Thr Ser Gly Arg Asn
1               5

<210> SEQ ID NO 177
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Ala Arg Asn Ser Arg Arg Tyr Gly Gly Tyr Asp Leu Phe Asp Val
1               5                   10                  15

<210> SEQ ID NO 178
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Gln Val Gln Leu Gln Glu Ser Gly Pro Gly Leu Val Lys Pro Ser Gln
1               5                   10                  15

Thr Leu Ser Leu Thr Cys Thr Val Ser Gly Ala Ser Ile Ser Ser Gly
                20                  25                  30

Ser Asp Tyr Trp Ser Trp Ile Arg Gln Pro Ala Gly Lys Gly Leu Glu
            35                  40                  45

Trp Ile Gly Arg Ile Tyr Thr Ser Gly Arg Asn Ser Tyr Asn Pro Ser
    50                  55                  60

Leu Lys Ser Arg Val Thr Ile Ala Val Asp Thr Ser Lys Asn Gln Phe
65                  70                  75                  80

Ser Leu Lys Leu Ser Ser Val Ser Ala Thr Asp Thr Ala Val Tyr Tyr
                85                  90                  95

Cys Ala Arg Asn Ser Arg Arg Tyr Gly Gly Tyr Asp Leu Phe Asp Val
            100                 105                 110

Trp Gly Gln Gly Thr Met Val Thr Val Ser Ser
        115                 120

<210> SEQ ID NO 179
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 179

-continued

```
caggtgcagc tgcaggagtc gggcccagga ctggtgaagc cttcacagac cctgtccctc    60
acctgcactg tctctggtgc ctccatcagc agtggtagtg actactggag ctggatccgg   120
cagcccgccg ggaagggact ggagtggatt gggcgtatct ataccagtgg gaggaacagc   180
tacaacccct ccctcaagag tcgagtcacc atagcagtag acacgtccaa gaaccagttc   240
tccctgaagc tgagtagtgt gagtgccaca gacacggccg tgtattactg tgcgaggaat   300
agcagaagat atggtggcta cgatctgttt gatgtctggg gccaagggac aatggtcacc   360
gtctcttca                                                            369
```

<210> SEQ ID NO 180
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 180

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Ala Ser Ile Ser Ser Gly
            20                  25                  30

Ser Asp Tyr Trp Ser Trp Ile Arg Gln Pro Ala Gly Lys Gly Leu Glu
        35                  40                  45

Trp Ile Gly Arg Ile Tyr Thr Ser Gly Arg Asn Ser Tyr Asn Pro Ser
    50                  55                  60

Leu Lys Ser Arg Val Thr Ile Ala Val Asp Thr Ser Lys Asn Gln Phe
65                  70                  75                  80

Ser Leu Lys Leu Ser Ser Val Ser Ala Thr Asp Thr Ala Val Tyr Tyr
                85                  90                  95

Cys Ala Arg Asn Ser Arg Arg Tyr Gly Gly Tyr Asp Leu Phe Asp Val
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 181
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 181
caggtgcagc tgcaggagtc gggcccagga ctggtgaagc cttcacagac cctgtccctc      60
acctgcactg tctctggtgc ctccatcagc agtggtagtg actactggag ctggatccgg     120
cagcccgccg ggaagggact ggagtggatt gggcgtatct ataccagtgg gaggaacagc     180
tacaaccccc tccctcaagag tcgagtcacc atagcagtag acacgtccaa gaaccagttc     240
tccctgaagc tgagtagtgt gagtgccaca gacacggccg tgtattactg tgcgaggaat     300 agcagaaagat atggtggcta cgatctgttt gatgtctggg gccaagggac aatggtcacc     360
gtctcttcag cctccaccaa gggcccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaaccac aagcccagca acaccaaggt ggacaagaga     660
gtggagccca gagctgcga caagacccac acctgccccc cctgcccagc cccagagctg     720
ctgggcggac cctccgtgtt cctgttcccc ccaagcccca aggacaccct gatgatcagc     780 aggaccccg aggtgacctg cgtggtggtg gacgtgagcc acgaggaccc agaggtgaag     840
ttcaactggt acgtggacgg cgtggaggtg cacaacgcca agaccaagcc agagaggag     900 cagtacaaca gcacctacag ggtggtgtcc gtgctgaccg tgctgcacca ggactggctg     960
aacggcaagg aatacaagtg caaggtctcc aacaaggccc tgccagcccc catcgaaaag    1020

```
accatcagca aggccaaggg ccagccacgg gagccccagg tgtacaccct gccccctcc      1080 cgggaggaga tgaccaagaa ccaggtgtcc ctgacctgtc tggtgaaggg cttctacccc      1140
agcgacatcg ccgtggagtg ggagagcaac ggccagcccg agaacaacta caagaccacc      1200
cccccagtgc tggacagcga cggcagcttc ttcctgtaca gcaagctgac cgtggacaag      1260
tccaggtggc agcagggcaa cgtgttcagc tgcagcgtga tgcacgaggc cctgcacaac      1320
cactacaccc agaagagcct gagcctgtcc cccggcaag                              1359
```

<210> SEQ ID NO 182
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Gly Gly Asn Asn Ile Gly Ser Lys Ser Val His
1               5                   10

<210> SEQ ID NO 183
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Tyr Asp Gly Asp Arg Pro Ser
1               5

<210> SEQ ID NO 184
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Gln Val Trp Asp Thr Ser Ser Asp His Pro Val
1               5                   10

<210> SEQ ID NO 185
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Gly Gly Asn Asn Ile Gly Ser Lys Ser Val His
1               5                   10

<210> SEQ ID NO 186
<211> LENGTH: 7
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 186

Tyr Asp Gly Asp Arg Pro Ser
1               5

<210> SEQ ID NO 187
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Gln Val Trp Asp Thr Ser Ser Asp His Pro Val
1               5                   10

<210> SEQ ID NO 188
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Asn Asn Ile Gly Ser Lys Ser
1               5

<210> SEQ ID NO 189
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Tyr Asp Gly
1

<210> SEQ ID NO 190
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Trp Asp Thr Ser Ser Asp His Pro
1               5

<210> SEQ ID NO 191
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 191

Asn Ile Gly Ser Lys Ser
1               5

<210> SEQ ID NO 192
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Tyr Asp Gly
1

<210> SEQ ID NO 193
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Gln Val Trp Asp Thr Ser Ser Asp His Pro Val
1               5                   10

<210> SEQ ID NO 194
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Ser Tyr Val Leu Thr Gln Pro Pro Ser Val Ser Glu Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Gly Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Pro Val Phe Gly Gly Gly Thr Lys Leu Thr Val Leu
                100                 105

<210> SEQ ID NO 195
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 195

```
tcctatgtgc tgactcagcc accctcagtg tcagaggccc caggaaagac ggccaggatt        60
acctgtgggg gaaacaacat tggaagtaaa agtgtgcact ggtaccagca gaagccaggc       120
caggccsctg tgctggtcat ctattatgat ggcgaccggc cctcagggat ccctgagcga       180
```
caggcccctg tgctggtcat ctattatgat ggcgaccggc cctcagggat ccctgagcga       180
```
ttctctggct ccaactctgg gaacacggcc accctgacca tcagcagggt cgaagccggg       240
gatgaggccg actattactg tcaggtgtgg gatactagta gtgatcaccc ggtgttcggc       300
ggagggacca agctgaccgt ccta                                              324
```

<210> SEQ ID NO 196
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

```
Ser Tyr Val Leu Thr Gln Pro Pro Ser Val Ser Glu Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Pro Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 197
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 197

```
tcctatgtgc tgactcagcc accctcagtg tcagaggccc caggaaagac ggccaggatt    60
acctgtgggg gaaacaacat tggaagtaaa agtgtgcact ggtaccagca gaagccaggc   120
caggcccctg tgctggtcat ctattatgat ggcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcaccc ggtgttcggc   300
ggagggacca agctgaccgt cctaggtcag cccaaggctg ccccctcggt cactctgttc   360
ccgcccctcc tctgaggagct tcaagccaac aaggccacac tggtgtgtct cataagtgac   420
ttctacccgg gagccgtgac agtggcctgg aaggcagata gcagcccgt caaggcggga   480
gtggagacca ccacaccctc caaacaaagc aacaacaagt acgccgccag cagctacctg   540
agcctgaccc ccgagcagtg gaagagccac agaagctaca gctgccaggt cacccacgag   600
ggcagcaccg tggagaaaac cgtggccccc accgagtgca gc                      642
```

<210> SEQ ID NO 198
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Gly Phe Thr Phe Ser Gly Tyr Asn Met His
1               5                   10

<210> SEQ ID NO 199
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Tyr Ile Ser Asn Ser Gly Arg Thr Ile Tyr Tyr Ala Asp Ser Val Lys
1               5                   10                  15
Gly

<210> SEQ ID NO 200
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Asp Arg Asp Pro Gln Trp Leu Gly Asn Asp Ala Leu Gln Ile
1               5                   10

<210> SEQ ID NO 201
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 201

Gly Tyr Asn Met His
1               5

<210> SEQ ID NO 202
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Tyr Ile Ser Asn Ser Gly Arg Thr Ile Tyr Tyr Ala Asp Ser Val Lys
1               5                   10                  15

Gly

<210> SEQ ID NO 203
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Asp Arg Asp Pro Gln Trp Leu Gly Asn Asp Ala Leu Gln Ile
1               5                   10

<210> SEQ ID NO 204
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Gly Phe Thr Phe Ser Gly Tyr
1               5

<210> SEQ ID NO 205
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Ser Asn Ser Gly Arg Thr
1               5

<210> SEQ ID NO 206
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206
```

Asp Arg Asp Pro Gln Trp Leu Gly Asn Asp Ala Leu Gln Ile
1               5                   10

<210> SEQ ID NO 207
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Gly Phe Thr Phe Ser Gly Tyr Asn
1               5

<210> SEQ ID NO 208
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Ile Ser Asn Ser Gly Arg Thr Ile
1               5

<210> SEQ ID NO 209
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Ala Arg Asp Arg Asp Pro Gln Trp Leu Gly Asn Asp Ala Leu Gln Ile
1               5                   10                  15

<210> SEQ ID NO 210
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 210

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Gly Tyr
            20                  25                  30

Asn Met His Trp Val Arg Gln Ala Pro Gly Lys Gly Leu Glu Trp Val
        35                  40                  45

Ser Tyr Ile Ser Asn Ser Gly Arg Thr Ile Tyr Tyr Ala Asp Ser Val
    50                  55                  60

Lys Gly Arg Phe Thr Leu Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Arg Asp Pro Gln Trp Leu Gly Asn Asp Ala Leu Gln Ile

```
            100                 105                 110
Trp Gly Gln Gly Thr Met Val Thr Val Ser Ser
        115                 120

<210> SEQ ID NO 211
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 211
caggtgcagc tggtggagtc tgggggaggc ttggtacagc ctggggggtc cctgaggctc      60
tcctgtgtag cctctggatt caccttcagt ggctataaca tgcactgggt ccgccaggct     120
ccagggaagg ggctggagtg ggtctcatac attagtaata gtggtagaac catatactac     180
gcagactctg tgaagggccg attcaccctg tccagagaca cgccaagaa ctcactgtat      240 ctgcagatga acagcctgag agccgaggac acggctgtct attttgtgc gagagatcgg      300 gatccccagt ggctgggaaa tgatgctctt caaatctggg gccaagggac aatggtcacc     360
gtctcttca                                                              369

<210> SEQ ID NO 212
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Gly Tyr
            20                  25                  30

Asn Met His Trp Val Arg Gln Ala Pro Gly Lys Gly Leu Glu Trp Val
        35                  40                  45

Ser Tyr Ile Ser Asn Ser Gly Arg Thr Ile Tyr Tyr Ala Asp Ser Val
    50                  55                  60

Lys Gly Arg Phe Thr Leu Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Arg Asp Pro Gln Trp Leu Gly Asn Asp Ala Leu Gln Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 213
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 213
caggtgcagc tggtggagtc tgggggaggc ttggtacagc ctggggggtc cctgagactc      60
tcctgtgtag cctctggatt caccttcagt ggctataaca tgcactgggt ccgccaggct     120
ccagggaagg ggctggagtg ggtctcatac attagtaata gtggtagaac catatactac     180
gcagactctg tgaagggccg attcaccctg tccagagaca cgccaagaa ctcactgtat     240 ctgcagatga acagcctgag agccgaggac acggctgtct attttgtgc gagagatcgg     300 gatccccagt ggctgggaaa tgatgctctt caaatctggg gccaagggac aatggtcacc     360
gtctcttcag cctccaccaa gggcccatcg gtcttccccc tggcaccctc ctccaagagc     420
acctctgggg gcacagcggc cctgggctgc ctggtcaagg actacttccc cgaaccggtg     480
```

```
acgtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaga    660
gtggagccca gagctgcga caagacccac acctgccccc cctgcccagc ccagagctg     720 ctgggcggac cctccgtgtt cctgttcccc cccaagccca aggacaccct gatgatcagc    780
aggacccccg aggtgacctg cgtggtggtg gacgtgagcc acgaggaccc agaggtgaag    840
ttcaactggt acgtggacgg cgtggaggtg cacaacgcca agaccaagcc cagagaggag    900
cagtacaaca gcacctacag ggtggtgtcc gtgctgaccg tgctgcacca ggactggctg    960
aacggcaagg aatacaagtg caaggtctcc aacaaggccc tgccagcccc catcgaaaag   1020
accatcagca aggccaaggg ccagccacgg gagcccagg tgtacaccct gcccccctcc    1080
cgggaggaga tgaccaagaa ccaggtgtcc ctgacctgtc tggtgaaggg cttctacccc   1140
agcgacatcg ccgtggagtg ggagagcaac ggccagcccg agaacaacta caagaccacc   1200
cccccagtgc tggacagcga cggcagcttc ttcctgtaca gcaagctgac cgtggacaag   1260
tccaggtggc agcagggcaa cgtgttcagc tgcagcgtga tgcacgaggc cctgcacaac   1320
cactacaccc agaagagcct gagcctgtcc cccggcaag                          1359
```

<210> SEQ ID NO 214
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Arg Ala Ser Gln Ser Val Ser Ser Gly Tyr Leu Ala
1               5                   10

<210> SEQ ID NO 215
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Gly Ala Ser Ser Arg Ala Thr
1               5

<210> SEQ ID NO 216
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Gln Gln Tyr Gly Thr Ser Arg Lys Thr
1               5

<210> SEQ ID NO 217
<211> LENGTH: 12
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Arg Ala Ser Gln Ser Val Ser Ser Gly Tyr Leu Ala
1               5                   10

<210> SEQ ID NO 218
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Gly Ala Ser Ser Arg Ala Thr
1               5

<210> SEQ ID NO 219
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Gln Gln Tyr Gly Thr Ser Arg Lys Thr
1               5

<210> SEQ ID NO 220
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Ser Gln Ser Val Ser Ser Gly Tyr
1               5

<210> SEQ ID NO 221
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Gly Ala Ser
1

<210> SEQ ID NO 222
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 222

Tyr Gly Thr Ser Arg Lys
1               5

<210> SEQ ID NO 223
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Gln Ser Val Ser Ser Gly Tyr
1               5

<210> SEQ ID NO 224
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Gly Ala Ser
1

<210> SEQ ID NO 225
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Gln Gln Tyr Gly Thr Ser Arg Lys Thr
1               5

<210> SEQ ID NO 226
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 226

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Thr Ser Arg
            85                  90                  95

Lys Thr Phe Gly Gln Gly Thr Lys Val Glu Ile Lys
            100                 105
```

<210> SEQ ID NO 227
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 227

```
gaaattgttt tgacgcagtc tccaggcacc ctgtctttgt ctccagggga aagagccacc    60
ctctcctgca gggccagtca gagtgttagc agtggctact tagcctggta tcagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttattgtcag cagtatggta cctcacgtaa gacgttcggc   300
caagggacca aggtggaaat caaa                                          324
```

<210> SEQ ID NO 228
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 228

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Arg
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
```

Ser Phe Asn Arg Gly Glu Cys
    210             215

<210> SEQ ID NO 229
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 229

```
gaaattgttt tgacgcagtc tccaggcacc ctgtctttgt ctccagggga aagagccacc      60
ctctcctgca gggccagtca gagtgttagc agtggctact tagcctggta tcagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttattgtcag cagtatggta cctcacgtaa gacgttcggc     300
caagggacca aggtggaaat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggacaacg ccctgcagag cggcaacagc     480
caggagagcg tcaccgagca ggacagcaag gactccacct acagcctgag cagcaccctg     540
accctgagca aggccgacta cgagaagcat aaggtgtacg cctgcgaggt gacccaccag     600
ggcctgtcca gccccgtgac caagagcttc aacaggggcg agtgc                     645
```

<210> SEQ ID NO 230
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Gly Gly Ser Ile Ser Gly Tyr Tyr Trp Ser
1               5                   10

<210> SEQ ID NO 231
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Leu Ile Tyr Glu Ser Gly Ser Ala Asn Tyr Asn Pro Ser Leu Lys Ser
1               5                   10                  15

<210> SEQ ID NO 232
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 232

Arg Val Arg Gly Trp Ser Tyr Gly Met Asp Val
1               5                   10

<210> SEQ ID NO 233
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Gly Tyr Tyr Trp Ser
1               5

<210> SEQ ID NO 234
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Leu Ile Tyr Glu Ser Gly Ser Ala Asn Tyr Asn Pro Ser Leu Lys Ser
1               5                   10                  15

<210> SEQ ID NO 235
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Arg Val Arg Gly Trp Ser Tyr Gly Met Asp Val
1               5                   10

<210> SEQ ID NO 236
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Gly Gly Ser Ile Ser Gly Tyr
1               5

<210> SEQ ID NO 237
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Tyr Glu Ser Gly Ser
1               5
```

```
<210> SEQ ID NO 238
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Arg Val Arg Gly Trp Ser Tyr Gly Met Asp Val
1               5                   10

<210> SEQ ID NO 239
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Gly Gly Ser Ile Ser Gly Tyr Tyr
1               5

<210> SEQ ID NO 240
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Ile Tyr Glu Ser Gly Ser Ala
1               5

<210> SEQ ID NO 241
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Ala Arg Arg Val Arg Gly Trp Ser Tyr Gly Met Asp Val
1               5                   10

<210> SEQ ID NO 242
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

Gln Val Gln Leu Val Gln Ser Gly Pro Gly Leu Val Lys Pro Ser Glu
1               5                   10                  15

Thr Leu Ser Leu Thr Cys Ser Val Ser Gly Gly Ser Ile Ser Gly Tyr
            20                  25                  30
```

Tyr Trp Ser Trp Ile Arg Gln Pro Pro Gly Lys Gly Leu Glu Trp Ile
            35                  40                  45

Gly Leu Ile Tyr Glu Ser Gly Ser Ala Asn Tyr Asn Pro Ser Leu Lys
        50                  55                  60

Ser Arg Val Thr Ile Ser Leu Asp Thr Ser Lys Asn Gln Phe Ser Leu
65                  70                  75                  80

Lys Leu Lys Ser Val Thr Ala Ala Asp Thr Ala Val Tyr Tyr Cys Ala
                85                  90                  95

Arg Arg Val Arg Gly Trp Ser Tyr Gly Met Asp Val Trp Gly Gln Gly
            100                 105                 110

Thr Thr Val Ala Val Ser Ser
        115

<210> SEQ ID NO 243
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 243
caggtgcagc tggtgcagtc tggcccagga ctggtgaagc cttcggagac cctgtccctc      60
acctgcagtg tctctggtgg ctccatcagt ggttactact ggagctggat ccggcagccc     120
ccagggaagg gactggagtg gatcggctta atttatgaga gtgggagcgc caactacaat     180
ccctccctca gagtcgagt caccatatcg ctagacacgt ccaagaatca gttctccctg     240
aagctgaagt ctgtgaccgc cgcggacacg gccgtgtatt actgtgcgag acgagtccgt     300
ggctggtctt acggtatgga cgtctggggc caagggacca cggtcgccgt ctcctca       357

<210> SEQ ID NO 244
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 244

Gln Val Gln Leu Val Gln Ser Gly Pro Gly Leu Val Lys Pro Ser Glu
1               5                   10                  15

Thr Leu Ser Leu Thr Cys Ser Val Ser Gly Gly Ser Ile Ser Gly Tyr
            20                  25                  30

Tyr Trp Ser Trp Ile Arg Gln Pro Pro Gly Lys Gly Leu Glu Trp Ile
        35                  40                  45

Gly Leu Ile Tyr Glu Ser Gly Ser Ala Asn Tyr Asn Pro Ser Leu Lys
    50                  55                  60

Ser Arg Val Thr Ile Ser Leu Asp Thr Ser Lys Asn Gln Phe Ser Leu
65                  70                  75                  80

Lys Leu Lys Ser Val Thr Ala Ala Asp Thr Ala Val Tyr Tyr Cys Ala
                85                  90                  95

Arg Arg Val Arg Gly Trp Ser Tyr Gly Met Asp Val Trp Gly Gln Gly
            100                 105                 110

Thr Thr Val Ala Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu

```
              130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 245
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 245
caggtgcagc tggtgcagtc tggcccagga ctggtgaagc cttcggagac cctgtccctc     60
acctgcagtg tctctggtgg ctccatcagt ggttactact ggagctggat ccggcagccc    120
ccagggaagg gactggagtg gatcggctta atttatgaga gtgggagcgc caactacaat    180
```

```
ccctccctca agagtcgagt caccatatcg ctagacacgt ccaagaatca gttctccctg    240
aagctgaagt ctgtgaccgc cgcggacacg gccgtgtatt actgtgcgag acgagtccgt    300
ggctggtctt acggtatgga cgtctggggc caagggacca cggtcgccgt ctcctcagcc    360
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaaccacaa gcccagcaac accaaggtgg acaagagagt tgagcccaaa    660
tcttgtgaca aaactcacac atgcccaccg tgcccagcac ctgaactcct ggggggaccg    660
agctgcgaca gacccacac ctgcccccc tgcccagccc cagagctgct gggcggaccc      720
tccgtgttcc tgttccccc caagcccaag gacaccctga tgatcagcag gaccccgag      780 gtgacctgcg tggtggtgga cgtgagccac gaggacccag aggtgaagtt caactggtac    840
gtggacggcg tggaggtgca caacgccaag accaagccca gaggagca gtacaacagc      900 acctacaggg tggtgtccgt gctgaccgtg ctgcaccagg actggctgaa cggcaaggaa    960
tacaagtgca aggtctccaa caaggccctg ccagccccca tcgaaaagac catcagcaag    1020 gccaagggc agccacggga gccccaggtg tacaccctgc cccctcccg ggaggagatg      1080 accaagaacc aggtgtccct gacctgtctg gtgaagggct tctacccag cgacatcgcc    1140 gtggagtggg agagcaacgg ccagcccgag aacaactaca agaccacccc cccagtgctg    1200
gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagagcctga gcctgtcccc cggcaag                                       1347
```

<210> SEQ ID NO 246
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Arg Ala Ser Gln Ile Leu Ser Ser Ser Phe Leu Ala
1               5                   10

<210> SEQ ID NO 247
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Ala Ala Ser Ser Arg Ala Thr
1               5

<210> SEQ ID NO 248
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

Gln His Tyr Gly Ser Ser Pro Pro Trp Thr
1               5                   10

<210> SEQ ID NO 249
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Arg Ala Ser Gln Ile Leu Ser Ser Ser Phe Leu Ala
1               5                   10

<210> SEQ ID NO 250
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Ala Ala Ser Ser Arg Ala Thr
1               5

<210> SEQ ID NO 251
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Gln His Tyr Gly Ser Ser Pro Pro Trp Thr
1               5                   10

<210> SEQ ID NO 252
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Ser Gln Ile Leu Ser Ser Ser Phe
1               5

<210> SEQ ID NO 253
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Ala Ala Ser

```
<210> SEQ ID NO 254
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Tyr Gly Ser Ser Pro Pro Trp
1               5

<210> SEQ ID NO 255
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Gln Ile Leu Ser Ser Ser Phe
1               5

<210> SEQ ID NO 256
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Ala Ala Ser
1

<210> SEQ ID NO 257
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Gln His Tyr Gly Ser Ser Pro Pro Trp Thr
1               5                   10

<210> SEQ ID NO 258
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 258

Asp Ile Val Leu Thr Gln Ser Pro Gly Thr Leu Ser Leu Ser Pro Gly
1               5                   10                  15

Glu Thr Ala Thr Leu Ser Cys Arg Ala Ser Gln Ile Leu Ser Ser Ser
            20                  25                  30
```

Phe Leu Ala Trp Phe Gln Gln Ile Pro Gly Gln Ala Pro Arg Leu Leu
         35                  40                  45

Ile Tyr Ala Ala Ser Ser Arg Ala Thr Gly Ile Pro Asp Arg Phe Ser
 50                  55                  60

Gly Ser Gly Ser Gly Thr Asp Phe Ser Leu Thr Ile Ser Arg Leu Glu
 65                  70                  75                  80

Pro Glu Asp Phe Ala Val Tyr Tyr Cys Gln His Tyr Gly Ser Ser Pro
                 85                  90                  95

Pro Trp Thr Phe Gly Gln Gly Thr Lys Val Glu Ile Lys
             100                 105

<210> SEQ ID NO 259
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 259
gatattgtgt tgacgcagtc tccaggcacc ctgtctttgt ctccagggga gacagccacc       60
ctctcctgca gggccagtca gattcttagc agcagcttct tagcctggtt ccagcagata      120
cctggccagg ctcccagact cctcatctat gctgcatcca gcagggccac tggcatccca      180
gacaggttca gtggcagtgg gtctgggaca gacttcagtc tcaccatcag cagactggag      240
cctgaagatt ttgcagtgta ttactgtcag cactatggta gctcacctcc ttggacgttc      300
ggccaaggga ccaaggtgga aatcaaa                                          327

<210> SEQ ID NO 260
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 260

Asp Ile Val Leu Thr Gln Ser Pro Gly Thr Leu Ser Leu Ser Pro Gly
 1               5                  10                  15

Glu Thr Ala Thr Leu Ser Cys Arg Ala Ser Gln Ile Leu Ser Ser Ser
                 20                  25                  30

Phe Leu Ala Trp Phe Gln Gln Ile Pro Gly Gln Ala Pro Arg Leu Leu
         35                  40                  45

Ile Tyr Ala Ala Ser Ser Arg Ala Thr Gly Ile Pro Asp Arg Phe Ser
 50                  55                  60

Gly Ser Gly Ser Gly Thr Asp Phe Ser Leu Thr Ile Ser Arg Leu Glu
 65                  70                  75                  80

Pro Glu Asp Phe Ala Val Tyr Tyr Cys Gln His Tyr Gly Ser Ser Pro
                 85                  90                  95

Pro Trp Thr Phe Gly Gln Gly Thr Lys Val Glu Ile Lys Arg Thr Val
             100                 105                 110

Ala Ala Pro Ser Val Phe Ile Phe Pro Pro Ser Asp Glu Gln Leu Lys
         115                 120                 125

Ser Gly Thr Ala Ser Val Val Cys Leu Leu Asn Asn Phe Tyr Pro Arg
     130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
            165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 261
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 261
gatattgtgt tgacgcagtc tccaggcacc ctgtctttgt ctccagggga gacagccacc       60
ctctcctgca gggccagtca gattcttagc agcagcttct tagcctggtt ccagcagata      120
cctggccagg ctcccagact cctcatctat gctgcatcca gcagggccac tggcatccca      180
gacaggttca gtggcagtgg gtctgggaca gacttcagtc tcaccatcag cagactggag      240
cctgaagatt ttgcagtgta ttactgtcag cactatggta gctcacctcc ttggacgttc      300
ggccaaggga ccaaggtgga aatcaaacga actgtggctg caccatctgt cttcatcttc      360
ccgccatctg atgagcagtt gaaatctgga actgcctctg ttgtgtgcct gctgaataac      420
ttctatccca gagaggccaa agtacagtgg aaggtggaca acgccctcca gagcggcaac      480
agccaggaga gcgtcaccga gcaggacagc aaggactcca cctacagcct gagcagcacc      540
ctgaccctga gcaaggccga ctacgagaag cataaggtgt acgcctgcga ggtgacccac      600
cagggcctgt ccagccccgt gaccaagagc ttcaacaggg gcgagtgc                   648

<210> SEQ ID NO 262
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Gly Tyr Thr Phe Thr Ser Tyr Asp Ile Ile
1               5                   10

<210> SEQ ID NO 263
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Arg Met Asn Pro Thr Gly Gly Asn Thr Asp Tyr Val Pro Lys Phe Gln
1               5                   10                  15

Gly

<210> SEQ ID NO 264
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Gly Val Lys Ser Leu Gly Val Ser Glu Ile Asp Tyr
1               5                   10

<210> SEQ ID NO 265
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Ser Tyr Asp Ile Ile
1               5

<210> SEQ ID NO 266
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Arg Met Asn Pro Thr Gly Gly Asn Thr Asp Tyr Val Pro Lys Phe Gln
1               5                   10                  15

Gly

<210> SEQ ID NO 267
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Gly Val Lys Ser Leu Gly Val Ser Glu Ile Asp Tyr
1               5                   10

<210> SEQ ID NO 268
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Gly Tyr Thr Phe Thr Ser Tyr
1               5

```
<210> SEQ ID NO 269
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Asn Pro Thr Gly Gly Asn
1               5

<210> SEQ ID NO 270
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Gly Val Lys Ser Leu Gly Val Ser Glu Ile Asp Tyr
1               5                   10

<210> SEQ ID NO 271
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Gly Tyr Thr Phe Thr Ser Tyr Asp
1               5

<210> SEQ ID NO 272
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Met Asn Pro Thr Gly Gly Asn Thr
1               5

<210> SEQ ID NO 273
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Ala Arg Gly Val Lys Ser Leu Gly Val Ser Glu Ile Asp Tyr
1               5                   10

<210> SEQ ID NO 274
<211> LENGTH: 121
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 274

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Ile Trp Val Arg Gln Ala Thr Gly Gln Gly Leu Glu Trp Met
        35                  40                  45

Gly Arg Met Asn Pro Thr Gly Gly Asn Thr Asp Tyr Val Pro Lys Phe
    50                  55                  60

Gln Gly Arg Val Thr Met Thr Arg Asp Ile Ser Leu Ser Thr Ala Tyr
65                  70                  75                  80

Met Glu Leu Arg Ser Leu Thr Ser Glu Asp Thr Ala Val Phe Tyr Cys
                85                  90                  95

Ala Arg Gly Val Lys Ser Leu Gly Val Ser Glu Ile Asp Tyr Trp Gly
            100                 105                 110

Gln Gly Thr Leu Val Thr Val Ser Ser
        115                 120
```

<210> SEQ ID NO 275
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 275

```
caggtgcagc tggtgcagtc tggggctgag gtgaagaaac ctggggcctc agtgaaggtc    60
tcctgcaagg cttctggata caccttcacc agttatgata tcatctgggt gcgacaggcc   120
actggacaag gccttgagtg gatgggaagg atgaacccta ccggtggtaa cacagactat   180
gtaccgaagt tccagggcag agtcaccatg accagggaca tctccttaag tacagcctac   240
atggagctgc gcagcctgac atctgaggac acggccgtgt tttactgtgc gagaggcgta   300
aagtctttag gagtttcgga aattgactac tggggccagg gaaccctggt caccgtctcc   360
tca                                                                 363
```

<210> SEQ ID NO 276
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 276

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Ile Trp Val Arg Gln Ala Thr Gly Gln Gly Leu Glu Trp Met
        35                  40                  45
```

```
Gly Arg Met Asn Pro Thr Gly Gly Asn Thr Asp Tyr Val Pro Lys Phe
    50                  55                  60

Gln Gly Arg Val Thr Met Thr Arg Asp Ile Ser Leu Ser Thr Ala Tyr
 65              70                  75                  80

Met Glu Leu Arg Ser Leu Thr Ser Glu Asp Thr Ala Val Phe Tyr Cys
                 85                  90                  95

Ala Arg Gly Val Lys Ser Leu Gly Val Ser Glu Ile Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
450
```

```
<210> SEQ ID NO 277
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 277
caggtgcagc tggtgcagtc tggggctgag gtgaagaaac ctggggcctc agtgaaggtc    60
tcctgcaagg cttctggata caccttcacc agttatgata tcatctgggt gcgacaggcc   120
actggacaag gcttgagtg gatgggaagg atgaaccctc ccggtggtaa cacagactat   180
gtaccgaagt tccagggcag agtcaccatg accagggaca tctccttaag tacagcctac   240
atggagctgc gcagcctgac atctgaggac acggccgtgt tttactgtgc gagaggcgta   300
aagtctttag gagtttcgga aattgactac tggggccagg gaaccctggt caccgtctcc   360
tcagcctcca ccaagggccc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa ccacaagccc agcaacacca aggtggacaa gagagttggag   660 cccaagagct gcgacaagac ccacacctgc cccccctgcc cagccccaga gctgctgggc   720
ggaccctccg tgttcctgtt cccccccaag cccaaggaca ccctgatgat cagcaggacc   780
cccgaggtga cctgcgtggt ggtggacgtg agccacgagg acccagaggt gaagttcaac   840
tggtacgtgg acggcgtgga ggtgcacaac gccaagacca gcccagaga ggagcagtac   900 aacagcacct acagggtggt gtccgtgctg accgtgctgc accaggactg gctgaacggc   960
aaggaataca agtgcaaggt ctccaacaag gccctgccag cccccatcga aaagaccatc  1020
agcaaggcca agggccagcc acgggagccc caggtgtaca ccctgccccc ctcccgggag  1080
gagatgacca gaaccaggt gtccctgacc tgtctggtga agggcttcta ccccagcgac  1140
atcgccgtgg agtgggagag caacggccag ccgagaaca actacaagac cacccccca  1200 gtgctggaca cgacggcag cttcttcctg tacagcaagc tgaccgtgga caagtccagg  1260
tggcagcagg gcaacgtgtt cagctgcagc gtgatgcacg aggccctgca caaccactac  1320
acccagaaga gcctgagcct gtccccggc aag                                1353

<210> SEQ ID NO 278
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Ser Gly Ser Thr Ser Asn Ile Ala Asn Asn Tyr Val Leu
1               5                   10

<210> SEQ ID NO 279
<211> LENGTH: 7
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 279

Asp Asn Asn Lys Arg Pro Ser
1               5

<210> SEQ ID NO 280
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Gly Thr Trp Asp Asn Ser Leu Ser Val Gly Val
1               5                   10

<210> SEQ ID NO 281
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Ser Gly Ser Thr Ser Asn Ile Ala Asn Asn Tyr Val Leu
1               5                   10

<210> SEQ ID NO 282
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Asp Asn Asn Lys Arg Pro Ser
1               5

<210> SEQ ID NO 283
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Gly Thr Trp Asp Asn Ser Leu Ser Val Gly Val
1               5                   10

<210> SEQ ID NO 284
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Ser Thr Ser Asn Ile Ala Asn Asn Tyr
1               5

<210> SEQ ID NO 285
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Asp Asn Asn
1

<210> SEQ ID NO 286
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Trp Asp Asn Ser Leu Ser Val Gly
1               5

<210> SEQ ID NO 287
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Thr Ser Asn Ile Ala Asn Asn Tyr
1               5

<210> SEQ ID NO 288
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Asp Asn Asn
1

<210> SEQ ID NO 289
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Gly Thr Trp Asp Asn Ser Leu Ser Val Gly Val
1               5                   10

<210> SEQ ID NO 290
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 290

Gln Ser Ala Leu Thr Gln Pro Pro Ser Val Ser Ala Ala Pro Gly Gln
1               5                   10                  15

Lys Val Thr Ile Ser Cys Ser Gly Ser Thr Ser Asn Ile Ala Asn Asn
            20                  25                  30

Tyr Val Leu Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Ala Asp Glu Ala Asp Tyr Tyr Cys Gly Thr Trp Asp Asn Ser Leu
                85                  90                  95

Ser Val Gly Val Phe Gly Gly Gly Thr Lys Leu Thr Val Leu
            100                 105                 110

<210> SEQ ID NO 291
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 291
cagtctgccc tgactcagcc tccctcagtg tctgcggccc caggacagaa ggtcaccatc    60
tcctgctctg gaagcaccte caacattgcg aataattatg tcttatggta ccagcaactc   120
ccaggaacag cccccaaact cctcatttat gacaataata gcgaccctc agggattcct    180 gaccgattct ccggctccaa gtctggcacg tcagccaccc tgggcatcac cggactccag   240
actgcggacg aggccgatta ctactgcgga acatgggata cagcctgag tgttggggtg    300 ttcggcggcg ggaccaagtt gaccgtccta                                    330

<210> SEQ ID NO 292
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 292

Gln Ser Ala Leu Thr Gln Pro Pro Ser Val Ser Ala Ala Pro Gly Gln
1               5                   10                  15

Lys Val Thr Ile Ser Cys Ser Gly Ser Thr Ser Asn Ile Ala Asn Asn
            20                  25                  30

Tyr Val Leu Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser

```
                 50                  55                  60
Gly Ser Lys Ser Gly Thr Ser Ala Thr Leu Gly Ile Thr Gly Leu Gln
 65                  70                  75                  80

Thr Ala Asp Glu Ala Asp Tyr Tyr Cys Gly Thr Trp Asp Asn Ser Leu
                 85                  90                  95

Ser Val Gly Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 293
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 293

```
cagtctgccc tgactcagcc tccctcagtg tctgcggccc caggacagaa ggtcaccatc    60
tcctgctctg gaagcaccct caacattgcg aataattatg tcttatggta ccagcaactc   120
ccaggaacag ccccccaaact cctcatttat gacaataata gcgaccctc agggattcct   180
gaccgattct ccggctccaa gtctggcacg tcagccaccc tgggcatcac cggactccag   240
actgcggacg aggccgatta ctactgcgga acatgggata cagcctgag tgttggggtg   300
ttcggcggcg ggaccaagtt gaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca caagtacgc cgccagcagc   540
tacctgagcc tgacgcctga gcagtggaag tcccacagaa gctacagctg ccaggtcacc   600
cacgagggca gcaccgtgga gaaaaccgtg gccccaccg agtgcagc              648
```

<210> SEQ ID NO 294
<211> LENGTH: 593
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 294

Met Glu Leu Gly Leu Cys Trp Leu Leu Leu Val Ala Ile Leu Lys Gly

-continued

```
  1               5                  10                 15
Val Gln Cys Glu Val Gln Leu Leu Glu Ser Gly Gly Gly Leu Val Gln
                 20                 25                 30
Pro Gly Gly Ser Leu Arg Leu Ser Cys Ala Ala Ser Gly Phe Ile Phe
                 35                 40                 45
Arg Asn Tyr Gly Met Ser Trp Leu Arg Gln Ala Pro Gly Lys Gly Leu
         50                 55                 60
Glu Trp Val Ser Ala Ile Ser Gly Ser Gly Ala Asn Thr Tyr Tyr Thr
 65                 70                 75                 80
Asp Ser Val Lys Gly Arg Phe Thr Ile Ser Arg Asp Asn Ser Lys Asn
                 85                 90                 95
Thr Leu Tyr Leu Gln Ile Tyr Ser Leu Thr Ala Glu Asp Thr Ala Leu
                100                105                110
Tyr Tyr Cys Ala Lys Ser Lys Gly Asp Gly Gly Ala Asp Ala Phe Asp
                115                120                125
Val Trp Gly Gln Gly Thr Leu Val Thr Val Ser Ser Gly Ser Ala Ser
            130                135                140
Ala Pro Thr Leu Phe Pro Leu Val Ser Cys Glu Asn Ser Pro Ser Asp
145                150                155                160
Thr Ser Ser Val Ala Val Gly Cys Leu Ala Gln Asp Phe Leu Pro Asp
                165                170                175
Ser Ile Thr Phe Ser Trp Lys Tyr Lys Asn Asn Ser Asp Ile Ser Ser
                180                185                190
Thr Arg Gly Phe Pro Ser Val Leu Arg Gly Gly Lys Tyr Ala Ala Thr
            195                200                205
Ser Gln Val Leu Leu Pro Ser Lys Asp Val Met Gln Gly Thr Asp Glu
210                215                220
His Val Val Cys Lys Val Gln His Pro Asn Gly Asn Lys Glu Lys Asn
225                230                235                240
Val Pro Leu Pro Val Ile Ala Glu Leu Pro Pro Lys Val Ser Val Phe
                245                250                255
Val Pro Pro Arg Asp Gly Phe Phe Gly Asn Pro Arg Lys Ser Lys Leu
            260                265                270
Ile Cys Gln Ala Thr Gly Phe Ser Pro Arg Gln Ile Gln Val Ser Trp
            275                280                285
Leu Arg Glu Gly Lys Gln Val Gly Ser Gly Val Thr Thr Asp Gln Val
            290                295                300
Gln Ala Glu Ala Lys Glu Ser Gly Pro Thr Thr Tyr Lys Val Thr Ser
305                310                315                320
Thr Leu Thr Ile Lys Glu Ser Asp Trp Leu Gly Gln Ser Met Phe Thr
                325                330                335
Cys Arg Val Asp His Arg Gly Leu Thr Phe Gln Gln Asn Ala Ser Ser
                340                345                350
Met Cys Val Pro Asp Gln Asp Thr Ala Ile Arg Val Phe Ala Ile Pro
            355                360                365
Pro Ser Phe Ala Ser Ile Phe Leu Thr Lys Ser Thr Lys Leu Thr Cys
            370                375                380
Leu Val Thr Asp Leu Thr Thr Tyr Asp Ser Val Thr Ile Ser Trp Thr
385                390                395                400
Arg Gln Asn Gly Glu Ala Val Lys Thr His Thr Asn Ile Ser Glu Ser
                405                410                415
His Pro Asn Ala Thr Phe Ser Ala Val Gly Glu Ala Ser Ile Cys Glu
                420                425                430
```

Asp Asp Trp Asn Ser Gly Glu Arg Phe Thr Cys Thr Val Thr His Thr
        435                 440                 445

Asp Leu Pro Ser Pro Leu Lys Gln Thr Ile Ser Arg Pro Lys Gly Val
    450                 455                 460

Ala Leu His Arg Pro Asp Val Tyr Leu Leu Pro Pro Ala Arg Glu Gln
465                 470                 475                 480

Leu Asn Leu Arg Glu Ser Ala Thr Ile Thr Cys Leu Val Thr Gly Phe
                485                 490                 495

Ser Pro Ala Asp Val Phe Val Gln Trp Met Gln Arg Gly Gln Pro Leu
            500                 505                 510

Ser Pro Glu Lys Tyr Val Thr Ser Ala Pro Met Pro Glu Pro Gln Ala
        515                 520                 525

Pro Gly Arg Tyr Phe Ala His Ser Ile Leu Thr Val Ser Glu Glu Glu
    530                 535                 540

Trp Asn Thr Gly Glu Thr Tyr Thr Cys Val Val Ala His Glu Ala Leu
545                 550                 555                 560

Pro Asn Arg Val Thr Glu Arg Thr Val Asp Lys Ser Thr Gly Lys Pro
                565                 570                 575

Thr Leu Tyr Asn Val Ser Leu Val Met Ser Asp Thr Ala Gly Thr Cys
            580                 585                 590

Tyr

<210> SEQ ID NO 295
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 295

Met Arg Leu Pro Ala Gln Leu Leu Gly Leu Leu Leu Leu Trp Leu Pro
1               5                   10                  15

Gly Ala Lys Cys Asp Ile Arg Met Thr Gln Ser Pro Ser Thr Leu Ser
            20                  25                  30

Ala Ser Val Gly Asp Arg Val Thr Ile Thr Cys Arg Ala Ser Gln Ser
        35                  40                  45

Ile Ser Arg Trp Leu Ala Trp Tyr Gln Gln Lys Pro Gly Lys Ala Pro
    50                  55                  60

Lys Leu Leu Ile Tyr Lys Ala Ser Ser Leu Glu Ser Gly Val Pro Ser
65                  70                  75                  80

Arg Phe Ser Gly Ser Gly Ser Ala Thr Glu Phe Thr Leu Thr Ile Ser
                85                  90                  95

Ser Leu Gln Pro Asp Asp Phe Ala Thr Tyr Tyr Cys Gln Gln Tyr Asn
            100                 105                 110

Ser Phe Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr

```
                    180                 185                 190
Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
            210                 215                 220

Thr Lys Ser Phe Asn Arg Gly Glu Cys
225                 230

<210> SEQ ID NO 296
<211> LENGTH: 600
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 296

Met Glu Leu Gly Leu Cys Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Pro Leu Ile Val Val Val Pro Ala Ala Ile
        115                 120                 125

Tyr Tyr Tyr Tyr Gly Met Asp Val Trp Gly Gln Gly Thr Thr Val Thr
    130                 135                 140

Val Ser Ser Gly Ser Ala Ser Ala Pro Thr Leu Phe Pro Leu Val Ser
145                 150                 155                 160

Cys Glu Asn Ser Pro Ser Asp Thr Ser Ser Val Ala Val Gly Cys Leu
                165                 170                 175

Ala Gln Asp Phe Leu Pro Asp Ser Ile Thr Phe Ser Trp Lys Tyr Lys
            180                 185                 190

Asn Asn Ser Asp Ile Ser Ser Thr Arg Gly Phe Pro Ser Val Leu Arg
        195                 200                 205

Gly Gly Lys Tyr Ala Ala Thr Ser Gln Val Leu Leu Pro Ser Lys Asp
    210                 215                 220

Val Met Gln Gly Thr Asp Glu His Val Val Cys Lys Val Gln His Pro
225                 230                 235                 240

Asn Gly Asn Lys Glu Lys Asn Val Pro Leu Pro Val Ile Ala Glu Leu
                245                 250                 255

Pro Pro Lys Val Ser Val Phe Val Pro Pro Arg Asp Gly Phe Phe Gly
            260                 265                 270

Asn Pro Arg Lys Ser Lys Leu Ile Cys Gln Ala Thr Gly Phe Ser Pro
        275                 280                 285

Arg Gln Ile Gln Val Ser Trp Leu Arg Glu Gly Lys Gln Val Gly Ser
    290                 295                 300
```

Gly Val Thr Thr Asp Gln Val Gln Ala Glu Ala Lys Glu Ser Gly Pro
305                 310                 315                 320

Thr Thr Tyr Lys Val Thr Ser Thr Leu Thr Ile Lys Glu Ser Asp Trp
            325                 330                 335

Leu Gly Gln Ser Met Phe Thr Cys Arg Val Asp His Arg Gly Leu Thr
                340                 345                 350

Phe Gln Gln Asn Ala Ser Ser Met Cys Val Pro Asp Gln Asp Thr Ala
            355                 360                 365

Ile Arg Val Phe Ala Ile Pro Pro Ser Phe Ala Ser Ile Phe Leu Thr
370                 375                 380

Lys Ser Thr Lys Leu Thr Cys Leu Val Thr Asp Leu Thr Thr Tyr Asp
385                 390                 395                 400

Ser Val Thr Ile Ser Trp Thr Arg Gln Asn Gly Glu Ala Val Lys Thr
                405                 410                 415

His Thr Asn Ile Ser Glu Ser His Pro Asn Ala Thr Phe Ser Ala Val
            420                 425                 430

Gly Glu Ala Ser Ile Cys Glu Asp Asp Trp Asn Ser Gly Glu Arg Phe
            435                 440                 445

Thr Cys Thr Val Thr His Thr Asp Leu Pro Ser Pro Leu Lys Gln Thr
        450                 455                 460

Ile Ser Arg Pro Lys Gly Val Ala Leu His Arg Pro Asp Val Tyr Leu
465                 470                 475                 480

Leu Pro Pro Ala Arg Glu Gln Leu Asn Leu Arg Glu Ser Ala Thr Ile
                485                 490                 495

Thr Cys Leu Val Thr Gly Phe Ser Pro Ala Asp Val Phe Val Gln Trp
                500                 505                 510

Met Gln Arg Gly Gln Pro Leu Ser Pro Glu Lys Tyr Val Thr Ser Ala
            515                 520                 525

Pro Met Pro Glu Pro Gln Ala Pro Gly Arg Tyr Phe Ala His Ser Ile
        530                 535                 540

Leu Thr Val Ser Glu Glu Glu Trp Asn Thr Gly Glu Thr Tyr Thr Cys
545                 550                 555                 560

Val Val Ala His Glu Ala Leu Pro Asn Arg Val Thr Glu Arg Thr Val
                565                 570                 575

Asp Lys Ser Thr Gly Lys Pro Thr Leu Tyr Asn Val Ser Leu Val Met
            580                 585                 590

Ser Asp Thr Ala Gly Thr Cys Tyr
            595                 600

<210> SEQ ID NO 297
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 297

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Thr Ser
        35                  40                  45

```
Gln Ser Ile Ser Ser Tyr Leu Asn Trp Tyr Gln Gln Lys Pro Gly Lys
     50                  55                  60

Ala Pro Lys Leu Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
                100                 105                 110

Ser Tyr Ser Thr Pro Ile Thr Phe Gly Gln Gly Thr Arg Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 298
<211> LENGTH: 591
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 298

Met Lys His Leu Trp Phe Phe Leu Leu Leu Val Ala Ala Pro Arg Trp
 1               5                  10                  15

Val Leu Ser Gln Leu Gln Leu Gln Glu Ser Gly Pro Gly Leu Val Lys
                 20                  25                  30

Pro Ser Glu Thr Leu Ser Leu Thr Cys Thr Val Ser Gly Gly Ser Ile
             35                  40                  45

Ser Ser Ser Ser Tyr Tyr Trp Gly Trp Ile Arg Gln Pro Pro Gly Lys
     50                  55                  60

Gly Leu Glu Trp Ile Gly Ser Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
            100                 105                 110

Val Tyr Tyr Cys Ala Arg Leu Gly Tyr Tyr Tyr Met Asp Val Trp
            115                 120                 125

Gly Lys Gly Thr Thr Val Thr Val Ser Ser Gly Ser Ala Ser Ala Pro
130                 135                 140

Thr Leu Phe Pro Leu Val Ser Cys Glu Asn Ser Pro Ser Asp Thr Ser
145                 150                 155                 160

Ser Val Ala Val Gly Cys Leu Ala Gln Asp Phe Leu Pro Asp Ser Ile
```

-continued

```
                165                 170                 175
Thr Phe Ser Trp Lys Tyr Lys Asn Asn Ser Asp Ile Ser Ser Thr Arg
            180                 185                 190

Gly Phe Pro Ser Val Leu Arg Gly Gly Lys Tyr Ala Ala Thr Ser Gln
            195                 200                 205

Val Leu Leu Pro Ser Lys Asp Val Met Gln Gly Thr Asp Glu His Val
210                 215                 220

Val Cys Lys Val Gln His Pro Asn Gly Asn Lys Glu Lys Asn Val Pro
225                 230                 235                 240

Leu Pro Val Ile Ala Glu Leu Pro Pro Lys Val Ser Val Phe Val Pro
            245                 250                 255

Pro Arg Asp Gly Phe Phe Gly Asn Pro Arg Lys Ser Lys Leu Ile Cys
            260                 265                 270

Gln Ala Thr Gly Phe Ser Pro Arg Gln Ile Gln Val Ser Trp Leu Arg
            275                 280                 285

Glu Gly Lys Gln Val Gly Ser Gly Val Thr Thr Asp Gln Val Gln Ala
            290                 295                 300

Glu Ala Lys Glu Ser Gly Pro Thr Thr Tyr Lys Val Thr Ser Thr Leu
305                 310                 315                 320

Thr Ile Lys Glu Ser Asp Trp Leu Gly Gln Ser Met Phe Thr Cys Arg
                325                 330                 335

Val Asp His Arg Gly Leu Thr Phe Gln Gln Asn Ala Ser Ser Met Cys
                340                 345                 350

Val Pro Asp Gln Asp Thr Ala Ile Arg Val Phe Ala Ile Pro Pro Ser
                355                 360                 365

Phe Ala Ser Ile Phe Leu Thr Lys Ser Thr Lys Leu Thr Cys Leu Val
370                 375                 380

Thr Asp Leu Thr Thr Tyr Asp Ser Val Thr Ile Ser Trp Thr Arg Gln
385                 390                 395                 400

Asn Gly Glu Ala Val Lys Thr His Thr Asn Ile Ser Glu Ser His Pro
                405                 410                 415

Asn Ala Thr Phe Ser Ala Val Gly Glu Ala Ser Ile Cys Glu Asp Asp
                420                 425                 430

Trp Asn Ser Gly Glu Arg Phe Thr Cys Thr Val Thr His Thr Asp Leu
            435                 440                 445

Pro Ser Pro Leu Lys Gln Thr Ile Ser Arg Pro Lys Gly Val Ala Leu
            450                 455                 460

His Arg Pro Asp Val Tyr Leu Leu Pro Pro Ala Arg Glu Gln Leu Asn
465                 470                 475                 480

Leu Arg Glu Ser Ala Thr Ile Thr Cys Leu Val Thr Gly Phe Ser Pro
                485                 490                 495

Ala Asp Val Phe Val Gln Trp Met Gln Arg Gly Gln Pro Leu Ser Pro
                500                 505                 510

Glu Lys Tyr Val Thr Ser Ala Pro Met Pro Glu Pro Gln Ala Pro Gly
            515                 520                 525

Arg Tyr Phe Ala His Ser Ile Leu Thr Val Ser Glu Glu Trp Asn
            530                 535                 540

Thr Gly Glu Thr Tyr Thr Cys Val Val Ala His Glu Ala Leu Pro Asn
545                 550                 555                 560

Arg Val Thr Glu Arg Thr Val Asp Lys Ser Thr Gly Lys Pro Thr Leu
                565                 570                 575

Tyr Asn Val Ser Leu Val Met Ser Asp Thr Ala Gly Thr Cys Tyr
            580                 585                 590
```

<210> SEQ ID NO 299
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 299

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Val Leu Tyr Ser Ser Asn Asn Lys Asn Tyr Leu Ala Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
                100                 105                 110

Tyr Cys Gln Gln Tyr Tyr Ser Thr Pro Pro Thr Phe Gly Gly Gly Thr
            115                 120                 125

Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240
```

<210> SEQ ID NO 300
<211> LENGTH: 592
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 300

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
                20                  25                  30

Pro Gly Glu Ser Leu Arg Leu Ser Cys Ala Ala Ser Gly Phe Thr Phe
            35                  40                  45
```

```
Ser Asn Tyr Phe Met His Trp Val Arg Gln Ala Pro Gly Met Gly Leu
    50                  55                  60

Glu Trp Val Ala Arg Ile Asn Thr Asp Gly Ser Val Thr Met Tyr Ala
 65                  70                  75                  80

Asp Ser Val Lys Gly Arg Phe Thr Ile Ser Arg Asp Asn Ala Lys Asn
                 85                  90                  95

Thr Val Tyr Leu Gln Met Asn Ser Leu Arg Ala Glu Asp Thr Ala Val
            100                 105                 110

Tyr Tyr Cys Val Arg Pro Asn Ser Val His Asp Lys Leu Leu Glu Asn
        115                 120                 125

Trp Gly Gln Gly Thr Leu Val Thr Val Ser Ser Gly Ser Ala Ser Ala
130                 135                 140

Pro Thr Leu Phe Pro Leu Val Ser Cys Glu Asn Ser Pro Ser Asp Thr
145                 150                 155                 160

Ser Ser Val Ala Val Gly Cys Leu Ala Gln Asp Phe Leu Pro Asp Ser
                165                 170                 175

Ile Thr Phe Ser Trp Lys Tyr Lys Asn Asn Ser Asp Ile Ser Ser Thr
            180                 185                 190

Arg Gly Phe Pro Ser Val Leu Arg Gly Gly Lys Tyr Ala Ala Thr Ser
        195                 200                 205

Gln Val Leu Leu Pro Ser Lys Asp Val Met Gln Gly Thr Asp Glu His
210                 215                 220

Val Val Cys Lys Val Gln His Pro Asn Gly Asn Lys Glu Lys Asn Val
225                 230                 235                 240

Pro Leu Pro Val Ile Ala Glu Leu Pro Pro Lys Val Ser Val Phe Val
                245                 250                 255

Pro Pro Arg Asp Gly Phe Phe Gly Asn Pro Arg Lys Ser Lys Leu Ile
            260                 265                 270

Cys Gln Ala Thr Gly Phe Ser Pro Arg Gln Ile Gln Val Ser Trp Leu
        275                 280                 285

Arg Glu Gly Lys Gln Val Gly Ser Gly Val Thr Thr Asp Gln Val Gln
290                 295                 300

Ala Glu Ala Lys Glu Ser Gly Pro Thr Thr Tyr Lys Val Thr Ser Thr
305                 310                 315                 320

Leu Thr Ile Lys Glu Ser Asp Trp Leu Gly Gln Ser Met Phe Thr Cys
                325                 330                 335

Arg Val Asp His Arg Gly Leu Thr Phe Gln Gln Asn Ala Ser Ser Met
            340                 345                 350

Cys Val Pro Asp Gln Asp Thr Ala Ile Arg Val Phe Ala Ile Pro Pro
        355                 360                 365

Ser Phe Ala Ser Ile Phe Leu Thr Lys Ser Thr Lys Leu Thr Cys Leu
370                 375                 380

Val Thr Asp Leu Thr Thr Tyr Asp Ser Val Thr Ile Ser Trp Thr Arg
385                 390                 395                 400

Gln Asn Gly Glu Ala Val Lys Thr His Thr Asn Ile Ser Glu Ser His
                405                 410                 415

Pro Asn Ala Thr Phe Ser Ala Val Gly Glu Ala Ser Ile Cys Glu Asp
            420                 425                 430

Asp Trp Asn Ser Gly Glu Arg Phe Thr Cys Thr Val Thr His Thr Asp
        435                 440                 445

Leu Pro Ser Pro Leu Lys Gln Thr Ile Ser Arg Pro Lys Gly Val Ala
450                 455                 460

Leu His Arg Pro Asp Val Tyr Leu Leu Pro Pro Ala Arg Glu Gln Leu
```

```
            465                 470                 475                 480
Asn Leu Arg Glu Ser Ala Thr Ile Thr Cys Leu Val Thr Gly Phe Ser
                485                 490                 495
Pro Ala Asp Val Phe Val Gln Trp Met Gln Arg Gly Gln Pro Leu Ser
                500                 505                 510
Pro Glu Lys Tyr Val Thr Ser Ala Pro Met Pro Glu Pro Gln Ala Pro
                515                 520                 525
Gly Arg Tyr Phe Ala His Ser Ile Leu Thr Val Ser Glu Glu Glu Trp
                530                 535                 540
Asn Thr Gly Glu Thr Tyr Thr Cys Val Val Ala His Glu Ala Leu Pro
545                 550                 555                 560
Asn Arg Val Thr Glu Arg Thr Val Asp Lys Ser Thr Gly Lys Pro Thr
                565                 570                 575
Leu Tyr Asn Val Ser Leu Val Met Ser Asp Thr Ala Gly Thr Cys Tyr
                580                 585                 590

<210> SEQ ID NO 301
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 301

Met Arg Leu Pro Ala Gln Leu Leu Gly Leu Leu Leu Leu Trp Leu Pro
1               5                   10                  15
Gly Ala Lys Cys Asp Ile Gln Met Thr Gln Ser Pro Ser Thr Leu Ser
                20                  25                  30
Ala Ser Val Gly Asp Arg Val Thr Ile Thr Cys Arg Ala Ser Gln Ser
            35                  40                  45
Ile Ser Ser Trp Leu Ala Trp Tyr Gln Gln Lys Pro Gly Lys Ala Pro
        50                  55                  60
Lys Leu Leu Ile Asn Lys Ala Ser Ser Leu Glu Ser Gly Val Pro Ser
65                  70                  75                  80
Arg Phe Ser Gly Ser Gly Ser Gly Thr Glu Phe Thr Leu Thr Ile Asn
                85                  90                  95
Ser Leu Gln Pro Asp Asp Phe Ala Thr Tyr Tyr Cys Gln Gln Tyr Tyr
                100                 105                 110
Thr Tyr Ser Ser Tyr Arg Phe Gly Gln Gly Thr Lys Leu Glu Ile Lys
            115                 120                 125
Arg Thr Val Ala Ala Pro Ser Val Phe Ile Phe Pro Pro Ser Asp Glu
        130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
                180                 185                 190
Thr Tyr Ser Leu Ser Ser Thr Leu Thr Leu Ser Lys Ala Asp Tyr Glu
            195                 200                 205
Lys His Lys Val Tyr Ala Cys Glu Val Thr His Gln Gly Leu Ser Ser
        210                 215                 220
Pro Val Thr Lys Ser Phe Asn Arg Gly Glu Cys
225                 230                 235
```

-continued

```
<210> SEQ ID NO 302
<211> LENGTH: 595
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (40)..(40)
<223> OTHER INFORMATION: Any amino acid

<400> SEQUENCE: 302

Met Ser Val Ser Phe Leu Leu Val Ala Ala Pro Arg Trp Val Leu
1               5                   10                  15

Ser Gln Gln Gln Leu Gln Glu Ser Gly Pro Gly Leu Val Lys Pro Ser
            20                  25                  30

Glu Thr Leu Ser Leu Thr Cys Xaa Val Ser Gly Gly Ser Ile Ser Ser
        35                  40                  45

Ser Ser Tyr Tyr Trp Gly Trp Ile Arg Gln Pro Pro Gly Lys Gly Leu
    50                  55                  60

Glu Trp Ile Gly Ser Ile Tyr Tyr Arg Gly Ser Thr Tyr Tyr Asn Pro
65                  70                  75                  80

Ser Leu Arg Ser Arg Val Thr Ala Ser Val Asp Thr Ser Arg Asn Gln
                85                  90                  95

Phe Ser Leu Arg Leu Ser Ser Val Thr Ala Ala Asp Thr Ala Val Tyr
            100                 105                 110

Tyr Cys Ala Arg Ser Tyr Cys Ser Gly Ser Cys Tyr Ala Val Gly Ala
        115                 120                 125

Phe Asp Met Trp Gly Gln Gly Thr Met Val Thr Val Ser Ser Gly Ser
    130                 135                 140

Ala Ser Ala Pro Thr Leu Phe Pro Leu Val Ser Cys Glu Asn Ser Pro
145                 150                 155                 160

Ser Asp Thr Ser Ser Val Ala Val Gly Cys Leu Ala Gln Asp Phe Leu
                165                 170                 175

Pro Asp Ser Ile Thr Phe Ser Trp Lys Tyr Lys Asn Asn Ser Asp Ile
            180                 185                 190

Ser Ser Thr Arg Gly Phe Pro Ser Val Leu Arg Gly Gly Lys Tyr Ala
        195                 200                 205

Ala Thr Ser Gln Val Leu Leu Pro Ser Lys Asp Val Met Gln Gly Thr
    210                 215                 220

Asp Glu His Val Val Cys Lys Val Gln His Pro Asn Gly Asn Lys Glu
225                 230                 235                 240

Lys Asn Val Pro Leu Pro Val Ile Ala Glu Leu Pro Pro Lys Val Ser
                245                 250                 255

Val Phe Val Pro Pro Arg Asp Gly Phe Phe Gly Asn Pro Arg Lys Ser
            260                 265                 270

Lys Leu Ile Cys Gln Ala Thr Gly Phe Ser Pro Arg Gln Ile Gln Val
        275                 280                 285

Ser Trp Leu Arg Glu Gly Lys Gln Val Gly Ser Gly Val Thr Thr Asp
    290                 295                 300

Gln Val Gln Ala Glu Ala Lys Glu Ser Gly Pro Thr Thr Tyr Lys Val
305                 310                 315                 320

Thr Ser Thr Leu Thr Ile Lys Glu Ser Asp Trp Leu Gly Gln Ser Met
                325                 330                 335
```

-continued

```
Phe Thr Cys Arg Val Asp His Arg Gly Leu Thr Phe Gln Gln Asn Ala
            340                 345                 350

Ser Ser Met Cys Val Pro Asp Gln Asp Thr Ala Ile Arg Val Phe Ala
            355                 360                 365

Ile Pro Pro Ser Phe Ala Ser Ile Phe Leu Thr Lys Ser Thr Lys Leu
            370                 375                 380

Thr Cys Leu Val Thr Asp Leu Thr Thr Tyr Asp Ser Val Thr Ile Ser
385                 390                 395                 400

Trp Thr Arg Gln Asn Gly Glu Ala Val Lys Thr His Thr Asn Ile Ser
            405                 410                 415

Glu Ser His Pro Asn Ala Thr Phe Ser Ala Val Gly Glu Ala Ser Ile
            420                 425                 430

Cys Glu Asp Asp Trp Asn Ser Gly Glu Arg Phe Thr Cys Thr Val Thr
            435                 440                 445

His Thr Asp Leu Pro Ser Pro Leu Lys Gln Thr Ile Ser Arg Pro Lys
450                 455                 460

Gly Val Ala Leu His Arg Pro Asp Val Tyr Leu Leu Pro Pro Ala Arg
465                 470                 475                 480

Glu Gln Leu Asn Leu Arg Glu Ser Ala Thr Ile Thr Cys Leu Val Thr
            485                 490                 495

Gly Phe Ser Pro Ala Asp Val Phe Val Gln Trp Met Gln Arg Gly Gln
            500                 505                 510

Pro Leu Ser Pro Glu Lys Tyr Val Thr Ser Ala Pro Met Pro Glu Pro
            515                 520                 525

Gln Ala Pro Gly Arg Tyr Phe Ala His Ser Ile Leu Thr Val Ser Glu
            530                 535                 540

Glu Glu Trp Asn Thr Gly Glu Thr Tyr Thr Cys Val Val Ala His Glu
545                 550                 555                 560

Ala Leu Pro Asn Arg Val Thr Glu Arg Thr Val Asp Lys Ser Thr Gly
            565                 570                 575

Lys Pro Thr Leu Tyr Asn Val Ser Leu Val Met Ser Asp Thr Ala Gly
            580                 585                 590

Thr Cys Tyr
            595

<210> SEQ ID NO 303
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 303

Met Ala Trp Thr Pro Leu Leu Phe Leu Thr Leu Leu Leu His Cys Thr
1               5                   10                  15

Gly Ser Leu Ser Gln Leu Val Leu Thr Gln Ser Pro Ser Ala Ser Ala
            20                  25                  30

Ser Leu Gly Ala Ser Val Lys Leu Thr Cys Thr Leu Ser Ser Gly His
            35                  40                  45

Ser Ser His Ala Ile Ala Trp His Gln Gln Gln Pro Glu Lys Gly Pro
            50                  55                  60

Arg Tyr Leu Ile Lys Leu Asn Ser Asp Gly Ser His Asn Lys Gly Asp
65                  70                  75                  80
```

-continued

```
Gly Ile Pro Asp Arg Phe Ser Gly Ser Ser Gly Ala Glu Arg Tyr
                85                  90                  95

Leu Thr Ile Ser Ser Leu Gln Ser Glu Asp Glu Ala Asp Tyr Tyr Cys
            100                 105                 110

Gln Thr Trp Asp Thr Gly Ile Val Val Phe Gly Gly Gly Thr Lys Leu
        115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235
```

<210> SEQ ID NO 304
<211> LENGTH: 596
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 304

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Phe Arg Gly Trp Gly Gly Gly Ser Gly Gly
        115                 120                 125

Ser Cys Gly Tyr Trp Gly Gln Gly Thr Leu Val Thr Val Ser Ser Gly
    130                 135                 140

Ser Ala Ser Ala Pro Thr Leu Phe Pro Leu Val Ser Cys Glu Asn Ser
145                 150                 155                 160

Pro Ser Asp Thr Ser Ser Val Ala Val Gly Cys Leu Ala Gln Asp Phe
                165                 170                 175

Leu Pro Asp Ser Ile Thr Phe Ser Trp Lys Tyr Lys Asn Asn Ser Asp
            180                 185                 190

Ile Ser Ser Thr Arg Gly Phe Pro Ser Val Leu Arg Gly Gly Lys Tyr
```

```
            195                 200                 205
Ala Ala Thr Ser Gln Val Leu Leu Pro Ser Lys Asp Val Met Gln Gly
210                 215                 220

Thr Asp Glu His Val Val Cys Lys Val Gln His Pro Asn Gly Asn Lys
225                 230                 235                 240

Glu Lys Asn Val Pro Leu Pro Val Ile Ala Glu Leu Pro Pro Lys Val
                245                 250                 255

Ser Val Phe Val Pro Pro Arg Asp Gly Phe Phe Gly Asn Pro Arg Lys
            260                 265                 270

Ser Lys Leu Ile Cys Gln Ala Thr Gly Phe Ser Pro Arg Gln Ile Gln
        275                 280                 285

Val Ser Trp Leu Arg Glu Gly Lys Gln Val Gly Ser Gly Val Thr Thr
    290                 295                 300

Asp Gln Val Gln Ala Glu Ala Lys Glu Ser Gly Pro Thr Thr Tyr Lys
305                 310                 315                 320

Val Thr Ser Thr Leu Thr Ile Lys Glu Ser Asp Trp Leu Gly Gln Ser
                325                 330                 335

Met Phe Thr Cys Arg Val Asp His Arg Gly Leu Thr Phe Gln Gln Asn
            340                 345                 350

Ala Ser Ser Met Cys Val Pro Asp Gln Asp Thr Ala Ile Arg Val Phe
        355                 360                 365

Ala Ile Pro Pro Ser Phe Ala Ser Ile Phe Leu Thr Lys Ser Thr Lys
    370                 375                 380

Leu Thr Cys Leu Val Thr Asp Leu Thr Thr Tyr Asp Ser Val Thr Ile
385                 390                 395                 400

Ser Trp Thr Arg Gln Asn Gly Glu Ala Val Lys Thr His Thr Asn Ile
                405                 410                 415

Ser Glu Ser His Pro Asn Ala Thr Phe Ser Ala Val Gly Glu Ala Ser
            420                 425                 430

Ile Cys Glu Asp Asp Trp Asn Ser Gly Glu Arg Phe Thr Cys Thr Val
        435                 440                 445

Thr His Thr Asp Leu Pro Ser Pro Leu Lys Gln Thr Ile Ser Arg Pro
    450                 455                 460

Lys Gly Val Ala Leu His Arg Pro Asp Val Tyr Leu Leu Pro Pro Ala
465                 470                 475                 480

Arg Glu Gln Leu Asn Leu Arg Glu Ser Ala Thr Ile Thr Cys Leu Val
                485                 490                 495

Thr Gly Phe Ser Pro Ala Asp Val Phe Val Gln Trp Met Gln Arg Gly
            500                 505                 510

Gln Pro Leu Ser Pro Glu Lys Tyr Val Thr Ser Ala Pro Met Pro Glu
        515                 520                 525

Pro Gln Ala Pro Gly Arg Tyr Phe Ala His Ser Ile Leu Thr Val Ser
    530                 535                 540

Glu Glu Glu Trp Asn Thr Gly Glu Thr Tyr Thr Cys Val Val Ala His
545                 550                 555                 560

Glu Ala Leu Pro Asn Arg Val Thr Glu Arg Thr Val Asp Lys Ser Thr
                565                 570                 575

Gly Lys Pro Thr Leu Tyr Asn Val Ser Leu Val Met Ser Asp Thr Ala
            580                 585                 590

Gly Thr Cys Tyr
        595

<210> SEQ ID NO 305
```

<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 305

```
Met Ala Leu Thr Pro Leu Leu Thr Leu Leu Ala His Cys Thr Gly
1               5                   10                  15

Ser Trp Ala Asn Phe Met Leu Thr Gln Pro His Ser Val Ser Glu Ser
            20                  25                  30

Pro Gly Lys Thr Val Thr Ile Ser Cys Thr Arg Ser Ser Gly Ser Ile
        35                  40                  45

Ala Ser Asn Tyr Val Gln Trp Tyr Gln Gln Arg Pro Gly Ser Ser Pro
    50                  55                  60

Thr Thr Val Ile Tyr Glu Asp Asn Gln Arg Pro Ser Gly Val Pro Asp
65                  70                  75                  80

Arg Phe Ser Gly Ser Ile Asp Ser Ser Ser Asn Ser Ala Ser Leu Thr
                85                  90                  95

Ile Ser Gly Leu Lys Thr Glu Asp Glu Ala Asp Tyr Tyr Cys Gln Ser
            100                 105                 110

Tyr Asp Ser Ser Asn Leu Tyr Val Phe Gly Thr Gly Thr Lys Val Thr
        115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235
```

<210> SEQ ID NO 306
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 306

```
Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Phe Met Ser Trp Val Arg Gln Thr Pro Gly Lys Gly Leu
    50                  55                  60
```

```
Glu Trp Leu Ser Tyr Met Ser Ser Asp Gly Thr Ile Ile His His Ala
 65                  70                  75                  80

Asp Ser Leu Lys Gly Arg Phe Thr Ile Ser Arg Asp Asn Ala Lys Asn
             85                  90                  95

Ser Leu Phe Leu Gln Met Asn Thr Leu Arg Ala Glu Asp Thr Ala Val
            100                 105                 110

Tyr Tyr Cys Ala Thr His Ile Leu Glu Thr Thr Ile Ala Ala Phe Glu
        115                 120                 125

Ile Trp Gly Arg Gly Thr Met Val Ile Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

```
<210> SEQ ID NO 307
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 307

Met Val Leu Gln Thr Gln Val Phe Ile Ser Leu Leu Trp Ile Ala
1               5                   10                  15

Gly Ala Tyr Gly Asp Ile Val Met Thr Gln Ser Pro Asp Ser Leu Ala
                20                  25                  30

Leu Ser Leu Gly Glu Arg Ala Thr Ile Asn Cys Arg Ser Ser His Ser
            35                  40                  45

Val Leu Tyr Arg Ser Asn Asn Asn Tyr Val Ala Trp Tyr Gln Gln
    50                  55                  60

Lys Pro Gly Gln Pro Pro Arg Leu Leu Ile Tyr Trp Ala Ser Asn Arg
65                  70                  75                  80

Ala Ser Gly Val Pro Asp Arg Phe Ser Gly Ser Gly Ser Gly Thr Asp
                85                  90                  95

Phe Thr Leu Thr Ile Ser Ser Leu Gln Pro Glu Asp Ala Ala Val Tyr
            100                 105                 110

Phe Cys Gln Gln Ile Leu Asp Thr Pro Phe Thr Phe Gly Pro Gly Thr
            115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 308
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (37)..(37)
<223> OTHER INFORMATION: Any amino acid

<400> SEQUENCE: 308

Met Glu Phe Gly Leu Ser Trp Leu Phe Leu Val Ala Thr Leu Lys Gly
1               5                   10                  15

Val Gln Cys Glu Val Gln Leu Leu Glu Ser Gly Gly Gly Leu Met Gln
                20                  25                  30

Pro Gly Gly Ser Xaa Arg Leu Ser Cys Ala Ala Ser Gly Phe Thr Phe
```

-continued

```
            35                  40                  45
Arg Ser Tyr Ala Met Asn Trp Val Arg Gln Ala Pro Gly Lys Gly Leu
50                  55                  60

Glu Trp Val Ser Thr Ile Ser Gly Asn Gly Gly Thr Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Ile
                100                 105                 110

Tyr Tyr Cys Ala Gln Gly Glu Pro Trp Ser Gly Tyr Leu Glu Pro Leu
            115                 120                 125

Phe Ala Ser Trp Gly Gln Gly Thr Leu Val Thr Val Ser Ser Ala Ser
            130                 135                 140

Thr Lys Gly Pro Ser Val Phe Pro Leu Ala Pro Cys Ser Arg Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460
```

```
Ser Leu Ser Leu Ser Pro Gly Lys
465                 470
```

```
<210> SEQ ID NO 309
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 309

Met Ala Trp Thr Pro Leu Trp Leu Thr Leu Leu Thr Leu Cys Ile Gly
1               5                   10                  15

Ser Val Val Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Asn
        35                  40                  45

Phe Tyr Ala Ser Trp Tyr Gln Gln Lys Pro Gly Gln Ala Pro Val Leu
    50                  55                  60

Val Ile Tyr Gly Lys Asn Asn Arg Pro Ser Gly Ile Pro Asp Arg Phe
65                  70                  75                  80

Ser Gly Ser Ser Ser Gly Asn Thr Val Ser Leu Thr Ile Thr Gly Ala
                85                  90                  95

Gln Ala Glu Asp Asp Ala Asp Tyr Tyr Cys Asn Ser Arg Asp Ser Ser
            100                 105                 110

Gly Asn His Val Ile Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

```
<210> SEQ ID NO 310
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 310

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val His
            20                  25                  30
```

```
Pro Gly Gly Ser Leu Arg Leu Ser Cys Ala Ala Ser Gly Phe Thr Phe
            35                  40                  45

Arg Thr Tyr Ile Met Asn Trp Val Arg Gln Ala Pro Gly Lys Gly Leu
 50                  55                  60

Glu Trp Ile Ser Tyr Ile Ser Ala Ser Ser Gly Thr Ile Tyr Tyr Ala
 65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Leu Asp Cys Ser Gly Gly Thr Cys Tyr Asp
            115                 120                 125

Gly Phe Asp Ser Trp Gly His Gly Thr Leu Val Thr Val Ser Ser Ser
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
            210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
```

450                 455                 460
Lys Ser Leu Ser Leu Ser Pro Gly Lys
465                 470

<210> SEQ ID NO 311
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 311

Met Ala Trp Thr Pro Leu Phe Leu Gly Val Leu Ala Tyr Cys Thr Gly
1               5                   10                  15

Ser Val Ala Ser Tyr Glu Leu Thr Gln Pro Pro Ser Leu Ser Val Ser
            20                  25                  30

Pro Gly Gln Thr Ala Ser Ile Thr Cys Ser Gly Asp Lys Leu Gly Asp
        35                  40                  45

Lys Tyr Ala Cys Trp Tyr Gln Gln Arg Pro Gly Gln Ser Pro Val Leu
    50                  55                  60

Val Ile Tyr Gln Asp Thr Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ser
            100                 105                 110

Thr Ala Val Phe Gly Gly Gly Thr Arg Leu Thr Val Leu Gly Gln Pro
        115                 120                 125

Lys Ala Ala Pro Ser Val Thr Leu Phe Pro Pro Ser Ser Glu Glu Leu
    130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
        195                 200                 205

Ser Tyr Ser Cys Gln Val Thr His Glu Gly Ser Thr Val Glu Lys Thr
    210                 215                 220

Val Ala Pro Thr Glu Cys Ser
225                 230

<210> SEQ ID NO 312
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 312

Met Glu Phe Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

```
Pro Gly Arg Ser Leu Arg Leu Ser Cys Ala Ala Ser Gly Phe Asn Phe
         35                  40                  45

Asp Asn Tyr Ala Met His Trp Val Arg Gln Val Pro Gly Lys Gly Leu
     50                  55                  60

Glu Trp Val Ser Gly Ile Asn Trp Asn Ser Gly Tyr Glu Gly Tyr Ala
 65                  70                  75                  80

Asp Ser Val Lys Gly Arg Phe Thr Ile Ser Arg Asp Asn Ala Gln Asn
                 85                  90                  95

Ser Leu Tyr Leu Gln Met Asp Ser Leu Arg Thr Asp Asp Thr Ala Leu
                100                 105                 110

Tyr Tyr Cys Thr Lys Asp Thr Ile Ala Ala Val Gly Arg Gly Ala Phe
            115                 120                 125

Asp Ile Trp Gly Gln Gly Thr Lys Val Thr Val Ser Ser Ala Ser Thr
        130                 135                 140

Lys Gly Pro Ser Val Phe Pro Leu Ala Pro Cys Ser Arg Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445
```

```
Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 313
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 313

```
Met Ala Trp Ile Pro Leu Leu Gly Leu Leu Ser His Cys Thr Gly
1               5                   10                  15

Ser Val Thr Ser Tyr Val Leu Thr Gln Pro Ser Val Ser Val Ala
                20                  25                  30

Pro Gly Lys Thr Ala Met Ile Thr Cys Gly Gly Asn Lys Ile Gly
            35                  40                  45

Lys Ser Val His Trp Tyr Gln Gln Lys Pro Gly Gln Ala Pro Val Leu
50                  55                  60

Val Ile Ser Tyr Asp Ser Asp Arg Pro Ser Gly Ile Pro Gln Arg Phe
65                  70                  75                  80

Ser Gly Ser Asn Ser Gly Asn Thr Ala Thr Leu Thr Ile Ser Arg Val
                85                  90                  95

Glu Ala Gly Asp Glu Ala Asp Tyr Tyr Cys Gln Val Trp Asp Thr Ser
                100                 105                 110

Ser Val His Arg Val Phe Gly Gly Gly Thr Lys Leu Thr Val Leu Gly
                115                 120                 125

Gln Pro Lys Ala Ala Pro Ser Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
                180                 185                 190

Tyr Ala Ala Ser Ser Tyr Leu Ser Leu Thr Pro Glu Gln Trp Lys Ser
                195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 314
<211> LENGTH: 476
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 314

```
Met Lys His Leu Trp Phe Phe Leu Leu Leu Val Ala Ala Pro Arg Trp
1               5                   10                  15

Val Leu Ser Gln Leu Gln Leu Arg Glu Ser Gly Pro Gly Leu Val Lys
```

```
                 20                  25                  30
Pro Ser Glu Thr Leu Ser Leu Thr Cys Ser Val Ser Gly Asp Ser Ile
             35                  40                  45

Ser Arg Ser Ser Asp Tyr Trp Gly Trp Ile Arg Gln Pro Pro Gly Arg
 50                  55                  60

Gly Leu Glu Trp Ile Gly Ser Ile Tyr Arg Thr Gly Ser Thr Tyr Tyr
 65                  70                  75                  80

Asn Pro Ser Leu Ser Ser Arg Val Thr Ile Ser Val Asp Thr Ser Lys
             85                  90                  95

Ser Gln Phe Ser Leu Ser Leu Ser Ser Val Thr Ala Ala Asp Thr Ala
            100                 105                 110

Leu Tyr Tyr Cys Ala Arg Val Arg His Asp Tyr Val Trp Gly Ser Ile
            115                 120                 125

Tyr Tyr Tyr Gly Met Asp Val Trp Gly Gln Gly Thr Thr Val Thr Val
            130                 135                 140

Ser Ser Pro Ser Thr Lys Gly Pro Ser Val Phe Pro Leu Ala Pro Cys
145                 150                 155                 160

Ser Arg Ser Thr Ser Gly Gly Thr Ala Ala Leu Gly Cys Leu Val Lys
            165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
            195                 200                 205

Tyr Ser Leu Ser Ser Val Val Thr Val Pro Ser Ser Ser Leu Gly Thr
210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
            245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
            290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
            325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
            370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445
```

Gly Asn Val Phe Ser Cys Ser Val Met His Glu Ala Leu His Asn His
            450                 455                 460

Tyr Thr Gln Lys Ser Leu Ser Leu Ser Pro Gly Lys
465                 470                 475

<210> SEQ ID NO 315
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 315

Met Ala Trp Ser Pro Leu Leu Leu Thr Gln Gly Thr Gly Ser Trp Ala
1               5                   10                  15

Gln Ser Ala Leu Thr Gln Pro Arg Ser Val Ser Gly Ser Pro Gly Gln
                20                  25                  30

Ser Val Thr Ile Ser Cys Thr Gly Thr Gly Ser Asp Val Gly Gly Tyr
            35                  40                  45

Thr Tyr Val Ser Trp Tyr Gln Gln His Pro Asp Lys Ala Pro Lys Leu
    50                  55                  60

Val Ile Tyr Asp Val Thr Lys Arg Pro Ser Gly Val Pro Asp Arg Phe
65                  70                  75                  80

Ser Gly Ser Lys Ser Gly Asn Thr Ala Ser Leu Thr Ile Ser Gly Leu
                85                  90                  95

Arg Ala Asp Asp Glu Ala Asp Tyr Tyr Cys Cys Ser Tyr Ala Gly Arg
            100                 105                 110

Tyr Ser Trp Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 316
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 316

Met Glu Phe Gly Leu Ser Trp Leu Phe Leu Val Ala Ile Leu Lys Gly
1               5                   10                  15

Val His Cys Glu Val Asp Leu Leu Glu Ser Gly Gly Gly Leu Ile Gln
            20                  25                  30

Pro Gly Gly Ser Leu Arg Leu Ser Cys Ala Ala Ser Gly Phe Thr Phe
                35                  40                  45

Arg Asn Tyr Ala Met Asn Trp Val Arg Gln Val Pro Gly Lys Gly Leu
            50                  55                  60

Glu Trp Val Ser Ser Val Ser Gly Ser Gly Gly Thr Thr Tyr Tyr Ala
65                  70                  75                  80

Asp Ser Val Lys Gly Arg Phe Ser Ile Ser Arg Asp Asn Ser Lys Asn
            85                  90                  95

Thr Leu Tyr Leu Gln Met Asn Gly Leu Arg Ala Gly Asp Thr Ala Ile
            100                 105                 110

Tyr Tyr Cys Ala Lys Gly Glu Ala Trp Ser Gly Tyr Leu Glu Pro Leu
            115                 120                 125

Cys Asp Phe Trp Gly His Gly Thr Leu Val Thr Val Ser Ser Ala Ser
            130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
            245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe

```
                    435                 440                 445
Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 317
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 317

Met Ala Leu Thr Pro Leu Trp Leu Thr Leu Thr Leu Cys Ile Gly
1               5                   10                  15

Ser Val Val Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Asp
            35                  40                  45

Phe Tyr Gly Ser Trp Tyr Gln Gln Lys Pro Gly Gln Ala Pro Val Leu
    50                  55                  60

Val Asn Phe Gly Tyr Asn Asn Arg Pro Ser Gly Ile Pro Asp Arg Phe
65                  70                  75                  80

Ser Gly Ser Arg Ser Gly Asn Thr Ala Ser Leu Thr Ile Thr Gly Ala
                85                  90                  95

Gln Ala Glu Asp Glu Ala Asp Tyr Tyr Cys Asn Ser Arg Asp Ile Ser
            100                 105                 110

Gly Asn Arg Val Val Phe Gly Gly Gly Thr Lys Leu Thr Val Val Gly
            115                 120                 125

Gln Pro Glu Ala Ala Pro Ser Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
            195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 318
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 318

Met Lys His Leu Trp Phe Phe Leu Leu Leu Val Ala Ala Pro Arg Trp
1               5                   10                  15
```

```
Val Leu Ser Gln Leu Gln Leu Gln Glu Ser Gly Ser Gly Leu Val Arg
                20                  25                  30

Pro Ser Gln Thr Leu Ser Leu Thr Cys Ala Val Ser Gly Ala Ser Ile
            35                  40                  45

Ser Ser Gly Gly Tyr Ser Trp Ser Trp Ile Arg Gln Pro Pro Gly Lys
 50                  55                  60

Gly Leu Glu Trp Ile Gly Tyr Ile Tyr His Ser Gly Ser Thr Ser Tyr
 65                  70                  75                  80

Asn Pro Ser Leu Lys Ser Arg Val Thr Ile Ser Glu Asp Lys Ser Asn
                85                  90                  95

Asn Gln Phe Ser Leu Lys Leu Ser Ser Val Thr Ala Ala Asp Thr Ala
                100                 105                 110

Val Tyr Tyr Cys Ala Arg Val Trp Ala Ser Phe Tyr Tyr Gly Ser Trp
                115                 120                 125

Thr Pro Pro Thr Trp Phe Asp Pro Trp Gly Pro Gly Thr Leu Val Thr
            130                 135                 140

Val Ser Ser Ala Ser Thr Lys Gly Pro Ser Val Phe Pro Leu Ala Pro
145                 150                 155                 160

Cys Ser Arg Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
                180                 185                 190

Leu Thr Ser Gly Val His Thr Phe Pro Ala Val Leu Gln Ser Ser Gly
            195                 200                 205

Leu Tyr Ser Leu Ser Ser Val Val Thr Val Pro Ser Ser Ser Leu Gly
210                 215                 220

Thr Gln Thr Tyr Ile Cys Asn Val Asn His Lys Pro Ser Asn Thr Lys
225                 230                 235                 240

Val Asp Lys Arg Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
                260                 265                 270

Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Lys
            290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
                340                 345                 350

Val Ser Asn Lys Ala Leu Pro Ala Pro Ile Glu Lys Thr Ile Ser Lys
                355                 360                 365

Ala Lys Gly Gln Pro Arg Glu Pro Gln Val Tyr Thr Leu Pro Pro Ser
            370                 375                 380

Arg Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430
```

```
Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
        450                 455                 460

His Tyr Thr Gln Lys Ser Leu Ser Leu Ser Pro Gly Lys
465                 470                 475

<210> SEQ ID NO 319
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 319

Met Ala Trp Ile Pro Leu Leu Leu Thr Gln Gly Thr Gly Ser Trp Ala
1               5                   10                  15

Gln Ser Ala Leu Thr Gln Pro Arg Ser Val Ser Gly Ser Pro Gly Gln
            20                  25                  30

Ser Val Thr Ile Ser Cys Thr Gly Thr Gly Ser Asn Val Gly Gly Tyr
        35                  40                  45

Thr Tyr Val Ser Trp Tyr Gln Gln His Pro Gly Lys Ala Pro Lys Leu
    50                  55                  60

Leu Ile Tyr Asp Val Ser Lys Arg Pro Ser Gly Val Pro Asp Arg Phe
65                  70                  75                  80

Ser Gly Ser Lys Ser Gly Asn Thr Ala Ser Leu Thr Ile Ser Gly Leu
                85                  90                  95

Gln Ala Asp Asp Glu Ala Asp Tyr His Cys Cys Ser Tyr Ala Gly Gly
            100                 105                 110

Tyr Thr Leu Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 320
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 320

Met Glu Leu Gly Leu Ser Trp Val Phe Leu Val Ala Ile Leu Glu Gly
```

-continued

```
1               5                   10                  15
Val Gln Cys Glu Val Gln Leu Val Glu Ser Gly Gly Gly Leu Val Gln
                20                  25                  30
Pro Gly Gly Ser Leu Arg Leu Ser Cys Ser Ala Ser Gly Phe Thr Phe
            35                  40                  45
Arg Ser Tyr Ile Ile Asn Trp Val Arg Gln Ala Pro Gly Lys Gly Leu
        50                  55                  60
Glu Trp Val Ser Tyr Ile Ser Gly Ser Ser Gly Thr Lys Asn Tyr Ala
65                  70                  75                  80
Asp Ser Val Lys Gly Arg Phe Thr Ile Ser Arg Asp Asn Ala Lys Asn
                85                  90                  95
Ser Val Tyr Leu Gln Met Asn Ser Leu Arg Ala Glu Asp Thr Ala Val
            100                 105                 110
Tyr Tyr Cys Ala Arg Asp Leu Asp Cys Ser Gly Gly Ser Cys Tyr Asp
        115                 120                 125
Gly Met Asp Val Trp Gly Gln Gly Thr Thr Val Thr Val Ser Ser Ala
    130                 135                 140
Ser Thr Lys Gly Pro Ser Val Phe Pro Leu Ala Pro Cys Ser Arg Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Arg
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Glu Glu Met
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
```

```
Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 321
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 321

Met Ala Trp Thr Pro Leu Leu Leu Gly Val Leu Ala Tyr Cys Thr Gly
1               5                   10                  15

Ser Val Ala Ser Phe Glu Leu Thr Gln Pro Pro Ser Val Ser Val Ser
            20                  25                  30

Pro Gly Gln Thr Ala Ser Ile Thr Cys Ser Gly Asp Lys Leu Gly His
        35                  40                  45

His Tyr Ala Tyr Trp Phe Gln Gln Arg Pro Gly Gln Ser Pro Val Leu
    50                  55                  60

Val Ile Tyr Gln His Thr Lys Arg Pro Ser Gly Ile Pro Glu Arg Phe
65                  70                  75                  80

Ser Gly Ser Lys Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ser
            100                 105                 110

Thr Tyr Val Val Phe Gly Gly Gly Thr Lys Val Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 322
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 322
```

Met Lys His Leu Trp Phe Phe Leu Leu Val Ala Ala Pro Arg Trp
1               5                   10                  15

Val Leu Ser Gln Val Gln Leu Gln Glu Ser Gly Pro Gly Leu Val Lys
        20                  25                  30

Pro Ser Gln Thr Leu Ser Leu Thr Cys Ser Val Ser Gly Gly Ser Ile
            35                  40                  45

Ser Ser Gly Ser His Tyr Trp Ser Trp Ile Arg Gln Pro Ala Gly Glu
    50                  55                  60

Ala Leu Glu Trp Ile Gly Arg Thr Tyr Thr Ser Gly Arg Thr Ser Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Thr Ser Val Thr Ala Ala Asp Thr Ala
                100                 105                 110

Val Tyr Tyr Cys Ala Arg Asn Ser Arg Ile Tyr Gly Gly Tyr Glu Leu
            115                 120                 125

Phe Asp Ile Trp Gly Gln Gly Thr Met Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 323
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 323

Met Ala Trp Thr Pro Leu Leu Gly Leu Leu Ser His Cys Thr Gly
1               5                   10                  15

Ser Leu Thr Ser Tyr Val Leu Thr Gln Pro Pro Ser Val Ser Val Ala
                20                  25                  30

Pro Gly Lys Thr Ala Arg Ile Pro Cys Gly Gly Asp Asn Ile Gly Asn
            35                  40                  45

Lys Gly Val His Trp Tyr Gln Gln Lys Ser Gly Gln Ala Pro Val Leu
    50                  55                  60

Leu Ile His Tyr Asp Ser Asp Arg Pro Ser Gly Ile Pro Glu Arg Phe
65                  70                  75                  80

Ser Gly Ser Asn Ser Gly Asn Thr Ala Thr Leu Ser Ile Ser Arg Val
                85                  90                  95

Glu Leu Gly Asp Glu Ala Asp Tyr Tyr Cys Gln Val Trp Asp Thr Ser
            100                 105                 110

Ser Asp Gln Pro Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 324
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 324

-continued

```
Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Arg Ser Tyr Met Met Asn Trp Val Arg Gln Ala Pro Gly Lys Gly Leu
        50                  55                  60

Glu Trp Val Ser Tyr Ile Ser Gly Ser Gly Gly Thr Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met His Ser Leu Arg Ala Glu Asp Thr Ala Val
            100                 105                 110

Tyr Tyr Cys Ala Arg Asp Leu Asp Cys Ser Gly Gly Thr Cys Tyr Asp
            115                 120                 125

Gly Met Asp Val Trp Gly Gln Gly Thr Thr Val Thr Val Ser Ser Ala
130                 135                 140

Ser Thr Lys Gly Pro Ser Val Phe Pro Leu Ala Pro Cys Ser Arg Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415
```

Tyr Lys Thr Thr Pro Pro Val Leu Asp Ser Asp Gly Ser Phe Phe Leu
            420             425                 430

Tyr Ser Lys Leu Thr Val Asp Lys Ser Arg Trp Gln Gln Gly Asn Val
        435             440                 445

Phe Ser Cys Ser Val Met His Glu Ala Leu His Asn His Tyr Thr Gln
        450             455                 460

Lys Ser Leu Ser Leu Ser Pro Gly Lys
465             470

<210> SEQ ID NO 325
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 325

Met Ala Trp Ala Pro Leu Leu Leu Gly Val Leu Ala Tyr Cys Thr Gly
1               5                   10                  15

Ser Val Ala Ser Tyr Glu Leu Ile Gln Pro Pro Ser Val Ser Val Ser
            20                  25                  30

Pro Gly Gln Thr Ala Ser Ile Thr Cys Ser Gly Asp Lys Leu Gly Asn
        35                  40                  45

Lys Tyr Val Tyr Trp Phe Gln His Arg Pro Gly Gln Ser Pro Val Leu
50              55                  60

Val Ile Tyr Gln His Thr Lys Arg Pro Ser Gly Ile Pro Glu Arg Phe
65                  70                  75                  80

Ser Gly Ser Lys Ser Gly Asn Thr Ala Thr Leu Ile Ile Ser Gly Thr
                85                  90                  95

Gln Ala Met Asp Glu Ala Asp Tyr Tyr Cys Gln Ala Trp Asp Ser Ser
            100                 105                 110

Val Val Ile Phe Gly Gly Gly Thr Lys Leu Thr Val Leu Gly Gln Pro
        115                 120                 125

Lys Ala Ala Pro Ser Val Thr Leu Phe Pro Pro Ser Ser Glu Glu Leu
130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
        195                 200                 205

Ser Tyr Ser Cys Gln Val Thr His Glu Gly Ser Thr Val Glu Lys Thr
210                 215                 220

Val Ala Pro Thr Glu Cys Ser
225                 230

<210> SEQ ID NO 326
<211> LENGTH: 476
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 326

Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Ser Val Ser Gly Asp Ser Ile
        35                  40                  45

Ser Arg Ser Ser Asp Tyr Trp Gly Trp Ile Arg Gln Pro Pro Gly Arg
    50                  55                  60

Gly Leu Glu Trp Ile Gly Ser Ile Tyr Arg Thr Gly Ser Thr Tyr Tyr
65                  70                  75                  80

Asn Pro Ser Leu Ser Ser Arg Val Thr Ile Ser Val Asp Thr Ser Lys
                85                  90                  95

Ser Gln Phe Ser Leu Ser Leu Ser Ser Val Thr Ala Ala Asp Thr Ala
            100                 105                 110

Leu Tyr Tyr Cys Ala Arg Val Arg His Asp Tyr Val Trp Gly Ser Ile
        115                 120                 125

Tyr Tyr Tyr Gly Met Asp Val Trp Gly Gln Gly Thr Thr Val Thr Val
130                 135                 140

Ser Ser Pro Ser Thr Lys Gly Pro Ser Val Phe Pro Leu Ala Pro Cys
145                 150                 155                 160

Ser Arg Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415
```

-continued

```
Glu Asn Asn Tyr Lys Thr Thr Pro Val Leu Asp Ser Asp Gly Ser
                420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
450                 455                 460

Tyr Thr Gln Lys Ser Leu Ser Leu Ser Pro Gly Lys
465                 470                 475

<210> SEQ ID NO 327
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 327

Met Ala Trp Ile Pro Leu Leu Leu Thr Gln Gly Thr Gly Ser Trp Ala
1               5                   10                  15

Gln Ser Ala Leu Thr Gln Pro Arg Ser Val Ser Gly Ser Pro Gly Gln
            20                  25                  30

Ser Val Thr Ile Ser Cys Thr Gly Thr Gly Ser Asp Val Gly Gly Tyr
        35                  40                  45

Thr Tyr Val Ser Trp Tyr Gln Gln His Pro Asp Lys Ala Pro Lys Leu
    50                  55                  60

Val Ile Tyr Asp Val Thr Lys Arg Pro Ser Gly Val Pro Asp Arg Phe
65                  70                  75                  80

Ser Gly Ser Lys Ser Gly Asn Thr Ala Ser Leu Thr Ile Ser Gly Leu
                85                  90                  95

Arg Ala Asp Asp Glu Ala Asp Tyr Tyr Cys Cys Ser Tyr Ala Gly Arg
            100                 105                 110

Tyr Ser Trp Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 328
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 328

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Gly Tyr Thr Phe
        35                  40                  45

Thr Ala Tyr His Leu His Trp Val Arg Gln Thr Pro Gly Gln Gly Leu
    50                  55                  60

Glu Trp Met Gly Trp Ile Asn Pro Asn Ser Gly Thr Asn Tyr Ala
65              70                  75                  80

Leu Lys Phe Gln Gly Arg Val Thr Val Thr Arg Asp Thr Ser Ile Ser
                85                  90                  95

Thr Val Tyr Met Glu Leu Thr Arg Leu Arg Ser Asp Asp Thr Ala Val
            100                 105                 110

Tyr Tyr Cys Ala Arg Glu Lys Glu Pro Leu Met Ala Ser Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn

```
                        405                 410                 415
Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 329
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 329

Met Ala Trp Ala Pro Leu Trp Leu Thr Leu Leu Thr Leu Cys Ile Gly
1               5                   10                  15

Ser Val Val Ser Ser Glu Val Thr Gln Asp Pro Ala Val Ser Val Ala
            20                  25                  30

Leu Gly Gln Thr Val Arg Ile Thr Cys Gln Gly Asp Ser Leu Arg Asn
        35                  40                  45

Tyr Tyr Thr Arg Trp Tyr Gln Gln Lys Pro Gly Gln Ala Pro Val Leu
    50                  55                  60

Val Ile Tyr Arg Glu Asn Asn Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Thr Ser Arg Ala Thr Asn
            100                 105                 110

Thr Asp His Leu Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 330
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 330

```
Met Lys His Leu Trp Phe Phe Leu Leu Val Ala Ala Pro Arg Trp
1               5                   10                  15

Val Leu Ser Gln Leu Gln Leu Gln Glu Ser Gly Ser Gly Leu Val Arg
            20                  25                  30

Pro Ser Gln Thr Leu Ser Leu Thr Cys Ala Val Ser Gly Ala Ser Ile
            35                  40                  45

Asn Ser Gly Gly Tyr Ser Trp Ser Trp Ile Arg Gln Pro Pro Gly Lys
        50                  55                  60

Gly Leu Glu Trp Ile Gly Tyr Ile Tyr His Ser Gly Ser Thr Ser Tyr
65                  70                  75                  80

Asn Pro Ser Leu Lys Ser Arg Val Thr Ile Ser Glu Asp Arg Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Val Trp Ala Ser Phe Tyr Tyr Gly Ser Trp
            115                 120                 125

Thr Pro Pro Thr Trp Leu Asp Pro Trp Gly Pro Gly Thr Leu Val Thr
            130                 135                 140

Val Ser Ser Ala Ser Thr Lys Gly Pro Ser Val Phe Pro Leu Ala Pro
145                 150                 155                 160

Cys Ser Arg Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
            195                 200                 205

Leu Tyr Ser Leu Ser Ser Val Val Thr Val Pro Ser Ser Ser Leu Gly
            210                 215                 220

Thr Gln Thr Tyr Ile Cys Asn Val Asn His Lys Pro Ser Asn Thr Lys
225                 230                 235                 240

Val Asp Lys Arg Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Lys
            290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
            370                 375                 380

Arg Glu Glu Met Thr Lys Asn Gln Val Ser Leu Thr Cys Leu Val Lys
385                 390                 395                 400
```

-continued

```
Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Val Leu Asp Ser Asp Gly
        420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 331
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 331

Met Ala Trp Ser Pro Leu Leu Leu Thr Gln Gly Thr Gly Ser Trp Ala
1               5                   10                  15

Gln Ser Ala Leu Thr Gln Pro Arg Ser Val Ser Gly Ser Pro Gly Gln
            20                  25                  30

Ser Val Thr Ile Ser Cys Thr Gly Thr Ser Asp Val Gly Gly Tyr
        35                  40                  45

Thr Tyr Val Ser Trp Tyr Gln Gln His Pro Gly Lys Ala Pro Lys Leu
    50                  55                  60

Met Ile Tyr Asp Val Ser Lys Arg Pro Ser Gly Val Pro Asp Arg Phe
65                  70                  75                  80

Ser Gly Ser Lys Ser Gly Asn Thr Ala Ser Leu Thr Ile Ser Gly Leu
                85                  90                  95

Gln Ala Asp Asp Glu Ala Asp Tyr Tyr Cys Cys Ser Tyr Ala Gly Gly
            100                 105                 110

Tyr Thr Leu Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val His Glu Gly Ser Thr Val Glu Lys
    210                 215                 220

Thr Val Ala Pro Thr Glu Cys Ser
225                 230

<210> SEQ ID NO 332
<211> LENGTH: 471
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 332

```
Met Glu Phe Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Asn Phe
        35                  40                  45

Asp Asn Tyr Ala Met His Trp Val Arg Gln Val Pro Gly Lys Gly Leu
    50                  55                  60

Glu Trp Val Ser Gly Ile Asn Trp Asn Ser Gly Tyr Glu Ala Tyr Ala
65                  70                  75                  80

Asp Ser Val Lys Gly Arg Phe Ile Ile Ser Arg Asp Asn Ala Gln Asn
                85                  90                  95

Ser Leu Tyr Leu Gln Met Asn Ser Leu Arg Ala Asp Asp Thr Ala Phe
            100                 105                 110

Tyr Tyr Cys Thr Lys Asp Thr Ile Ala Ala Val Gly Arg Gly Ala Phe
        115                 120                 125

Asp Ile Trp Gly Gln Gly Thr Val Ser Val Ser Pro Ala Ser Thr
    130                 135                 140

Lys Gly Pro Ser Val Phe Pro Leu Ala Pro Cys Ser Arg Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400
```

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465             470

<210> SEQ ID NO 333
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 333

Met Ala Trp Ile Pro Leu Leu Gly Leu Leu Ser His Cys Thr Gly
1               5                   10                  15

Ser Val Thr Ser Tyr Leu Leu Thr Gln Pro Pro Ser Val Ser Val Ala
            20                  25                  30

Pro Gly Lys Thr Ala Met Ile Thr Cys Gly Gly Ser Lys Ile Gly Gly
            35                  40                  45

Lys Ser Val His Trp Tyr Gln Gln Lys Pro Gly Gln Ala Pro Val Leu
        50                  55                  60

Val Ile Ser Tyr Asp Ser Asp Arg Pro Ser Gly Ile Pro Lys Arg Phe
65                  70                  75                  80

Ser Gly Ser Asn Ser Gly Asn Thr Ala Thr Leu Thr Ile Ser Gly Val
                85                  90                  95

Glu Ala Gly Asp Glu Ala Asp Tyr Tyr Cys Gln Val Trp Asp Ser Ser
            100                 105                 110

Asn Val His Arg Val Phe Gly Gly Gly Thr Lys Leu Thr Val Leu Ser
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 334
<211> LENGTH: 476
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 334

```
Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Ser Val Ser Gly Asp Ser Ile
        35                  40                  45

Ser Arg Ser Ser Asp Tyr Trp Gly Trp Ile Arg Gln Pro Pro Gly Arg
    50                  55                  60

Gly Leu Glu Trp Ile Gly Ser Ile Tyr Arg Thr Gly Ser Thr Tyr Tyr
65                  70                  75                  80

Asn Pro Ser Leu Ser Ser Arg Val Thr Ile Ser Val Asp Thr Ser Lys
                85                  90                  95

Ser Gln Phe Ser Leu Ser Leu Ser Val Thr Ala Ala Asp Thr Ala
            100                 105                 110

Leu Tyr Tyr Cys Ala Arg Val Arg His Asp Tyr Val Trp Gly Ser Ile
        115                 120                 125

Tyr Tyr Tyr Gly Met Asp Val Trp Gly Gln Gly Thr Thr Val Thr Val
    130                 135                 140

Ser Ser Pro Ser Thr Lys Gly Pro Ser Val Phe Pro Leu Ala Pro Cys
145                 150                 155                 160

Ser Arg Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Leu Gly Thr
    210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
```

```
                385                 390                 395                 400
Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Phe Leu Tyr Ser Lys Leu Thr Val Asp Lys Ser Arg Trp Gln Gln
                435                 440                 445

Gly Asn Val Phe Ser Cys Ser Val Met His Glu Ala Leu His Asn His
            450                 455                 460

Tyr Thr Gln Lys Ser Leu Ser Leu Ser Pro Gly Lys
465                 470                 475

<210> SEQ ID NO 335
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 335

Met Ala Trp Ile Pro Leu Leu Leu Thr Gln Gly Thr Gly Ser Trp Ala
1               5                   10                  15

Gln Ser Ala Leu Thr Gln Pro Arg Ser Val Ser Gly Ser Pro Gly Gln
                20                  25                  30

Ser Val Thr Ile Ser Cys Thr Gly Thr Gly Ser Asp Val Gly Gly Tyr
            35                  40                  45

Thr Tyr Val Ser Trp Tyr Gln Gln His Pro Asp Lys Ala Pro Lys Leu
        50                  55                  60

Val Ile Tyr Asp Val Thr Lys Arg Pro Ser Gly Val Pro Asp Arg Phe
65                  70                  75                  80

Ser Gly Ser Lys Ser Gly Asn Thr Ala Ser Leu Thr Ile Ser Gly Leu
                85                  90                  95

Arg Ala Asp Asp Glu Ala Asp Tyr Tyr Cys Cys Ser Tyr Ala Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
210                 215

<210> SEQ ID NO 336
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 336

```
Met Glu Leu Gly Leu Cys Trp Val Phe Leu Val Ala Ile Leu Glu Gly
 1               5                  10                  15

Val Gln Cys Glu Val Gln Leu Val Glu Ser Gly Gly Gly Leu Val Gln
             20                  25                  30

Pro Gly Gly Ser Leu Arg Leu Ser Cys Ser Ala Ser Gly Phe Thr Phe
         35                  40                  45

Arg Ser Tyr Ile Ile Asn Trp Val Arg Gln Ala Pro Gly Lys Gly Leu
     50                  55                  60

Glu Trp Val Ser Tyr Ile Ser Gly Ser Ser Gly Thr Lys Asn Tyr Ala
 65                  70                  75                  80

Asp Ser Val Lys Gly Arg Phe Thr Ile Ser Arg Asp Asn Ala Lys Asn
                 85                  90                  95

Ser Val Tyr Leu Gln Met Asn Ser Leu Arg Ala Glu Asp Thr Ala Val
            100                 105                 110

Tyr Tyr Cys Ala Arg Asp Leu Asp Cys Ser Gly Gly Ser Cys Tyr Asp
        115                 120                 125

Gly Met Asp Val Trp Gly Gln Gly Thr Thr Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400
```

-continued

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 337
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 337

Met Ala Trp Thr Pro Leu Phe Leu Gly Val Leu Ala Tyr Cys Thr Gly
1               5                   10                  15

Ser Val Ala Ser Phe Glu Leu Thr Gln Pro Pro Ser Val Ser Val Ser
            20                  25                  30

Pro Gly Gln Thr Ala Ser Ile Thr Cys Ser Gly Asp Lys Leu Gly His
        35                  40                  45

His Tyr Ala Tyr Trp Phe Gln Gln Arg Pro Gly Gln Ser Pro Val Leu
    50                  55                  60

Val Ile Tyr Gln His Thr Lys Arg Pro Ser Gly Ile Pro Glu Arg Phe
65                  70                  75                  80

Ser Gly Ser Lys Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ser
            100                 105                 110

Thr Tyr Val Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 338
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 338

```
Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser Tyr Met Met Asn Trp Val Arg Gln Ala Pro Gly Lys Gly Leu
    50                  55                  60

Glu Trp Val Ser Tyr Ile Ser Gly Ser Gly Gly Thr Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met His Ser Leu Arg Ala Glu Asp Thr Ala Val
            100                 105                 110

Tyr Tyr Cys Ala Arg Asp Leu Asp Cys Ser Gly Gly Thr Cys Tyr Asp
        115                 120                 125

Gly Met Asp Val Trp Gly Gln Gly Thr Thr Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400
```

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
        420                 425                 430

Tyr Ser Lys Leu Thr Val Asp Lys Ser Arg Trp Gln Gln Gly Asn Val
    435                 440                 445

Phe Ser Cys Ser Val Met His Glu Ala Leu His Asn His Tyr Thr Gln
    450                 455                 460

Lys Ser Leu Ser Leu Ser Pro Gly Lys
465             470

<210> SEQ ID NO 339
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 339

Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
            20                  25                  30

Pro Gly Gln Thr Ala Ser Ile Thr Cys Ser Gly Asp Lys Leu Gly His
        35                  40                  45

Lys Tyr Val Tyr Trp Phe Gln His Arg Pro Gly Gln Ser Pro Val Leu
    50                  55                  60

Val Ile Tyr Gln His Thr Lys Arg Pro Ser Gly Ile Pro Glu Arg Phe
65                  70                  75                  80

Ser Gly Ser Lys Ser Gly Asn Thr Ala Thr Leu Thr Ile Ser Gly Thr
            85                  90                  95

Gln Ala Leu Asp Glu Ala Asp Tyr Tyr Cys Gln Ala Trp Asp Ser Ser
            100                 105                 110

Val Val Ile Phe Gly Gly Gly Thr Lys Leu Thr Val Leu Gly Gln Pro
        115                 120                 125

Lys Ala Ala Pro Ser Val Thr Leu Phe Pro Pro Ser Ser Glu Glu Leu
130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
        195                 200                 205

Ser Tyr Ser Cys Gln Val Thr His Glu Gly Ser Thr Val Glu Lys Thr
    210                 215                 220

Val Ala Pro Thr Glu Cys Ser
225                 230

<210> SEQ ID NO 340
<211> LENGTH: 473
<212> TYPE: PRT
<213> ORGANISM: Artificial Sequence
<220> FEATURE:

<220> NAME/KEY: source
<223> OTHER INFORMATION: /note="Description of Artificial Sequence: Synthetic polypeptide"

<400> SEQUENCE: 340

```
Met Asp Trp Thr Trp Arg Ile Leu Phe Leu Val Ala Ala Val Thr Gly
1               5                   10                  15

Ala His Ser Gln Val Gln Leu Val Gln Ser Gly Pro Glu Val Lys Arg
            20                  25                  30

Pro Gly Ala Ser Val Lys Val Ser Cys Lys Ala Ser Gly Tyr Thr Leu
        35                  40                  45

Thr Thr Ser Ser Ile His Trp Val Arg Gln Ala Pro Gly Gln Arg Leu
    50                  55                  60

Glu Trp Met Gly Trp Ile Asn Thr Gly Asn Asp Asn Thr Met Tyr Ser
65                  70                  75                  80

Gln Lys Phe Gln Gly Arg Val Leu Ile Thr Thr Asp Thr Ser Ala Ser
                85                  90                  95

Thr Ala Tyr Leu Glu Leu Arg Ser Leu Arg Ser Glu Asp Thr Ala Val
            100                 105                 110

Phe Tyr Cys Ala Arg Gly Pro Leu Pro Tyr Tyr Tyr Asp Ser Ser Gly
        115                 120                 125

Pro Leu Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
```

```
                385                 390                 395                 400
Ser Asp Ile Ala Val Glu Trp Glu Ser Asn Gly Gln Pro Glu Asn Asn
                    405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 341
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 341

Met Ala Trp Ile Pro Leu Leu Leu Gly Leu Leu Ser His Cys Thr Gly
1               5                   10                  15

Ser Val Thr Ser Tyr Val Leu Thr Gln Pro Pro Ser Val Ser Val Ala
                20                  25                  30

Pro Gly Lys Thr Ala Thr Phe Thr Cys Gly Gly Asp Asn Ile Gly Thr
            35                  40                  45

Lys Ser Val His Trp Tyr Arg Gln Lys Pro Gly Gln Ala Pro Val Leu
50                  55                  60

Val Val Tyr Asp Asp Ser Asp Arg Pro Ser Gly Asp Pro Glu Arg Phe
65                  70                  75                  80

Ser Gly Ser Asn Ser Gly Asn Thr Ala Thr Leu Thr Ile Ser Arg Val
                85                  90                  95

Glu Ala Gly Asp Glu Ala Asp Tyr Phe Cys Gln Val Trp Ile Ser Ser
            100                 105                 110

Arg Asp His Pro Val Phe Gly Glu Gly Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 342
<211> LENGTH: 474
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 342

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Gly Tyr Thr Phe
            35                  40                  45

Thr Ala Tyr His Met His Trp Val Arg Gln Ala Pro Gly Gln Gly Leu
50                  55                  60

Glu Trp Met Gly Trp Ile Asn Pro Asn Ser Gly Gly Thr Asn Tyr Ala
65                  70                  75                  80

Gln Asn Phe Gln Gly Arg Val Thr Val Thr Arg Asp Thr Ser Ile Ser
                85                  90                  95

Thr Val Tyr Met Glu Leu Thr Arg Leu Arg Ser Asp Asp Thr Ala Val
            100                 105                 110

Tyr Tyr Cys Ala Arg Glu Arg Glu Pro Leu Met Ala Ser Tyr Tyr Tyr
            115                 120                 125

Tyr Gly Met Asp Val Trp Gly Gln Gly Thr Thr Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
370                 375                 380
```

```
Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 343
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 343

```
Met Ala Trp Ala Thr Leu Leu Leu Thr Leu Cys Ile Gly Ser Val Val
1               5                   10                  15

Ser Ser Glu Val Thr Gln Asp Pro Ala Val Ser Val Ala Leu Gly Gln
            20                  25                  30

Thr Val Arg Ile Thr Cys Gln Gly Asp Ser Leu Arg Asn Tyr Tyr Thr
        35                  40                  45

Arg Trp Tyr Gln Gln Lys Pro Gly Gln Ala Pro Ile Leu Val Ile Tyr
    50                  55                  60

Arg Glu Asn Asn Arg Pro Ser Gly Ile Pro Asp Arg Phe Ser Gly Ser
65                  70                  75                  80

Asn Ser Gly Asn Thr Ala Ser Leu Thr Ile Thr Gly Ala Gln Ala Glu
                85                  90                  95

Asp Glu Ala Asp Tyr Tyr Cys Thr Ser Arg Ala Ser Gly Ser Asp His
            100                 105                 110

Leu Val Phe Gly Gly Gly Thr Lys Leu Thr Val Leu Gly Gln Pro Lys
        115                 120                 125

Ala Ala Pro Ser Val Thr Leu Phe Pro Pro Ser Ser Glu Glu Leu Gln
130                 135                 140

Ala Asn Lys Ala Thr Leu Val Cys Leu Ile Ser Asp Phe Tyr Pro Gly
145                 150                 155                 160

Ala Val Thr Val Ala Trp Lys Ala Asp Ser Ser Pro Val Lys Ala Gly
                165                 170                 175

Val Glu Thr Thr Thr Pro Ser Lys Gln Ser Asn Asn Lys Tyr Ala Ala
            180                 185                 190

Ser Ser Tyr Leu Ser Leu Thr Pro Glu Gln Trp Lys Ser His Arg Ser
        195                 200                 205

Tyr Ser Cys Gln Val Thr His Glu Gly Ser Thr Val Glu Lys Thr Val
    210                 215                 220

Ala Pro Thr Glu Cys Ser
225                 230
```

<210> SEQ ID NO 344
<211> LENGTH: 474
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 344

Met Asp Trp Thr Trp Arg Ile Leu Phe Leu Val Ala Ala Ala Thr Gly
1               5                   10                  15

Ala His Ser Arg Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ala Tyr His Met His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Arg Phe Gln Gly Arg Val Thr Met Thr Arg Asp Thr Ser Ser Ser
                85                  90                  95

Thr Ala Tyr Met Asp Leu Thr Arg Leu Arg Ser Asp Asp Thr Ala Val
            100                 105                 110

Tyr Tyr Cys Ala Arg Glu Arg Glu Pro Leu Met Ala Ser Phe Tyr His
        115                 120                 125

Tyr Gly Leu Gly Val Trp Gly Gln Gly Thr Thr Val Ala Val Ser Ser
    130                 135                 140

Ala Ser Thr Lys Gly Pro Ser Val Phe Pro Leu Ala Pro Cys Ser Arg
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380
```

```
Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
        420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 345
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 345

Met Ala Trp Thr Pro Leu Leu Thr Leu Cys Ile Gly Ser Gly Gly Ser
1               5                   10                  15

Ser Glu Leu Thr Gln Asp Pro Ala Val Ser Val Ala Leu Gly Gln Thr
            20                  25                  30

Val Thr Ile Thr Cys Gln Gly Asp Ser Leu Arg Ile Tyr Ala Ser
        35                  40                  45

Trp Tyr Gln Gln Lys Pro Gly Gln Ala Pro Ile Leu Val Ile Tyr Asp
    50                  55                  60

Thr Asn Lys Arg Pro Ser Gly Ile Pro Asp Arg Phe Ser Gly Ser Ser
65                  70                  75                  80

Ser Gly Asn Thr Ala Ser Leu Thr Ile Thr Gly Ala Gln Ala Glu Asp
                85                  90                  95

Glu Ala Glu Tyr Tyr Cys Asp Ser Arg Asp Ser Ser Gly Asp His Leu
            100                 105                 110

Leu Phe Gly Gly Gly Thr Arg Val Thr Val Leu Gly Gln Pro Lys Ala
        115                 120                 125

Ala Pro Ser Val Thr Leu Phe Pro Pro Ser Ser Glu Glu Leu Gln Ala
    130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Ser Ser Pro Val Lys Ala Gly Val
                165                 170                 175

Glu Thr Thr Thr Pro Ser Lys Gln Ser Asn Asn Lys Tyr Ala Ala Ser
            180                 185                 190

Ser Tyr Leu Ser Leu Thr Pro Glu Gln Trp Lys Ser His Arg Ser Tyr
        195                 200                 205

Ser Cys Gln Val Thr His Glu Gly Ser Thr Val Glu Lys Thr Val Ala
    210                 215                 220

Pro Thr Glu Cys Ser
225

<210> SEQ ID NO 346
<211> LENGTH: 476
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 346

Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Ser Val Ser Gly Asp Ser Ile
        35                  40                  45

Ser Arg Ser Ser Asp Tyr Trp Gly Trp Ile Arg Gln Pro Pro Gly Arg
    50                  55                  60

Gly Leu Glu Trp Ile Gly Ser Ile Tyr Arg Thr Gly Ser Thr Tyr Tyr
65                  70                  75                  80

Asn Pro Ser Leu Ser Ser Arg Val Thr Ile Ser Val Asp Thr Ser Lys
                85                  90                  95

Ser Gln Phe Ser Leu Ser Leu Ser Ser Val Thr Ala Ala Asp Thr Ala
            100                 105                 110

Leu Tyr Tyr Cys Ala Arg Val Arg His Asp Tyr Val Trp Gly Ser Ile
        115                 120                 125

Tyr Tyr Tyr Gly Met Asp Val Trp Gly Gln Gly Thr Thr Val Thr Val
    130                 135                 140

Ser Ser Pro Ser Thr Lys Gly Pro Ser Val Phe Pro Leu Ala Pro Cys
145                 150                 155                 160

Ser Arg Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
```

370                 375                 380
Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475

<210> SEQ ID NO 347
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 347

Met Ala Trp Thr Val Leu Leu Leu Ser Leu Leu Thr Gln Gly Thr Gly
1               5                   10                  15

Ser Trp Ala Gln Ser Ala Leu Thr Gln Pro Arg Ser Val Ser Gly Ser
            20                  25                  30

Pro Gly Gln Ser Val Thr Ile Ser Cys Thr Gly Thr Gly Ser Asp Val
        35                  40                  45

Gly Gly Tyr Thr Tyr Val Ser Trp Tyr Gln Gln His Pro Asp Lys Ala
    50                  55                  60

Pro Lys Leu Val Ile Tyr Asp Val Thr Lys Arg Pro Ser Gly Val Pro
65                  70                  75                  80

Asp Arg Phe Ser Gly Ser Lys Ser Gly Asn Thr Ala Ser Leu Thr Ile
                85                  90                  95

Ser Gly Leu Arg Ala Asp Asp Glu Ala Asp Tyr Tyr Cys Cys Ser Tyr
            100                 105                 110

Ala Gly Arg Tyr Ser Trp Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 348

```
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 348
```

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Gly Tyr Thr Phe
        35                  40                  45

Thr Ala Tyr His Met His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65              70                  75                  80

Gln Lys Phe Gln Gly Arg Val Thr Val Thr Arg Asp Thr Ser Ile Ser
            85                  90                  95

Thr Val Tyr Met Glu Leu Thr Arg Leu Arg Ser Asp Asp Thr Ala Val
        100                 105                 110

Tyr Tyr Cys Ala Arg Glu Arg Glu Pro Leu Met Ala Ser Tyr Tyr Tyr
    115                 120                 125

Tyr Gly Met Asp Val Trp Gly Gln Gly Thr Thr Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Gly Gly Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
    195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
            245                 250                 255

Pro Ala Pro Glu Leu Leu Gly Gly Pro Ser Val Phe Leu Phe Pro Pro
        260                 265                 270

Lys Pro Lys Asp Thr Leu Met Ile Ser Arg Thr Pro Glu Val Thr Cys
    275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
        340                 345                 350

Lys Ala Leu Pro Ala Pro Ile Glu Lys Thr Ile Ser Lys Ala Lys Gly
    355                 360                 365

```
Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 349
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 349

Met Ala Trp Ile Pro Leu Trp Leu Thr Leu Leu Thr Leu Cys Ile Gly
1               5                   10                  15

Ser Val Val Ser Ser Glu Val Thr Gln Asp Pro Ala Val Ser Val Ala
                20                  25                  30

Leu Gly Gln Thr Val Arg Ile Thr Cys Gln Gly Asp Ser Leu Arg Asn
            35                  40                  45

Tyr Tyr Thr Arg Trp Tyr Gln Gln Lys Pro Gly Gln Ala Pro Val Leu
        50                  55                  60

Val Ile Tyr Arg Glu Asn Asn Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Thr Ser Arg Ala Ser Ser
                100                 105                 110

Thr Asp His Leu Val Phe Gly Gly Gly Thr Lys Leu Thr Val Leu Gly
            115                 120                 125

Gln Pro Lys Ala Ala Pro Ser Val Thr Leu Phe Pro Pro Ser Ser Glu
        130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

```
<210> SEQ ID NO 350
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 350
```

Met Glu Leu Gly Leu Ser Trp Leu Phe Leu Val Ala Thr Leu Lys Gly
1               5                   10                  15

Val Gln Cys Glu Val Gln Leu Leu Glu Ser Gly Gly Gly Leu Met Gln
            20                  25                  30

Pro Gly Gly Ser Leu Arg Leu Ser Cys Ala Ala Ser Gly Phe Thr Phe
        35                  40                  45

Arg Ser Tyr Ala Met Asn Trp Val Arg Gln Ala Pro Gly Lys Gly Leu
    50                  55                  60

Glu Trp Val Ser Thr Ile Ser Gly Asn Gly Thr Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Ile
            100                 105                 110

Tyr Tyr Cys Ala Gln Gly Glu Pro Trp Ser Gly Tyr Leu Glu Pro Leu
        115                 120                 125

Phe Ala Ser Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

```
Arg Glu Pro Gln Val Tyr Thr Leu Pro Pro Ser Arg Glu Glu Met Thr
        370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
        450                 455                 460

Ser Leu Ser Leu Ser Pro Gly Lys
465                 470
```

<210> SEQ ID NO 351
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 351

```
Met Ala Leu Thr Pro Leu Trp Leu Thr Leu Thr Pro Cys Ile Gly
1               5                   10                  15

Ser Val Val Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Asn
            35                  40                  45

Phe Tyr Ala Ser Trp Tyr Gln Gln Lys Pro Gly Gln Ala Pro Val Leu
        50                  55                  60

Val Ile Tyr Gly Lys Asn Asn Arg Pro Ser Gly Ile Pro Asp Arg Phe
65                  70                  75                  80

Ser Gly Ser Ser Ser Gly Asn Thr Val Ser Leu Thr Ile Thr Gly Ala
                85                  90                  95

Gln Ala Glu Asp Asp Ala Asp Tyr Tyr Cys Asn Ser Arg Asp Ser Ser
                100                 105                 110

Gly Asn His Val Ile Phe Gly Gly Gly Thr Lys Leu Thr Val Leu Gly
            115                 120                 125

Gln Pro Lys Ala Ala Pro Ser Val Thr Leu Phe Pro Pro Ser Ser Glu
        130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
                180                 185                 190

Tyr Ala Ala Ser Ser Tyr Leu Ser Leu Thr Pro Glu Gln Trp Lys Ser
            195                 200                 205

His Arg Ser Tyr Ser Cys Gln Val Thr His Glu Gly Ser Thr Val Glu
        210                 215                 220

Lys Thr Val Ala Pro Thr Glu Cys Ser
225                 230
```

<210> SEQ ID NO 352
<211> LENGTH: 475
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 352

Met Glu Leu Gly Leu Arg Trp Val Phe Leu Val Ala Ile Leu Glu Gly
1               5                   10                  15

Val His Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Ser Ile Ser Thr Ser Lys Asn Tyr Lys Lys Tyr Ala
65                  70                  75                  80

Asp Ser Val Lys Gly Arg Phe Thr Ile Ser Arg Asp Asn Ala Glu Asn
                85                  90                  95

Ser Leu Tyr Leu Gln Met Asn Ser Leu Arg Ala Glu Asp Thr Ala Ile
            100                 105                 110

Tyr Tyr Cys Ala Arg Val Asp Tyr Asp Tyr Ile Trp Gly Ser Tyr Arg
        115                 120                 125

Glu Lys Ala Met Asp Val Trp Gly His Gly Thr Thr Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys

```
                355                 360                 365
Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 353
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 353

Met Ala Trp Ser Pro Leu Leu Leu Thr Gln Gly Thr Gly Ser Trp Ala
1               5                   10                  15

Gln Ser Ala Leu Thr Gln Pro Arg Ser Val Ser Gly Ser Pro Gly Gln
            20                  25                  30

Ser Val Thr Ile Ser Cys Thr Gly Thr Gly Ser Asp Val Gly Gly Tyr
        35                  40                  45

Asn Tyr Val Ser Trp Tyr Gln Gln His Pro Gly Lys Ala Pro Lys Val
    50                  55                  60

Ile Ile Tyr Asp Val Ser Lys Arg Pro Ser Gly Val Pro Asp Arg Phe
65                  70                  75                  80

Ser Gly Ser Lys Ser Gly Asn Thr Ala Ser Leu Thr Ile Ser Gly Leu
                85                  90                  95

Gln Ala Glu Asp Glu Ala Asp Tyr His Cys Cys Ser Tyr Ala Gly Thr
            100                 105                 110

Tyr Thr Trp Val Phe Gly Gly Gly Thr Lys Val Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230
```

<210> SEQ ID NO 354
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 354

Met Glu Phe Gly Leu Arg Trp Leu Phe Leu Val Ala Ile Leu Lys Gly
1               5                   10                  15

Val Gln Cys Glu Val Gln Leu Leu Glu Ser Gly Gly Gly Ser Val Gln
                20                  25                  30

Pro Gly Gly Ser Leu Arg Leu Ser Cys Ala Ala Ser Gly Phe Thr Phe
            35                  40                  45

Arg Asn Tyr Ala Met Asn Trp Val Arg Gln Ser Pro Gly Lys Gly Leu
        50                  55                  60

Glu Trp Val Ser Thr Ile Ser Gly Thr Gly Gly Thr Thr Tyr Tyr Ala
65                  70                  75                  80

Asp Ser Val Lys Gly Arg Phe Ser Ile Ser Arg Asp Asn Ser Arg Asn
                85                  90                  95

Thr Leu Tyr Leu Asn Met Asn Asn Leu Arg Val Glu Asp Thr Ala Ile
            100                 105                 110

Tyr Tyr Cys Ala Lys Gly Glu Pro Trp Ser Asn Tyr Leu Glu Pro Leu
        115                 120                 125

Phe Asp His Trp Gly Gln Gly Thr Leu Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

```
Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 355
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 355

Met Ala Leu Thr Pro Leu Leu Thr Leu Cys Ile Gly Ser Val Val
1               5                   10                  15

Ser Ser Glu Leu Thr Gln Asp Pro Ala Val Ser Val Ala Leu Gly Gln
            20                  25                  30

Thr Val Arg Ile Thr Cys Gln Gly Asp Ser Leu Arg Asn Phe Tyr Ala
        35                  40                  45

Thr Trp Tyr Gln Gln Lys Pro Gly Gln Ala Pro Val Phe Val Met Tyr
    50                  55                  60

Asp Lys Thr Asn Arg Pro Ser Gly Ile Pro Asp Arg Phe Ser Gly Ser
65                  70                  75                  80

Arg Ser Gly Asn Thr Ala Tyr Leu Thr Ile Thr Gly Ala Gln Ala Glu
                85                  90                  95

Asp Glu Ala Asp Tyr Tyr Cys Asn Ser Arg Asp Ser Ser Gly Asn Tyr
            100                 105                 110

Val Ile Phe Gly Gly Gly Thr Lys Leu Thr Val Leu Gly Gln Pro Lys
        115                 120                 125

Ala Ala Pro Ser Val Thr Leu Phe Pro Pro Ser Ser Glu Glu Leu Gln
    130                 135                 140

Ala Asn Lys Ala Thr Leu Val Cys Leu Ile Ser Asp Phe Tyr Pro Gly
145                 150                 155                 160

Ala Val Thr Val Ala Trp Lys Ala Asp Ser Ser Pro Val Lys Ala Gly
                165                 170                 175

Val Glu Thr Thr Thr Pro Ser Lys Gln Ser Asn Asn Lys Tyr Ala Ala
            180                 185                 190

Ser Ser Tyr Leu Ser Leu Thr Pro Glu Gln Trp Lys Ser His Arg Ser
        195                 200                 205

Tyr Ser Cys Gln Val Thr His Glu Gly Ser Thr Val Glu Lys Thr Val
    210                 215                 220

Ala Pro Thr Glu Cys Ser
225                 230
```

225         230

<210> SEQ ID NO 356
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 356

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Met Arg
            20                  25                  30

Pro Gly Ala Ser Leu Lys Val Ser Cys Lys Ala Ser Gly Tyr Ser Phe
        35                  40                  45

Thr Met Tyr Ser Ile His Trp Val Arg Gln Ala Pro Gly His Arg Leu
    50                  55                  60

Glu Trp Met Gly Trp Ile Asn Ala Ala Asn Gly Asn Thr Ile Tyr Ser
65                  70                  75                  80

Gln Asn Phe Gln Gly Arg Val Thr Ile Ser Arg Asp Thr Ser Ala Thr
                85                  90                  95

Thr Ala His Met Glu Leu Gly Ser Leu Arg Ser Glu Asp Thr Ala Val
            100                 105                 110

Tyr Phe Cys Ala Arg Gly Pro Ile Pro Tyr Tyr Tyr Asp His Ser Gly
        115                 120                 125

Pro Phe Asp Tyr Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

```
Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470
```

<210> SEQ ID NO 357
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 357

```
Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Pro Thr Leu Ser
            20                  25                  30

Val Ser Pro Gly Glu Arg Ala Ile Leu Ser Cys Arg Ala Ser Gln Ser
        35                  40                  45

Val Ser Ser Asp Leu Ala Trp Tyr Gln Gln Ala Gly Gln Ala Pro
    50                  55                  60

Arg Leu Leu Ile Tyr Gly Ala Ser Thr Arg Ala Thr Gly Ile Pro Pro
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Lys Trp Val Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220
```

```
Thr Lys Ser Phe Asn Arg Gly Glu Cys
225                 230
```

<210> SEQ ID NO 358
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 358

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Arg Thr Ser Gly Tyr Thr Phe
            35                  40                  45

Thr Ala Tyr His Met His Trp Val Arg Gln Ala Pro Gly Gln Gly Leu
        50                  55                  60

Glu Trp Met Gly Trp Ile Asn Pro Asn Ser Gly Gly Thr Asn Tyr Ala
65                  70                  75                  80

Gln Lys Phe Gln Gly Arg Val Thr Val Thr Arg Asp Thr Ser Leu Arg
                85                  90                  95

Thr Val Tyr Met Glu Val Thr Ser Leu Arg Ser Asp Asp Thr Ala Val
            100                 105                 110

Tyr Tyr Cys Ala Arg Glu Arg Glu Pro Leu Met Ala Ser Tyr Tyr Tyr
        115                 120                 125

Tyr Gly Leu Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
```

```
                340                 345                 350
Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
    435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 359
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 359

Met Ala Trp Ala Pro Leu Trp Leu Thr Leu Leu Thr Leu Cys Ile Gly
1               5                   10                  15

Ser Val Val Ser Ser Glu Val Thr Gln Asp Pro Ala Val Ser Val Ala
                20                  25                  30

Leu Gly Gln Thr Val Arg Ile Thr Cys Gln Gly Asp Ser Leu Arg Asn
            35                  40                  45

Tyr Tyr Thr Arg Trp Tyr Gln Gln Lys Pro Gly Gln Ala Pro Ile Leu
    50                  55                  60

Val Ile Tyr Arg Glu Asn Asn Arg Pro Ser Gly Ile Pro Asp Arg Phe
65                  70                  75                  80

Ser Gly Thr Asn Ser Gly Asn Thr Ala Ser Leu Thr Ile Thr Gly Ala
                85                  90                  95

Gln Ala Glu Asp Glu Ala Asp Tyr Tyr Cys Thr Ser Arg Ala Ser Gly
            100                 105                 110

Thr Asp His Leu Val Phe Gly Arg Gly Thr Lys Leu Thr Val Leu Gly
    115                 120                 125

Gln Pro Lys Ala Ala Pro Ser Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
    195                 200                 205

His Arg Ser Tyr Ser Cys Gln Val Thr His Glu Gly Ser Thr Val Glu
210                 215                 220
```

Lys Thr Val Ala Pro Thr Glu Cys Ser
225                 230

<210> SEQ ID NO 360
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 360

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Gly Tyr Ala Phe
            35                  40                  45

Thr Ala Phe His Leu His Trp Val Arg Gln Ala Pro Gly Gln Gly Leu
        50                  55                  60

Glu Trp Met Gly Trp Ile Asn Pro Asn Ser Gly Asp Thr Asn Tyr Ala
65                  70                  75                  80

Gln Lys Phe Gln Gly Arg Val Thr Val Thr Arg Asp Thr Ser Ile Ser
                85                  90                  95

Thr Val Tyr Met Glu Leu Thr Arg Leu Arg Ser Asp Asp Thr Ala Val
            100                 105                 110

Tyr Tyr Cys Ala Arg Glu Arg Glu Pro Leu Met Ala Ser Tyr Tyr Tyr
            115                 120                 125

Tyr Gly Met Asp Val Trp Gly Gln Gly Thr Thr Val Thr Val Ser Ser
        130                 135                 140

Ala Ser Thr Lys Gly Pro Ser Val Phe Pro Leu Ala Pro Cys Ser Arg
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
        210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
            370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
            450                 455                 460

Gln Lys Ser Leu Ser Leu Ser Pro Gly Lys
465                 470

<210> SEQ ID NO 361
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 361

Met Ala Trp Ala Pro Leu Leu Leu Thr Leu Cys Ile Gly Ser Val Val
1               5                   10                  15

Ser Ser Glu Val Thr Gln Asp Pro Ala Val Ser Val Ala Leu Gly Gln
            20                  25                  30

Thr Val Arg Ile Thr Cys Gln Gly Asp Ser Leu Arg Lys Tyr Tyr Thr
            35                  40                  45

Arg Trp Tyr Gln Gln Lys Pro Gly Gln Ala Pro Val Leu Val Ile Tyr
50                  55                  60

Arg Glu Asn Asn Arg Pro Ser Gly Ile Pro Asp Arg Phe Ser Gly Ser
65                  70                  75                  80

Ser Ser Gly Asn Thr Ala Ser Leu Thr Ile Thr Gly Ala Gln Ala Glu
            85                  90                  95

Asp Glu Ala Asp Tyr Tyr Cys Ser Ser Arg Ala Ser Ser Thr Asp His
            100                 105                 110

Leu Val Phe Gly Gly Gly Thr Lys Leu Thr Val Leu Gly Gln Pro Lys
            115                 120                 125

Ala Ala Pro Ser Val Thr Leu Phe Pro Pro Ser Ser Glu Glu Leu Gln
            130                 135                 140

Ala Asn Lys Ala Thr Leu Val Cys Leu Ile Ser Asp Phe Tyr Pro Gly
145                 150                 155                 160

Ala Val Thr Val Ala Trp Lys Ala Asp Ser Ser Pro Val Lys Ala Gly
            165                 170                 175

Val Glu Thr Thr Thr Pro Ser Lys Gln Ser Asn Asn Lys Tyr Ala Ala
            180                 185                 190

Ser Ser Tyr Leu Ser Leu Thr Pro Glu Gln Trp Lys Ser His Arg Ser
            195                 200                 205

Tyr Ser Cys Gln Val Thr His Glu Gly Ser Thr Val Glu Lys Thr Val

```
            210                 215                 220

Ala Pro Thr Glu Cys Ser
225             230

<210> SEQ ID NO 362
<211> LENGTH: 476
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 362

Met Lys His Leu Trp Phe Phe Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Ser Val Ser Gly Asp Ser Ile
        35                  40                  45

Ser Arg Ser Ser Asp Tyr Trp Gly Trp Ile Arg Gln Pro Pro Gly Arg
    50                  55                  60

Gly Leu Glu Trp Ile Gly Ser Ile Tyr Arg Thr Gly Ser Thr Tyr Tyr
65                  70                  75                  80

Asn Pro Ser Leu Ser Ser Arg Val Thr Ile Ser Val Asp Thr Ser Lys
                85                  90                  95

Ser Gln Phe Ser Leu Ser Leu Ser Ser Val Thr Ala Ala Asp Thr Ala
            100                 105                 110

Leu Tyr Tyr Cys Ala Arg Val Arg His Asp Tyr Val Trp Gly Ser Ile
        115                 120                 125

Tyr Tyr Tyr Gly Met Asp Val Trp Gly Gln Gly Thr Thr Val Thr Val
    130                 135                 140

Ser Ser Pro Ser Thr Lys Gly Pro Ser Val Phe Pro Leu Ala Pro Cys
145                 150                 155                 160

Ser Arg Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335
```

```
Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
        370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475
```

<210> SEQ ID NO 363
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: MOD_RES
<222> LOCATION: (4)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (32)..(32)
<223> OTHER INFORMATION: Any amino acid

<400> SEQUENCE: 363

```
Met Ala Trp Xaa Xaa Xaa Xaa Ser Xaa Leu Thr Gln Gly Thr Gly
1               5                   10                  15

Ser Trp Ala Arg Ser Ala Leu Thr Gln Pro Arg Ser Val Ser Gly Xaa
                20                  25                  30

Pro Gly Gln Ser Val Thr Ile Ser Cys Thr Gly Thr Gly Ser Asp Val
            35                  40                  45

Gly Gly Tyr Thr Tyr Val Ser Trp Tyr Gln Gln His Pro Asp Lys Ala
    50                  55                  60

Pro Lys Leu Val Ile Tyr Asp Val Thr Lys Arg Pro Ser Gly Val Pro
65                  70                  75                  80

Asp Arg Phe Ser Gly Ser Lys Ser Gly Asn Thr Ala Ser Leu Thr Ile
                85                  90                  95

Ser Gly Leu Arg Ala Asp Asp Glu Ala Asp Tyr Tyr Cys Cys Ser Tyr
            100                 105                 110

Ala Gly Arg Tyr Ser Trp Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140
```

```
Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 364
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 364

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Ser Gly Ser His Tyr Trp Ser Trp Ile Arg Gln Pro Ala Gly Lys
    50                  55                  60

Gly Leu Glu Trp Ile Gly Arg Ile Tyr Thr Ser Gly Arg Asn Ser Tyr
65                  70                  75                  80

Asn Pro Ser Leu Lys Ser Arg Val Thr Ile Ser Val Asp Thr Phe Lys
                85                  90                  95

Asn Gln Phe Ser Leu Lys Val Ser Ser Val Thr Ala Ala Asp Thr Ala
            100                 105                 110

Val Tyr Tyr Cys Ala Arg Asn Asn Arg Ile Tyr Gly Gly Tyr Glu Leu
        115                 120                 125

Phe Asp Ile Trp Gly Gln Gly Thr Thr Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
```

```
                260                 265                 270
Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 365
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 365

Met Ala Trp Ser Pro Leu Leu Leu Gly Leu Leu Ser His Cys Thr Val
1               5                   10                  15

Ser Val Thr Ser Phe Val Leu Thr Gln Pro Pro Ser Val Ser Val Ala
            20                  25                  30

Pro Gly Lys Thr Ala Arg Phe Ser Cys Gly Gly Asp Asn Ile Gly Ser
        35                  40                  45

Lys Pro Val His Trp Tyr Gln Gln Lys Pro Gly Gln Ala Pro Ala Leu
    50                  55                  60

Val Ile Tyr Tyr Asp Ser Asp Arg Pro Ser Gly Ile Pro Glu Arg Phe
65                  70                  75                  80

Ser Gly Ser Asn Ser Gly Asn Thr Ala Thr Leu Thr Ile Ser Arg Val
                85                  90                  95

Glu Ala Gly Asp Glu Ala Asp Tyr Tyr Cys Gln Val Trp Asp Thr Ser
            100                 105                 110

Gly Asp His Pro Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140
```

```
Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 366
<211> LENGTH: 475
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 366

Met Glu Leu Gly Leu Cys Trp Val Phe Leu Val Ala Ile Leu Glu Gly
1               5                   10                  15

Val His Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Ser Ile Ser Thr Ser Lys Asn Tyr Lys Lys Tyr Ala
65                  70                  75                  80

Asp Ser Val Lys Gly Arg Phe Thr Ile Ser Arg Asp Asn Ala Glu Asn
                85                  90                  95

Ser Leu Tyr Leu Gln Met Asn Ser Leu Arg Ala Glu Asp Thr Ala Ile
            100                 105                 110

Tyr Tyr Cys Ala Arg Val Asp Tyr Asp Tyr Ile Trp Gly Ser Tyr Arg
        115                 120                 125

Glu Lys Ala Met Asp Val Trp Gly His Gly Thr Thr Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255
```

```
Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 367
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 367

Met Ala Trp Ile Pro Leu Leu Leu Thr Gln Gly Thr Gly Ser Trp Ala
1               5                   10                  15

Gln Ser Ala Leu Thr Gln Pro Arg Ser Val Ser Gly Ser Pro Gly Gln
            20                  25                  30

Ser Val Thr Ile Ser Cys Thr Gly Thr Gly Ser Asp Val Gly Gly Tyr
        35                  40                  45

Asn Tyr Val Ser Trp Tyr Gln Gln His Pro Gly Lys Ala Pro Lys Val
    50                  55                  60

Ile Ile Tyr Asp Val Ser Lys Arg Pro Ser Gly Val Pro Asp Arg Phe
65                  70                  75                  80

Ser Gly Ser Lys Ser Gly Asn Thr Ala Ser Leu Thr Ile Ser Gly Leu
                85                  90                  95

Gln Ala Glu Asp Glu Ala Asp Tyr His Cys Cys Ser Tyr Ala Gly Thr
            100                 105                 110

Tyr Thr Trp Val Phe Gly Gly Gly Thr Lys Val Thr Val Leu Gly Gln
        115                 120                 125

Pro Lys Ala Ala Pro Ser Val Thr Leu Phe Pro Pro Ser Ser Glu Glu
```

```
                130             135              140
Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
            195                 200                 205

Arg Ser Tyr Ser Cys Gln Val Thr His Glu Gly Ser Thr Val Glu Lys
            210                 215                 220

Thr Val Ala Pro Thr Glu Cys Ser
225                 230
```

<210> SEQ ID NO 368
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 368

```
Met Asp Trp Thr Trp Arg Val Phe Cys Leu Leu Ala Val Ala Pro Gly
1               5                   10                  15

Val His Ser Gln Val Gln Leu Val Gln Ser Gly Ala Glu Val Lys Lys
            20                  25                  30

Pro Gly Ala Ser Val Arg Val Ser Cys Lys Ala Ser Gly Tyr Thr Phe
        35                  40                  45

Thr Asn Tyr Tyr Met His Trp Val Arg Gln Ala Pro Gly Gln Gly Leu
    50                  55                  60

Glu Trp Thr Gly Ile Val Asn Pro Ser Gly Gly Ser Thr Asn Tyr Ala
65                  70                  75                  80

Gln Lys Leu Gln Gly Arg Val Thr Met Thr Ile Asp Thr Ser Thr Ser
                85                  90                  95

Thr Val Tyr Met Glu Leu Asn Ser Leu Thr Ser Glu Asp Thr Ala Val
            100                 105                 110

Tyr Tyr Cys Ala Arg Ala Arg Lys His Tyr Phe Gly Ser Gly Thr Asp
        115                 120                 125

Tyr Lys Gly Arg Tyr Thr Ala His Ala Leu Asp Leu Trp Gly Gln Gly
    130                 135                 140

Thr Met Val Ile Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Arg Val Glu Pro Lys Ser Cys Asp Lys
                245                 250                 255
```

```
Thr His Thr Cys Pro Pro Cys Pro Ala Pro Glu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Glu Glu Met Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys

<210> SEQ ID NO 369
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 369

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Tyr Thr Ser Asn Asn Lys Asn Tyr Leu Ala Trp Tyr Gln Gln
    50                  55                  60

Lys Ala Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ser Glu Asp Val Ala Val Tyr
            100                 105                 110

Tyr Cys Gln Gln Tyr Tyr Ser Thr Pro Gln Thr Phe Gly Gln Gly Thr
```

```
            115                 120                 125
Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 370
<211> LENGTH: 476
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 370

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Arg Leu Val Lys
            20                  25                  30

Pro Ser Gln Thr Leu Ser Leu Thr Cys Ser Val Ser Gly Gly Thr Val
        35                  40                  45

Arg Thr Gly Asp Tyr Tyr Trp Ser Trp Ile Arg Gln Pro Pro Gly Lys
    50                  55                  60

Gly Leu Glu Trp Ile Gly Phe Ile His Tyr Ser Gly Ser Thr Tyr Tyr
65                  70                  75                  80

Asn Pro Ser Leu Lys Ser Arg Val Thr Ile Ser Leu Asp Thr Ser Arg
                85                  90                  95

Asn Gln Phe Ser Leu Lys Leu Ser Ser Val Thr Ala Ala Asp Thr Ala
            100                 105                 110

Val Tyr Phe Cys Ala Arg Ile Tyr Tyr Asp Ser Ser Gly Tyr Leu His
        115                 120                 125

Ser Leu Lys Ile Ile Asp Ser Trp Gly Gln Gly Thr Leu Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240
```

```
Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 371
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 371

Met Arg Leu Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Ala Ser Pro Gly Glu Arg Ala Thr Leu Ser Cys Arg Ala Ser Gln Ser
            35                  40                  45

Val Ser Ser Asn Leu Ala Trp Tyr Arg Gln Lys Pro Gly Gln Ser Pro
        50                  55                  60

Arg Leu Leu Ile Tyr Gly Ala Ser Ala Arg Ala Thr Gly Ile Pro Ala
65                  70                  75                  80

Arg Phe Gly Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110
```

-continued

```
Asn Trp Pro Leu Thr Phe Gly Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 372
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 372

Met Asp Trp Thr Trp Arg Ile Leu Phe Leu Val Ala Ala Ala Thr Gly
1               5                   10                  15

Ala His Ser Gln Val Gln Leu Val Gln Ser Gly Thr Glu Val Lys Lys
            20                  25                  30

Pro Gly Ala Ser Val Lys Val Ser Cys Lys Ala Ser Gly Tyr Thr Phe
        35                  40                  45

Asn Lys Tyr Ala Met Asn Trp Val Arg Gln Ala Pro Gly Gln Arg Leu
    50                  55                  60

Glu Trp Met Gly Tyr Ile Asn Ala Asp Asn Gly Asn Thr Lys Tyr Ser
65                  70                  75                  80

Gln Lys Phe Arg Asp Arg Val Thr Ile Thr Arg Asp Thr Ser Ala Ser
                85                  90                  95

Ile Val Tyr Met Glu Leu Arg Ser Leu Arg Ser Glu Asp Thr Ala Met
            100                 105                 110

Tyr Tyr Cys Ala Arg Asp Gly Gly Trp Ser Thr Thr Val Asn Asn Gln
        115                 120                 125

Pro Tyr Tyr Tyr Gly Met Asp Val Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
```

```
                225                 230                 235                 240
Val Asp Lys Arg Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 373
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 373

Met Arg Leu Leu Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Phe
            35                  40                  45

Val Gly Ser Lys Tyr Met Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Phe
            100                 105                 110
```

```
Gly Ser Ser Pro Pro Met Tyr Ala Phe Gly Gln Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Cys
225                 230                 235
```

<210> SEQ ID NO 374
<211> LENGTH: 475
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 374

```
Met Lys His Leu Trp Phe Phe Leu Leu Leu Val Ala Val Pro Arg Trp
1               5                   10                  15

Val Leu Ser Gln Val Gln Leu Gln Glu Ser Gly Pro Arg Leu Val Lys
            20                  25                  30

Pro Ser Gln Thr Leu Ser Leu Thr Cys Thr Val Ser Gly Gly Ser Ile
        35                  40                  45

Ser Ser Gly Asp Tyr Tyr Trp Ser Trp Ile Arg Gln Ala Pro Gly Thr
    50                  55                  60

Gly Leu Glu Trp Ile Gly Phe Ile Tyr Asn Thr Glu Thr Thr Tyr Tyr
65                  70                  75                  80

Ser Pro Ser Leu Arg Ser Arg Val Ser Met Ser Leu Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Glu Arg Pro Ser His Tyr Asp Ser Gly
        115                 120                 125

Gly Tyr Ser Leu Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220
```

```
Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
                340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Glu
370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475

<210> SEQ ID NO 375
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 375

Met Glu Ala Pro Ala Gln Leu Leu Phe Leu Leu Leu Leu Trp Leu Pro
1               5                   10                  15

Asp Ser Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Ala Ile Ser
                85                  90                  95

Ser Leu Gln Ser Glu Asp Phe Ala Leu Tyr Tyr Cys Gln Gln Tyr Asn
```

```
            100                 105                 110
Asn Trp Pro Arg Thr Phe Gly Gln Gly Thr Lys Val Glu Ile Lys Arg
            115                 120                 125

Thr Val Ala Ala Pro Ser Val Phe Ile Phe Pro Ser Asp Glu Gln
            130                 135             140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                    165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230
```

<210> SEQ ID NO 376
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 376

```
Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Lys
                20                  25                  30

Pro Gly Gly Ser Leu Arg Leu Ser Cys Ala Ala Ser Gly Phe Thr Phe
            35                  40                  45

Ser Thr Tyr Ser Met Asn Trp Val Arg Gln Ala Pro Gly Lys Gly Leu
        50                  55                  60

Glu Trp Val Ser Ser Ile Ser Ser Ser Gly Thr Tyr Thr Tyr Tyr Ala
65                  70                  75                  80

Asp Ser Val Lys Gly Arg Phe Thr Ile Ser Arg Asp Asn Ala Lys Asp
                    85                  90                  95

Ser Leu Tyr Leu Gln Met Asn Ser Leu Arg Ala Asp Asp Thr Ala Val
                100                 105                 110

Tyr Tyr Cys Ala Arg Ala Pro Tyr Asp Tyr Gly Asp Tyr Arg Gly Gly
            115                 120                 125

Arg Tyr Phe Asp Leu Trp Gly Arg Gly Ser Leu Val Thr Val Ser Ser
        130                 135                 140

Ala Ser Thr Lys Gly Pro Ser Val Phe Pro Leu Ala Pro Cys Ser Arg
145                 150                 155                 160

Ser Thr Ser Gly Gly Thr Ala Ala Leu Gly Cys Leu Val Lys Asp Tyr
                    165                 170                 175

Phe Pro Glu Pro Val Thr Val Ser Trp Asn Ser Gly Ala Leu Thr Ser
                180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
        210                 215                 220
```

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
            245                 250                 255

Pro Ala Pro Glu Leu Leu Gly Gly Pro Ser Val Phe Leu Phe Pro Pro
        260                 265                 270

Lys Pro Lys Asp Thr Leu Met Ile Ser Arg Thr Pro Glu Val Thr Cys
    275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
        340                 345                 350

Lys Ala Leu Pro Ala Pro Ile Glu Lys Thr Ile Ser Lys Ala Lys Gly
    355                 360                 365

Gln Pro Arg Glu Pro Gln Val Tyr Thr Leu Pro Pro Ser Arg Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
        420                 425                 430

Leu Tyr Ser Lys Leu Thr Val Asp Lys Ser Arg Trp Gln Gln Gly Asn
    435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 377
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 377

Met Arg Leu Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Lys Leu Ala Trp Tyr Gln Gln Lys Pro Gly Gln Ala Pro
    50                  55                  60

Arg Leu Leu Ile Phe Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Arg Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 378
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 378

Met Asp Thr Leu Cys Ser Thr Leu Leu Leu Thr Ile Pro Ser Trp
1               5                   10                  15

Val Leu Ser Gln Ile Thr Leu Lys Glu Ser Gly Pro Thr Leu Val Lys
            20                  25                  30

Pro Thr Gln Thr Leu Met Leu Thr Cys Thr Phe Ser Gly Phe Ser Leu
        35                  40                  45

Ser Thr Ser Gly Val Gly Val Gly Trp Ile Arg Gln Pro Pro Gly Lys
50                  55                  60

Ala Leu Glu Trp Leu Ala Phe Ile Tyr Trp Asn Thr Asp Lys Arg Tyr
65                  70                  75                  80

Asn Pro Ser Leu Lys Thr Arg Leu Thr Ile Thr Lys Asp Thr Ser Lys
                85                  90                  95

Thr Gln Val Val Leu Thr Met Thr Asn Leu Asp Pro Val Asp Thr Gly
            100                 105                 110

Thr Tyr Tyr Cys Val His His Asp Gly Tyr Leu Ala Glu Tyr Phe Asn
        115                 120                 125

His Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn

```
                210               215               220
Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly Lys
465                 470

<210> SEQ ID NO 379
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 379

Met Ala Leu Thr Pro Leu Leu Leu Thr Leu Leu Ile His Cys Thr Gly
1               5                   10                  15

Ser Trp Ala Gln Ser Val Leu Thr Gln Pro Pro Ser Val Ser Ala Ala
                20                  25                  30

Pro Gly Gln Arg Val Thr Ile Ser Cys Ser Gly Thr Thr Ser Asn Ile
                35                  40                  45

Gly Asn Tyr Tyr Val Ser Trp Tyr Gln Glu Val Pro Gly Thr Ala Pro
                50                  55                  60

Lys Leu Leu Ile Tyr Asp Asn Val Lys Arg Pro Ser Gly Ile Pro Asp
65                  70                  75                  80

Arg Phe Ser Ala Ser Lys Ser Gly Thr Ser Ala Thr Leu Gly Ile Ser
                85                  90                  95
```

```
Gly Leu Gln Thr Gly Asp Glu Ala Asp Tyr Tyr Cys Gly Thr Trp Asp
                100                 105                 110

Gly Arg Leu Ser Ala Trp Val Phe Gly Gly Gly Thr Lys Leu Thr Val
            115                 120                 125

Leu Gly Gln Pro Lys Ala Ala Pro Ser Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
                195                 200                 205

Lys Ser His Arg Ser Tyr Ser Cys Gln Val Thr His Glu Gly Ser Thr
            210                 215                 220

Val Glu Lys Thr Val Ala Pro Thr Glu Cys Ser
225                 230                 235
```

<210> SEQ ID NO 380
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 380

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Arg
            20                  25                  30

Pro Ser Glu Thr Leu Ser Leu Thr Cys Gly Val Ser Gly Gly Ala Leu
        35                  40                  45

Ser Gly Tyr Ile Trp Ser Trp Ile Arg Gln Pro Pro Gly Lys Gly Leu
    50                  55                  60

Glu Trp Ile Gly Glu Ile Asn His Ser Gly Thr Thr Asn Tyr Ser Pro
65                  70                  75                  80

Ser Leu Lys Ser Arg Val Thr Ile Ser Val Asp Thr Ser Lys Asn His
                85                  90                  95

Phe Ser Leu Arg Leu Ser Ser Val Thr Ala Ala Asp Ser Ala Met Tyr
            100                 105                 110

Tyr Cys Ala Arg Gly Gly Val Arg Asn Trp Gln Leu Gly Pro Ala Leu
        115                 120                 125

Asp Phe Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205
```

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 381
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 381

Met Arg Leu Pro Ala Gln Leu Leu Gly Leu Leu Leu Leu Trp Leu Pro
1               5                   10                  15

Gly Ala Arg Cys Ala Ile Gln Leu Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Ser Ser Phe Leu Ala Trp Phe Gln Gln Lys Pro Gly Arg Ala Pro
    50                  55                  60

Lys Leu Leu Leu Tyr Ala Ala Ser Thr Leu Gln Ser Gly Val Pro Ser
65                  70                  75                  80

Arg Phe Ser Gly Ser Gly Ser Gly Thr Asp Phe Ser Leu Thr Ile Gly

```
                85                  90                  95
Ser Leu Gln Pro Glu Asp Phe Ala Thr Tyr Tyr Cys Gln Ser Leu Asn
            100                 105                 110

Asn Tyr Pro Arg Ser Phe Thr Phe Gly Pro Gly Thr Lys Val Asp Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 382
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 382

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Ser Val Ser Gly Asp Ser Met
        35                  40                  45

Ala Ser Asp Tyr Trp Ser Trp Ile Arg Gln Pro Pro Gly Lys Gly Leu
    50                  55                  60

Glu Trp Ile Gly Tyr Val Ser Tyr Ser Gly Thr Thr Tyr Tyr Ile Pro
65                  70                  75                  80

Ser Leu Lys Ser Arg Val Thr Ile Ser Leu Asp Arg Ser Arg Thr Gln
                85                  90                  95

Phe Ser Leu Lys Val Thr Ser Val Thr Ser Ala Asp Thr Ala Val Tyr
            100                 105                 110

Tyr Cys Ala Arg Gly Arg Gly His Ser Ser Gly Trp Gly Ile
            115                 120                 125

Glu Phe Phe His Gln Trp Gly Gln Gly Thr Leu Val Thr Val Ser Pro
            130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205
```

Leu Arg Ser Val Val Thr Val Pro Ser Ser Leu Gly Thr Gln Thr
            210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 383
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 383

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Thr Leu Ser
            20                  25                  30

Val Ser Pro Gly Glu Arg Ala Thr Leu Ser Cys Arg Ala Ser Gln Ser
        35                  40                  45

Val Ser Ser Asp Leu Ala Trp Tyr Gln Gln Gln Ala Gly Gln Ala Pro
    50                  55                  60

Arg Leu Leu Ile Tyr Asp Ala Ser Thr Arg Ala Thr Gly Ile Pro Pro
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
                100                 105                 110

Lys Trp Val Thr Phe Gly Gly Gly Thr Lys Val Glu Ile Lys Arg Thr
                115                 120                 125

Val Ala Ala Pro Ser Val Phe Ile Phe Pro Pro Ser Asp Glu Gln Leu
                130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
                210                 215                 220

Thr Lys Ser Phe Asn Arg Gly Glu Cys
225                 230

<210> SEQ ID NO 384
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 384

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Met Arg
                20                  25                  30

Pro Gly Ala Ser Leu Lys Val Ser Cys Lys Ala Ser Gly Tyr Ser Phe
                35                  40                  45

Thr Met Tyr Ser Ile His Trp Val Arg Gln Ala Pro Gly His Arg Leu
                50                  55                  60

Glu Trp Met Gly Trp Ile Asn Ala Ala Asn Gly Asn Thr Ile Tyr Ser
65                  70                  75                  80

Gln Asn Phe Gln Gly Arg Val Thr Ile Ser Arg Asp Thr Ser Ala Thr
                85                  90                  95

Thr Ala His Met Glu Leu Gly Ser Leu Arg Ser Glu Asp Thr Ala Val
                100                 105                 110

Tyr Phe Cys Ala Arg Gly Pro Ile Pro Tyr Tyr Asp His Ser Gly
                115                 120                 125

Pro Phe Asp Tyr Trp Gly Gln Gly Thr Leu Val Thr Val Ser Ser Ala
                130                 135                 140

Ser Thr Lys Gly Pro Ser Val Phe Pro Leu Ala Pro Cys Ser Arg Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu

```
                195                 200                 205
Ser Ser Val Val Thr Val Pro Ser Ser Leu Gly Thr Gln Thr Tyr
    210                 215                 220
Ile Cys Asn Val Asn His Lys Pro Ser Asn Thr Lys Val Asp Lys Arg
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Glu Glu Met
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
    450                 455                 460
Lys Ser Leu Ser Leu Ser Pro Gly Lys
465                 470

<210> SEQ ID NO 385
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 385

Met Glu Ala Pro Ala Gln Leu Leu Phe Leu Leu Leu Leu Trp Leu Pro
1               5                   10                  15
Asp Thr Thr Gly Glu Ile Val Met Thr Gln Ser Pro Thr Leu Ser
            20                  25                  30
Val Ser Pro Gly Glu Arg Ala Ile Leu Ser Cys Arg Ala Ser Gln Ser
        35                  40                  45
Val Ser Ser Asp Leu Ala Trp Tyr Gln Gln Gln Ala Gly Gln Ala Pro
    50                  55                  60
Arg Leu Leu Ile Tyr Gly Ala Ser Thr Arg Ala Thr Gly Ile Pro Pro
65                  70                  75                  80
```

```
Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
                100                 105                 110

Lys Trp Val Thr Phe Gly Gly Gly Thr Lys Val Glu Ile Lys Arg Thr
                115                 120                 125

Val Ala Ala Pro Ser Val Phe Ile Phe Pro Pro Ser Asp Glu Gln Leu
            130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
            210                 215                 220

Thr Lys Ser Phe Asn Arg Gly Glu Cys
225                 230

<210> SEQ ID NO 386
<211> LENGTH: 15
<212> TYPE: PRT
<213> ORGANISM: Human polyomavirus BKV

<400> SEQUENCE: 386

Arg Val Asp Gly Gln Pro Met Tyr Gly Met Glu Ser Gln Val Glu
1               5                   10                  15

<210> SEQ ID NO 387
<211> LENGTH: 15
<212> TYPE: PRT
<213> ORGANISM: Human polyomavirus BKV

<400> SEQUENCE: 387

Lys Val Asp Gly Gln Pro Met Tyr Gly Met Glu Ser Gln Val Glu
1               5                   10                  15

<210> SEQ ID NO 388
<211> LENGTH: 15
<212> TYPE: PRT
<213> ORGANISM: Human polyomavirus BKV

<400> SEQUENCE: 388

Lys Val Asp Gly Gln Pro Met Tyr Gly Met Glu Ser Gln Val Glu
1               5                   10                  15

<210> SEQ ID NO 389
<211> LENGTH: 15
<212> TYPE: PRT
<213> ORGANISM: Human polyomavirus BKV

<400> SEQUENCE: 389

Arg Val Asp Gly Gln Pro Met Tyr Gly Met Glu Ser Gln Val Glu
1               5                   10                  15

<210> SEQ ID NO 390
<211> LENGTH: 15
<212> TYPE: PRT
```

<213> ORGANISM: Human polyomavirus JCV

<400> SEQUENCE: 390

Arg Val Asp Gly Gln Pro Met Tyr Gly Met Asp Ala Gln Val Glu
1               5                   10                  15

<210> SEQ ID NO 391
<211> LENGTH: 15
<212> TYPE: PRT
<213> ORGANISM: Merkel cell polyomavirus

<400> SEQUENCE: 391

Lys Val Ser Gly Gln Pro Met Glu Gly Lys Asp Asn Gln Val Glu
1               5                   10                  15

<210> SEQ ID NO 392
<211> LENGTH: 12
<212> TYPE: PRT
<213> ORGANISM: Human polyomavirus BKV

<400> SEQUENCE: 392

Asn Pro Thr Ala Gln Ser Gln Val Met Asn Thr Asp
1               5                   10

<210> SEQ ID NO 393
<211> LENGTH: 12
<212> TYPE: PRT
<213> ORGANISM: Human polyomavirus BKV

<400> SEQUENCE: 393

Asn Pro Thr Ala Gln Ser Gln Val Met Asn Thr Asp
1               5                   10

<210> SEQ ID NO 394
<211> LENGTH: 12
<212> TYPE: PRT
<213> ORGANISM: Human polyomavirus BKV

<400> SEQUENCE: 394

Asn Pro Thr Ala Gln Ser Gln Val Met Asn Thr Asp
1               5                   10

<210> SEQ ID NO 395
<211> LENGTH: 12
<212> TYPE: PRT
<213> ORGANISM: Human polyomavirus BKV

<400> SEQUENCE: 395

Asn Pro Thr Ala Gln Ser Gln Val Met Asn Thr Asp
1               5                   10

<210> SEQ ID NO 396
<211> LENGTH: 12
<212> TYPE: PRT
<213> ORGANISM: Human polyomavirus JCV

<400> SEQUENCE: 396

Asn Ala Thr Val Gln Ser Gln Val Met Asn Thr Glu
1               5                   10

<210> SEQ ID NO 397
<211> LENGTH: 12
<212> TYPE: PRT
<213> ORGANISM: Merkel cell polyomavirus

```
<400> SEQUENCE: 397

Lys Met Thr Pro Lys Asn Gln Gly Leu Asp Pro Gln
1               5                   10

<210> SEQ ID NO 398
<211> LENGTH: 6
<212> TYPE: PRT
<213> ORGANISM: Human polyomavirus BKV

<400> SEQUENCE: 398

Pro Asp Glu Asn Leu Arg
1               5

<210> SEQ ID NO 399
<211> LENGTH: 6
<212> TYPE: PRT
<213> ORGANISM: Human polyomavirus BKV

<400> SEQUENCE: 399

Pro Asp Asp Asn Leu Arg
1               5

<210> SEQ ID NO 400
<211> LENGTH: 6
<212> TYPE: PRT
<213> ORGANISM: Human polyomavirus BKV

<400> SEQUENCE: 400

Pro Asp Asp Asn Leu Arg
1               5

<210> SEQ ID NO 401
<211> LENGTH: 6
<212> TYPE: PRT
<213> ORGANISM: Human polyomavirus BKV

<400> SEQUENCE: 401

Pro Asp Asn Asn Leu Arg
1               5

<210> SEQ ID NO 402
<211> LENGTH: 6
<212> TYPE: PRT
<213> ORGANISM: Human polyomavirus JCV

<400> SEQUENCE: 402

Pro Asp Glu His Leu Arg
1               5

<210> SEQ ID NO 403
<211> LENGTH: 6
<212> TYPE: PRT
<213> ORGANISM: Merkel cell polyomavirus

<400> SEQUENCE: 403

Asn Ser Pro Asp Leu Pro
1               5

<210> SEQ ID NO 404
<211> LENGTH: 7
<212> TYPE: PRT
<213> ORGANISM: Human polyomavirus BKV

<400> SEQUENCE: 404
```

Pro Glu Arg Lys Met Leu Pro
1               5

<210> SEQ ID NO 405
<211> LENGTH: 7
<212> TYPE: PRT
<213> ORGANISM: Human polyomavirus BKV

<400> SEQUENCE: 405

Pro Asp Lys Lys Met Leu Pro
1               5

<210> SEQ ID NO 406
<211> LENGTH: 7
<212> TYPE: PRT
<213> ORGANISM: Human polyomavirus BKV

<400> SEQUENCE: 406

Pro Asp Arg Lys Met Leu Pro
1               5

<210> SEQ ID NO 407
<211> LENGTH: 7
<212> TYPE: PRT
<213> ORGANISM: Human polyomavirus BKV

<400> SEQUENCE: 407

Pro Asp Arg Lys Met Leu Pro
1               5

<210> SEQ ID NO 408
<211> LENGTH: 7
<212> TYPE: PRT
<213> ORGANISM: Human polyomavirus JCV

<400> SEQUENCE: 408

Pro Ser Lys Asp Met Leu Pro
1               5

<210> SEQ ID NO 409
<211> LENGTH: 7
<212> TYPE: PRT
<213> ORGANISM: Merkel cell polyomavirus

<400> SEQUENCE: 409

Pro Ile Lys Glu Asn Leu Pro
1               5

<210> SEQ ID NO 410
<211> LENGTH: 5
<212> TYPE: PRT
<213> ORGANISM: Human polyomavirus BKV

<400> SEQUENCE: 410

Lys Tyr Pro Asp Gly
1               5

<210> SEQ ID NO 411
<211> LENGTH: 5
<212> TYPE: PRT
<213> ORGANISM: Human polyomavirus BKV

<400> SEQUENCE: 411

Lys Tyr Pro Gln Gly
1               5

```
<210> SEQ ID NO 412
<211> LENGTH: 5
<212> TYPE: PRT
<213> ORGANISM: Human polyomavirus BKV

<400> SEQUENCE: 412

Lys Tyr Pro Gln Gly
1               5

<210> SEQ ID NO 413
<211> LENGTH: 5
<212> TYPE: PRT
<213> ORGANISM: Human polyomavirus BKV

<400> SEQUENCE: 413

Lys Tyr Pro Glu Gly
1               5

<210> SEQ ID NO 414
<211> LENGTH: 5
<212> TYPE: PRT
<213> ORGANISM: Human polyomavirus JCV

<400> SEQUENCE: 414

Lys Tyr Pro Asp Gly
1               5

<210> SEQ ID NO 415
<211> LENGTH: 5
<212> TYPE: PRT
<213> ORGANISM: Merkel cell polyomavirus

<400> SEQUENCE: 415

Glu Tyr Pro Lys Thr
1               5

<210> SEQ ID NO 416
<211> LENGTH: 4
<212> TYPE: PRT
<213> ORGANISM: Human polyomavirus BKV

<400> SEQUENCE: 416

Leu Asp Lys Asn
1

<210> SEQ ID NO 417
<211> LENGTH: 4
<212> TYPE: PRT
<213> ORGANISM: Human polyomavirus BKV

<400> SEQUENCE: 417

Leu Asp Lys Asn
1

<210> SEQ ID NO 418
<211> LENGTH: 4
<212> TYPE: PRT
<213> ORGANISM: Human polyomavirus BKV

<400> SEQUENCE: 418

Leu Asp Lys Asn
1
```

-continued

```
<210> SEQ ID NO 419
<211> LENGTH: 4
<212> TYPE: PRT
<213> ORGANISM: Human polyomavirus BKV

<400> SEQUENCE: 419

Leu Asp Lys Asn
1

<210> SEQ ID NO 420
<211> LENGTH: 4
<212> TYPE: PRT
<213> ORGANISM: Human polyomavirus JCV

<400> SEQUENCE: 420

Leu Asp Lys Asn
1

<210> SEQ ID NO 421
<211> LENGTH: 4
<212> TYPE: PRT
<213> ORGANISM: Merkel cell polyomavirus

<400> SEQUENCE: 421

Leu Asp Lys Asp
1

<210> SEQ ID NO 422
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: SITE
<222> LOCATION: (1)..(12)
<223> OTHER INFORMATION: /note="Variant residues given in the sequence
      have no preference with respect to those in the annotations
      for variant positions"

<400> SEQUENCE: 422

Gly Gly Ser Ile Ser Gly Gly Gly Tyr Tyr Trp Ser
1               5                   10

<210> SEQ ID NO 423
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: VARIANT
<222> LOCATION: (6)..(6)
<223> OTHER INFORMATION: /replace="Gly"
<220> FEATURE:
<221> NAME/KEY: VARIANT
<222> LOCATION: (7)..(7)
<223> OTHER INFORMATION: /replace="Ser"
<220> FEATURE:
```

```
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 423

Tyr Ile Tyr Tyr Asn Arg Gly Thr
1               5

<210> SEQ ID NO 424
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (15)..(15)
<223> OTHER INFORMATION: /replace="Ile"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"

<400> SEQUENCE: 424

Ala Arg Cys Val Leu Gly Gly Tyr Gly Ser Asp Ala Phe Asp Arg
1               5                   10                  15

<210> SEQ ID NO 425
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (9)..(9)
<223> OTHER INFORMATION: /replace="Tyr"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 425

Arg Ala Ser Gln Ser Val Ser Ser His Leu Ala
1               5                   10

<210> SEQ ID NO 426
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Asn"
<220> FEATURE:
<221> NAME/KEY: VARIANT
<222> LOCATION: (8)..(8)
<223> OTHER INFORMATION: /replace="Thr"
<220> FEATURE:
```

-continued

```
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 426

Tyr Asp Ala Ser Ser Arg Ala Asn
1               5

<210> SEQ ID NO 427
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Asn"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 427

Gln Gln Arg Ser Ser Trp Pro Pro Ser Leu Thr
1               5                   10
```